United States Patent
Zhang

(10) Patent No.: US 10,370,406 B2
(45) Date of Patent: Aug. 6, 2019

(54) SALTS AND POLYMORPHS OF SCY-078

(71) Applicant: SCYNEXIS, INC., Jersey City, NJ (US)

(72) Inventor: Yi Zhang, Suzhou (CN)

(73) Assignee: SCYNEXIS, INC., Jersey City, NJ (US)

( * ) Notice: Subject to any disclaimer, the term of this patent is extended or adjusted under 35 U.S.C. 154(b) by 0 days.

(21) Appl. No.: 16/203,273

(22) Filed: Nov. 28, 2018

(65) Prior Publication Data

US 2019/0153024 A1     May 23, 2019

Related U.S. Application Data

(60) Division of application No. 14/995,593, filed on Jan. 14, 2016, now Pat. No. 10,174,074, which is a continuation of application No. PCT/CN2015/070967, filed on Jan. 19, 2015.

(51) Int. Cl.
| | |
|---|---|
| *C07D 405/14* | (2006.01) |
| *C07J 71/00* | (2006.01) |
| *C07C 59/265* | (2006.01) |

(52) U.S. Cl.
CPC ......... *C07J 71/0005* (2013.01); *C07C 59/265* (2013.01); *C07D 405/14* (2013.01)

(58) Field of Classification Search
None
See application file for complete search history.

(56) References Cited

U.S. PATENT DOCUMENTS 8,188,085 B2 * 5/2012 Greenlee ............. A01N 43/653
                                                                   514/252.05
2016/0207956 A1    7/2016 Zhang

FOREIGN PATENT DOCUMENTS

WO    WO 2010/019203 A1    2/2010

OTHER PUBLICATIONS

Bhattacharya, S. et al., "Thermoanalytical and Crystallographic Methods," Polymorphism in Pharmaceutical Solids, H.G. Brittain ed., Informa Healthcare, 2009, pp. 318-335.
International Search Report and Written Opinion issued from the European Patent Office for PCT/US2016/013356, dated Mar. 31, 2016 (9 pages).
Ivanisevic, I. et al., "Uses of X-Ray Powder Diffraction in the Pharmaceutical Industry," Pharmaceutical Formulation & Quality, Aug./Sep. 2011, pp. 30-33.
Mauludin, R. et al., "Kinetic solubility and dissolution velocity of rutin nanocrystals," European Journal of Pharmaceutical Sciences, vol. 36, 2009, pp. 502-510.
Saal, C. et al., "Optimizing solubility: Kinetic versus thermodynamic solubility temptations and risks," European Journal of Pharmaceutical Sciences, vol. 47, 2012, pp. 589-595.
Wiser, L. et al., "Solubility of Pharmaceutical Solids," Oral Bioavailability: Basic Principles, Advanced Concepts, and Applications, Hu, M. and Li Xiaoling eds., Chapter 3, New York John Wiley, 2011.

\* cited by examiner

*Primary Examiner* — Heidi Reese
(74) *Attorney, Agent, or Firm* — Finnegan, Henderson, Farabow, Garrett & Dunner L.L.P.

(57) ABSTRACT

SCY-078 is a glucan synthase inhibitor with antimicrobial activity. Novel salts and polymorph forms of SCY-078 are disclosed herein. The disclosure also relates to pharmaceutical compositions, methods of use, and methods of preparing the novel salts and polymorphs of SCY-078.

37 Claims, 128 Drawing Sheets

DSC/TGA of SCY-078 glycolate Type A

XRPD of SCY-078 mesylate Type A

DVS of SCY-078 hippurate Type B scaled-up

DSC/TGA of SCY-078 mesylate Type A scaled-up

DVS plot of Type A

DVS plot of Type A after process development

DVS plot of Type M

XRPD pattern of Type S

DVS plot of Type S

XRPD patterns overlay of disproportionated forms

XRPD overlay of Type S after stability study

Solubility curves of trifluoroacetate and hydrochloride in SGF

XRPD overlay of trifluoroacetate Type A from Example 59

XRPD overlay of trifluoroacetate Type B from Example 59

Solubility curves of trifluoroacetate and hydrochloride from Example 60

XRPD overlay of hydrochloride Type I from Example 60

Solubility curves of trifluoroacetate and hydrochloride from Example 61

Solubility curves of trifluoroacetate and hydrochloride from Example 62

XRPD overlay of trifluoroacetate Type A from Example 62

XRPD Overlay of hydrochloride Type I under 60 °C condition

SALTS AND POLYMORPHS OF SCY-078

This application is a divisional of U.S. patent application Ser. No. 14/995,593, filed Jan. 14, 2016, currently pending, which application claims the benefit of priority to International Application No. PCT/CN2015/070967, filed Jan. 19, 2015, all of which are incorporated by reference in their entirety.

SCY-078 (or "compound 1") is a glucan synthase inhibitor useful as an antifungal compound. SCY-078 is useful for treating, among other things, *Invasive Candidiasis* and *Invasive Aspergillosis*. Other antimicrobial utilities of SCY-078 are disclosed, for example, in U.S. Pat. No. 8,188,085, the relevant portions of which are incorporated herein by reference. SCY-078 has the following chemical structure:

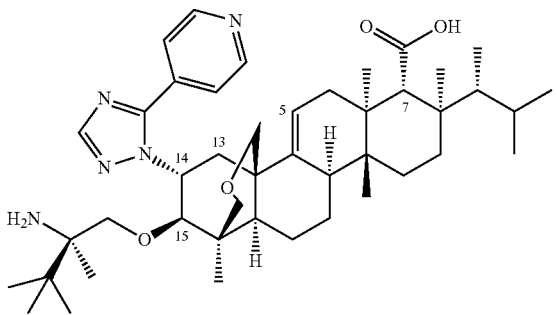

The present disclosure is directed to, among other things, pharmaceutically acceptable salts of SCY-078 and polymorphs of those salts. In another embodiment, the salts and polymorphs thereof exhibit certain kinetic solubilities. Higher kinetic solubilities can be importance in formulations, such as intravenous formulations. In yet another embodiment, the salts and polymorphs thereof exhibit certain hygroscopicities. Hygroscopity has been found to play an important role in the preparation of solid dosage forms and the selection of excipients. The present disclosure is further directed to, among other things, methods of preparing pharmaceutically acceptable salts of SCY-078 and polymorphs thereof.

The present disclosure is additionally directed to, among other things, pharmaceutical compositions comprising pharmaceutically acceptable salts of SCY-078 and polymorphs thereof. In another embodiment, the disclosure relates to methods of preparing pharmaceutical compositions comprising pharmaceutically acceptable salts of SCY-078 and polymorphs thereof suitable for injection or intravenous administration. In yet another embodiment, the present disclosure relates to method of treating fungal infections by administering pharmaceutically acceptable salts of SCY-078 and polymorphs thereof.

BRIEF DESCRIPTION OF DRAWINGS

FIG. 120 is an XRPD overlay of SCY-078 Trifluoroacetate Type A under 25° C./60% RH from Example 63.

FIG. 121 is an XRPD overlay of SCY-078 Trifluoroacetate Type A under 40° C./75% RH from Example 63.

FIG. 122 is an XRPD overlay of SCY-078 Trifluoroacetate Type A under 60° C. from Example 63.

FIG. 123 is an XRPD overlay of SCY-078 Trifluoroacetate Type B under 25° C./60% RH from Example 63.

FIG. 124 is an XRPD overlay of SCY-078 Trifluoroacetate Type B under 40° C./75% RH from Example 63.

FIG. 125 is an XRPD overlay of SCY-078 Trifluoroacetate Type B under 60° C. from Example 63.

FIG. 126 is an XRPD overlay of SCY-078 HCl Type I under 25° C./60% RH from Example 63.

FIG. 127 is an XRPD overlay of SCY-078 HCl Type I under 40° C./75% RH from Example 63.

FIG. 128 is an XRPD overlay of SCY-078 HCl Type I under 60° C. from Example 63.

DETAILED DESCRIPTION

Figure 1:
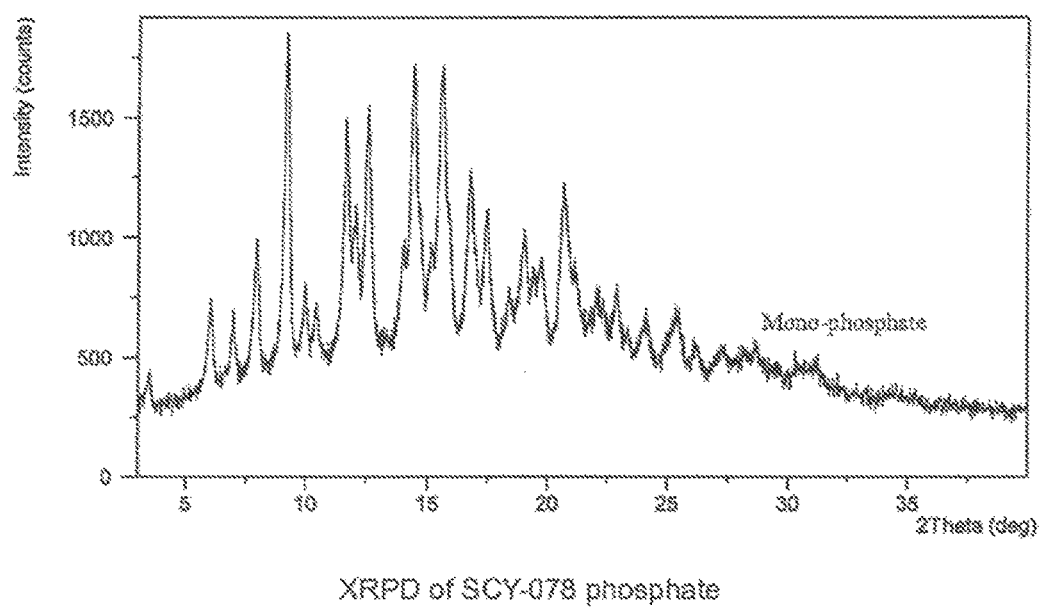
FIG. 1 is an X-ray Powder Diffraction "XRPD" pattern of SCY-078 phosphate from Example 1.

All numbers used herein, including those in the examples and claims, should be understood as being modified by the term "about" unless otherwise stated, such as with a specified precision. Unless expressly stated to the contrary, all ranges cited herein are inclusive.

As used herein, the singular forms "a," "an," and "the" include plural reference unless the context dictates otherwise.

The terms "SCY-078" and "compound 1" refer to the compound shown below, and refer to the freebase form unless otherwise indicated. Another name for SCY-078 is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a, 10b,11,12,12a-dodecahydro-1,6a,8,10a-tetramethyl-4H-4a-propano-2H-phenanthro[1,2-c]pyran-7-carboxylic acid.

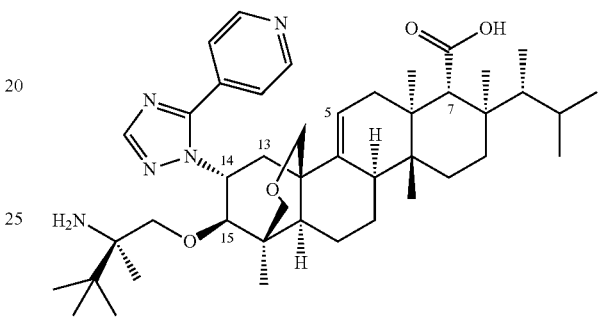

The term "HCl" refers to hydrochloric acid. The term "Ca" refers to calcium.

The terms "pharmaceutically acceptable salt" and the like should be understood to include, but not limited to, citrate salts, hippurate salts, fumarate salts, glycolate salts, mesylate salts, and calcium salts.

As used here, phrases such as "SCY-078 salt," "SCY-078 salts," "salt of SCY-078," "salts of SCY-078," "pharmaceutically acceptable salt of SCY-078," and "pharmaceutically acceptable salts thereof" should be understood to be salts in various forms, for example, the polymorphs disclosed herein. In addition, as used here, phrases such as "SCY-078 phosphate," "SCY-078 citrate," "SCY-078 hippurate," "SCY-078 glycolate," "SCY-078 mesylate," "SCY-078 fumarate," and "SCY-078 calcium" should be understood to be salts in various forms, for example, the polymorphs disclosed herein.

The term "solvent" and the like refer to any appropriate aqueous or organic solvent. Solvents include, but are not limited to, methanol, acetic acid, tetrahydrofuran, 2 methyltetrahydrofuran, 1,4-dioxane, n-methyl-2-pyrrolidone, dimethyl sulfoxide, dimethylacetamide, isopropyl alcohol, acetonitrile, acetone, ethyl acetate, water and mixtures thereof.

The term "pharmaceutically acceptable carrier" and the like refer to an ingredient that is compatible with SCY-078 and is not harmful to a patient's health. Pharmaceutically acceptable carriers include, but are not limited to, one or more of the following: aqueous vehicles and solvents, such as water, saline solutions, and alcohols; buffers; surface active agents; dispersing agents; inert diluents; preservatives; suspending agents; emulsifying agents; demulcents; thickening agents; emulsifying agents; antioxidants; and stabilizing agents. Other additional ingredients that may be included in the pharmaceutical compositions of the disclosure are generally known in the art and may be described, for example, in *Remington's Pharmaceutical Sciences*, Mack Publishing Co., Easton, Pa., which is incorporated by reference herein.

The term "injection" and the like refer to the insertion of a composition into the body by syringe, hollow needle, or the like. The term "injection" and the like include, but are not limited to, intravenous injections, including those entailing administering using an IV bag containing a diluent.

The term "effective amount" refers to an amount of the active ingredient that, when administered to a subject, alleviates at least some of the symptoms or stops the progression of the identified disease or condition. The terms "disease" or "condition" include, but are not limited to, infections such as fungal infections. Exemplary dosage amounts can be found, for example, in U.S. Pat. No. 8,188,085, the relevant portions of which are incorporated herein by reference.

The term "Å" refers to angstroms. Terms such as "2θ" or "2 Th." refer to degrees 2 theta.

The XRPD peaks recited herein should be understood to reflect a precision of ±0.2 for the 2 theta peaks, and the equivalent precision for d-spacings as per Bragg's law. The present disclosure also fully incorporates section 941 of the United States Pharmacopeia. The National Formulary from 2014 (USP 37/NF 32, volume 1) relating to characterization of crystalline and partially crystalline solids by X-ray Powder Diffraction.

The present disclosure relates to, among other things, pharmaceutically acceptable salts of SCY-078, wherein the salt is selected from citrate, hippurate, glycolate, mesylate, fumarate, and calcium. In one embodiment, the salt is selected from citrate, hippurate, mesylate, and fumarate. In a further embodiment, the SCY-078 salt is selected from SCY-078 hippurate Type A, SCY-078 hippurate Type B, and SCY-078 hippurate Type C. In another embodiment, the SCY-078 salt is selected from SCY-078 fumarate Type A and SCY-078 fumarate Type B. In yet another embodiment, the salt is a SCY-078 citrate salt. In yet a further embodiment, the salt is SCY-078 citrate Type A.

The present disclosure further relates to pharmaceutically acceptable salts of SCY-078 that have a chemical purity of at least 90%. In another embodiment, pharmaceutically acceptable salts of SCY-078 have a chemical purity of at least 95%. In a further embodiment, pharmaceutically acceptable salts of SCY-078 have a chemical purity of at least 98%. In yet another embodiment, pharmaceutically acceptable salts of SCY-078 have a chemical purity of at least 99%. In still another embodiment, the present disclosure relates to pharmaceutically acceptable salts of SCY-078, wherein the salt is selected from citrate, hippurate, mesylate, and fumarate, and wherein the salt has a chemical purity of at least 90%, at least 95%, at least 98%, or at least 99%.

The present disclosure additionally relates to pharmaceutically acceptable salts of SCY-078 that have a kinetic solubility of at least 2 mg/mL at 4 hours in dextrose buffer at pH 5.5. In one embodiment, the pharmaceutically acceptable salts of SCY-078 have a kinetic solubility of at least 4 mg/mL at 4 hours in dextrose buffer at pH 5.5. In another embodiment, the pharmaceutically acceptable salts of SCY-078 have a kinetic solubility of from 2 mg/mL to 5 mg/mL at 4 hours in dextrose buffer at pH 5.5. In yet another embodiment, the pharmaceutically acceptable salts of SCY-078 have a kinetic solubility of from 4 mg/mL to 5 mg/mL at 4 hours in dextrose buffer at pH 5.5. In still another embodiment, the pharmaceutically acceptable salts of SCY-078 have a kinetic solubility greater than SCY-078 (as a freebase) at 4 hours in dextrose buffer at pH 5.5.

The present disclosure additionally relates to pharmaceutically acceptable salts of SCY-078 that have a kinetic solubility of at least 2 mg/mL at 24 hours in dextrose buffer at pH 5.5. In one embodiment, the pharmaceutically acceptable salts of SCY-078 have a kinetic solubility of at least 4 mg/mL at 24 hours in dextrose buffer at pH 5.5. In another embodiment, the pharmaceutically acceptable salts of SCY-078 have a kinetic solubility of at least 8 mg/mL at 24 hours in dextrose buffer at pH 5.5. In a further embodiment, the pharmaceutically acceptable salts of SCY-078 have a kinetic solubility of from 2 mg/mL to 9 mg/mL at 24 hours in dextrose buffer at pH 5.5. In yet another embodiment, the pharmaceutically acceptable salts of SCY-078 have a kinetic solubility of from 4 mg/mL to 9 mg/mL at 24 hours in dextrose buffer at pH 5.5. In still another embodiment, the pharmaceutically acceptable salts of SCY-078 have a kinetic solubility of from 8 mg/mL to 9 mg/mL at 24 hours in dextrose buffer at pH 5.5.

The present disclosure additionally relates to pharmaceutically acceptable salts of SCY-078, wherein the salt is selected from citrate, hippurate, mesylate, and fumarate, and wherein the salt has a kinetic solubility of from 2 mg/mL to 5 mg/mL at 4 hours in dextrose buffer at pH 5.5. In one embodiment, the disclosure relates to pharmaceutically acceptable salts of SCY-078, wherein the salt is selected from citrate, hippurate, mesylate, and fumarate, and wherein the salt has a kinetic solubility of from 4 mg/mL to 5 mg/mL at 4 hours in dextrose buffer at pH 5.5.

In yet another embodiment, the disclosure relates to pharmaceutically acceptable salts of SCY-078, wherein the salt is selected from citrate, hippurate, mesylate, and fumarate, and wherein the salt has a kinetic solubility of from 2 mg/mL to 9 mg/mL at 24 hours in dextrose buffer at pH 5.5. In still another embodiment, the disclosure also relates to pharmaceutically acceptable salts of SCY-078, wherein the salt is selected from citrate, hippurate, mesylate, and fumarate, and wherein the salt has a kinetic solubility of from 4 mg/mL to 9 mg/mL at 24 hours in dextrose buffer at pH 5.5. In another embodiment, the disclosure relates to pharmaceutically acceptable salts of SCY-078, wherein the salt is selected from citrate, hippurate, mesylate, and fumarate, and wherein the salt has a kinetic solubility of from 8 mg/mL to 9 mg/mL at 24 hours in dextrose buffer at pH 5.5.

The present disclosure additionally relates to pharmaceutically acceptable salts of SCY-078 that have a kinetic solubility of at least 2 mg/mL at 4 hours in phosphate buffer at pH 6.0. In one embodiment, the pharmaceutically acceptable salts of SCY-078 have a kinetic solubility of at least 4 mg/mL at 4 hours in phosphate buffer at pH 6.0. In another embodiment, the pharmaceutically acceptable salts of SCY-078 have a kinetic solubility of from 2 mg/mL to 5 mg/mL at 4 hours in phosphate buffer at pH 6.0. In yet another embodiment, the pharmaceutically acceptable salts of SCY-078 have a kinetic solubility of from 4 mg/mL to 5 mg/mL at 4 hours in phosphate buffer at pH 6.0.

In still another embodiment, the pharmaceutically acceptable salts of SCY-078 have a kinetic solubility of at least 4.5 mg/mL at 24 hours in phosphate buffer at pH 6.0. In one embodiment, the pharmaceutically acceptable salts of SCY-078 have a kinetic solubility of at least 7 mg/mL at 24 hours in phosphate buffer at pH 6.0. In another embodiment, the pharmaceutically acceptable salts of SCY-078 have a kinetic solubility of from 4.5 mg/mL to 8 mg/mL at 24 hours in phosphate buffer at pH 6.0. In yet another embodiment, the pharmaceutically acceptable salts of SCY-078 have a kinetic solubility of from 7 mg/mL to 8 mg/mL at 24 hours in phosphate buffer at pH 6.0.

The present disclosure additionally relates to pharmaceutically acceptable salts of SCY-078, wherein the salt is selected from citrate, hippurate, mesylate, and fumarate, and wherein the salt has a kinetic solubility of from 1 mg/mL to 5 mg/mL at 4 hours in phosphate buffer at pH 6.0. In one embodiment, the disclosure relates to pharmaceutically acceptable salts of SCY-078, wherein the salt is selected from citrate, hippurate, mesylate, and fumarate, and wherein the salt has a kinetic solubility of from 4 mg/mL to 5 mg/mL at 4 hours in phosphate buffer at pH 6.0.

In another embodiment, the disclosure relates to pharmaceutically acceptable salts of SCY-078, wherein the salt is selected from citrate, hippurate, mesylate, and fumarate, and wherein the salt has a kinetic solubility of from 4 mg/mL to 8 mg/mL at 24 hours in phosphate buffer at pH 6.0. In yet another embodiment, the disclosure relates to pharmaceutically acceptable salts of SCY-078, wherein the salt is selected from citrate, hippurate, mesylate, and fumarate, and wherein the salt has a kinetic solubility of from 7 mg/mL to 8 mg/mL at 24 hours in phosphate buffer at pH 6.0.

The present disclosure additionally relates to pharmaceutically acceptable salts of SCY-078 that have a kinetic solubility of at least 16 mg/mL at 1 hour in SGF media. In one embodiment, the pharmaceutically acceptable salts of SCY-078 have a kinetic solubility of at least 17 mg/mL at 1 hour in SGF media. In another embodiment, the pharmaceutically acceptable salts of SCY-078 have a kinetic solubility of at least 18 mg/mL at 1 hour in SGF media. In yet another embodiment, the pharmaceutically acceptable salts of SCY-078 have a kinetic solubility of at least 20 mg/mL at 1 hour in SGF media.

The present disclosure additionally relates to pharmaceutically acceptable salts of SCY-078 that have a kinetic solubility of from 17 mg/mL to 21 mg/mL at 1 hour in SGF media. In another embodiment, the pharmaceutically acceptable salts of SCY-078 have a kinetic solubility of from 18 mg/mL to 21 mg/mL at 1 hour in SGF media. In yet another embodiment, the pharmaceutically acceptable salts of SCY-078 have a kinetic solubility of from 20 mg/mL to 21 mg/mL at 1 hour in SGF media.

The present disclosure additionally relates to pharmaceutically acceptable salts of SCY-078, wherein the salt is selected from citrate, hippurate, mesylate, and fumarate, and wherein the salt has a kinetic solubility of from 12 mg/mL to 21 mg/mL at 1 hour in SGF media. In one embodiment, the disclosure relates to pharmaceutically acceptable salts of SCY-078, wherein the salt is selected from citrate, hippurate, mesylate, and fumarate, and wherein the salt has a kinetic solubility of from 13 mg/mL to 21 mg/mL at 1 hour in SGF media. In another embodiment, the disclosure relates to pharmaceutically acceptable salts of SCY-078, wherein the salt is selected from citrate, hippurate, mesylate, and fumarate, and wherein the salt has a kinetic solubility of from 18 mg/mL to 21 mg/mL at 1 hour in SGF media. In yet another embodiment, the disclosure relates to pharmaceutically acceptable salts of SCY-078, wherein the salt is selected from citrate, hippurate, mesylate, and fumarate, and wherein the salt has a kinetic solubility of from 20 mg/mL to 21 mg/mL at 1 hour in SGF media.

The present disclosure additionally relates to pharmaceutically acceptable salts of SCY-078 that have a kinetic solubility of at least 17 mg/mL at 24 hours in FaSSIF media. In one embodiment, the pharmaceutically acceptable salts of SCY-078 have a kinetic solubility of at least 22 mg/mL at 24 hours in FaSSIF media. In another embodiment, the pharmaceutically acceptable salts of SCY-078 have a kinetic solubility of from 17 mg/mL to 22 mg/mL at 24 hours in FaSSIF media. In yet another embodiment, the pharmaceutically acceptable salts of SCY-078 have a kinetic solubility of from 21 mg/mL to 22 mg/mL at 24 hours in FaSSIF media.

The present disclosure additionally relates to pharmaceutically acceptable salts of SCY-078, wherein the salt is selected from citrate, hippurate, mesylate, and fumarate, and wherein the salt has a kinetic solubility of from 17 mg/mL to 22 mg/mL at 24 hours in FaSSIF media. In one embodiment, the disclosure relates to pharmaceutically acceptable salts of SCY-078, wherein the salt is selected from citrate, hippurate, mesylate, and fumarate, and wherein the salt has a kinetic solubility of from 21 mg/mL to 22 mg/mL at 24 hours in FaSSIF media.

The present disclosure additionally relates to pharmaceutically acceptable salts of SCY-078 having any of the disclosed kinetic solubilities and having a water sorption of not greater than 7% at 25° C. and 80% relative humidity as determined by DVS. In one embodiment, the pharmaceutically acceptable salts of SCY-078 have a water sorption of from 2% to 7% at 25° C. and 80% relative humidity as determined by DVS. In another embodiment, the pharmaceutically acceptable salts of SCY-078 have a water sorption of from 3% to 7% at 25° C. and 80% relative humidity as determined by DVS. In yet another embodiment, the pharmaceutically acceptable salts of SCY-078 have a water sorption of from 6% to 7% at 25° C. and 80% relative humidity as determined by DVS.

The present disclosure additionally relates to pharmaceutically acceptable salts of SCY-078, wherein the salt is selected from citrate, hippurate, mesylate, and fumarate, and wherein the salt has a water sorption of from 2% to 7% at 25° C. and 80% relative humidity as determined by DVS. In one embodiment, the disclosure relates to pharmaceutically acceptable salts of SCY-078, wherein the salt is selected from citrate, hippurate, mesylate, and fumarate, and wherein the salt has a water sorption of from 3% to 7% at 25° C. and 80% relative humidity as determined by DVS. In one embodiment, the disclosure relates to pharmaceutically acceptable salts of SCY-078, wherein the salt is selected from citrate, hippurate, mesylate, and fumarate, and wherein the salt has a water sorption of from 6% to 7% at 25° C. and 80% relative humidity as determined by DVS.

The present disclosure further relates to hippurate salts of SCY-078, such as SCY-078 hippurate Type A, SCY-078 hippurate Type B, and SCY-078 hippurate Type C. In one embodiment, the SCY-078 hippurate Type A has an XRPD pattern comprising peaks at one or more of the following locations:

TABLE A

| Pos. [°2 Th.] | Height [cts] | FWHM Left [°2 Th.] | d-spacing [Å] | Rel. Int. [%] |
|---|---|---|---|---|
| 6.276484 | 353.472400 | 0.102336 | 14.08226 | 12.90 |
| 7.023845 | 139.782300 | 0.307008 | 12.58545 | 5.10 |
| 7.900725 | 1475.766000 | 0.127920 | 11.19048 | 53.85 |
| 8.241444 | 302.522300 | 0.102336 | 10.72859 | 11.04 |
| 9.723080 | 945.921800 | 0.089544 | 9.09681 | 34.52 |
| 11.283030 | 414.659200 | 0.102336 | 7.84238 | 15.13 |
| 11.492390 | 300.886600 | 0.076752 | 7.69998 | 10.98 |
| 12.610210 | 2740.558000 | 0.089544 | 7.01982 | 100.00 |
| 12.910370 | 765.158500 | 0.063960 | 6.85728 | 27.92 |
| 13.561180 | 243.791900 | 0.153504 | 6.52963 | 8.90 |
| 14.149930 | 371.812900 | 0.102336 | 6.25924 | 13.57 |

TABLE A-continued

| Pos. [°2 Th.] | Height [cts] | FWHM Left [°2 Th.] | d-spacing [Å] | Rel. Int. [%] |
|---|---|---|---|---|
| 15.182550 | 1607.490000 | 0.102336 | 5.83577 | 58.66 |
| 15.806230 | 690.955800 | 0.179088 | 5.60688 | 25.21 |
| 16.673670 | 482.323700 | 0.179088 | 5.31709 | 17.60 |
| 17.068480 | 365.833300 | 0.127920 | 5.19498 | 13.35 |
| 18.200570 | 206.779900 | 0.153504 | 4.87432 | 7.55 |
| 18.933070 | 395.979900 | 0.153504 | 4.68736 | 14.45 |
| 19.293830 | 277.037400 | 0.102336 | 4.60052 | 10.11 |
| 19.924160 | 251.428800 | 0.204672 | 4.45638 | 9.17 |
| 20.583290 | 158.800000 | 0.204672 | 4.31514 | 5.79 |
| 21.951230 | 220.614300 | 0.153504 | 4.04923 | 8.05 |
| 23.477450 | 72.922780 | 0.409344 | 3.78934 | 2.66 |
| 24.511240 | 99.987140 | 0.255840 | 3.63181 | 3.65 |
| 24.954920 | 117.325600 | 0.153504 | 3.56824 | 4.28 |
| 25.993010 | 108.058000 | 0.204672 | 3.42804 | 3.94 |
| 28.257860 | 72.489400 | 0.409344 | 3.15822 | 2.65 |
| 31.063590 | 95.037750 | 0.179088 | 2.87907 | 3.47 |
| 31.653730 | 62.090590 | 0.307008 | 2.82673 | 2.27 |

For example, the SCY-078 hippurate Type A has an XRPD pattern comprising one or more peaks at d-spacings of 11.20, 7.02, and 5.84 Å. In another example, the SCY-078 hippurate Type A has an XRPD pattern comprising one or more peaks at degrees 2 theta of 7.90, 12.6, and 15.18.

In one embodiment, the SCY-078 hippurate Type B has an XRPD pattern comprising peaks at one or more of the following locations:

TABLE B

| Pos. [°2 Th.] | Height [cts] | FWHM Left [°2 Th.] | d-spacing [Å] | Rel. Int. [%] |
|---|---|---|---|---|
| 5.887601 | 118.925500 | 0.102336 | 15.01151 | 9.56 |
| 6.889384 | 462.675400 | 0.063960 | 12.83077 | 37.19 |
| 7.277837 | 251.176000 | 0.051168 | 12.14678 | 20.19 |
| 8.767134 | 927.066800 | 0.076752 | 10.08643 | 74.52 |
| 9.945603 | 1143.995000 | 0.102336 | 8.89377 | 91.96 |
| 10.843500 | 681.448200 | 0.102336 | 8.15925 | 54.78 |
| 11.822440 | 140.502200 | 0.127920 | 7.48575 | 11.29 |
| 12.417990 | 1244.014000 | 0.089544 | 7.12805 | 100.00 |
| 13.714490 | 435.466500 | 0.089544 | 6.45698 | 35.00 |
| 14.608760 | 1242.496000 | 0.102336 | 6.06367 | 99.88 |
| 15.050420 | 474.015800 | 0.102336 | 5.88670 | 38.10 |
| 16.071560 | 476.890000 | 0.127920 | 5.51491 | 38.33 |
| 16.476910 | 708.831400 | 0.102336 | 5.38014 | 56.98 |
| 16.857150 | 185.689200 | 0.102336 | 5.25963 | 14.93 |
| 17.289970 | 422.781900 | 0.127920 | 5.12893 | 33.99 |
| 17.612420 | 996.474200 | 0.089544 | 5.03575 | 80.10 |
| 18.405510 | 186.288500 | 0.153504 | 4.82051 | 14.97 |
| 19.118560 | 303.851800 | 0.127920 | 4.64230 | 24.43 |
| 19.623870 | 158.474700 | 0.153504 | 4.52389 | 12.74 |
| 20.218430 | 314.377200 | 0.153504 | 4.39218 | 25.27 |
| 21.746130 | 200.050600 | 0.153504 | 4.08695 | 16.08 |
| 23.075880 | 129.668200 | 0.204672 | 3.85436 | 10.42 |
| 23.853540 | 106.856400 | 0.204672 | 3.73044 | 8.59 |
| 25.372290 | 96.670350 | 0.204672 | 3.51048 | 7.77 |
| 29.216870 | 66.396300 | 0.230256 | 3.05670 | 5.34 |
| 32.714200 | 31.053470 | 0.614016 | 2.73748 | 2.50 |

For example, the SCY-078 hippurate Type B has an XRPD pattern comprising one or more peaks at d-spacings of 8.90, 7.13, and 6.10 Å. In another example, the SCY-078 hippurate Type B has an XRPD pattern comprising one or more peaks at degrees 2 theta of 9.95, 12.42, and 14.61.

In one embodiment, the SCY-078 hippurate Type C has an XRPD pattern comprising peaks at one or more of the following locations:

TABLE C

| Pos. [°2 Th.] | Height [cts] | FWHM Left [°2 Th.] | d-spacing [Å] | Rel. Int. [%] |
|---|---|---|---|---|
| 3.027072 | 11818.150000 | 0.051168 | 29.18766 | 100.00 |
| 5.916137 | 351.270000 | 0.102336 | 14.93916 | 2.97 |
| 6.916698 | 947.910600 | 0.102336 | 12.78016 | 8.02 |
| 7.251646 | 624.847700 | 0.076752 | 12.19059 | 5.29 |
| 8.761702 | 1828.733000 | 0.076752 | 10.09268 | 15.47 |
| 9.962105 | 2404.236000 | 0.102336 | 8.87907 | 20.34 |
| 10.897800 | 1593.408000 | 0.102336 | 8.11872 | 13.48 |
| 11.868550 | 552.254500 | 0.102336 | 7.45677 | 4.67 |
| 12.432300 | 2880.441000 | 0.127920 | 7.11988 | 24.37 |
| 12.857840 | 525.634600 | 0.076752 | 6.88518 | 4.45 |
| 13.091360 | 511.764400 | 0.115128 | 6.76288 | 4.33 |
| 13.709840 | 1112.219000 | 0.102336 | 6.45916 | 9.41 |
| 14.555290 | 3086.294000 | 0.153504 | 6.08582 | 26.11 |
| 14.984610 | 1215.693000 | 0.102336 | 5.91241 | 10.29 |
| 15.341160 | 506.870800 | 0.153504 | 5.77579 | 4.29 |
| 16.136210 | 1315.742000 | 0.089544 | 5.49296 | 11.13 |
| 16.453540 | 1710.358000 | 0.153504 | 5.38772 | 14.47 |
| 16.897030 | 606.324900 | 0.102336 | 5.24730 | 5.13 |
| 17.280760 | 1171.798000 | 0.127920 | 5.13164 | 9.92 |
| 17.591700 | 2258.867000 | 0.102336 | 5.04163 | 19.11 |
| 18.190770 | 538.754800 | 0.127920 | 4.87692 | 4.56 |
| 18.425670 | 516.831300 | 0.179088 | 4.81526 | 4.37 |
| 19.151570 | 950.084500 | 0.102336 | 4.63437 | 8.04 |
| 19.602330 | 487.956400 | 0.127920 | 4.52881 | 4.13 |
| 20.234760 | 861.917600 | 0.153504 | 4.38867 | 7.29 |
| 20.860030 | 424.598600 | 0.153504 | 4.25851 | 3.59 |
| 21.725360 | 459.496200 | 0.307008 | 4.09081 | 3.89 |
| 22.532320 | 498.240700 | 0.102336 | 3.94610 | 4.22 |
| 23.078810 | 380.947900 | 0.127920 | 3.85388 | 3.22 |
| 23.551950 | 208.488500 | 0.409344 | 3.77752 | 1.76 |
| 23.874020 | 377.598600 | 0.102336 | 3.72728 | 3.20 |
| 25.381750 | 351.553600 | 0.102336 | 3.50919 | 2.97 |
| 25.844490 | 207.070300 | 0.204672 | 3.44740 | 1.75 |
| 27.188450 | 192.463400 | 0.153504 | 3.27997 | 1.63 |
| 27.681830 | 144.369000 | 0.307008 | 3.22262 | 1.22 |
| 29.319670 | 172.870900 | 0.511680 | 3.04622 | 1.46 |
| 30.833510 | 86.432220 | 0.307008 | 2.90002 | 0.73 |
| 34.979000 | 90.330020 | 0.204672 | 2.56525 | 0.76 |
| 35.588330 | 69.479680 | 0.307008 | 2.52271 | 0.59 |
| 37.270360 | 55.666410 | 0.307008 | 2.41264 | 0.47 |

For example, the SCY-078 hippurate Type C has an XRPD pattern comprising one or more peaks at d-spacings of 29.19, 8.88, 7.12, and 6.09 Å. In another example, the SCY-078 hippurate Type C has an XRPD pattern comprising one or more peaks at degrees 2 theta of 3.03, 9.96, 12.43, and 14.56.

The present disclosure further relates to fumarate salts of SCY-078, such as SCY-078 fumarate Type A and SCY-078 fumarate Type B. In one embodiment, the SCY-078 fumarate Type A has an XRPD pattern comprising peaks at one or more of the following locations:

TABLE D

| Pos. [°2 Th.] | Height [cts] | FWHM Left [°2 Th.] | d-spacing [Å] | Rel. Int. [%] |
|---|---|---|---|---|
| 7.747007 | 167.350400 | 0.153504 | 11.41218 | 2.00 |
| 8.493147 | 8373.572000 | 0.102336 | 10.41119 | 100.00 |
| 9.346397 | 181.715800 | 0.204672 | 9.46257 | 2.17 |
| 9.931064 | 167.355100 | 0.153504 | 8.90676 | 2.00 |
| 10.442940 | 371.960600 | 0.089544 | 8.47130 | 4.44 |
| 10.706620 | 463.482500 | 0.076752 | 8.26326 | 5.54 |
| 11.231160 | 490.618200 | 0.153504 | 7.87848 | 5.86 |
| 13.030860 | 311.426800 | 0.102336 | 6.79415 | 3.72 |
| 13.700070 | 569.254300 | 0.102336 | 6.46374 | 6.80 |
| 14.895760 | 234.024600 | 0.153504 | 5.94748 | 2.79 |
| 15.204970 | 269.752200 | 0.153504 | 5.82722 | 3.22 |
| 16.350790 | 434.953000 | 0.127920 | 5.42135 | 5.19 |
| 16.976580 | 3015.489000 | 0.115128 | 5.22289 | 36.01 |
| 17.726110 | 1152.135000 | 0.230256 | 5.00370 | 13.76 |
| 18.205910 | 303.920500 | 0.102336 | 4.87290 | 3.63 |

TABLE D-continued

| Pos. [°2 Th.] | Height [cts] | FWHM Left [°2 Th.] | d-spacing [Å] | Rel. Int. [%] |
|---|---|---|---|---|
| 18.863510 | 267.939100 | 0.153504 | 4.70449 | 3.20 |
| 20.164360 | 63.804870 | 0.409344 | 4.40383 | 0.76 |
| 20.898390 | 184.877000 | 0.102336 | 4.25078 | 2.21 |
| 21.419940 | 168.417300 | 0.102336 | 4.14844 | 2.01 |
| 22.228150 | 318.867400 | 0.127920 | 3.99940 | 3.81 |
| 23.936960 | 77.330220 | 0.307008 | 3.71763 | 0.92 |
| 25.533030 | 318.681700 | 0.089544 | 3.48874 | 3.81 |
| 26.114530 | 59.303240 | 0.204672 | 3.41236 | 0.71 |
| 26.883130 | 111.136200 | 0.204672 | 3.31652 | 1.33 |
| 30.876670 | 38.684340 | 0.614016 | 2.89607 | 0.46 |

For example, the SCY-078 fumarate Type A has an XRPD pattern comprising one or more peaks at d-spacings of 10.41, 5.22, and 5.00 Å. In another example, the SCY-078 fumarate Type A has an XRPD pattern comprising one or more peaks at degrees 2 theta of 8.49, 16.98, and 17.73.

In one embodiment, the SCY-078 fumarate Type B has an XRPD pattern comprising peaks at one or more of the following locations:

TABLE E

| Pos. [°2 Th.] | Height [cts] | FWHM Left [°2 Th.] | d-spacing [Å] | Rel. Int. [%] |
|---|---|---|---|---|
| 5.449312 | 94.567020 | 0.307008 | 16.21786 | 19.92 |
| 6.318422 | 110.456500 | 0.409344 | 13.98888 | 23.26 |
| 9.799620 | 153.670200 | 0.614016 | 9.02593 | 32.36 |
| 10.577440 | 403.264100 | 0.255840 | 8.36388 | 84.93 |
| 10.995710 | 322.682700 | 0.089544 | 8.04665 | 67.96 |
| 11.970210 | 133.555200 | 0.307008 | 7.39367 | 28.13 |
| 13.136230 | 472.855300 | 0.102336 | 6.73989 | 99.58 |
| 13.551710 | 408.076200 | 0.102336 | 6.53417 | 85.94 |
| 14.201760 | 320.510900 | 0.204672 | 6.23651 | 67.50 |
| 15.712210 | 472.732700 | 0.076752 | 5.64022 | 99.56 |
| 16.216750 | 474.828900 | 0.076752 | 5.46586 | 100.00 |
| 16.849640 | 211.687300 | 0.204672 | 5.26195 | 44.58 |
| 20.391740 | 103.586500 | 0.358176 | 4.35524 | 21.82 |
| 21.343910 | 97.997770 | 0.409344 | 4.16305 | 20.64 |
| 28.564840 | 34.739620 | 0.614016 | 3.12498 | 7.32 |

For example, the SCY-078 fumarate Type B has an XRPD pattern comprising one or more peaks at d-spacings of 8.36, 6.74, 6.53, 5.64, and 5.47 Å. In another example, the SCY-078 fumarate Type B has an XRPD pattern comprising one or more peaks at degrees 2 theta of 10.58, 13.14, 13.55, 15.71, and 16.22.

The present disclosure further relates to glycolate salts of SCY-078. In one embodiment, the SCY-078 glycolate has an XRPD pattern comprising peaks at one or more of the following locations:

TABLE F

| Pos. [°2 Th.] | Height [cts] | FWHM Left [°2 Th.] | d-spacing [Å] | Rel. Int [%] |
|---|---|---|---|---|
| 7.879599 | 291.814000 | 0.127920 | 11.22044 | 54.74 |
| 8.983378 | 233.086200 | 0.204672 | 9.84412 | 43.72 |
| 9.855934 | 117.677600 | 0.153504 | 8.97448 | 22.07 |
| 11.483230 | 269.580500 | 0.204672 | 7.70610 | 50.56 |
| 12.311460 | 163.106800 | 0.358176 | 7.18949 | 30.59 |
| 14.259570 | 285.813400 | 0.179088 | 6.21136 | 53.61 |
| 14.651000 | 437.366100 | 0.102336 | 6.04628 | 82.04 |
| 15.433320 | 533.138100 | 0.102336 | 5.74151 | 100.00 |
| 16.892280 | 103.441500 | 0.614016 | 5.24877 | 19.40 |
| 18.826490 | 177.863500 | 0.204672 | 4.71365 | 33.36 |
| 20.401140 | 101.236200 | 0.307008 | 4.35325 | 18.99 |
| 21.743970 | 54.436950 | 0.614016 | 4.08735 | 10.21 |
| 24.981860 | 29.298130 | 0.614016 | 3.56445 | 5.50 |

For example, the SCY-078 glycolate has an XRPD pattern comprising one or more peaks at d-spacings of 11.22, 6.21, 6.05, and 5.74 Å. In another example, the SCY-078 glycolate has an XRPD pattern comprising one or more peaks at degrees 2 theta of 7.88, 14.26, 14.65, and 15.43.

The present disclosure further relates to mesylate salts of SCY-078. In one embodiment, the SCY-078 mesylate has an XRPD pattern comprising peaks at one or more of the following locations:

TABLE G

| Pos. [°2 Th.] | Height [cts] | FWHM Left [°2 Th.] | d-spacing [Å] | Rel. Int. [%] |
|---|---|---|---|---|
| 5.321569 | 44.016770 | 0.307008 | 16.60688 | 3.75 |
| 6.654286 | 233.467600 | 0.076752 | 13.28355 | 19.89 |
| 8.041747 | 243.835400 | 0.204672 | 10.99455 | 20.77 |
| 9.224843 | 236.712900 | 0.153504 | 9.58698 | 20.16 |
| 10.179890 | 547.128100 | 0.089544 | 8.68960 | 46.60 |
| 10.532080 | 592.551800 | 0.089544 | 8.39980 | 50.47 |
| 11.692820 | 225.932500 | 0.409344 | 7.56843 | 19.24 |
| 12.670270 | 361.926000 | 0.102336 | 6.98668 | 30.83 |
| 14.316750 | 537.652200 | 0.102336 | 6.18668 | 45.80 |
| 14.751260 | 1174.011000 | 0.102336 | 6.00541 | 100.00 |
| 15.645660 | 347.928600 | 0.204672 | 5.66406 | 29.64 |
| 16.537910 | 485.586600 | 0.179088 | 5.36043 | 41.36 |
| 17.477180 | 328.731900 | 0.127920 | 5.07441 | 28.00 |
| 18.838670 | 252.134300 | 0.307008 | 4.71063 | 21.48 |
| 19.613670 | 351.448500 | 0.153504 | 4.52622 | 29.94 |
| 21.008230 | 254.102200 | 0.204672 | 4.22880 | 21.64 |
| 22.068870 | 130.646600 | 0.307008 | 4.02791 | 11.13 |
| 23.475460 | 151.601600 | 0.204672 | 3.78965 | 12.91 |
| 25.592960 | 130.952000 | 0.153504 | 3.48071 | 11.15 |

For example, the SCY-078 mesylate has an XRPD pattern comprising one or more peaks at d-spacings of 10.99, 6.99, and 6.01 Å. In another example, the SCY-078 mesylate has an XRPD pattern comprising one or more peaks at degrees 2 theta of 8.04, 12.67, and 14.75.

The present disclosure further relates to calcium salts of SCY-078. In one embodiment, the SCY-078 Calcium has an XRPD pattern comprising peaks at one or more of the following locations:

TABLE H

| Pos. [°2 Th.] | Height [cts] | FWHM Left [°2 Th.] | d-spacing [Å] | Rel. Int. [%] |
|---|---|---|---|---|
| 5.330948 | 1222.647000 | 0.063960 | 16.57768 | 100.00 |
| 8.684942 | 82.143680 | 0.307008 | 10.18170 | 6.72 |
| 9.624508 | 215.229600 | 0.127920 | 9.18975 | 17.60 |
| 10.625810 | 286.722000 | 0.153504 | 8.32591 | 23.45 |
| 13.358050 | 110.336200 | 0.307008 | 6.62846 | 9.02 |
| 14.092620 | 101.325400 | 0.307008 | 6.28456 | 8.29 |
| 15.952080 | 1188.492000 | 0.153504 | 5.55594 | 97.21 |
| 16.282720 | 334.685300 | 0.153504 | 5.44386 | 27.37 |
| 17.853110 | 104.842700 | 0.153504 | 4.96839 | 8.58 |
| 19.638160 | 74.407610 | 0.307008 | 4.52063 | 6.09 |
| 29.434580 | 171.668200 | 0.204672 | 3.03457 | 14.04 |
| 30.178030 | 59.353870 | 0.153504 | 2.96150 | 4.85 |
| 31.428330 | 37.765730 | 0.307008 | 2.84648 | 3.09 |

For example, the SCY-078 calcium has an XRPD pattern comprising one or more peaks at d-spacings of 16.58, 5.56, and 5.44 Å. In another example, the SCY-078 calcium has an XRPD pattern comprising one or more peaks at degrees 2 theta of 5.33, 15.95, and 16.28.

The present disclosure further relates to citrate salts of SCY-078, such as SCY-078 citrate Type A, Type B, Type E, Type F, Type M, Type N, Type O, Type Q, Type R, and Type S. In one embodiment, the citrate salt of SCY-078 comprises at least one of Type A, Type B, Type E, Type F, Type M, Type N, Type O, Type Q, Type R, and Type S.

The present disclosure further relates to a citrate salt of SCY-078 comprising Type A. In one embodiment, the citrate salt of SCY-078 consists essentially of Type A. In another embodiment, the citrate salt of SCY-078 comprises at least 98% Type A. In a further embodiment, the citrate salt of SCY-078 comprises at least 99% Type A.

In one embodiment, the SCY-078 citrate Type A is stable for at least 1 week when stored at 60° C. In another embodiment, the SCY-078 citrate Type A is stable for at least 1 week when stored at 25° C. and 60% relative humidity. In a further embodiment, the SCY-078 citrate Type A is stable for at least 1 week when stored at 40° C. and 75% relative humidity.

In a further embodiment, the SCY-078 citrate Type A has an equilibrium solubility of 38 mg/mL in non-buffered water at ambient temperature. In yet another embodiment, the SCY-078 citrate Type A has an approximate solubility of from 40 mg/mL to 42 mg/mL at room temperature in at least one solvent selected from methanol, isopropyl alcohol, acetic acid, tetrahydrofuran, 2 methyl-tetrahydrofuran, 1,4-dioxane, n-methyl-2-pyrrolidone, dimethyl sulfoxide, and dimethylacetamide. In still another embodiment, the SCY-078 citrate Type A has a water sorption of 6% at 25° C. and 80% relative humidity as determined by DVS.

In one embodiment, the SCY-078 citrate Type A has a kinetic solubility of 4 mg/mL at 4 hours in dextrose buffer at pH 5.5. In another embodiment, the SCY-078 citrate Type A has a kinetic solubility of 8 mg/mL at 24 hours in dextrose buffer at pH 5.5. In a further embodiment, the SCY-078 citrate Type A has a kinetic solubility of 5 mg/mL at 4 hours in phosphate buffer at pH 6.0. In still another embodiment, the SCY-078 citrate Type A has a kinetic solubility of 8 mg/mL at 24 hours in phosphate buffer at pH 6.0.

In one embodiment, the SCY-078 citrate Type A has a kinetic solubility of 21 mg/mL at 1 hour in SGF media. In another embodiment, the SCY-078 citrate Type A has a kinetic solubility of 4 mg/mL at 24 hours in FeSSIF media. In yet another embodiment, the SCY-078 citrate Type A has a kinetic solubility of 10 mg/mL at 1 hour in FaSSIF media. In a further embodiment, the SCY-078 citrate Type A has a kinetic solubility of 21 mg/mL at 4 hours in FaSSIF media.

The present disclosure further relates to a citrate salt of SCY-078 comprising SCY-078 citrate Type A. In one embodiment, the SCY-078 citrate Type A has an XRPD pattern comprising peaks at one or more of the following locations:

TABLE I

| Pos. [°2 Th.] | Height [cts] | FWHM Left [°2 Th.] | d-spacing [Å] | Rel. Int. [%] |
|---|---|---|---|---|
| 5.400273 | 434.322700 | 0.102336 | 16.36502 | 3.34 |
| 7.453872 | 13000.820000 | 0.191880 | 11.86031 | 100.00 |
| 9.201639 | 691.948300 | 0.204672 | 9.61110 | 5.32 |
| 10.831710 | 404.555000 | 0.153504 | 8.16811 | 3.11 |
| 11.485080 | 936.115200 | 0.179088 | 7.70486 | 7.20 |
| 12.491050 | 954.805500 | 0.179088 | 7.08652 | 7.34 |
| 13.191360 | 1776.320000 | 0.204672 | 6.71184 | 13.66 |
| 15.020350 | 1342.537000 | 0.204672 | 5.89842 | 10.33 |
| 15.664830 | 532.278900 | 0.179088 | 5.65717 | 4.09 |
| 15.955570 | 613.057500 | 0.127920 | 5.55474 | 4.72 |
| 16.751250 | 951.729000 | 0.153504 | 5.29264 | 7.32 |
| 17.978130 | 170.323300 | 0.204672 | 4.93412 | 1.31 |
| 19.591770 | 472.971000 | 0.204672 | 4.53123 | 3.64 |
| 22.213400 | 146.982900 | 0.204672 | 4.00202 | 1.13 |
| 23.845740 | 34.469910 | 0.614016 | 3.73164 | 0.27 |
| 25.160050 | 117.741100 | 0.307008 | 3.53961 | 0.91 |

TABLE I-continued

| Pos. [°2 Th.] | Height [cts] | FWHM Left [°2 Th.] | d-spacing [Å] | Rel. Int. [%] |
|---|---|---|---|---|
| 28.761350 | 129.234400 | 0.255840 | 3.10407 | 0.99 |
| 30.356250 | 332.945100 | 0.230256 | 2.94452 | 2.56 |
| 32.317870 | 87.151140 | 0.307008 | 2.77014 | 0.67 |
| 34.725480 | 74.664570 | 0.511680 | 2.58339 | 0.57 |

For example, the SCY-078 citrate Type A has an XRPD pattern comprising one or more peaks at d-spacings of 11.86, 7.70, 7.09, 6.71, 5.90, and 5.29 Å. In another example, the SCY-078 citrate Type A has an XRPD pattern comprising one or more peaks at degrees 2 theta of 7.45, 11.49, 12.49, 13.19, 15.02, and 16.75.

The present disclosure further relates to a citrate salt of SCY-078 comprising SCY-078 citrate Type B. In one embodiment, the SCY-078 citrate Type B has an XRPD pattern comprising peaks at one or more of the following locations:

TABLE J

| Pos. [°2 Th.] | Height [cts] | FWHM Left [°2 Th.] | d-spacing [Å] | Rel. Int. [%] |
|---|---|---|---|---|
| 5.561437 | 214.772000 | 0.127920 | 15.89114 | 18.87 |
| 6.920576 | 1138.274000 | 0.115128 | 12.77301 | 100.00 |
| 9.319721 | 77.009080 | 0.307008 | 9.48959 | 6.77 |
| 11.144180 | 155.075600 | 0.153504 | 7.93978 | 13.62 |
| 11.729970 | 201.281900 | 0.153504 | 7.54455 | 17.68 |
| 13.405240 | 187.402700 | 0.358176 | 6.60523 | 16.46 |
| 15.225970 | 237.746900 | 0.204672 | 5.81923 | 20.89 |
| 16.813690 | 449.144100 | 0.153504 | 5.27312 | 39.46 |
| 18.219030 | 148.764600 | 0.204672 | 4.86942 | 13.07 |
| 19.324790 | 108.017600 | 0.153504 | 4.59322 | 9.49 |
| 20.531330 | 143.254500 | 0.127920 | 4.32594 | 12.59 |
| 23.721410 | 34.728650 | 0.307008 | 3.75092 | 3.05 |
| 26.000800 | 68.151450 | 0.204672 | 3.42703 | 5.99 |
| 29.343000 | 18.852780 | 0.614016 | 3.04385 | 1.66 |

For example, the SCY-078 citrate Type B has an XRPD pattern comprising one or more peaks at d-spacings of 15.89, 12.77, 7.54, 5.82, and 5.27 Å. In another example, the SCY-078 citrate Type B has an XRPD pattern comprising one or more peaks at degrees 2 theta of 5.56, 6.92, 11.73, 15.23, and 16.81.

The present disclosure further relates to a citrate salt of SCY-078 comprising SCY-078 citrate Type E. In one embodiment, the SCY-078 citrate Type E has an XRPD pattern comprising peaks at one or more of the following locations:

TABLE K

| Pos. [°2 Th.] | Height [cts] | FWHM Left [°2 Th.] | d-spacing [Å] | Rel. Int. [%] |
|---|---|---|---|---|
| 5.524293 | 92.779970 | 0.307008 | 15.99790 | 5.74 |
| 7.256628 | 1616.341000 | 0.179088 | 12.18224 | 100.00 |
| 11.438900 | 216.111400 | 0.281424 | 7.73586 | 13.37 |
| 14.135060 | 246.012400 | 0.255840 | 6.26579 | 15.22 |
| 15.755470 | 336.295500 | 0.255840 | 5.62483 | 20.81 |
| 16.331430 | 208.920100 | 0.255840 | 5.42773 | 12.93 |
| 17.088060 | 99.712520 | 0.409344 | 5.18907 | 6.17 |
| 21.127980 | 46.130650 | 0.614016 | 4.20511 | 2.85 |
| 31.562360 | 23.421260 | 0.614016 | 2.83470 | 1.45 |

For example, the SCY-078 citrate Type E has an XRPD pattern comprising one or more peaks at d-spacings of 12.18, 7.74, 6.27, 5.62, and 5.43 Å. In another example, the SCY-078 citrate Type E has an XRPD pattern comprising one or more peaks at degrees 2 theta of 7.26, 11.44, 14.14, 15.76, and 16.33.

The present disclosure further relates to a citrate salt of SCY-078 comprising SCY-078 citrate Type F. In one embodiment, the SCY-078 citrate Type F has an XRPD pattern comprising peaks at one or more of the following locations:

TABLE L

| Pos. [°2 Th.] | Height [cts] | FWHM Left [°2 Th.] | d-spacing [Å] | Rel. Int. [%] |
|---|---|---|---|---|
| 3.633823 | 273.473300 | 0.204672 | 24.31535 | 100.00 |
| 8.094996 | 83.291080 | 0.307008 | 10.92235 | 30.46 |
| 14.004250 | 57.266020 | 0.818688 | 6.32402 | 20.94 |
| 17.742840 | 88.241520 | 0.307008 | 4.99902 | 32.27 |

For example, the SCY-078 citrate Type F has an XRPD pattern comprising one or more peaks at d-spacings of 24.32 and 5.00 Å. In another example, the SCY-078 citrate Type F has an XRPD pattern comprising one or more peaks at degrees 2 theta of 3.63 and 17.74.

The present disclosure further relates to a citrate salt of SCY-078 comprising SCY-078 citrate Type M. In one embodiment, the SCY-078 citrate Type M has an XRPD pattern comprising peaks at one or more of the following locations:

TABLE M

| Pos. [°2 Th.] | Height [cts] | FWHM Left [°2 Th.] | d-spacing [Å] | Rel. Int. [%] |
|---|---|---|---|---|
| 5.572099 | 251.586000 | 0.179088 | 15.86076 | 9.89 |
| 7.341430 | 2543.546000 | 0.332592 | 12.04171 | 100.00 |
| 9.506812 | 193.442600 | 0.307008 | 9.30326 | 7.61 |
| 11.507120 | 612.058600 | 0.281424 | 7.69016 | 24.06 |
| 12.151790 | 217.504900 | 0.255840 | 7.28359 | 8.55 |
| 14.166310 | 475.291100 | 0.179088 | 6.25204 | 18.69 |
| 15.796090 | 798.112100 | 0.255840 | 5.61046 | 31.38 |
| 16.373100 | 704.236700 | 0.179088 | 5.41401 | 27.69 |
| 17.342680 | 236.560600 | 0.511680 | 5.11346 | 9.30 |
| 18.264100 | 127.099200 | 0.307008 | 4.85751 | 5.00 |
| 20.028560 | 111.330700 | 0.307008 | 4.43338 | 4.38 |
| 21.230190 | 166.125100 | 0.255840 | 4.18509 | 6.53 |
| 22.124240 | 151.032300 | 0.358176 | 4.01795 | 5.94 |
| 23.019390 | 107.550400 | 0.307008 | 3.86369 | 4.23 |
| 25.286220 | 144.601600 | 0.511680 | 3.52223 | 5.69 |
| 27.656070 | 79.447100 | 0.358176 | 3.22556 | 3.12 |
| 28.430390 | 56.622940 | 0.409344 | 3.13945 | 2.23 |
| 29.646340 | 75.432070 | 0.614016 | 3.01339 | 2.97 |
| 32.376530 | 74.417430 | 0.307008 | 2.76525 | 2.93 |
| 36.534050 | 34.760060 | 0.614016 | 2.45955 | 1.37 |
| 38.139080 | 26.017290 | 0.614016 | 2.35966 | 1.02 |

For example, the SCY-078 citrate Type M has an XRPD pattern comprising one or more peaks at d-spacings of 12.04, 7.69, 6.25, 5.61, and 5.41 Å. In another example, the SCY-078 citrate Type M has an XRPD pattern comprising one or more peaks at degrees 2 theta of 7.34, 11.51, 14.17, 15.80, and 16.37.

The present disclosure further relates to a citrate salt of SCY-078 comprising SCY-078 citrate Type N. In one embodiment, the SCY-078 citrate Type N has an XRPD pattern comprising peaks at one or more of the following locations:

TABLE N

| Pos. [°2 Th.] | Height [cts] | FWHM Left [°2 Th.] | d-spacing [Å] | Rel. Int. [%] |
|---|---|---|---|---|
| 5.410849 | 486.098000 | 0.076752 | 16.33306 | 9.13 |
| 7.067553 | 5326.844000 | 0.089544 | 12.50771 | 100.00 |
| 10.838060 | 670.175200 | 0.063960 | 8.16333 | 12.58 |
| 11.383920 | 1260.568000 | 0.089544 | 7.77310 | 23.66 |
| 11.924900 | 315.766000 | 0.153504 | 7.42166 | 5.93 |
| 12.367310 | 352.822800 | 0.153504 | 7.15714 | 6.62 |
| 12.923310 | 1574.956000 | 0.089544 | 6.85044 | 29.57 |
| 14.132120 | 1282.157000 | 0.102336 | 6.26708 | 24.07 |
| 15.162450 | 1604.350000 | 0.102336 | 5.84346 | 30.12 |
| 16.256930 | 1496.153000 | 0.089544 | 5.45244 | 28.09 |
| 16.676790 | 891.116500 | 0.115128 | 5.31610 | 16.73 |
| 16.898590 | 608.961300 | 0.102336 | 5.24682 | 11.43 |
| 17.769210 | 633.106100 | 0.127920 | 4.99166 | 11.89 |
| 18.512560 | 1119.245000 | 0.102336 | 4.79287 | 21.01 |
| 20.764100 | 264.835400 | 0.102336 | 4.27797 | 4.97 |
| 21.599360 | 277.781400 | 0.127920 | 4.11439 | 5.21 |
| 22.726850 | 204.007000 | 0.102336 | 3.91276 | 3.83 |
| 23.066060 | 336.013100 | 0.153504 | 3.85598 | 6.31 |
| 24.489610 | 243.365100 | 0.127920 | 3.63497 | 4.57 |
| 28.491330 | 175.736200 | 0.179088 | 3.13287 | 3.30 |
| 30.668850 | 84.372280 | 0.307008 | 2.91522 | 1.58 |
| 33.097360 | 34.363080 | 0.614016 | 2.70666 | 0.65 |
| 36.308500 | 40.510880 | 0.716352 | 2.47431 | 0.76 |

For example, the SCY-078 citrate Type N has an XRPD pattern comprising one or more peaks at d-spacings of 12.51, 7.77, 6.85, 6.27, 5.84, 5.45, and 4.79 Å. In another example, the SCY-078 citrate Type N has an XRPD pattern comprising one or more peaks at degrees 2 theta of 7.07, 11.38, 12.92, 14.13, 15.16, 16.26, and 18.51.

The present disclosure further relates to a citrate salt of SCY-078 comprising SCY-078 citrate Type O. In one embodiment, the SCY-078 citrate Type O has an XRPD pattern comprising peaks at one or more of the following locations:

TABLE O

| Pos. [°2 Th.] | Height [cts] | FWHM Left [°2 Th.] | d-spacing [Å] | Rel. Int. [%] |
|---|---|---|---|---|
| 3.214240 | 359.101800 | 0.409344 | 27.48844 | 9.56 |
| 5.562890 | 564.632100 | 0.102336 | 15.88699 | 15.03 |
| 7.082335 | 3757.717000 | 0.115128 | 12.48164 | 100.00 |
| 11.908250 | 1208.103000 | 0.089544 | 7.43200 | 32.15 |
| 14.197590 | 602.552700 | 0.115128 | 6.23833 | 16.04 |
| 16.178670 | 447.137400 | 0.179088 | 5.47864 | 11.90 |
| 16.755170 | 956.290800 | 0.115128 | 5.29141 | 25.45 |
| 28.567280 | 48.759020 | 0.307008 | 3.12472 | 1.30 |

For example, the SCY-078 citrate Type O has an XRPD pattern comprising one or more peaks at d-spacings of 12.48, 7.43, and 5.29 Å. In another example, the SCY-078 citrate Type O has an XRPD pattern comprising one or more peaks at degrees 2 theta of 7.08, 11.91, and 16.76.

The present disclosure further relates to a citrate salt of SCY-078 comprising SCY-078 citrate Type Q. In one embodiment, the SCY-078 citrate Type Q has an XRPD pattern comprising peaks at one or more of the following locations:

TABLE P

| Pos. [°2 Th.] | Height [cts] | FWHM Left [°2 Th.] | d-spacing [Å] | Rel. Int. [%] |
|---|---|---|---|---|
| 5.686347 | 449.970600 | 0.102336 | 15.54234 | 13.51 |
| 6.300879 | 3329.599000 | 0.140712 | 14.02779 | 100.00 |
| 6.890776 | 1871.585000 | 0.076752 | 12.82818 | 56.21 |

TABLE P-continued

| Pos. [°2 Th.] | Height [cts] | FWHM Left [°2 Th.] | d-spacing [Å] | Rel. Int. [%] |
|---|---|---|---|---|
| 8.441730 | 95.233120 | 0.153504 | 10.47449 | 2.86 |
| 9.785571 | 136.396600 | 0.153504 | 9.03885 | 4.10 |
| 11.334590 | 1386.986000 | 0.140712 | 7.80682 | 41.66 |
| 11.733060 | 826.632000 | 0.102336 | 7.54257 | 24.83 |
| 12.939760 | 265.781600 | 0.409344 | 6.84177 | 7.98 |
| 13.691820 | 190.778000 | 0.153504 | 6.46762 | 5.73 |
| 14.156830 | 332.781500 | 0.153504 | 6.25620 | 9.99 |
| 14.496570 | 455.453300 | 0.102336 | 6.11034 | 13.68 |
| 15.135910 | 594.105600 | 0.153504 | 5.85365 | 17.84 |
| 15.903400 | 540.737100 | 0.127920 | 5.57284 | 16.24 |
| 17.010910 | 1588.263000 | 0.127920 | 5.21243 | 47.70 |
| 17.296950 | 476.914900 | 0.127920 | 5.12687 | 14.32 |
| 18.962100 | 570.585000 | 0.204672 | 4.68025 | 17.14 |
| 20.190720 | 395.466100 | 0.102336 | 4.39814 | 11.88 |
| 20.646480 | 601.591200 | 0.153504 | 4.30207 | 18.07 |
| 21.298380 | 208.197100 | 0.153504 | 4.17185 | 6.25 |
| 22.025220 | 160.183700 | 0.307008 | 4.03579 | 4.81 |
| 22.719750 | 205.611500 | 0.204672 | 3.91397 | 6.18 |
| 23.633070 | 128.288000 | 0.307008 | 3.76474 | 3.85 |
| 25.991160 | 157.744000 | 0.204672 | 3.42828 | 4.74 |
| 27.462080 | 37.389280 | 0.307008 | 3.24790 | 1.12 |
| 28.950740 | 597.140100 | 0.140712 | 3.08419 | 17.93 |
| 34.085010 | 29.835660 | 0.511680 | 2.63046 | 0.90 |

For example, the SCY-078 citrate Type Q has an XRPD pattern comprising one or more peaks at d-spacings of 14.03, 12.83, 7.81, 7.54, and 5.21 Å. In another example, the SCY-078 citrate Type Q has an XRPD pattern comprising one or more peaks at degrees 2 theta of 6.30, 6.89, 11.33, 11.73, and 17.01.

The present disclosure further relates to a citrate salt of SCY-078 comprising SCY-078 citrate Type R. In one embodiment, the SCY-078 citrate Type R has an XRPD pattern comprising peaks at one or more of the following locations:

TABLE Q

| Pos. [°2 Th.] | Height [cts] | FWHM Left [°2 Th.] | d-spacing [Å] | Rel. Int. [%] |
|---|---|---|---|---|
| 6.143884 | 611.904200 | 0.153504 | 14.38589 | 100.00 |
| 11.248800 | 143.606900 | 0.255840 | 7.86616 | 23.47 |
| 14.059410 | 351.488100 | 0.204672 | 6.29933 | 57.44 |
| 14.636960 | 372.993000 | 0.204672 | 6.05205 | 60.96 |
| 16.413500 | 550.672100 | 0.102336 | 5.40078 | 89.99 |
| 17.742000 | 362.377400 | 0.614016 | 4.99926 | 59.22 |
| 19.697290 | 248.048100 | 0.307008 | 4.50719 | 40.54 |
| 22.159300 | 133.589200 | 0.409344 | 4.01167 | 21.83 |
| 30.197650 | 27.706020 | 0.614016 | 2.95963 | 4.53 |

For example, the SCY-078 citrate Type R has an XRPD pattern comprising one or more peaks at d-spacings of 14.39, 6.05, 5.40, and 5.00 Å. In another example, the SCY-078 citrate Type R has an XRPD pattern comprising one or more peaks at degrees 2 theta of 6.14, 14.64, 16.41, and 17.74.

The present disclosure further relates to a citrate salt of SCY-078 comprising SCY-078 citrate Type S. In one embodiment, the SCY-078 citrate Type S has an XRPD pattern comprising peaks at one or more of the following locations:

TABLE R

| Pos. [°2 Th.] | Height [cts] | FWHM Left [°2 Th.] | d-spacing [Å] | Rel. Int. [%] |
|---|---|---|---|---|
| 5.512446 | 1020.013000 | 0.089544 | 16.03226 | 16.16 |
| 7.296105 | 6310.710000 | 0.153504 | 12.11641 | 100.00 |

TABLE R-continued

| Pos. [°2 Th.] | Height [cts] | FWHM Left [°2 Th.] | d-spacing [Å] | Rel. Int. [%] |
|---|---|---|---|---|
| 8.443163 | 252.219900 | 0.230256 | 10.47272 | 4.00 |
| 11.057440 | 582.228600 | 0.179088 | 8.00186 | 9.23 |
| 12.004950 | 2714.326000 | 0.166296 | 7.37235 | 43.01 |
| 14.346070 | 536.999100 | 0.204672 | 6.17410 | 8.51 |
| 16.812800 | 1626.861000 | 0.127920 | 5.27340 | 25.78 |
| 19.482230 | 106.142000 | 0.358176 | 4.55646 | 1.68 |
| 22.188280 | 88.048920 | 0.409344 | 4.00650 | 1.40 |
| 24.046320 | 53.183810 | 0.818688 | 3.70096 | 0.84 |

For example, the SCY-078 citrate Type S has an XRPD pattern comprising one or more peaks at d-spacings of 16.03, 12.12, 7.37, and 5.27 Å. In another example, the SCY-078 citrate Type S has an XRPD pattern comprising one or more peaks at degrees 2 theta of 5.51, 7.30, 12.00, and 16.81.

The present disclosure further relates to a method for preparing a pharmaceutically acceptable salt of SCY-078 comprising combining at least components: (i) a free base of SCY-078; (ii) a weak organic acid; and (iii) a liquid carrier. The weak organic acid may be chosen from those known in the art. In one embodiment, the weak organic acid is selected from citric acid, fumaric acid, methanesulfonic acid, and hippuric acid. In another embodiment, the weak organic acid is citric acid. In a further embodiment, the liquid carrier is a solvent or solvent mixture, and at least one of the free base of SCY-078 and the weak organic acid is soluble in the solvent or solvent mixture. In still another embodiment, the liquid carrier comprises at least one of ethanol, isopropyl alcohol, acetonitrile, acetone, ethyl acetate, and tetrahydrofuran/water mixture. In yet another embodiment, the liquid carrier comprises ethanol. In one embodiment, the method further comprises combining (iv) an anti-solvent. In another embodiment, the anti-solvent comprises N-heptane.

In one embodiment, the method further comprises agitating the combination of at least components (i)-(iii). In a further embodiment, the method further comprises agitating the combination of at least components (i)-(iii) for at least 24 hours. In another embodiment, the method further comprises agitating and heating the combination of at least components (i)-(iii). In a further embodiment, the method further comprises agitating and heating the combination of at least components (i)-(iii) to a temperature of from 40° C. to 60° C. In still another embodiment, the method further comprises agitating and heating the combination of at least components (i)-(iii) to a temperature of from 40° C. to 60° C. for at least 60 minutes.

In one embodiment, the method further comprises agitating and heating the combination of at least components (i)-(iii) and adding to the combination of at least components (i)-(iii) an anti-solvent after at least 14 hours. In yet another embodiment, the anti-solvent is N-heptane.

In one embodiment, the method further comprises agitating and heating the combination of at least components (i)-(iii); adding to the combination of at least components (i)-(iii) an anti-solvent after at least 14 hours; and cooling the combination of at least components (i)-(iii). In a further embodiment, the cooling is from 0° C. to 20° C. In another embodiment, the cooling is from 0° C. to 20° C. at a rate of 0.25° C./min.

The present disclosure further relates to methods for preparing citrate Type A salt of SCY-078. In one embodiment, the method comprises desolvating at least one of Type B, Type N, and Type Q citrate salt of SCY-078. In a further embodiment, the desolvating comprises drying under nitrogen. In yet another embodiment, the desolvating comprises drying under vacuum filtration.

The present disclosure additionally relates to pharmaceutical compositions comprising a pharmaceutically acceptable salt of SCY-078, and a pharmaceutically acceptable carrier. The pharmaceutically acceptable carrier may be chosen from, among other things, one or more of the following: water, saline solutions, buffers, and alcohols. In one embodiment, the pharmaceutically acceptable salt in the pharmaceutical composition is selected from citrate, hippurate, mesylate, and fumarate. In yet another embodiment, the pharmaceutically acceptable salt is a citrate salt. In still another embodiment, the pharmaceutically acceptable salt of SCY-078 is SCY-078 citrate Type A.

According to certain embodiments, the pharmaceutically acceptable salt of SCY-078 may consist essentially of a specified crystal form. According to certain embodiments, the pharmaceutically acceptable salt of SCY-078 may comprise a specified crystal in combination with one or more other crystal forms. The pharmaceutically acceptable salt of SCY-078 may, for example, contain a specified crystal form together with less than 10% of another crystal form(s), such as less than 5%, less than 2%, or less than 1%.

In one embodiment, the pharmaceutical composition is made by dissolving the pharmaceutically acceptable salt of SCY-078 in a pharmaceutically acceptable carrier. The pharmaceutically acceptable carrier may be chosen from, among other things, one or more of the following: water, saline solutions, buffers, and alcohols. In another embodiment, the pharmaceutical composition is suitable for injection into a human. In a further embodiment, the pharmaceutical composition is suitable for intravenous injection into a human. In another embodiment, the pharmaceutically acceptable salt is a citrate salt. In still another embodiment, the pharmaceutically acceptable salt of SCY-078 is SCY-078 citrate Type A.

The present disclosure further relates to methods of preparing a pharmaceutical composition comprising pharmaceutically acceptable salts of SCY-078, and a pharmaceutically acceptable carrier. The pharmaceutically acceptable carrier may be chosen from, among other things, one or more of the following: water, saline solutions, buffers, and alcohols. In one embodiment, the pharmaceutically acceptable salt of SCY-078 is dissolved in the pharmaceutically acceptable carrier within 1 hour. In another embodiment, the pharmaceutically acceptable salt of SCY-078 is dissolved in the pharmaceutically acceptable carrier within 24 hours. In a further embodiment, the pharmaceutically acceptable salt is a citrate salt. In still another embodiment, the pharmaceutically acceptable salt of SCY-078 is SCY-078 citrate Type A.

The present disclosure additionally relates to methods of treating a fungal infection in a patient in need thereof. For example, the methods include treating *Invasive Candidiasis* and *Invasive Aspergillosis*. In one embodiment, the method comprises administering to the patient in need thereof a pharmaceutical composition comprising an effective amount of a pharmaceutically acceptable salt of SCY-078. In another embodiment, the pharmaceutically acceptable salt is a citrate salt. In a further embodiment, the pharmaceutically acceptable salt of SCY-078 is SCY-078 citrate Type A. In another embodiment, the pharmaceutical composition is suitable for injection into a human. In yet another embodiment, the pharmaceutical composition is suitable for intravenous injection into a human.

EXAMPLES

Methods and Materials

The following describes the materials and methods used for all examples unless otherwise stated.

TABLE 1

| Type | Abbreviation/Acronym | Full Name/Description |
|---|---|---|
| Solvent | ACN | Acetonitrile |
| | DCM | Dichloromethane |
| | DMA | Dimethylamine |
| | DMAc | Dimethylacetamide |
| | DMSO | Dimethyl sulfoxide |
| | EtOH | Ethanol |
| | EtOAc | Ethyl Acetate |
| | IPA | Isopropyl alcohol |
| | IPAc | Isopropyl acetate |
| | MeOH | Methanol |
| | MIBK | Methyl isobutyl ketone |
| | MTBE | Methyl tert-butyl ether |
| | NMP | N-methyl-2-pyrrolidone |
| | THF | Tetrahydrofuran |
| Bio-Relevant Media | SGF | Simulated gastric fluid |
| | FaSSIF | Fasted state simulated intestinal fluid |
| | FeSSIF | Fed state simulated intestinal fluid |
| Techniques | DSC | Differential scanning calorimetry |
| | DVS | Dynamic Vapor Sorption |
| | HPLC | High Performance Liquid Chromatography |
| | TGA | Thermogravimetric analysis |
| | XRPD | X-ray power diffraction |
| Other | FB | Freebase |
| | NF | New form |
| | RH | Relative humidity |
| | RT | Room temperature |

X-Ray Powder Diffraction (XRPD)—

To perform XRPD analysis, a PANanalytical Empryean X-ray powder diffractometer was used. The typical XRPD parameters used are listed below. Data Viewer (version 1.4a) from PANanalytic was used for analysis.

| | |
|---|---|
| X-Ray Wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence split | Automatic |
| Scan mood | Continuous |
| Scan range (°2 TH) | 3°-40° |
| Step size (°2 TH) | 0.0130 or 0.0170 |
| Scan speed (°/min) | ~10 |

Differential Scanning Calorimetry (DSC)—

DSC was performed with a TA Q2000 DSC from TA Instruments. To perform DSC, the sample was ramped from room temperature to the desired temperature at a heating rate of 10° C./min, using $N_2$ as the purge gas and with the pan crimped. Universal Analysis 2000 (TA Instruments) was used to analyze the results.

Thermogravimetric Analysis (TGA)—

TGA was performed with a TA Q500/Q5000 TGA from TA Instruments. To perform TGA, the sample was ramped from room temperature to the desired temperature at a heating rate of 10° C./min, using $N_2$ as the purge gas. Universal Analysis 2000 (TA Instruments) was used to analyze the results. The temperature was calibrated using nickel and the weight using TA-supplied standard weights and verified against calcium oxalate monohydrate dehydration and decomposition.

Dynamic Vapor Sorption (DVS)—

The term "DVS" means the procedure described in below. The relative humidity at 25° C. was calibrated against deliquescence point of LiCl, $Mg(NO_3)_2$ and KCl.

| | |
|---|---|
| Temperature | 25° C. |
| Gas Flow and Rate | $N_2$, 200 mL/min |
| dm/dt | 0.002%/min |
| Min. dm/dt stability duration | 10 min |
| Max. equilibrium time | 180 min |
| RH range | 95% RH-0% RH-95% RH |
| RH step size | 10% (90% RH-0% RH-90% RH) |
| | 5% (90% RH-95% RH-90% RH) |

The DVS of SCY-078 salts were tested according to the above method, using a 10-20 mg sample size. The DVS was measured using a Surface Measurement Systems (SMS) DVS Intrinsic.

High Power Liquid Chromatography (HPLC) Method—

An Agilent 1260 HPLC with DAD detector was utilized to test solubility or to test purity and stability. For all compounds tested other than the trifluoroacetate salts (Type A and B) and the HCl Type I and II salts, the conditions and parameters used for measuring solubility are shown in Table 2A and for measuring stability are showing in Table 3 Å. The conditions and parameters used for the solubility of the trifluoroacetate salts (Type A and B) and the HCl Type I and II salts are shown in Table 2B and for stability are shown in Table 3B. System suitability was tested by injecting standard solutions five times in each sample sequence, and the relative standard deviation of the peak areas was less than 2%.

TABLE 2A

| | | | |
|---|---|---|---|
| Column | 53#: Eclipse plus C18, 4.6 * 150 mm, 3.5 μm | | |
| Mobile Phase | A: 0.1% $HClO_4$ in $H_2O$B: ACN | | |
| Gradient Table | Time (mins) | % A | % B |
| | 0 | 70 | 30 |
| | 1 | 70 | 30 |
| | 7 | 5 | 95 |
| | 8 | 5 | 95 |
| | 8.1 | 70 | 30 |
| | 12 | 70 | 30 |
| Flow Rate | 1.0 mL/min | | |
| Injection Volume | 10 μL | | |
| Detector Wavelength | 255 nm | | |
| Run Time | 12 min | | |
| Column Temperature | 40° C. | | |
| Autosampler Temperature | RT | | |

TABLE 2B

| | | |
|---|---|---|
| Column | Waters C18 110A, 4.6 * 150 mm, 5 μm | |
| Mobile Phase | A: 0.1% TFA in $H_2O$; B: 0.1% TFA in acetonitrile | |
| Gradient Table | Time (mins) | % B |
| | 0 | 5 |
| | 1 | 5 |
| | 9 | 95 |
| | 11 | 95 |
| | 11.1 | 5 |
| | 15 | 5 |
| Flow Rate | 1.0 mL/min | |
| Injection Volume | 10 μL | |
| Detector Wavelength | UV at 255 nm | |
| Run Time | 15 min | |
| Column Temperature | 40° C. | |
| Autosampler Temperature | RT | |

TABLE 3A

| | | | |
|---|---|---|---|
| Column | Phenomenex, Gemini C18, 4.6 × 150 mm, 3 mm | | |
| Mobile Phase | A: 0.1% $HClO_4$ in $H_2O$ B: ACN | | |
| Gradient Table | Time (mins) | % A | % B |
| | 0.0 | 63 | 37 |
| | 5.0 | 43 | 57 |
| | 15.0 | 38 | 62 |
| | 20.0 | 10 | 90 |
| | 30.0 | 10 | 90 |
| | 31.0 | 63 | 37 |
| | 36.0 | 63 | 37 |
| Flow Rate | 1.0 mL/min | | |
| Injection Volume | 10 μL | | |
| Detector Wavelength | UV at 210 min | | |
| Run Time | 36.0 min | | |
| Column Temperature | 40° C. | | |
| Sampler Temperature | RT | | |
| Diluent | ACN | | |

TABLE 3B

| | | |
|---|---|---|
| Column | Waters C18 110A, 4.6 * 150 mm, 5 μm | |
| Mobile Phase | A: 0.1% TFA in $H_2O$; B: 0.1% TFA in acetonitrile | |
| Gradient Table | Time (mins) | % B |
| | 0.0 | 5 |
| | 23 | 95 |
| | 27 | 95 |
| | 27.1 | 5 |
| | 30 | 5 |
| Flow Rate | 1.0 mL/min | |
| Injection Volume | 10 μL | |
| Detector Wavelength | 270 min | |
| Run Time | 30.0 min | |
| Column Temperature | 40° C. | |
| Sampler Temperature | RT | |

SGF Media Preparation—

The term "SGF media" means a solution prepared according to the following method. Sodium chloride (0.2 g) and Triton X-100 (0.1 g) were combined in a 100 mL flask. Then deionized water was added. The mixture was stirred until all solids were dissolved. Then 12 N HCl (200 μL) was added and the pH value was checked with a pH meter. The pH was adjusted to 1.8 with 1N HCl or 1N NaOH. Once the desired pH was established, the solution was diluted to volume with deionized water.

FaSSIF Media Preparation—

The term "FaSSIF media" means a solution prepared according to the following method. A FaSSIF Dissolving Buffer was prepared by dissolving maleic acid (0.222 g) in 45 mL of purified water. The pH was adjusted to exactly 6.4 using 1N NaOH.

FaSSIF media was prepared by adding sodium taurocholate (0.161 g), sodium chloride (0.398 g), and lecithin (0.0156 g) into a 100-mL volumetric flask. Then 40 mL of deionized water was added. The solution was sonicated until clear. Next 45 mL of the FaSSIF Dissolving Buffer was added. The pH was adjusted to 6.5 with 1N NaOH or 1N HCl. Once the desired pH was reached, the solution was diluted to volume with deionized water.

An alternative media ("FaSSIF alternative media") was used to study the trifluoroacetate salts (Type A and B) and the HCl Type I salt. More specifically, the media was prepared by weighing 0.17 g of sodium phosphate monobasic (NaH2PO4, anhydrous), 0.021 g of sodium hydroxide, and 0.31 g of sodium chloride into a 50-mL volumetric flask and was dissolve with approximately 48 mL of purified water. The pH was adjusted to exactly 6.5 using 1 M HCl or 1 M NaOH and diluted to volume with purified water. 0.11 g of SIF powder was then added, stirred and sonicated until all the powder was completely dissolved. The solution was equilibrated for 2 hours at RT before use. The solution can be stored at RT for 48 hours or 4° C. for 7 days and should be equilibrated to RT before use FeSSIF Preparation—

The term "FeSSIF media" means a solution prepared according to the following method. A FeSSIF Dissolving Buffer was prepared by dissolving maleic acid (0.638 g) and NaCl (0.728 g) in 100 mL of purified water. The pH was adjusted to exactly 5.8 using 1N NaOH or 1N HCl.

FeSSIF media was prepared by adding sodium taurocholate (0.269 g), lecithin (0.078 g), sodium oleate (0.012 g), and glyceryl monooleate (0.089) into a 50-mL flask. Then 2.5 mL of the FeSSIF Dissolving Buffer was added. The solution was sonicated. An additional 12.5 mL of the FeSSIF Dissolving Buffer was then added 1 mL stepwise forming an emulsion. The solution was transferred to a 50-mL volumetric flask and diluted to volume with the FeSSIF Dissolving Buffer.

An alternative media ("FeSSIF alternative media") was used to study the trifluoroacetate salts (Type A and B) and the HCl Type I salt. More specifically, the media was prepared by transferring 0.41 mL of glacial acid and weighing 0.20 g of sodium hydroxide, 0.59 g of sodium chloride into a 50-mL volumetric flask. This was dissolved with approximately 48 mL of purified water. The pH was adjusted to exactly 5.0 using 1 M HCl or 1 M NaOH and diluted to volume with purified water. 0.56 g of SIF powder was added, stirred and sonicated until all the powder is completely dissolved. The solution can be stored at RT for 48 hours or 4° C. for 7 days and should be equilibrated to RT before use.

Dextrose Buffer (pH 5.5) Preparation—

The terms "dextrose buffer at pH 5.5" and "dextrose buffer (pH 5.5)" mean a solution prepared according to the following method. Dextrose (0.5 g) was added to a 100-mL volumetric flask. Then 1M HCl or 1M NaOH was added to adjust the pH of the buffer to pH 5.5.

Acetate Buffer (DH 5.5) Preparation—

The acetate buffer (pH 5.5) used for the trifluoroacetate salts (Type A and B) and the HCl Type I salt was prepared by placing 0.60 g sodium acetate ($NaC_2H_3O_2 \cdot 3H_2O$) in a 100-mL volumetric flask, adding 3 mL of 2 M acetic acid solution, and then adding purified water to volume.

Phosphate Buffer (DH 6.0) Preparation—

The terms "phosphate buffer at pH 6.0" and "phosphate buffer (pH 6.0)" mean a solution prepared according to the following method. A solution of 0.2 M $KH_2PO_4$ (25 mL) and 0.2 M NaOH (5.6 mL) was prepared in a 100-mL volumetric flask. The pH was checked by pH meter. Then water was added to volume.

An alternative media ("phosphate (pH 6.0) alternative media") was used to study the trifluoroacetate salts (Type A and B) and the HCl Type I salt. More specifically, the media was prepared by dissolving 2.72 g of 0.2 M monobasic potassium phosphate ($KH_2PO_4$) in purified water, and diluting with purified water to 100 mL. 0.8 g of 0.2 M sodium hydroxide in purified water was diluted with purified water to 100 mL. Then 50 mL of the 0.2 M monobasic potassium phosphate solution was placed in a 200-mL volumetric flask, 5.6 mL of 0.2 M sodium hydroxide solution was added, and then purified water was added to volume.

Phosphate Buffer (pH 7.5) Preparation—

The terms "phosphate buffer at pH 7.5" and "phosphate buffer (pH 7.5)" mean a solution prepared according to the following method. A solution of 0.2 M $KH_2PO_4$ (25 mL) and 0.2 M NaOH (40.2 mL) was prepared in a 100-mL volumetric flask. The pH was checked by pH meter. Then water was added to volume.

Kinetic Solubility of SCY-078 Salts—

The term "kinetic solubility" with respect to SCY-078 salts means the following procedure. First, 15 mg, 50 mg, or 100 mg of one of the SCY-078 salts was placed into a 4-mL plastic centrifuge tubes along with 1.7 mL of relevant media or 2.0 mL of water. For dextrose buffer at pH 5.5, phosphate buffer at pH 6.0, and phosphate buffer at pH 7.5, 15 mg of the SCY-078 salt was used. For SGF media, FeSSIF media, and FaSSIF media, 50 mg of the SCY-078 salt was used. For water, 100 mg of the SCY-078 salt was used. The actual weight of each sample was recorded. The tube was subsequently capped and the suspension samples were stirred on a rolling incubator (25 rpm) at room temperature. Samples were taken at 1 hour, 4 hours, and 24 hours respectively. For each sample, a 0.5 mL aliquot of the suspension was transferred into a 1.5-mL centrifuge filtration tube and centrifuged. The samples were then filtered through the centrifuge filtration tube (0.45 μm) at 8,000 rpm at room temperature for 3 minutes.

The trifluoroacetate salts (Type A and B) and the HCl Type I salt were tested using the following alternative procedure. First, 15 mg, 36 mg or 90 mg solid was weighted into a 4-mL plastic tube, and 3 mL of relevant media was added before leaving the suspension on a rolling incubator (25 r/min). For SCF, 90 mg of solid was used. For FaSSIF, acetate buffer (pH 5.5), and phosphate buffer (pH 6.0), 15 mg solid was used. For FeSSIF, 36 mg of solid was used. 1.0 mL aliquot of the suspension was sampled for centrifugation with the supernatant submitted for HPLC and pH measurement and solid for XRPD characterization at 1 hr, 4 hr and/or 24 hrs.

Approximate Solubility of SCY-078 Salts—

The term "approximate solubility" with respect to SCY-078 salts means the procedure described in this paragraph. To conduct each experiment, a sample of a SCY-078 salt (~2 mg) was added into a 3-mL glass vial. Then a solvent was added step-wise (100 μL per step) into the vials until the solids were dissolved or a total volume of 2 mL was reached.

Equilibrium Solubility of SCY-078 Salts—

The term "equilibrium solubility" with respect to SCY-078 salts means the procedure described in this paragraph. The equilibrium solubility of a SCY-078 salt was evaluated in water at room temperature. First, the SCY-078 salt (~50 mg) was weighed into a 1.5-mL vial followed by addition of 1.0 mL water, and then the sample was stirred (800 rpm) at room temperature for 24 hours. The sample was centrifuged with the residual solid analyzed by XRPD and supernatant concentration measured by HPLC.

Polarized Light Microscopic Imaging—

Polarized light microscopic (PLM) images was captured at room temperature using Axio Lab A1 upright microscope equipped with ProgRes® CT3 camera. The sample was sandwiched between a glass slide and a top cover before placed under the polarized light microscopy for imaging.

Example 1

SCY-078 Phosphate: The phosphate salt of SCY-078 was prepared from SCY-078 freebase, which was prepared using known procedures. See, e.g., U.S. Pat. No. 8,188,085. SCY-078 freebase (10.0 g) was placed in a 250 mL reactor.

Ethanol (50 mL), ethyl acetate (30 mL), acetic acid (1.5 mL) and water (1 mL) were added and the mixture was stirred at room temperature over 10 minutes. The resulting homogeneous solution was heated to 50° C. and phosphoric acid (1.74 g) solution in ethyl acetate was slowly added to the solution at 50° C. for 1 hour. The resulting slurry was slowly cooled to room temperature and stirred overnight at room temperature. The slurry was filtered, and the wet cake was washed with 20 mL mixed solvents (ethanol:ethyl acetate: water=5:5:0.1) two times, then twice with ethyl acetate (1 mL). The wet cake was dried under vacuum with nitrogen sweep over three hours, and then dried in a vacuum oven overnight to obtain 11.08 g of an off-white crystal. The retention time of the compound was 4.08 minutes, as measured by HPLC using an Ascentis Express C18 column with standard gradient: 10-95% of B in 6 minutes (A=0.1% phosphoric acid, B=acetonitrile), 2 minute hold 2 minute post; flow rate: 1.8 mL/minute (UV detection at 245 nm, 40° C.).

Figure 2:
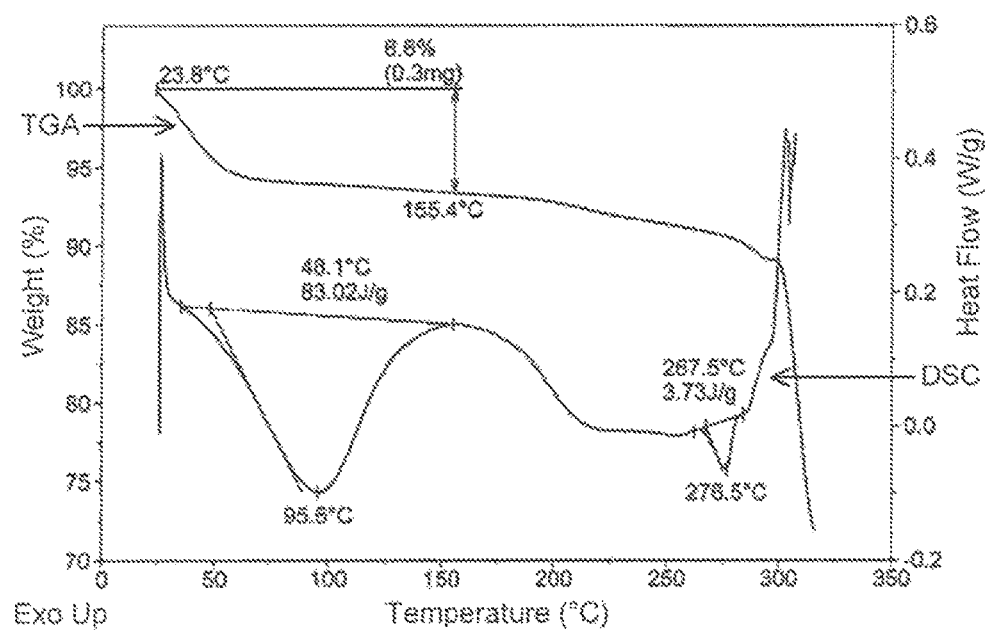
FIG. 2 is a DSC curve and a TGA curve of SCY-078 phosphate from Example 1.

SCY-078 phosphate was characterized by XRPD, which evidenced that the compound is crystalline (FIG. 1). The 2 theta and d-spacing values are summarized in Table 4. The DSC curve of SCY-078 phosphate exhibited two endothermic peaks at 48.1° C. and 267° C. (FIG. 2). A weight loss of 6.6% was observed up to 155.4° C. in the TGA curve (FIG. 2).

TABLE 4

| Pos. [°2Th.] | Height [cts] | FWHM Left [°2Th.] | d-spacing [Å] | Rel. Int. [%] |
|---|---|---|---|---|
| 3.446579 | 121.838400 | 0.153504 | 25.63591 | 8.36 |
| 6.002339 | 410.263500 | 0.127920 | 14.72481 | 28.14 |
| 6.926787 | 321.574500 | 0.153504 | 12.76157 | 22.05 |
| 7.923199 | 635.487400 | 0.179088 | 11.15879 | 43.58 |
| 9.163023 | 1458.149000 | 0.230256 | 9.65152 | 100.00 |
| 9.949172 | 420.112200 | 0.153504 | 8.89059 | 28.81 |
| 10.395180 | 355.706200 | 0.204672 | 8.51011 | 24.39 |
| 11.606700 | 1098.847000 | 0.179088 | 7.62440 | 75.36 |
| 11.998390 | 742.370400 | 0.153504 | 7.37637 | 50.91 |
| 12.509650 | 1152.457000 | 0.230256 | 7.07603 | 79.04 |
| 14.390130 | 1325.262000 | 0.179088 | 6.15529 | 90.89 |
| 15.561700 | 1295.270000 | 0.230256 | 5.69443 | 88.83 |
| 16.742160 | 847.559600 | 0.230256 | 5.29549 | 58.13 |
| 17.427190 | 694.495600 | 0.179088 | 5.08885 | 47.63 |
| 18.989620 | 584.788500 | 0.204672 | 4.67353 | 40.10 |
| 19.700330 | 472.891400 | 0.204672 | 4.50650 | 32.43 |
| 20.641180 | 788.029700 | 0.153504 | 4.30316 | 54.04 |
| 22.864060 | 331.310800 | 0.204672 | 3.88959 | 22.72 |
| 24.026930 | 187.756700 | 0.307008 | 3.70391 | 12.88 |
| 25.365620 | 208.707200 | 0.358176 | 3.51139 | 14.31 |
| 28.405150 | 77.468630 | 0.614016 | 3.14218 | 5.31 |
| 30.814330 | 70.380370 | 0.818688 | 2.90179 | 4.83 |

Example 2

SCY-078 Crystalline Freebase (MeOH desolvate): The MeOH desolvate was prepared as follows. SCY-078 phosphate salt (10.0 g) was charged into a 250 mL reactor. Sodium carbonate (50 mL of a 10% solution) was added at 20° C. and agitated. 2-methyltetrahydrofuan (100 mL) was added and agitated strongly at 20° C. until all the solids dissolved. The mixture was left to stand for 30 minutes to leave two clear layers which were separated and the organic layer was washed twice with deionized water (40 mL). The washed organic layer was transferred to a 125-mL reaction vessel and agitated at 500 rpm, heated to 50° C. and distilled under partial vacuum at 50° C. down to 40 mL volume. Methanol (80 mL) was added to the reaction vessel at 50° C., which was then cooled to 40° C.; after 2 hours, crystals formed. The volume was then distilled down to 50 mL at 40° C. under partial vacuum over 16 hours. There was then constant volume distillation at 40° C. while adding methanol (40 mL) over 2 hours. Water (20 mL) was then added over 2 hours. The reaction vessel was then cooled to 20° C. over 2 hours and then slurry aged at 20° C. for 2 hours. The mixture was then filtered and the resulting wet cake washed with 20 mL of a 4:1 solution of methanol and water. The wet cake was dried under nitrogen sweep at room temperature for 16 hours. XRPD analysis confirmed that the dry cake is desolvated methanol solvate (yield 89%, purity: 99.1%).

Figure 3:
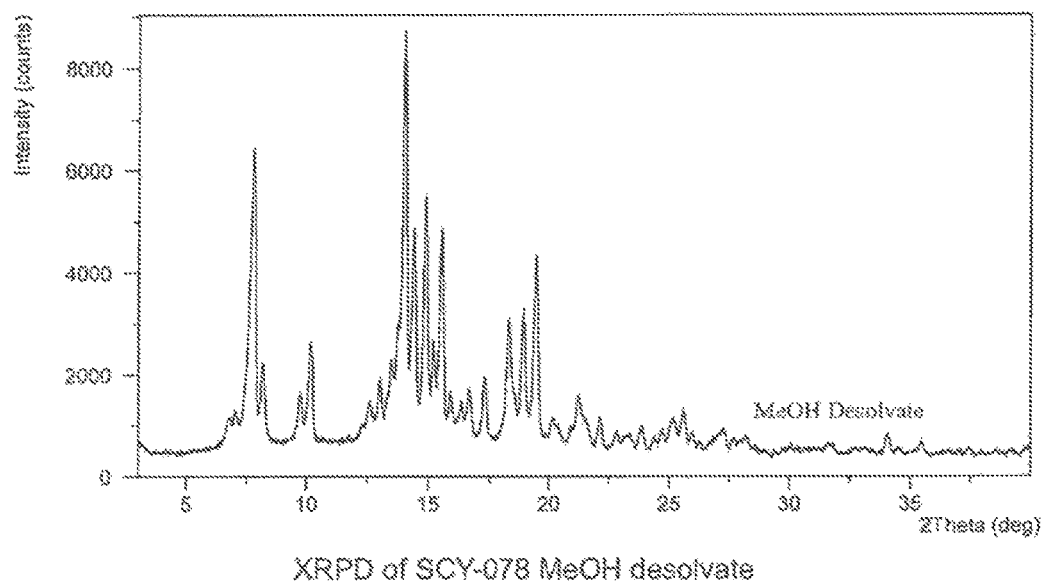
FIG. 3 is an XRPD of SCY-078 crystalline freebase (MeOH desolvate), batch 1 from Example 2.
Figure 4:
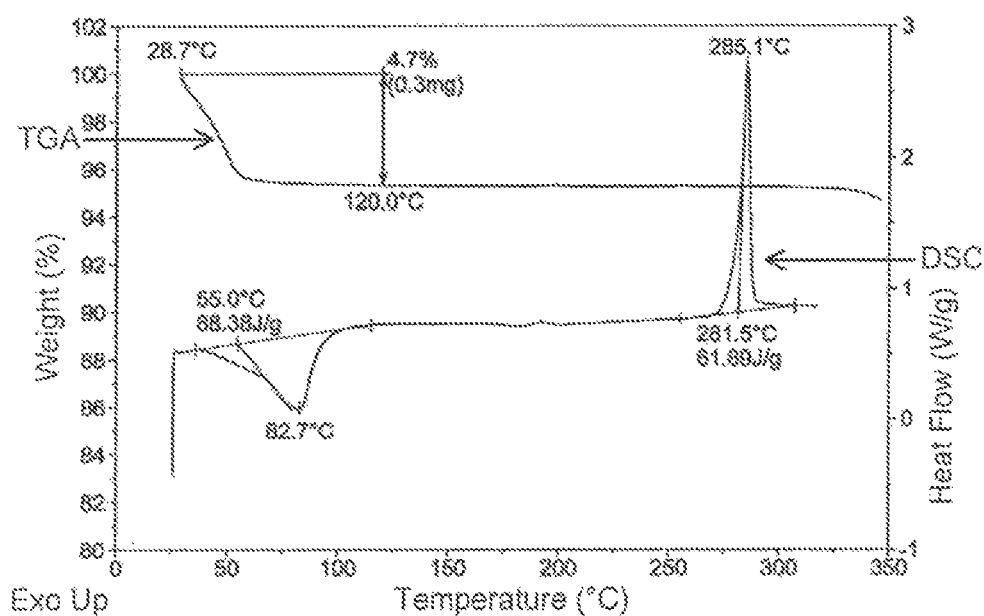
FIG. 4 is a DSC curve and a TGA curve of SCY-078 crystalline freebase (MeOH desolvate), batch 1 from Example 2.
Figure 5:
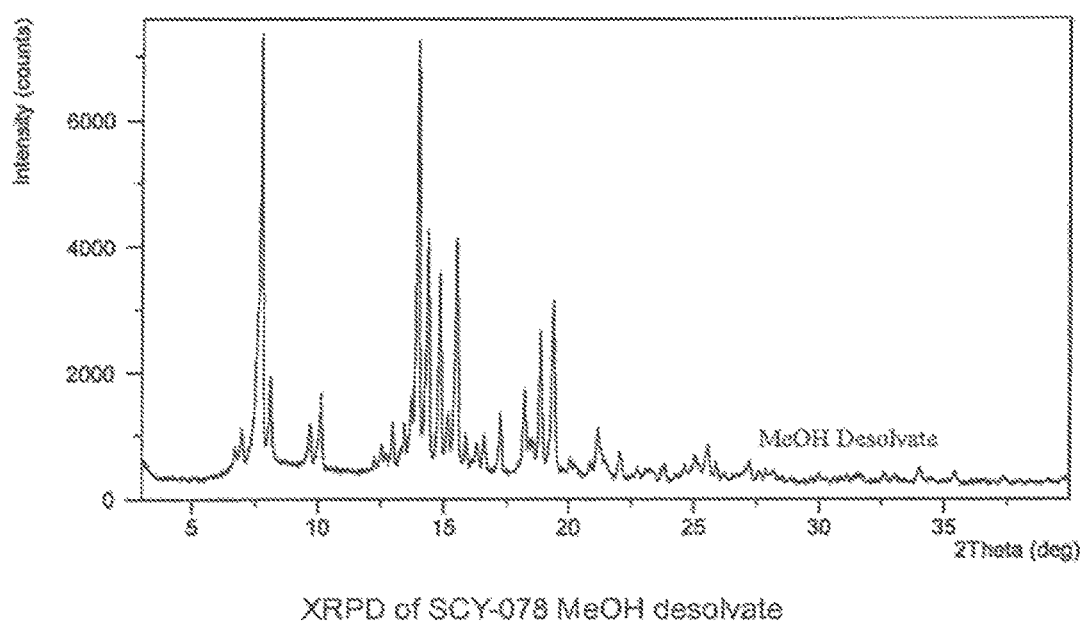
FIG. 5 is an XRPD of SCY-078 crystalline freebase (MeOH desolvate), batch 2 from Example 2.

Two batches of MeOH desolvate were prepared and characterized by XRPD, DSC, and TGA (FIGS. 3-5). XRPD patterns evidenced that the compound is crystalline. The 2 theta and d-spacing values from Batch 1 and Batch 2 are summarized in Tables 5a and 5b, respectively. The DSC curve of MeOH desolvate Batch 1 exhibited an endotherm at ~55.0° C. and an exotherm at ~281.5° C. The DSC curve of MeOH desolvate Batch 2 exhibited an endotherm at ~56.1° C. and an exotherm at ~279.2° C. The TGA curve of Batch 1 showed a weight loss of 4.7% before 120° C. The TGA curve of Batch 1 showed a weight loss of 0.6.6% before 120° C. The TGA curve of Batch 2 showed a weight loss of 4.9% before 120° C.

TABLE 5a

| Pos. [°2Th.] | Height [cts] | FWHM Left [°2Th.] | d-spacing [Å] | Rel. Int. [%] |
|---|---|---|---|---|
| 6.763088 | 656.275900 | 0.153504 | 13.07009 | 7.96 |
| 7.007256 | 762.055000 | 0.127920 | 12.61520 | 9.24 |
| 7.747366 | 5938.858000 | 0.179088 | 11.41165 | 72.02 |
| 8.156786 | 1751.303000 | 0.179088 | 10.83975 | 21.24 |
| 9.712988 | 1115.822000 | 0.153504 | 9.10623 | 13.53 |
| 10.141860 | 2106.808000 | 0.076752 | 8.72210 | 25.55 |
| 12.584090 | 950.310500 | 0.153504 | 7.03433 | 11.52 |
| 13.014360 | 1356.119000 | 0.127920 | 6.80272 | 16.45 |
| 13.486330 | 1749.145000 | 0.102336 | 6.56570 | 21.21 |
| 13.729600 | 2433.802000 | 0.076752 | 6.44991 | 29.52 |
| 14.005940 | 8245.783000 | 0.166296 | 6.32326 | 100.00 |
| 14.405120 | 4246.837000 | 0.140712 | 6.14892 | 51.50 |
| 14.876760 | 4956.689000 | 0.127920 | 5.95503 | 60.11 |
| 15.210400 | 2019.649000 | 0.089544 | 5.82515 | 24.49 |
| 15.545740 | 4247.989000 | 0.153504 | 5.70024 | 51.52 |
| 15.924930 | 1123.799000 | 0.127920 | 5.56535 | 13.63 |
| 16.357440 | 911.992900 | 0.102336 | 5.41916 | 11.06 |
| 16.653970 | 1230.506000 | 0.153504 | 5.32333 | 14.92 |
| 17.281780 | 1476.632000 | 0.115128 | 5.13134 | 17.91 |
| 18.290550 | 2584.896000 | 0.127920 | 4.85054 | 31.35 |
| 18.910970 | 2762.926000 | 0.089544 | 4.69279 | 33.51 |
| 19.423650 | 3792.983000 | 0.166296 | 4.57006 | 46.00 |
| 20.154410 | 631.061700 | 0.153504 | 4.40598 | 7.65 |
| 21.211700 | 1085.950000 | 0.153504 | 4.18870 | 13.17 |
| 22.103930 | 642.381300 | 0.153504 | 4.02160 | 7.79 |
| 22.813500 | 357.089200 | 0.153504 | 3.89809 | 4.33 |
| 23.851840 | 485.307900 | 0.204672 | 3.73070 | 5.89 |
| 24.372350 | 254.224300 | 0.153504 | 3.65219 | 3.08 |
| 25.127990 | 631.886600 | 0.204672 | 3.54405 | 7.66 |
| 25.582260 | 817.763400 | 0.230256 | 3.48214 | 9.92 |
| 25.946780 | 361.733700 | 0.127920 | 3.43404 | 4.39 |
| 27.215450 | 399.894700 | 0.204672 | 3.27677 | 4.85 |
| 31.598700 | 117.418900 | 0.358176 | 2.83152 | 1.42 |
| 34.043420 | 360.328100 | 0.179088 | 2.63357 | 4.37 |
| 35.453150 | 228.142700 | 0.204672 | 2.53202 | 2.77 |
| 37.397760 | 89.968660 | 0.204672 | 2.40471 | 1.09 |

TABLE 5b

| Pos. [°2Th.] | Height [cts] | FWHM Left [°2Th.] | d-spacing [Å] | Rel. Int. [%] |
|---|---|---|---|---|
| 6.689568 | 495.508900 | 0.076752 | 13.21357 | 7.10 |
| 6.958760 | 795.039300 | 0.076752 | 12.70301 | 11.39 |
| 7.719929 | 6977.127000 | 0.102336 | 11.45214 | 100.00 |

TABLE 5b-continued

| Pos. [°2Th.] | Height [cts] | FWHM Left [°2Th.] | d-spacing [Å] | Rel. Int. [%] |
|---|---|---|---|---|
| 8.113519 | 1569.148000 | 0.076752 | 10.89746 | 22.49 |
| 9.660554 | 883.585800 | 0.089544 | 9.15554 | 12.66 |
| 10.105090 | 1377.370000 | 0.063960 | 8.75376 | 19.74 |
| 12.511740 | 551.167400 | 0.076752 | 7.07485 | 7.90 |
| 12.972470 | 906.794200 | 0.102336 | 6.82459 | 13.00 |
| 13.432450 | 898.612700 | 0.051168 | 6.59191 | 12.88 |
| 13.698610 | 1280.818000 | 0.063960 | 6.46442 | 18.36 |
| 13.963580 | 6943.854000 | 0.102336 | 6.34235 | 99.52 |
| 14.354450 | 3936.292000 | 0.102336 | 6.17051 | 56.42 |
| 14.833880 | 3242.652000 | 0.102336 | 5.97215 | 46.48 |
| 15.161830 | 1072.948000 | 0.102336 | 5.84370 | 15.38 |
| 15.499310 | 3840.597000 | 0.115128 | 5.71721 | 55.05 |
| 15.870270 | 694.539900 | 0.063960 | 5.58440 | 9.95 |
| 16.294450 | 561.885100 | 0.102336 | 5.43997 | 8.05 |
| 16.589520 | 716.170000 | 0.076752 | 5.34387 | 10.26 |
| 17.231620 | 1048.768000 | 0.089544 | 5.14616 | 15.03 |
| 18.228150 | 1455.529000 | 0.089544 | 4.86701 | 20.86 |
| 18.853630 | 2320.288000 | 0.102336 | 4.70693 | 33.26 |
| 19.358690 | 2769.789000 | 0.127920 | 4.58525 | 39.70 |
| 20.105050 | 319.040400 | 0.153504 | 4.41669 | 4.57 |
| 21.158160 | 854.556900 | 0.089544 | 4.19918 | 12.25 |
| 22.060990 | 457.091300 | 0.127920 | 4.02933 | 6.55 |
| 22.755630 | 189.699300 | 0.153504 | 3.90788 | 2.72 |
| 23.818130 | 259.770000 | 0.102336 | 3.73590 | 3.72 |
| 24.629730 | 250.065300 | 0.153504 | 3.61461 | 3.58 |
| 25.034030 | 415.901700 | 0.102336 | 3.55714 | 5.96 |
| 25.544070 | 535.863500 | 0.179088 | 3.48726 | 7.68 |
| 25.883800 | 303.412800 | 0.102336 | 3.44225 | 4.35 |
| 27.200370 | 321.682800 | 0.102336 | 3.27856 | 4.61 |
| 27.597540 | 179.014900 | 0.102336 | 3.23227 | 2.57 |
| 28.068430 | 126.035900 | 0.409344 | 3.17911 | 1.81 |
| 29.974950 | 124.045000 | 0.153504 | 2.98110 | 1.78 |
| 31.402190 | 89.293980 | 0.614016 | 2.84879 | 1.28 |
| 32.603460 | 118.588300 | 0.204672 | 2.74652 | 1.70 |
| 33.988800 | 247.854700 | 0.179088 | 2.63768 | 3.55 |
| 35.391040 | 161.830400 | 0.153504 | 2.53632 | 2.32 |

Example 3

SCY-078 Amorphous Freebase: To prepare SCY-078 amorphous freebase, MeOH desolvate (50 mg) was added to a 3-mL vial. Then DCM (0.5 mL) was added to the vial of MeOH desolvate. The resulting solution of MeOH desolvate and DCM formed a clear solution. The solution was evaporated to dryness from an open vial at 50° C.

Figure 6:
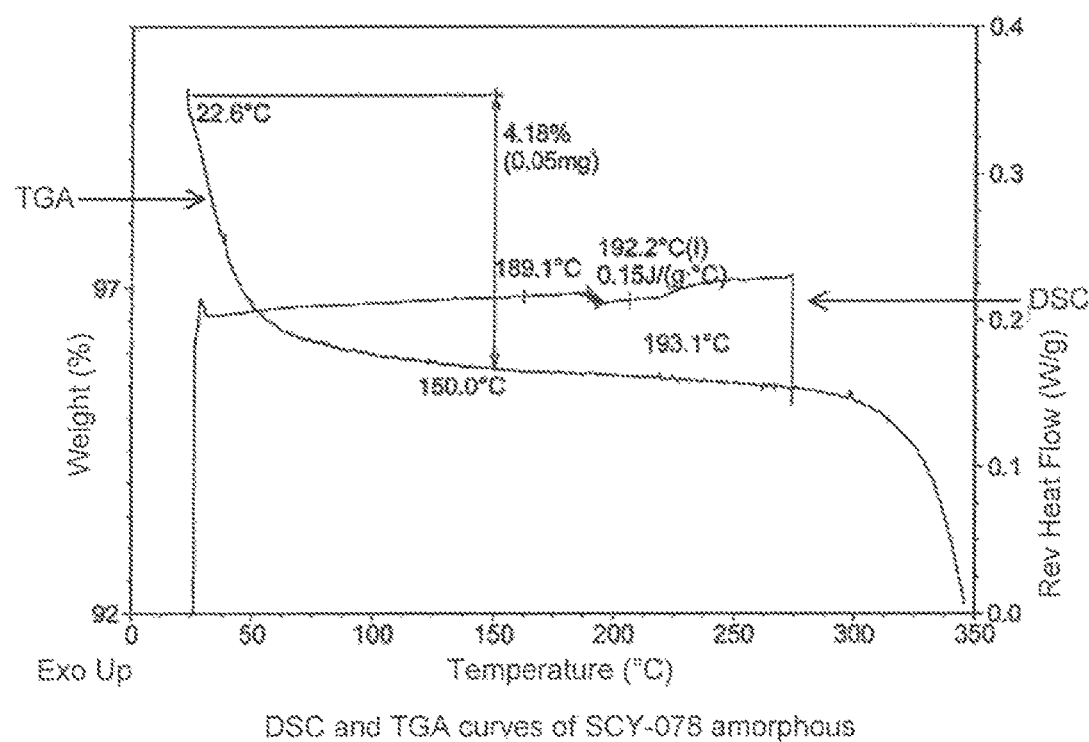
FIG. 6 is a DSC curve and a TGA curve of SCY-078 amorphous freebase from Example 3.

The solid obtained after evaporation was characterized by XRPD, TGA, DSC, and DVS. The XRPD pattern evidenced that the tested sample is amorphous. The DSC and TGA curves of the amorphous sample exhibited a glass transition at ~189.1° C. (FIG. 6). The TGA curve demonstrated a weight loss of 4.2% before 150° C. The DVS curve demonstrated that the sample is hygroscopic with a water uptake of ~4.8% at 80% RH, 25° C. An XRPD pattern performed after DVS demonstrated no form change.

Example 4

Kinetic Solubility of SCY-078 Freebase: The kinetic solubility of SCY-078 MeOH desolvate and SCY-078 amorphous freebase was evaluated in SGF media, FaSSIF media, FeSSIF media, dextrose buffer (pH 5.5), phosphate buffer (pH 6.0), and phosphate buffer (pH 7.5) at room temperature. First, solid SCY-078 MeOH desolvate or SCY-078 amorphous freebase (~15 mg) was weighed into a 4-mL vial. Then the relevant media (3.0 mL) was added and the suspensions were stirred on a rolling incubator (25 rpm) at room temperature for 1 hour, 4 hours, and 24 hours respectively. After stirring, 0.5 mL of suspension was centrifuged and filtered (0.45 µm). The residual solids were analyzed by XRPD, and the supernatant was measured by HPLC and pH meter.

The results (Table 6) suggested that both the MeOH desolvate and the amorphous freebase display high solubility in SGF and FeSSIF. The results also showed that both the MeOH desolvate and the amorphous freebase are only sparingly soluble in FaSSIF and pH 5.5, pH 6.0, and pH 7.5 buffers.

Solid form change was observed during the solubility measurements of the MeOH desolvate in FeSSIF, FaSSIF, pH 5.5 and 6.0 buffers. Additionally, three new crystal forms were discovered (Table 6). The three new forms are identified as New Form 1, 2, and 3.

TABLE 6

Kinetic solubility of SCY-078 freebase

| Solvent | Starting Form | Time (hours) | Solubility (mg/mL) | pH | Form |
|---|---|---|---|---|---|
| SGF | Desolv.$ | 1 | >5.3* | 2.8 | N/A |
|  |  | 4 | >5.3* | 2.8 | N/A |
|  |  | 24 | >5.3* | 2.8 | N/A |
|  | Amorph. | 1 | >5.2* | 2.1 | N/A |
|  |  | 4 | >5.2* | 2.2 | N/A |
|  |  | 24 | >5.2* | 2.2 | N/A |
| FeSSIF | Desolv. | 1 | 3.3 | 5.1 | NF 1 |
|  |  | 4 | 3.5 | 5.1 | NF 1 |
|  |  | 24 | 3.5 | 5.1 | NF 1 |
|  | Amorph. | 1 | 3.0 | 5.1 | Amorph. |
|  |  | 4 | 3.7 | 5.1 | Amorph. |
|  |  | 24 | 3.8 | 5.1 | Amorph. |
| FaSSIF | Desolv. | 1 | ND | 6.6 | NF 1 |
|  |  | 4 | ND | 6.6 | NF 1 |
|  |  | 24 | ND | 6.6 | NF 1 |
|  | Amorph. | 1 | 0.017 | 6.6 | Amorph. |
|  |  | 4 | <0.51 µg/mL | 6.6 | Amorph. |
|  |  | 24 | ND | 6.6 | Amorph. |
| pH 5.5 buffer | Desolv. | 1 | N/A | N/A | N/A |
|  |  | 4 | 0.0008 | 7.2 | NF 2 |
|  |  | 24 | ND | 7.1 | NF 2 |
|  | Amorph. | 1 | N/A | N/A | N/A |
|  |  | 4 | ND | 6.8 | Amorph. |
|  |  | 24 | ND | 6.9 | Amorph. |
| pH 6.0 buffer | Desolv. | 1 | N/A | N/A | N/A |
|  |  | 4 | 0.045 | 6.2 | NF 1 |
|  |  | 24 | 0.60 | 6.1 | NF 3 |
|  | Amorph. | 1 | N/A | N/A | N/A |
|  |  | 4 | <0.51 µg/mL | 6.1 | Amorph. |
|  |  | 24 | 0.0024 | 6.1 | Amorph, |
| pH 7.5 buffer | Desolv. | 1 | N/A | N/A | N/A |
|  |  | 4 | 0.0024 | 7.3 | Desolv. |
|  |  | 24 | 0.0025 | 7.4 | Desolv. |
|  | Amorph. | 1 | N/A | N/A | N/A |
|  |  | 4 | ND | 7.4 | Amorph. |
|  |  | 24 | ND | 7.4 | Amorph. |

*Clear solution was obtained
NF: New Form
ND: Not Detected
$MeOH desolvate
N/A: Not available
Desolv.: Desolvate
Amorph.: Amorphous Example 5

Approximate Solubility of SCY-078 MeOH Desolvate: The approximate solubility of SCY-078 MeOH desolvate was measured in 20 solvents at room temperature (25±3° C.). First, MeOH desolvate (~2 mg) was added to a 3-mL glass vial. Then the corresponding solvent was added step wise (100 µL) until the solution was visually clear or a total volume of 2 mL was reached. The results appear in Table 7.

TABLE 7

Approximate solubility of SCY-078 freebase at RT

| Solvent | Solubility (mg/mL) |
|---|---|
| MeOH | 5.4 < S < 6.3 |
| EtOH | 2.6 < S < 3.0 |
| IPA | 7.0 < S < 11.0 |
| Acetic Acid | S > 25.0 |
| ACN | 2.6 < S < 2.9 |
| Acetone | 8.3 < S < 12.5 |
| MIBK | S > 29.0 |
| EtOAc | S > 23.0 |
| iPrOAc | 10.5 < S < 21.0 |
| MTBE | S > 23.0 |
| THF | S > 23.0 |
| 2-MeTHF | S > 25.0 |
| 1,4-Dioxane | S > 37.0 |
| NMP | S > 45.0 |
| DMSO | S > 32.0 |
| CHCl$_3$ | S > 33.0 |
| Toluene | 6.8 < S < 8.5 |

TABLE 7-continued

Approximate solubility of SCY-078 freebase at RT

| Solvent | Solubility (mg/mL) |
|---|---|
| Heptane | S < 2.2 |
| DMA | S > 40.0 |
| H$_2$O | S < 1.9 |

Example 6

Salt Study of SCY-078 Freebase: A salt study of the SCY-078 MeOH desolvate freebase was performed using 108 different conditions developed through 18 acids in 6 solvents (Table 8). The salt study was performed by first preparing a solution of SCY-078 MeOH desolvate freebase and mixing with an equi-molar acid solution. This solution was stirred at room temperature overnight.

For precipitates, the solids were isolated and analyzed by XRPD. Clear solutions were evaporated slowly to dryness at room temperature.

The salt study (Table 8) showed that seven crystalline salts (eight crystal forms) of SCY-078 were found: HCl Type A, citrate Type A, hippurate Type A, fumarate Type A, fumarate Type B, glycolate Type A, mesylate Type A, and Ca salt Type A. Four crystal forms of SCY-078 freebase were discovered during the salt study and were identified as freebase ("FB") Type A, B, C, and D.

TABLE 8

| | Solvent | | | | | |
|---|---|---|---|---|---|---|
| Acid | EtOH (A) | IPA (B) | ACN (C) | Acetone (D) | EtOAc (E) | THF/Hp (19:1, v/v) (F) |
| HCl | oil | oil | HCl salt Type A | HCl salt Type A | amorphous | oil |
| H$_3$PO$_4$ | oil | oil | oil | oil | oil | oil |
| Maleic Acid | amorphous | amorphous | FB Type A | amorphous | amorphous | amorphous |
| Citric Acid | amorphous | amorphous | Citrate Type A | amorphous | FB Type A | amorphous |
| Hippuric Acid | FB Type B | FB Type B | Hippurate Type A | Hippurate Type A | Hippurate Type A | Low crystallinity |
| Adipic Acid | amorphous | FB Type A | FB Type A | FB Type C | amorphous | amorphous |
| Fumaric Acid | amorphous | amorphous | Fumarate Type A | FB Tape D | Fumarate Type B | amorphous |
| Glutaric Acid | amorphous | FB Type A | FB Type A | FB Type C | FB Type A | amorphous |
| Glycolic Acid | FB Type B | FB Type B | FB Type B | FB Type C | FB Type A | Glycolate Type A |
| D-Glutamic Acid | MeOH desolvate + acid | FB Type A | FB Type A | FB Type C | FB Type A | amorphous |
| Acetic Acid | oil | oil | amorphous | amorphous | amorphous | oil |
| Mucic Acid | amorphous | amorphous | FB Type D | FB Type D | FB Type D | amorphous |
| L-Malic Acid | amorphous | amorphous | | | | amorphous |
| Benzoic acid | MeOH Desolvate | FB Type A | FB Type A | FB Type C | FB Type A | amorphous |
| Methanesulfonic Acid | amorphous | amorphous | FB Type B | Mesylate Type A | FB Type B | amorphous |
| Malonic Acid | amorphous | amorphous | FB Type A | amorphous | FB Type A | amorphous |
| Ethanesulfonic Acid | amorphous | oil | FB Type B | FB Type B | FB Type B | amorphous |
| Ca(OH)$_2$ | Ca(OH)$_2$ | Ca(OH)$_2$ | FB Type A | FB Type C | Ca(OH)$_2$ | Ca salt Type A |

All the above salt formation experiments were performed at RT using 1.0 mole equivalency of acid.
FB: freebase

Example 7

Figure 7:
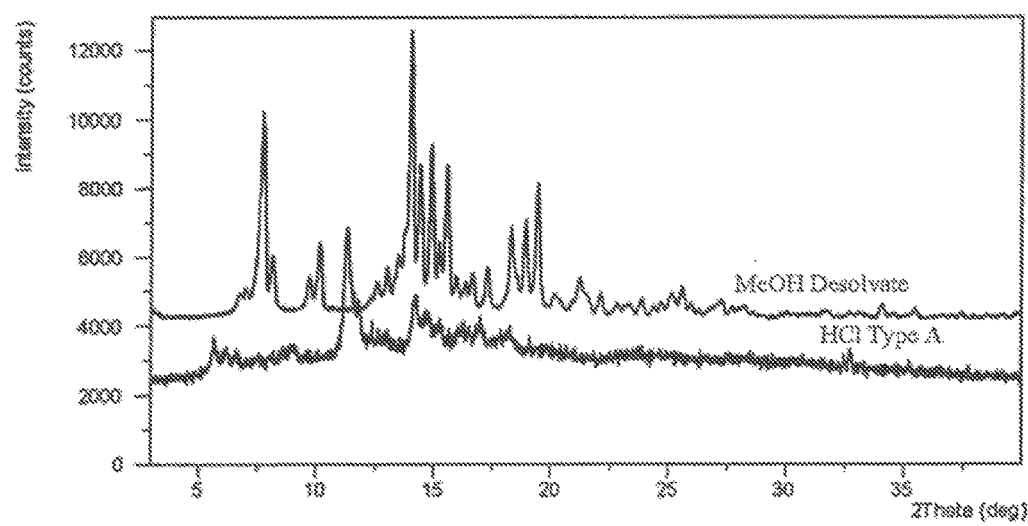
FIG. 7 is an XRPD of SCY-078 HCl Type A from Example 7.
Figure 8:
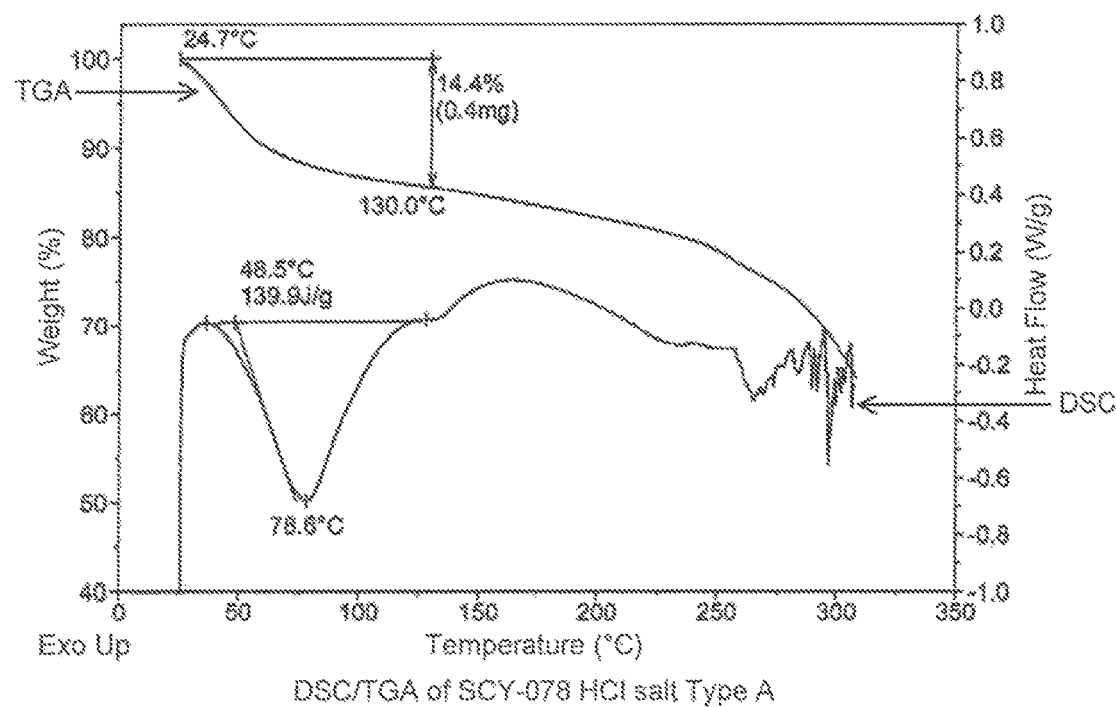
FIG. 8 is a DSC curve and a TGA curve of SCY-078 HCl Type A from Example 7.

SCY-078 HCl Type A: SCY-078 HCl Type A prepared from the salt study in Example 6 was characterized by XRPD, DSC, and TGA (FIGS. 7-8). The resulting XRPD pattern evidenced that SCY-078 HCl Type A is weakly crystalline and has a unique form as compared to the freebase MeOH desolvate. The 2 theta and d-spacing values are summarized in Table 9. The DSC curve displayed an endotherm at 48.5° C. (onset temperature). The TGA curve showed a weight loss of 14.4% before 130° C.

TABLE 9

| Pos. [°2Th.] | Height [cts] | FWHM Left [°2Th.] | d-spacing [Å] | Rel. Int. [%] |
|---|---|---|---|---|
| 5.635436 | 167.080400 | 0.153504 | 15.68264 | 21.28 |
| 9.023307 | 62.106750 | 0.307008 | 9.80065 | 7.91 |
| 11.313240 | 785.111500 | 0.179088 | 7.82150 | 100.00 |
| 14.217720 | 329.207600 | 0.179088 | 6.22955 | 41.93 |
| 16.983670 | 169.700900 | 0.204672 | 5.22073 | 21.61 |
| 18.224350 | 96.247500 | 0.409344 | 4.86801 | 12.26 |
| 32.709530 | 91.332090 | 0.153504 | 2.73786 | 11.63 |

Example 8

Figure 9:
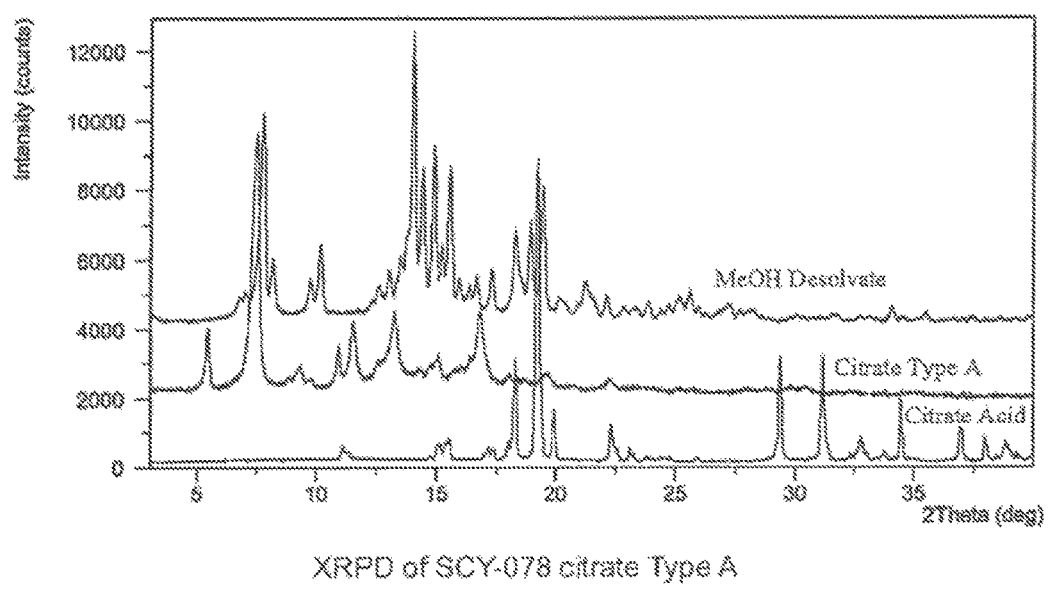
FIG. 9 is an XRPD of SCY-078 citrate Type A from Example 8.
Figure 10:
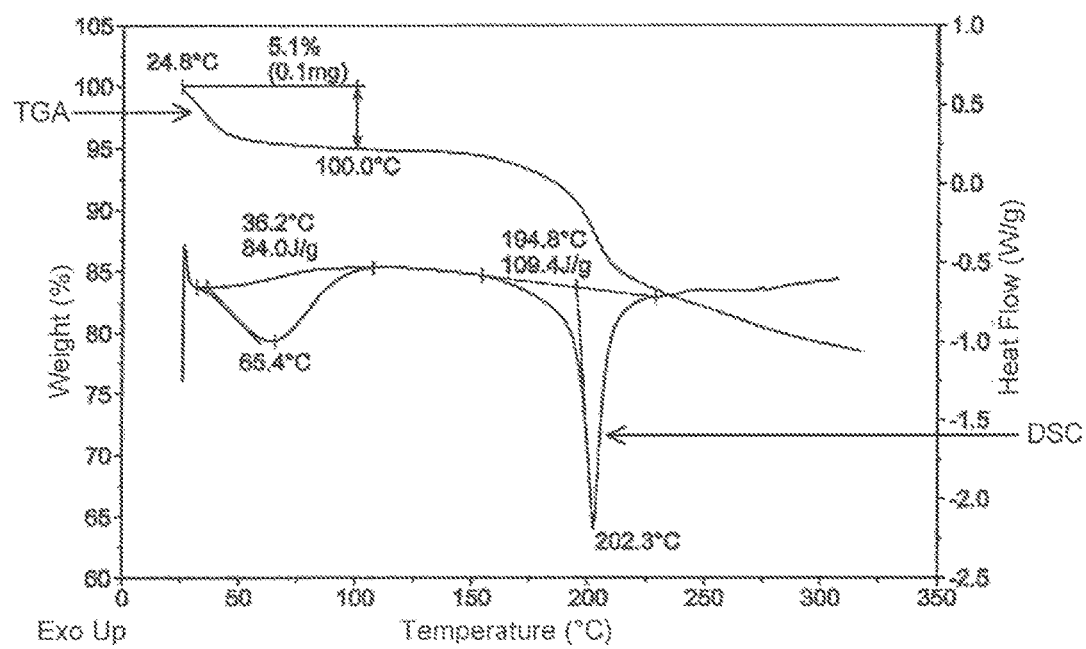
FIG. 10 is a DSC curve and a TGA curve of SCY-078 citrate Type A from Example 8.

SCY-078 Citrate Type A (Molar Equivalency—counter ion/API 1): SCY-078 citrate Type A prepared from the salt study in Example 6 was characterized by XRPD, DSC, and TGA (FIGS. 9-10). The resulting XRPD pattern evidenced that SCY-078 citrate Type A is crystalline and is a unique form compared to the freebase MeOH desolvate. The 2 theta and d-spacing values are summarized in Table 10. The DSC curve displayed two endotherms at 36.2° C. and 194.8° C. (onset temperature). The TGA curve demonstrated 5.1% before 100° C.

A sample was heated to 100° C. and then cooled to room temperature. XRPD was performed after heating and cooling to room temperature. The resulting XRPD pattern showed that there was no change in form. DSC and TGA characterization was also performed after heating and cooling. The DSC curve demonstrated two endotherms at 39.9° C. and 194.8° C. (onset temperatures). The TGA curve showed a weight loss of 5.3% before 100° C.

TABLE 10

| Pos. [°2Th.] | Height [cts] | FWHM Left [°2Th.] | d-spacing [Å] | Rel. Int. [%] |
|---|---|---|---|---|
| 5.448309 | 886.677500 | 0.140712 | 16.22084 | 29.56 |
| 7.551316 | 2999.844000 | 0.153504 | 11.70747 | 100.00 |
| 9.280401 | 338.350200 | 0.204672 | 9.52971 | 11.28 |
| 10.933390 | 532.481900 | 0.102336 | 8.09237 | 17.75 |
| 11.525650 | 1003.802000 | 0.140712 | 7.67783 | 33.46 |
| 12.550580 | 416.868300 | 0.204672 | 7.05304 | 13.90 |
| 13.236060 | 1150.251000 | 0.153504 | 6.68928 | 38.34 |
| 15.063710 | 476.465200 | 0.153504 | 5.88154 | 15.88 |
| 16.766510 | 1157.775000 | 0.204672 | 5.28786 | 38.59 |
| 18.032270 | 212.464400 | 0.153504 | 4.91943 | 7.08 |
| 19.686700 | 214.063600 | 0.307008 | 4.50959 | 7.14 |
| 22.220460 | 123.975800 | 0.153504 | 4.00077 | 4.13 |
| 30.421720 | 65.589230 | 0.358176 | 2.93833 | 2.19 |
| 34.915250 | 28.764450 | 0.614016 | 2.56979 | 0.96 |

Example 9

Figure 11:
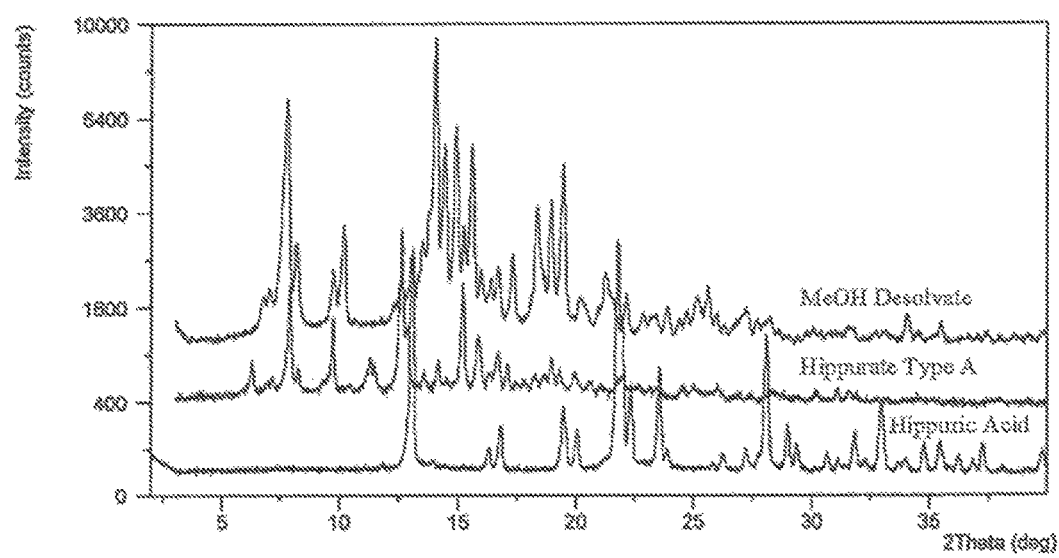
FIG. 11 is an XRPD of SCY-078 hippurate Type A from Example 9.
Figure 12:
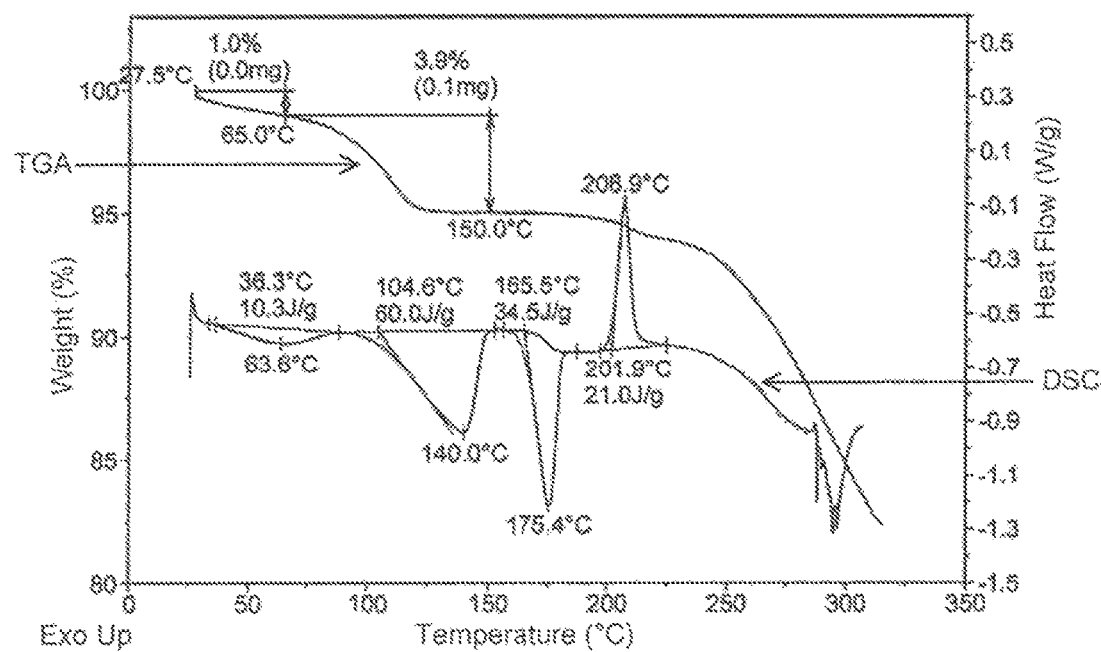
FIG. 12 is a DSC curve and a TGA curve of SCY-078 hippurate Type A from Example 9.

SCY-078 Hippurate Type A (Molar equivalency counter ion/API 2.0): SCY-078 hippurate Type A prepared from the salt study in Example 6 was characterized by XRPD, DSC, and TGA (FIGS. 11-12). The XRPD pattern of SCY-078 hippurate Type A indicated that the sample is crystalline and has a unique form as compared to the freebase MeOH desolvate. The DSC curve displayed three endotherms at 36.3° C., 104.6° C., and 165.5° C. (onset temperatures) and one exotherm at 201.9° C. (onset temperature). The TGA curve showed a weight loss of 4.9% before 150° C.

Example 10

Figure 13:
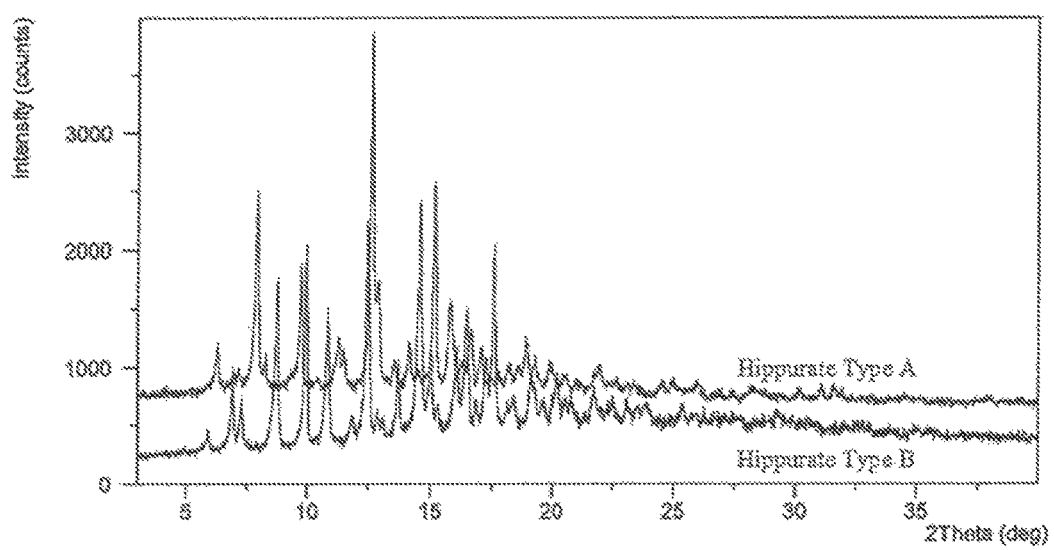
FIG. 13 is an XRPD of SCY-078 hippurate Type B from Example 10 overlaid on an XRPD of SCY-078 hippurate Type A from Example 9.
Figure 14:
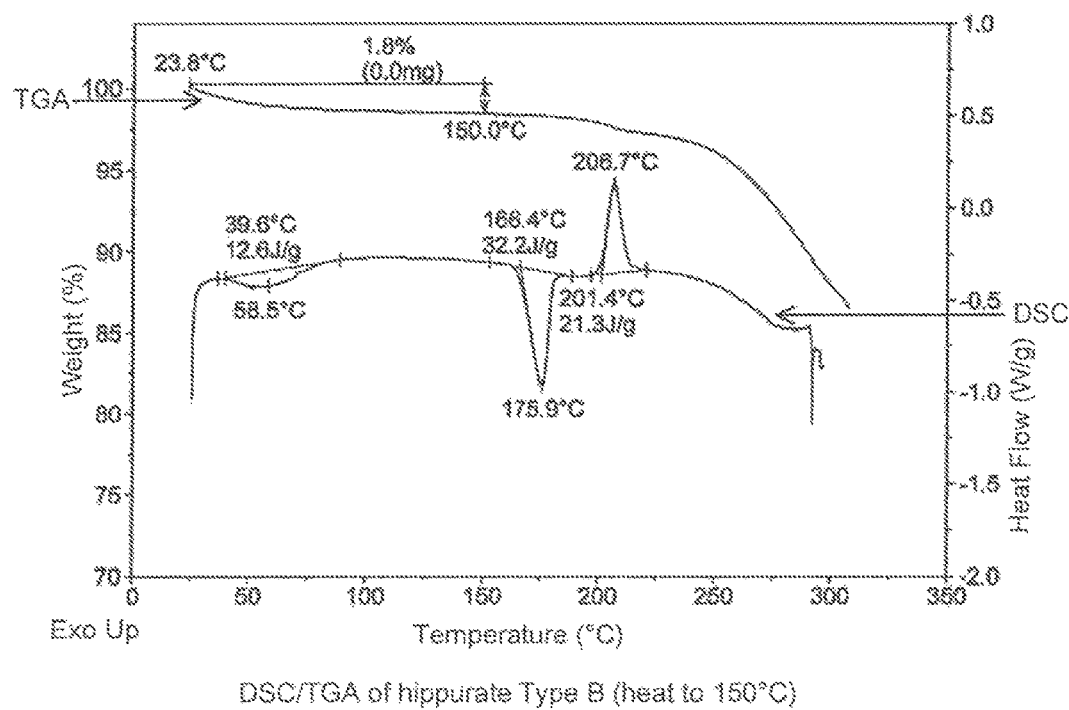
FIG. 14 is a DSC curve and a TGA curve of SCY-078 hippurate Type B from Example 10.

SCY-078 Hippurate Type B: SCY-078 hippurate Type B is produced from heating hippurate Type A to 150° C. and then cooling the sample to room temperature. SCY-078 hippurate Type B was characterized by XRPD, DSC, and TGA (FIGS. 13-14). The XRPD pattern showed that the sample is crystalline and a unique form compared to SCY-078 hippurate Type A. The DSC curve displayed two endotherms at 39.6° C. and 166.4° C. (onset temperatures) and one exotherm at 201.4° C. (onset temperature). The TGA curve demonstrated a weight loss of 1.8% before 150° C.

Example 11

Figure 15:
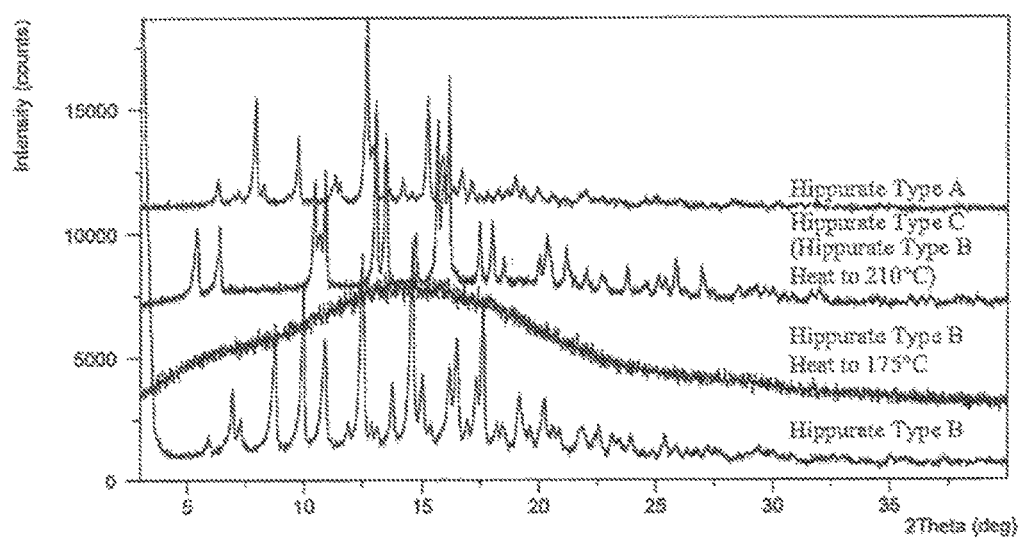
FIG. 15 is an XRPD of SCY-078 hippurate Type C from Example 11 overlaid on the XPRDs of SCY-078 hippurate Type A, hippurate Type B, and hippurate Type B heated to 175° C.
Figure 16:
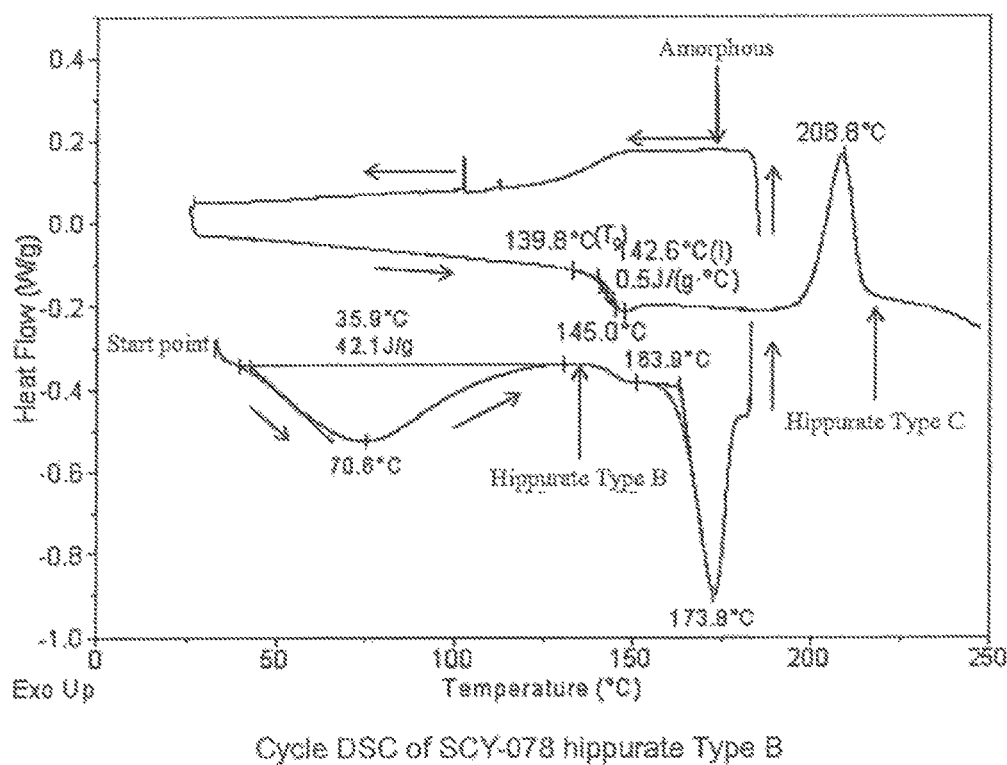
FIG. 16 is a cycle DSC curve of SCY-078 hippurate Type B and SCY-078 hippurate Type C from Example 11.

SCY-078 Hippurate Type C: Cycle DSC and XRPD were performed to investigate the phase transition events during the heating-cooling process of SCY-078 hippurate Type B (FIGS. 15-16). The XRPD overlay and DSC curve suggested the melting point of SCY-078 hippurate Type B at 163.9° C. followed by amorphous phase recrystallizing at 208.8° C. and a new anhydrate phase being formed. The new anhydrate phase is SCY-078 hippurate Type C.

Example 12

Figure 17:
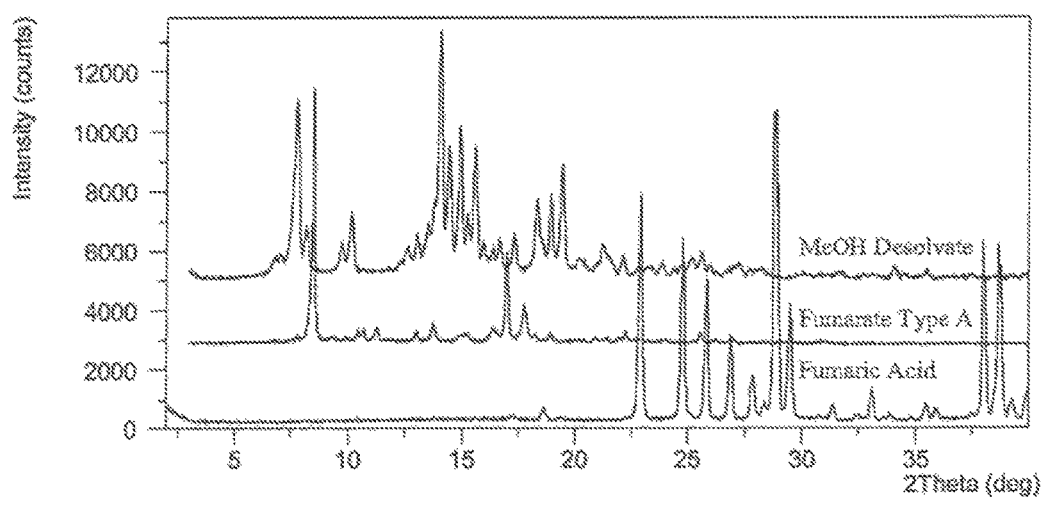
FIG. 17 is an XRPD of SCY-078 fumarate Type A from Example 12.
Figure 18:
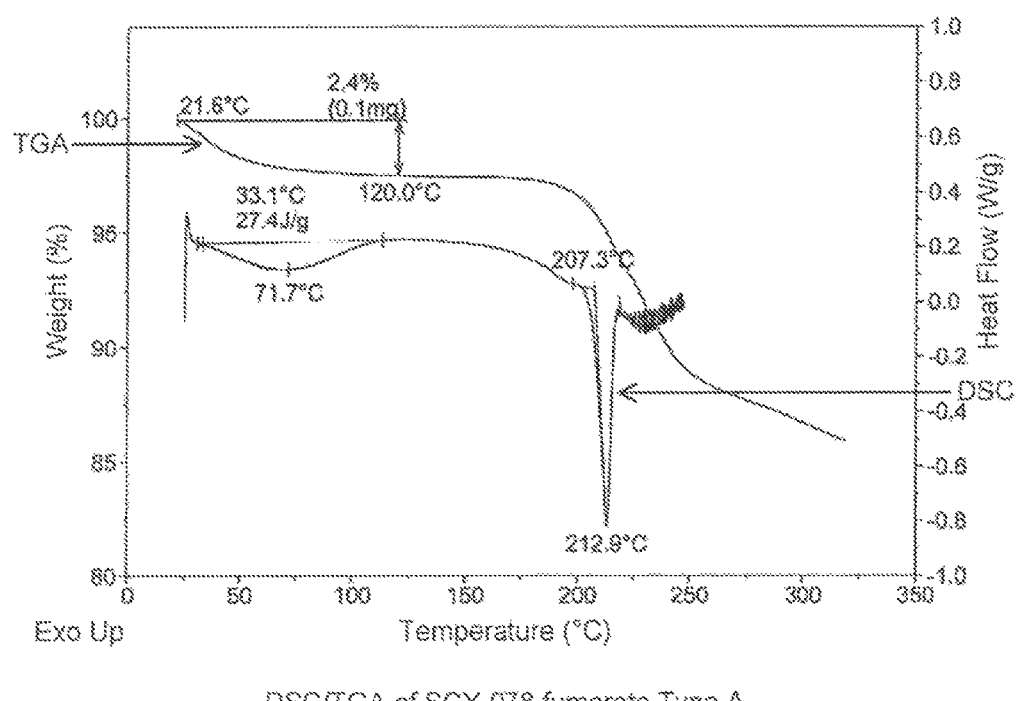
FIG. 18 is a DSC curve and a TGA curve of SCY-078 fumarate Type A from Example 12.

SCY-078 Fumarate Type A (Molar equivalency counter ion/API 1.0): SCY-078 fumarate Type A prepared from the salt study in Example 6 was characterized by XRPD, DSC, and TGA (FIGS. 17-18). The XRPD pattern indicated that the sample is crystalline and a unique form compared to the freebase MeOH desolvate. The DSC curve of SCY-078 fumarate Type A showed an endotherm at 33.1° C. and a melting point at 207.3° C. (onset temperature). The TGA curve displayed a weight loss of 2.4% before 120° C.

A sample of SCY-078 fumarate Type A was heated to 120° C. and then allowed to cool to room temperature. Characterization by XRPD, DSC, and TGA were then repeated. The XRPD pattern displayed no form change after heating and cooling. The DSC curve of heated-cooled SCY-078 fumarate Type A exhibited two endotherms at 38.4° C. and 207.1° C. (onset temperatures). The TGA curve of heated-cooled SCY-078 fumarate Type A showed a weight loss of 2.0% before 120° C.

Example 13

Figure 19:
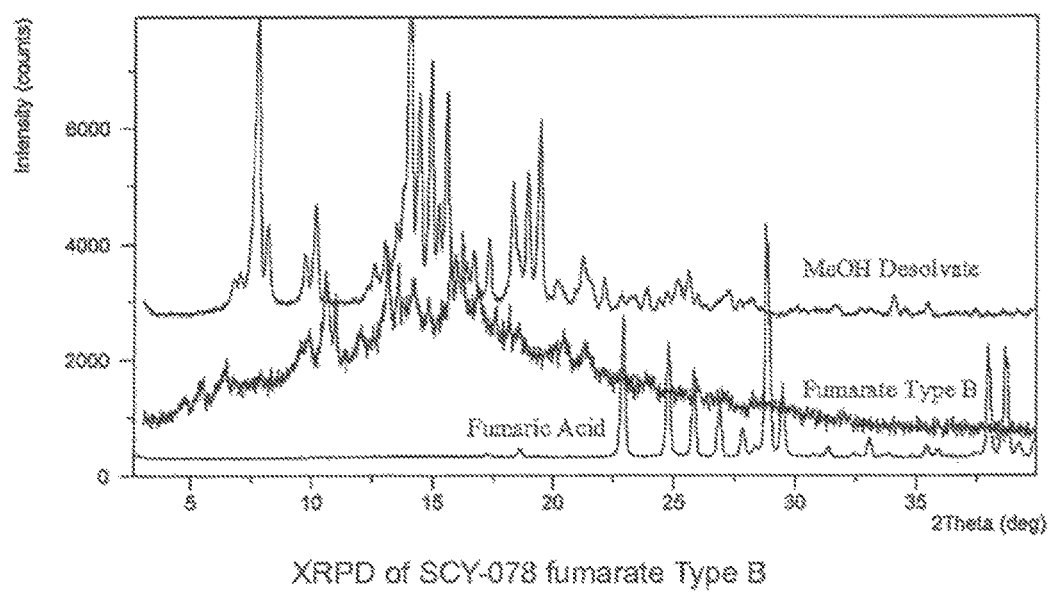
FIG. 19 is an XRPD of SCY-078 fumarate Type B from Example 13.
Figure 20:
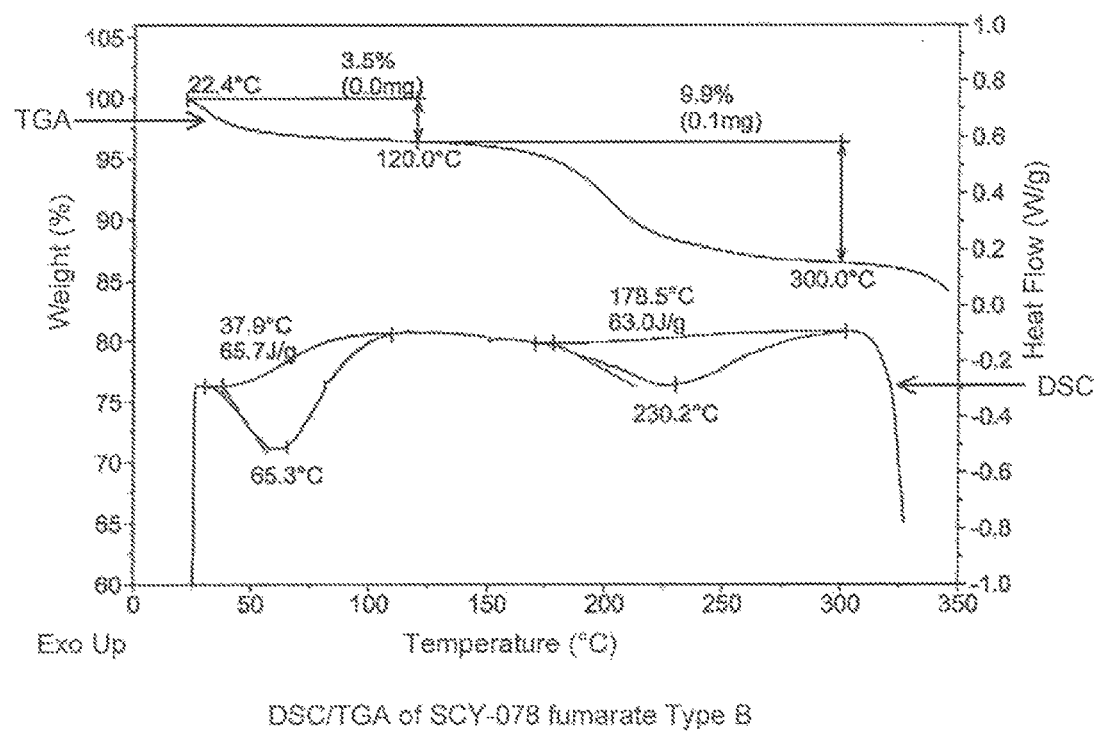
FIG. 20 is a DSC curve and a TGA curve of SCY-078 fumarate Type B from Example 13.

SCY-078 Fumarate Type B (Molar equivalency counter ion/API 0.8): SCY-078 fumarate Type B prepared from the salt study in Example 6 was characterized by XRPD, DSC, and TGA (FIGS. 19-20). The XRPD pattern of SCY-078 fumarate Type B indicated that the sample is weakly crystalline and that it is a unique form compared to the freebase MeOH desolvate. The DSC curve of SCY-078 fumarate Type B showed two endotherms at 37.9° C. and 178.5° C. (onset temperature). The TGA curve demonstrated a weight loss of 13.4% before 300° C.

Example 14

Figure 21:
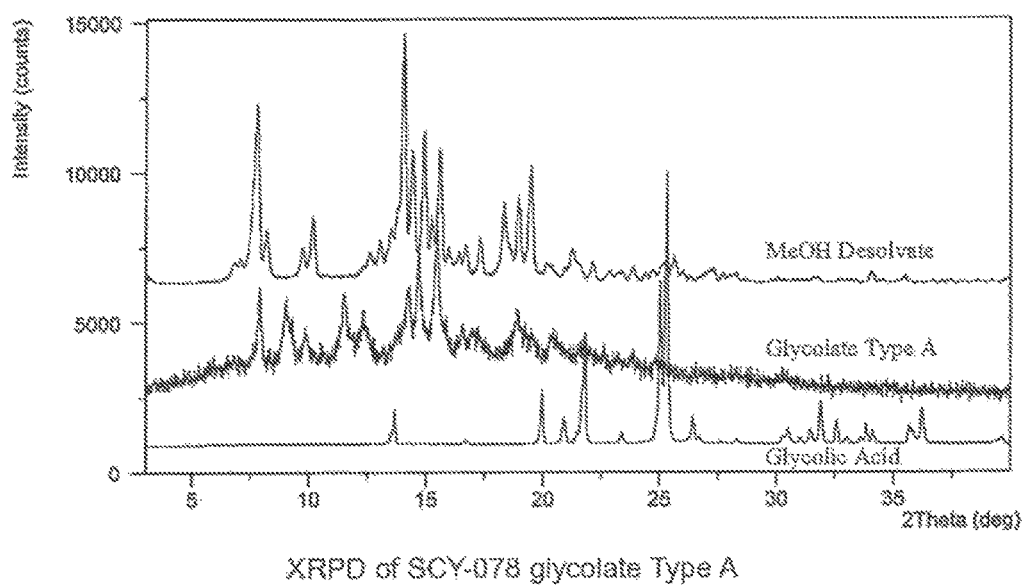
FIG. 21 is an XRPD of SCY-078 glycolate Type A from Example 14.
Figure 22:
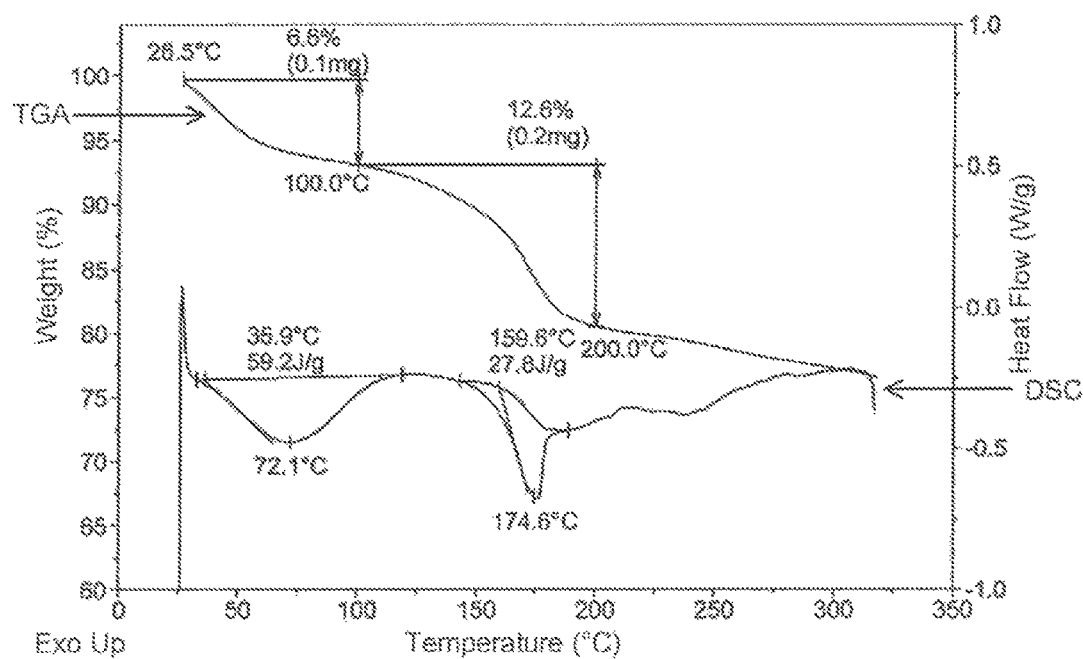
FIG. 22 is a DSC curve and a TGA curve of SCY-078 glycolate Type A from Example 14.

SCY-078 Glycolate Type A (Molar equivalency counter ion/API 2.0): SCY-078 glycolate Type A prepared from the salt study in Example 6 was characterized by XRPD, DSC, and TGA (FIGS. 21-22). The XRPD pattern of SCY-078 glycolate Type A indicated that the sample is crystalline and a unique form compared to the freebase MeOH solvate. The DSC curve of the sample displayed two endotherms at 35.9° C. and 159.6° C. (onset temperatures). The TGA curve showed a weight loss of 6.6% before 100° C.

Example 15

Figure 23:
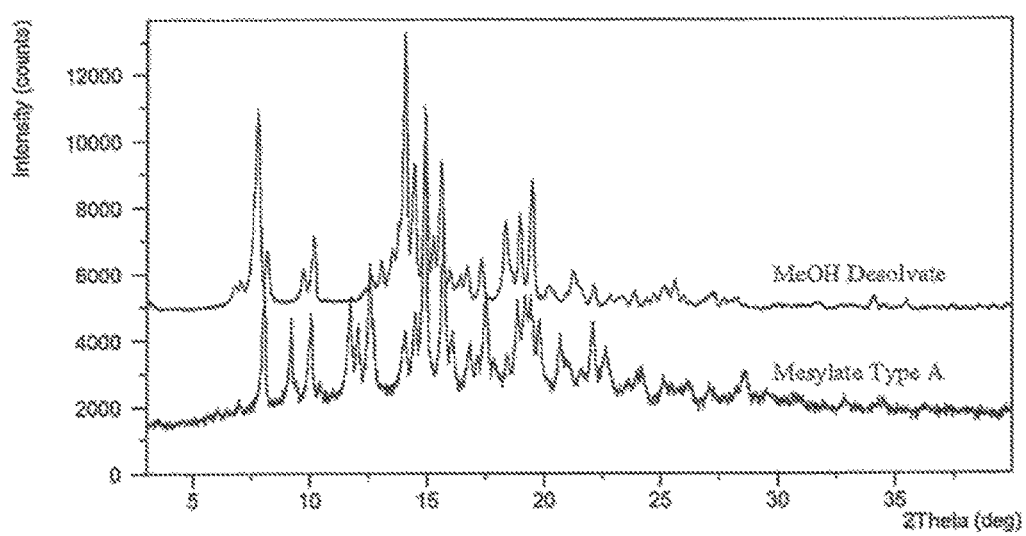
FIG. 23 is an XRPD of SCY-078 mesylate Type A from Example 15.
Figure 24:
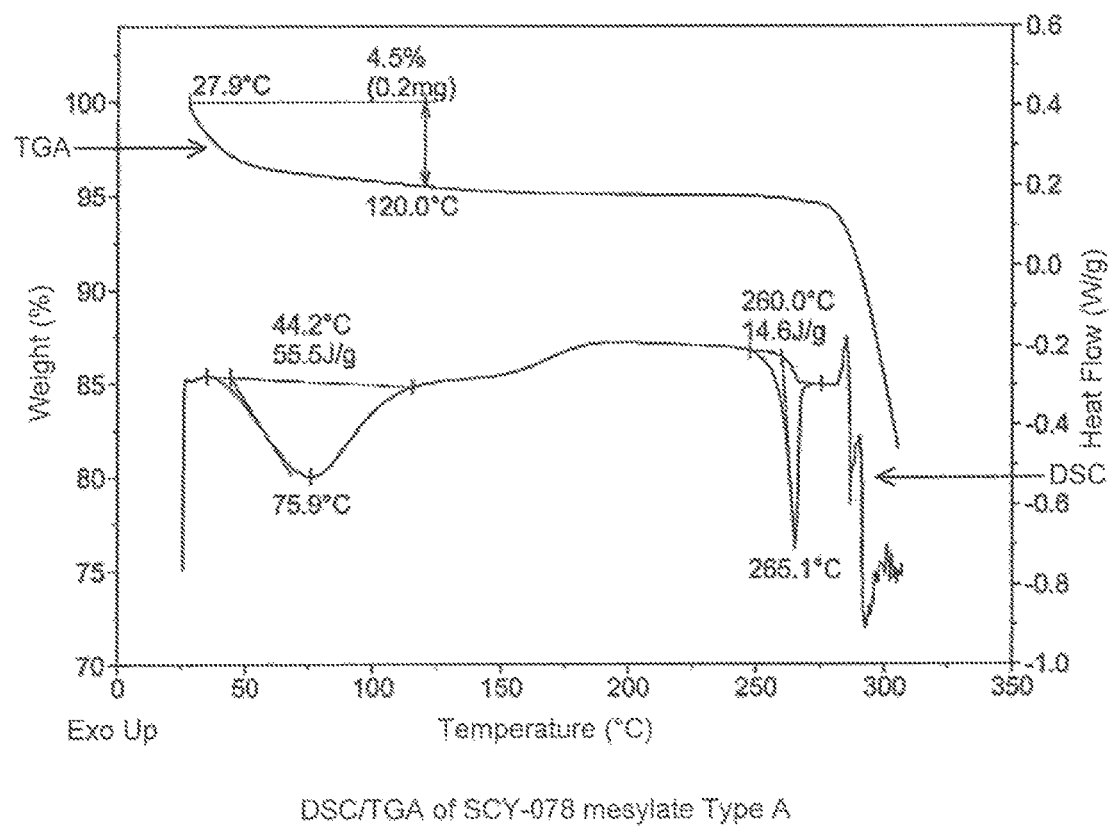
FIG. 24 is a DSC curve and a TGA curve of SCY-078 mesylate Type A from Example 15.

SCY-078 Mesylate Type A (Molar equivalency counter ion/API 1.0): SCY-078 mesylate Type A prepared from the salt study in Example 6 was characterized by XRPD, DSC, and TGA (FIGS. 23-24). The XRPD pattern indicated that the sample is crystalline and a unique form compared to the freebase MeOH desolvate. The DSC curve displayed an endotherm at 44.2° C. and a melting point at 260.0° C. (onset temperatures). The TGA showed a weight loss of 4.5% before 120° C.

Next, a sample of SCY-078 mesylate Type A was heated to 120° C. and then allowed to cool to room temperature. Characterization by XRPD, DSC, and TGA was then repeated. The XRPD pattern displayed no form change after heating and cooling. The DSC curve of the heated-cooled SCY-078 mesylate Type A exhibited an endotherm at 59.7° C. and a melting point at 257.4° C. (onset temperatures). The TGA curve of the heated-cooled SCY-078 mesylate Type A showed a weight loss of 9.4% before 120° C.

Example 16

Figure 25:
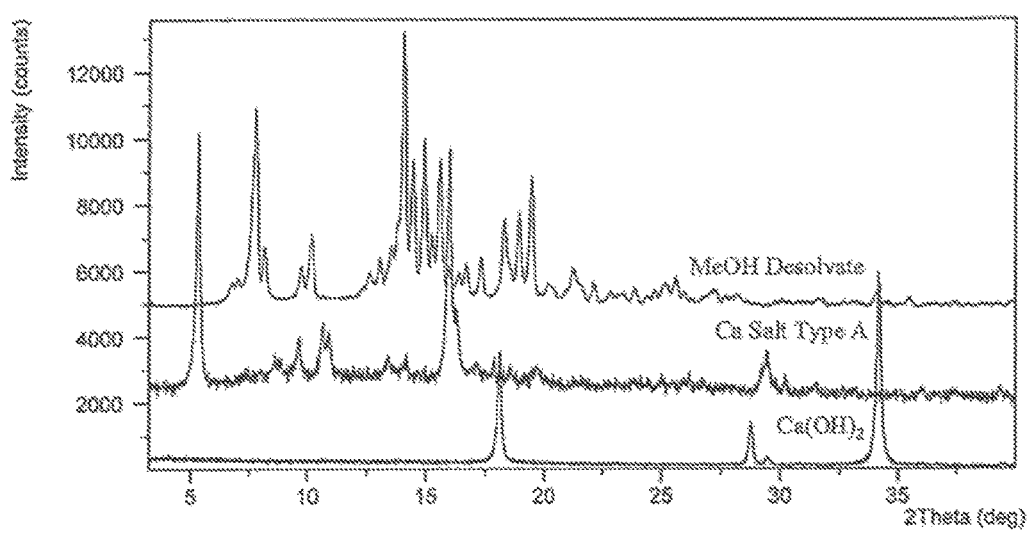
FIG. 25 is an XRPD of SCY-078 calcium Type A from Example 16.
Figure 26:
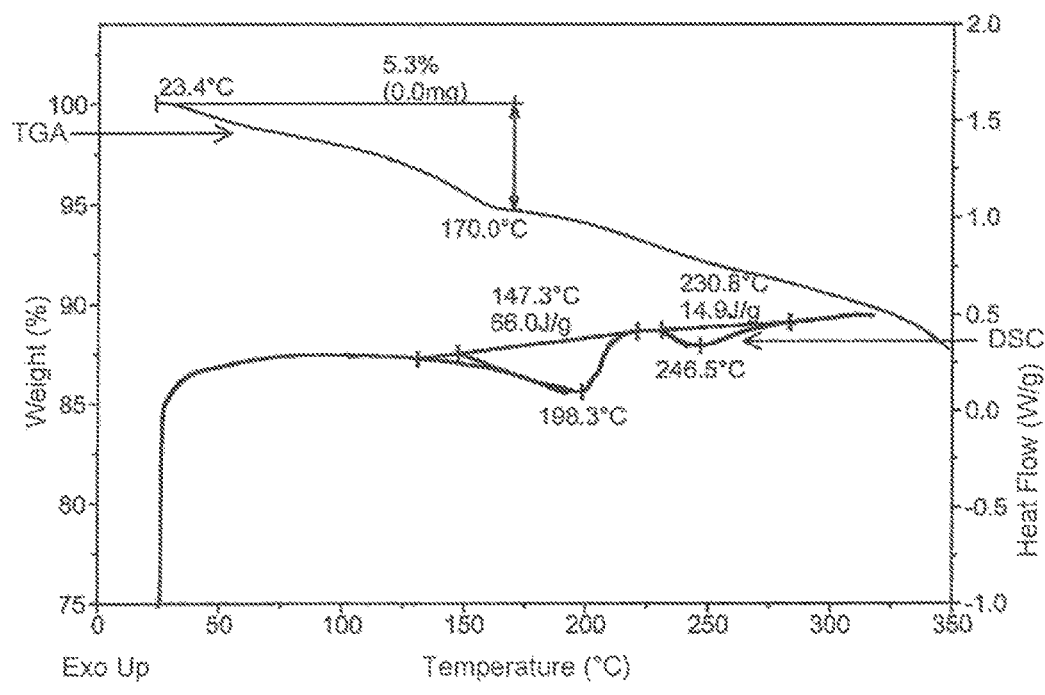
FIG. 26 is a DSC curve and a TGA curve of SCY-078 calcium Type A from Example 16.
Figure 27:
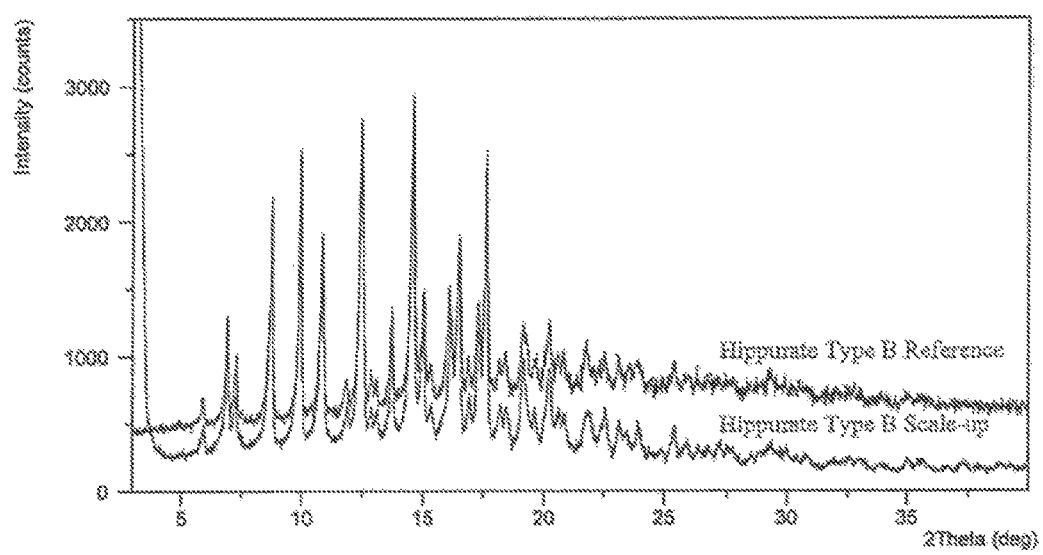
FIG. 27 is an XRPD of scaled-up SCY-078 hippurate Type B from Example 17.
Figure 28:
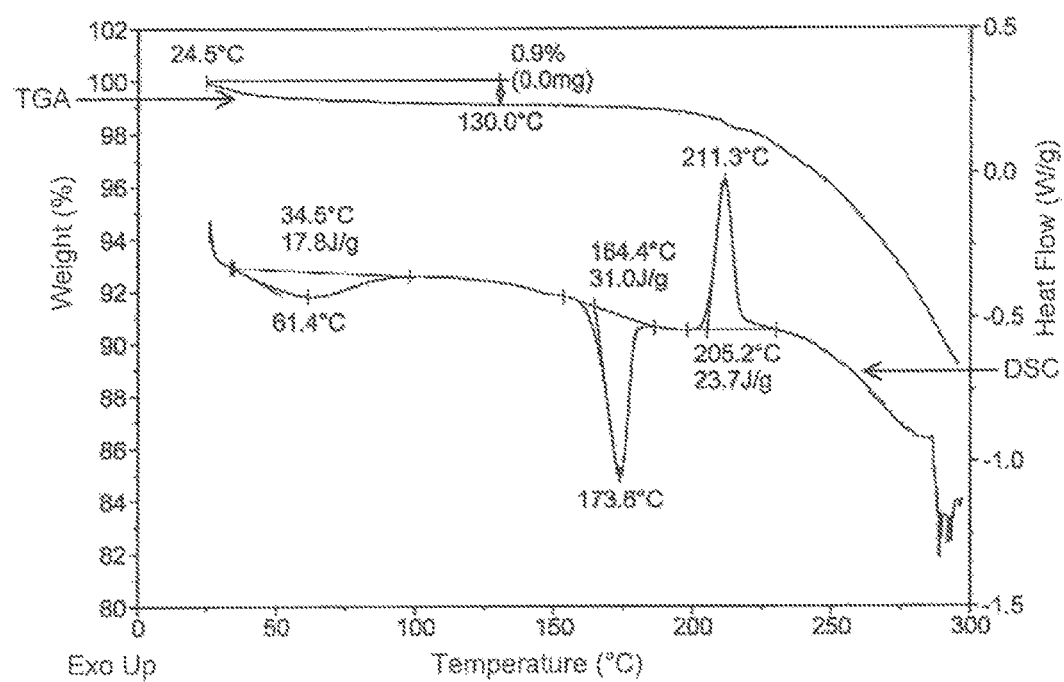
FIG. 28 is a DSC curve and a TGA curve of scaled-up SCY-078 hippurate Type B from Example 17.
Figure 29:
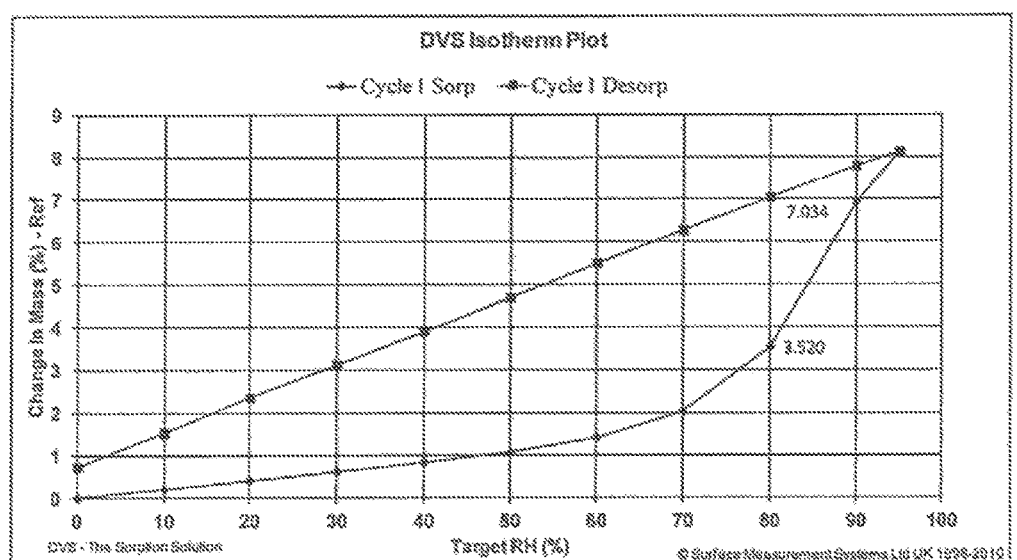
FIG. 29 is a DVS isotherm plot of scaled-up SCY-078 hippurate Type B from Example 17.
Figure 30:
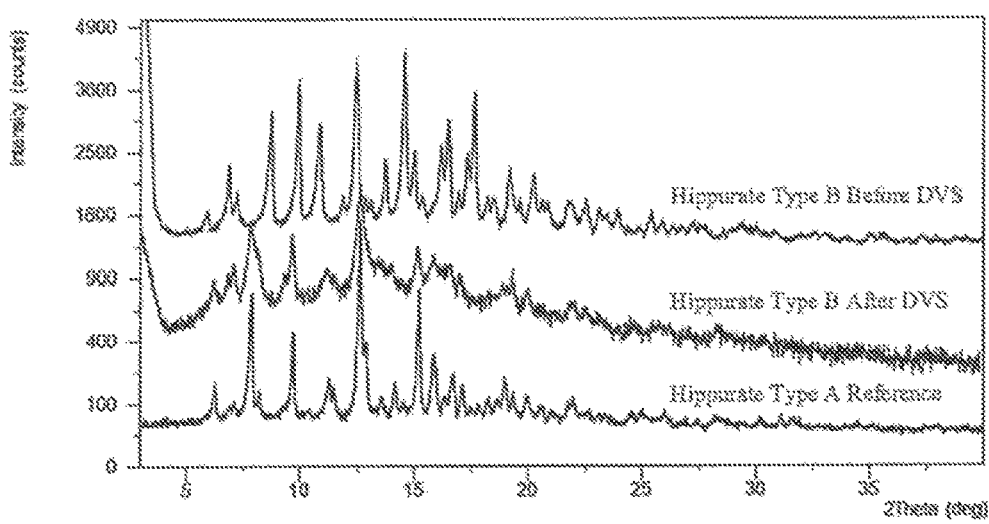
FIG. 30 is an XRPD of scaled-up SCY-078 hippurate Type B before DVS, after DVS, and compared to hippurate Type A from Example 17.

SCY-078 Calcium Type A: SCY-078 calcium Type A prepared from the salt study in Example 6 was characterized by XRPD, DSC, and TGA (FIGS. 25-26). The XRPD pattern indicated that the sample is crystalline and a unique form compared to the freebase MeOH desolvate. The DSC curve displayed two endotherms at 147.3° C. and 230.8° C. (onset temperatures). The TGA curve showed a weight loss of 5.3% before 170° C.

Example 17

Preparation and Characterization of Scaled-Up SCY-078 Hippurate Type B: To scale-up SCY-078 hippurate Type B, a solution of hippuric acid (122.8 mg) and SCY-078 MeOH desolvate (500.3 mg) in ACN (5.0 mL) was prepared. The suspension was then stirred (500 rpm) at room temperature for 28 hours. Following stirring, some slurry was filtered and the isolated solid was checked by XRPD to confirm SCY-078 hippurate Type A. The suspension was filtered and dried at 150° C. for 1 hour before characterization. Finally, the solid was check by XRPD to confirm to SCY-078 hippurate Type B.

The scaled-up SCY-078 hippurate Type B was analyzed by XRPD, DSC, TGA, and DVS (FIGS. 27-30). The resulting XRPD pattern evidenced that SCY-078 hippurate Type B was successfully scaled up. The 2 theta and d-spacing values are summarized in Table 11. The DSC curve showed two endotherms at 34.5° C. and 164.4° C. and one exotherm at 205.2° C. (onset temperatures). The TGA curve showed a weight loss of 0.9% before 130° C. The DVS curve showed that the sample is hygroscopic with a water uptake of ~3.5% at 25° C. and 80% RH. A second XRPD pattern performed after DVS showed SCY-078 hippurate Type B converted to SCY-078 hippurate Type A after DVS experiment.

TABLE 11

| Pos. [°2Th.] | Height [cts] | FWHM Left [°2Th.] | d-spacing [Å] | Rel. Int. [%] |
|---|---|---|---|---|
| 3.027072 | 11818.150000 | 0.051168 | 29.18766 | 100.00 |
| 5.916137 | 351.270000 | 0.102336 | 14.93916 | 2.97 |
| 6.916698 | 947.910600 | 0.102336 | 12.78016 | 8.02 |
| 7.251646 | 624.847700 | 0.076752 | 12.19059 | 5.29 |
| 8.761702 | 1828.733000 | 0.076752 | 10.09268 | 15.47 |
| 9.962105 | 2404.236000 | 0.102336 | 8.87907 | 20.34 |
| 10.897800 | 1593.408000 | 0.102336 | 8.11872 | 13.48 |
| 11.868550 | 552.254500 | 0.102336 | 7.45677 | 4.67 |
| 12.432300 | 2880.441000 | 0.127920 | 7.11988 | 24.37 |
| 12.857840 | 525.634600 | 0.076752 | 6.88518 | 4.45 |

TABLE 11-continued

| Pos. [°2Th.] | Height [cts] | FWHM Left [°2Th.] | d-spacing [Å] | Rel. Int. [%] |
|---|---|---|---|---|
| 13.091360 | 511.764400 | 0.115128 | 6.76288 | 4.33 |
| 13.709840 | 1112.219000 | 0.102336 | 6.45916 | 9.41 |
| 14.555290 | 3086.294000 | 0.153504 | 6.08582 | 26.11 |
| 14.984610 | 1215.693000 | 0.102336 | 5.91241 | 10.29 |
| 15.341160 | 506.870800 | 0.153504 | 5.77579 | 4.29 |
| 16.136210 | 1315.742000 | 0.089544 | 5.49296 | 11.13 |
| 16.453540 | 1710.358000 | 0.153504 | 5.38772 | 14.47 |
| 16.897030 | 606.324900 | 0.102336 | 5.24730 | 5.13 |
| 17.280760 | 1171.798000 | 0.127920 | 5.13164 | 9.92 |
| 17.591700 | 2258.867000 | 0.102336 | 5.04163 | 19.11 |
| 18.190770 | 538.754800 | 0.127920 | 4.87692 | 4.56 |
| 18.425670 | 516.831300 | 0.179088 | 4.81528 | 4.37 |
| 19.151570 | 950.084500 | 0.102336 | 4.63437 | 8.04 |
| 19.602330 | 487.956400 | 0.127920 | 4.52881 | 4.13 |
| 20.234760 | 861.917600 | 0.153504 | 4.38867 | 7.29 |
| 20.860030 | 424.598600 | 0.153504 | 4.25851 | 3.59 |
| 21.725360 | 459.496200 | 0.307008 | 4.09081 | 3.89 |
| 22.532320 | 498.240700 | 0.102336 | 3.94610 | 4.22 |
| 23.078810 | 380.947900 | 0.127920 | 3.85388 | 3.22 |
| 23.551950 | 208.488500 | 0.409344 | 3.77752 | 1.76 |
| 23.874020 | 377.598600 | 0.102336 | 3.72728 | 3.20 |
| 25.381750 | 351.553600 | 0.102336 | 3.50919 | 2.97 |
| 25.844490 | 207.070300 | 0.204672 | 3.44740 | 1.75 |
| 27.188450 | 192.463400 | 0.153504 | 3.27997 | 1.63 |
| 27.681830 | 144.369000 | 0.307008 | 3.22262 | 1.22 |
| 29.319670 | 172.870900 | 0.511680 | 3.04622 | 1.46 |
| 30.833510 | 86.432220 | 0.307008 | 2.90002 | 0.73 |
| 34.979000 | 90.330020 | 0.204672 | 2.56525 | 0.76 |
| 35.588330 | 69.479680 | 0.307008 | 2.52271 | 0.59 |
| 37.270360 | 55.666410 | 0.307008 | 2.41264 | 0.47 |

Example 18

Preparation and Characterization of Scaled-Up SCY-078 Fumarate Type A: To scale-up SCY-078 fumarate Type A, a solution of fumaric acid (79.8 mg) and SCY-078 MeOH desolvate (501.9 mg) in ACN (15.0 mL) was prepared. The suspension was then stirred (500 rpm) at room temperature for 28 hours. Following stirring, some slurry was filtered and the isolated solid was checked by XRPD to confirm SCY-078 fumarate Type A. Finally, the suspension was filtered and dried at 30° C. for 4 hours in vacuum before characterization.

Figure 31:
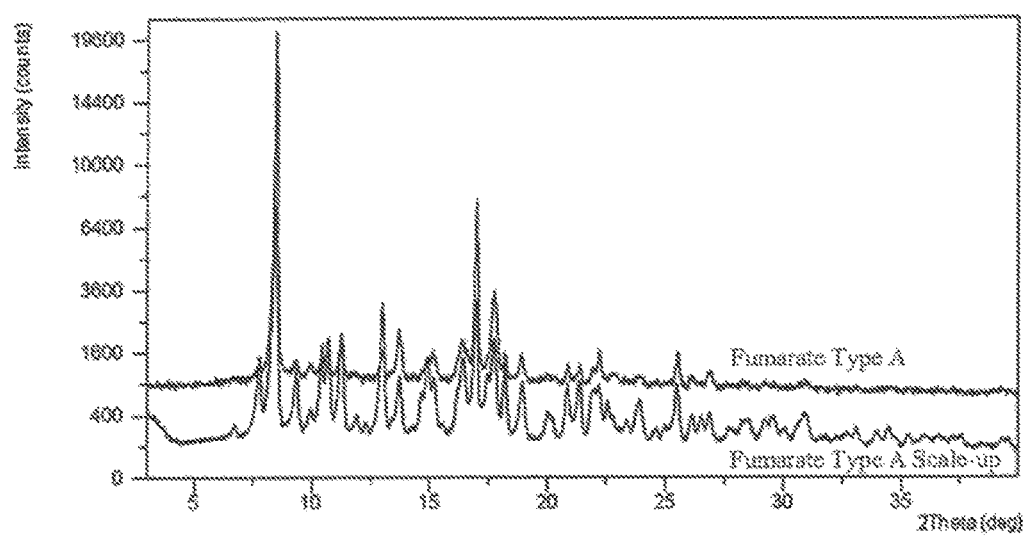
FIG. 31 is an XRPD of scaled-up SCY-078 fumarate Type A from Example 18.
Figure 32:
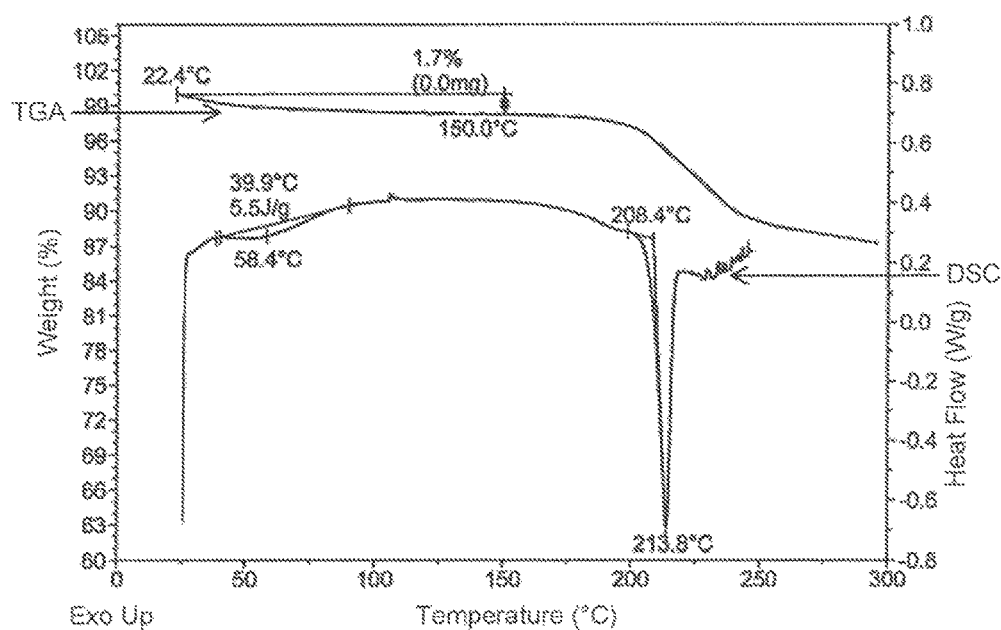
FIG. 32 is a DSC curve and a TGA curve of scaled-up SCY-078 fumarate Type A from Example 18.
Figure 33:
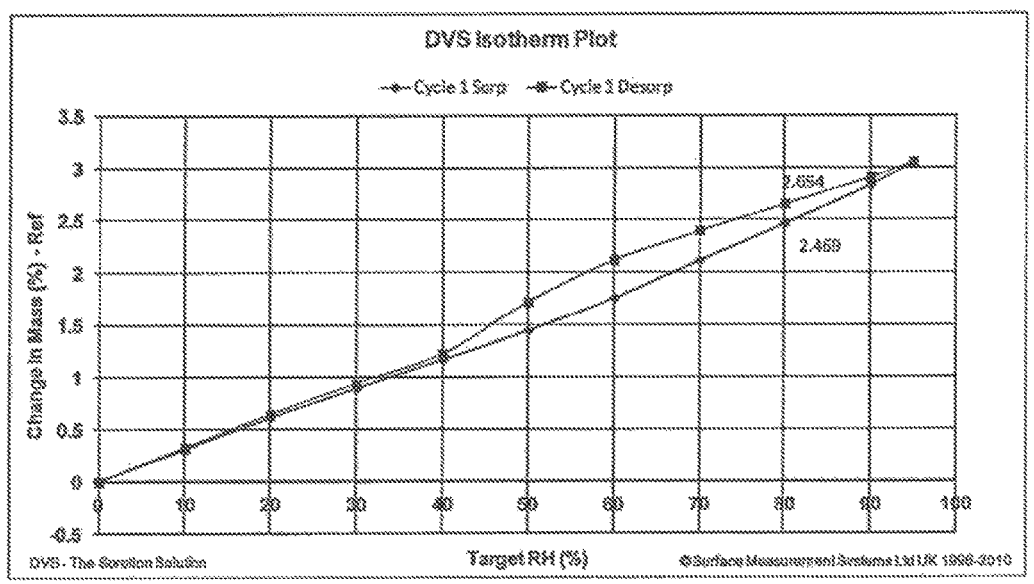
FIG. 33 is a DVS isotherm plot of scaled-up SCY-078 fumarate Type A from Example 18.

Characterization of scaled-up SCY-078 fumarate Type A included XRPD, DSC, TGA, and DVS (FIGS. 31-33). The resulting XRPD pattern evidenced that SCY-078 fumarate Type A was successfully scaled up. The 2 theta and d-spacing values are summarized in Table 12. The DSC curve showed an endotherm at 39.9° C. and a melting endotherm at 208.4° C. (onset temperatures). The TGA curve showed a weight loss of 1.7% before 150° C. The DVS curve showed that the sample is hygroscopic with a water uptake of 2.5% at 80% RH, 25° C. A second XRPD pattern performed after DVS showed SCY-078 fumarate Type A had no form change.

TABLE 12

| Pos.[°2Th.] | Height [cts] | FWHM Left [°2Th.] | d-spacing [Å] | Rel. Int. [%] |
|---|---|---|---|---|
| 6.708362 | 290.801200 | 0.153504 | 13.17659 | 2.14 |
| 7.779830 | 2540.992000 | 0.102336 | 11.36410 | 18.74 |
| 8.490587 | 13558.710000 | 0.127920 | 10.41433 | 100.00 |
| 9.362659 | 1986.519000 | 0.102336 | 9.44617 | 14.65 |
| 9.964151 | 661.033600 | 0.127920 | 8.87725 | 4.88 |
| 10.417770 | 2882.948000 | 0.115128 | 8.49171 | 21.26 |
| 10.694630 | 3478.282000 | 0.127920 | 8.27250 | 25.65 |

TABLE 12-continued

| Pos.[°2Th.] | Height [cts] | FWHM Left [°2Th.] | d-spacing [Å] | Rel. Int. [%] |
|---|---|---|---|---|
| 11.221780 | 3785.363000 | 0.140712 | 7.88504 | 27.92 |
| 11.875520 | 519.613200 | 0.153504 | 7.45241 | 3.83 |
| 12.271310 | 357.834700 | 0.127920 | 7.21292 | 2.64 |
| 13.008060 | 5831.607000 | 0.140712 | 6.80600 | 43.01 |
| 13.729940 | 1780.661000 | 0.127920 | 6.44975 | 13.13 |
| 14.640000 | 1169.640000 | 0.076752 | 6.05080 | 8.63 |
| 14.888350 | 2319.347000 | 0.078000 | 5.94549 | 17.11 |
| 14.955620 | 2471.802000 | 0.076752 | 5.92381 | 18.23 |
| 15.225230 | 1608.774000 | 0.089544 | 5.81951 | 11.87 |
| 16.171470 | 1276.652000 | 0.076752 | 5.48106 | 9.42 |
| 16.429100 | 2604.447000 | 0.140712 | 5.39569 | 19.21 |
| 16.942700 | 6000.498000 | 0.140712 | 5.23326 | 44.26 |
| 17.442280 | 1878.502000 | 0.063960 | 5.08448 | 13.85 |
| 17.749440 | 3552.116000 | 0.140712 | 4.99718 | 26.20 |
| 18.202980 | 2297.875000 | 0.127920 | 4.87368 | 16.95 |
| 18.928920 | 1597.690000 | 0.140712 | 4.68838 | 11.78 |
| 20.028870 | 591.031400 | 0.127920 | 4.43332 | 4.36 |
| 20.258840 | 480.204800 | 0.102336 | 4.38351 | 3.54 |
| 20.868380 | 1498.769000 | 0.127920 | 4.25683 | 11.05 |
| 21.397940 | 1555.987000 | 0.089544 | 4.15266 | 11.48 |
| 21.879750 | 1130.218000 | 0.127920 | 4.06229 | 8.34 |
| 22.217300 | 1475.131000 | 0.102336 | 4.00133 | 10.88 |
| 22.591130 | 913.600300 | 0.102336 | 3.93596 | 6.74 |
| 23.385000 | 425.684600 | 0.153504 | 3.80411 | 3.14 |
| 23.950880 | 915.135300 | 0.204672 | 3.71550 | 6.75 |
| 24.627720 | 245.047100 | 0.153504 | 3.61490 | 1.81 |
| 25.499420 | 1445.187000 | 0.089544 | 3.49326 | 10.66 |
| 26.148510 | 509.814300 | 0.179088 | 3.40800 | 3.76 |
| 26.502880 | 512.161300 | 0.127920 | 3.36323 | 3.78 |
| 26.881710 | 614.926800 | 0.153504 | 3.31669 | 4.54 |
| 27.716900 | 269.647600 | 0.255840 | 3.21862 | 1.99 |
| 28.552140 | 414.549300 | 0.153504 | 3.12634 | 3.06 |
| 29.217330 | 471.259100 | 0.153504 | 3.05666 | 3.48 |
| 29.558860 | 525.910500 | 0.204672 | 3.02211 | 3.88 |
| 30.043740 | 270.781000 | 0.204672 | 2.97444 | 2.00 |
| 30.962340 | 570.115500 | 0.307008 | 2.88825 | 4.20 |
| 33.133860 | 264.449500 | 0.179088 | 2.70376 | 1.95 |
| 33.967430 | 212.730600 | 0.179088 | 2.63929 | 1.57 |
| 34.456190 | 314.358700 | 0.179088 | 2.60297 | 2.32 |
| 35.316070 | 163.009400 | 0.179088 | 2.54153 | 1.20 |
| 35.928310 | 161.442300 | 0.307008 | 2.49962 | 1.19 |
| 37.556590 | 162.885200 | 0.153504 | 2.39491 | 1.20 |

Example 19

Preparation and Characterization of Scaled-Up SCY-078 Mesylate Type A: To scale up SCY-078 mesylate Type A, a solution of methanesulfonic acid (66.7 mg) and SCY-078 MeOH desolvate (500.00 mg) in ACN (6.0 mL) was prepared. The suspension was then stirred (500 rpm) at room temperature for 28 hours. Following stirring, some slurry was filtered and the isolated solid was checked by XRPD to confirm to SCY-078 mesylate Type A. Finally, the suspension was filtered and dried at 30° C. for 4 hours in vacuum before characterization.

Figure 34:
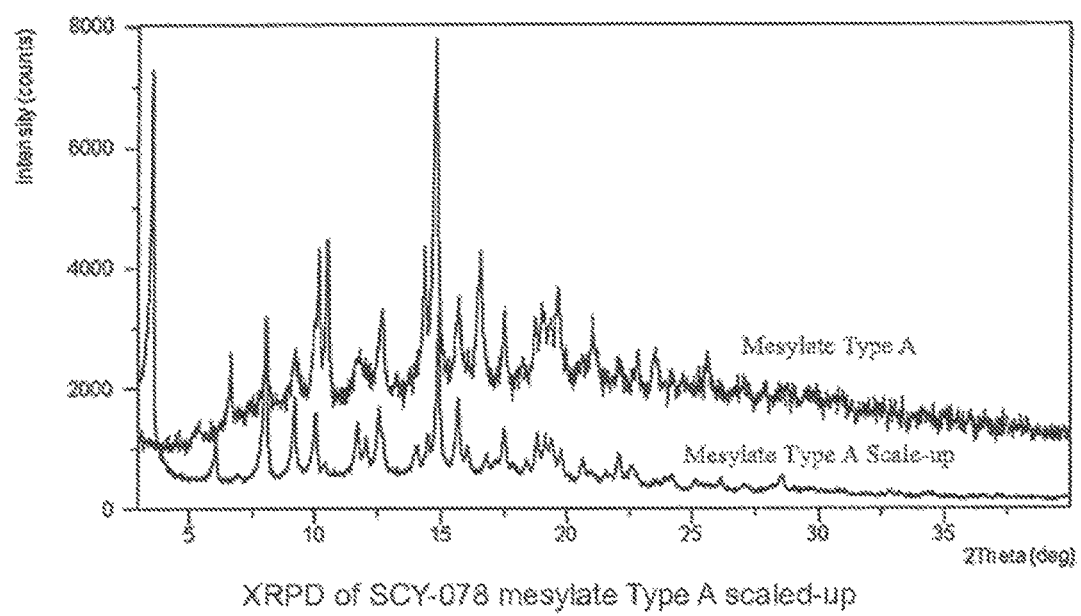
FIG. 34 is an XRPD of scaled-up SCY-078 mesylate Type A from Example 19.
Figure 35:
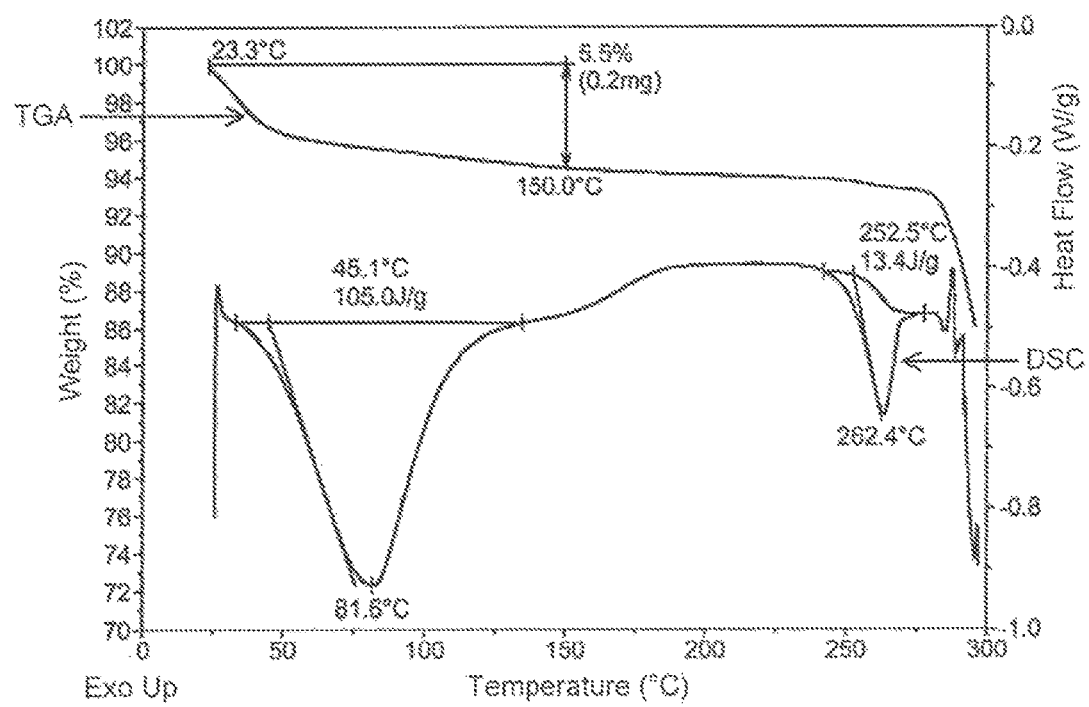
FIG. 35 is a DSC curve and a TGA curve of scaled-up SCY-078 mesylate Type A from Example 19.
Figure 36:
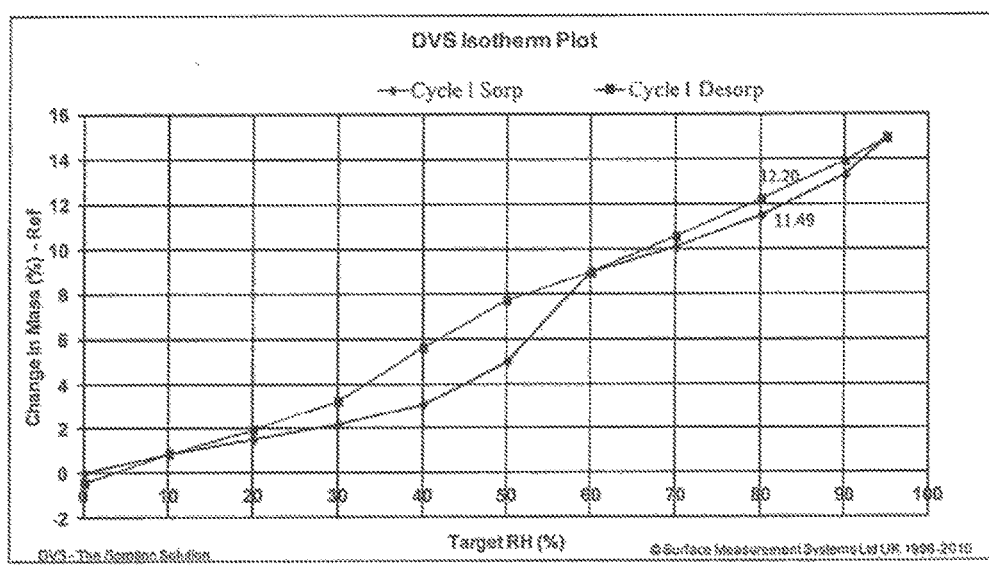
FIG. 36 is a DVS isotherm plot of scaled-up SCY-078 mesylate Type A from Example 19.

Characterization of scaled-up SCY-078 mesylate Type A included XRPD, DSC, TGA, and DVS (FIGS. 34-36). The resulting XRPD pattern evidenced that SCY-078 mesylate Type A was successfully scaled up. The 2 theta and d-spacing values are summarized in Table 13. The DSC curve showed an endotherm at 45.1° C. and a melting endotherm at 252.5° C. (onset temperatures). The TGA curve showed a weight loss of 5.5% before 150° C. The DVS curve showed that the sample is hygroscopic with a water uptake of 11.5% at 25° C. and 80% RH. A second XRPD pattern performed after DVS showed SCY-078 mesylate Type A had no form change.

TABLE 13

| Pos. [°2Th.] | Height [cts] | FWHM Left [°2Th.] | d-spacing [Å] | Rel. Int. [%] |
|---|---|---|---|---|
| 3.460873 | 6386.923000 | 0.076752 | 25.53007 | 100.00 |
| 5.977580 | 779.662100 | 0.063960 | 14.78574 | 12.21 |
| 7.966391 | 2528.494000 | 0.089544 | 11.09839 | 39.59 |
| 9.108506 | 1390.758000 | 0.089544 | 9.70916 | 21.78 |
| 9.950825 | 1211.786000 | 0.102336 | 8.88911 | 18.97 |
| 11.611990 | 1031.845000 | 0.076752 | 7.62094 | 16.16 |
| 11.923410 | 791.823600 | 0.102336 | 7.42258 | 12.40 |
| 12.425240 | 1268.865000 | 0.089544 | 7.12391 | 19.87 |
| 13.944550 | 688.156900 | 0.102336 | 6.35096 | 10.77 |
| 14.380410 | 848.725700 | 0.102336 | 6.15943 | 13.29 |
| 14.769580 | 2671.218000 | 0.089544 | 5.99800 | 41.82 |
| 15.556400 | 1399.797000 | 0.102336 | 5.69636 | 21.92 |
| 15.933420 | 664.503200 | 0.102336 | 5.56241 | 10.40 |
| 16.662350 | 540.586700 | 0.102336 | 5.32067 | 8.46 |
| 17.361270 | 955.468500 | 0.127920 | 5.10802 | 14.96 |
| 18.265030 | 453.378300 | 0.153504 | 4.85726 | 7.10 |
| 18.734480 | 812.380000 | 0.102336 | 4.73660 | 12.72 |
| 19.019690 | 850.304100 | 0.102336 | 4.66621 | 13.31 |
| 19.260210 | 762.325000 | 0.153504 | 4.60847 | 11.94 |
| 19.645310 | 613.773700 | 0.127920 | 4.51900 | 9.61 |
| 20.566280 | 436.518500 | 0.127920 | 4.31867 | 6.83 |
| 21.974920 | 571.254200 | 0.127920 | 4.04491 | 8.94 |
| 22.483420 | 374.000100 | 0.255840 | 3.95457 | 5.86 |
| 24.101950 | 210.447500 | 0.153504 | 3.69255 | 3.29 |
| 25.009440 | 137.497300 | 0.204672 | 3.56058 | 2.15 |
| 26.043990 | 151.416700 | 0.204672 | 3.42144 | 2.37 |
| 27.012060 | 72.724460 | 0.307008 | 3.30098 | 1.14 |
| 28.443410 | 214.270100 | 0.153504 | 3.13804 | 3.35 |
| 34.283540 | 45.493190 | 0.511680 | 2.61568 | 0.71 |

Example 20

Preparation and Characterization of Scaled-Up SCY-078 Phosphate Type A: To scale up SCY-078 phosphate Type A, a solution of phosphoric acid (87.2 mg) and SCY-078 MeOH desolvate (501.1 mg) in EtOH/EtOAc/acetic acid/H$_2$O (6.0 mL, 5:3:0.15:0.1; v/v/v/v) was prepared. The suspension was then stirred (500 rpm) at room temperature for 28 hours. Following stirring, some slurry was filtered and the isolated solid was checked by XRPD and named as SCY-078 phosphate Type A. Finally, the suspension was filtered and dried at 30° C. for 4 hours in vacuum before characterization.

Figure 37:
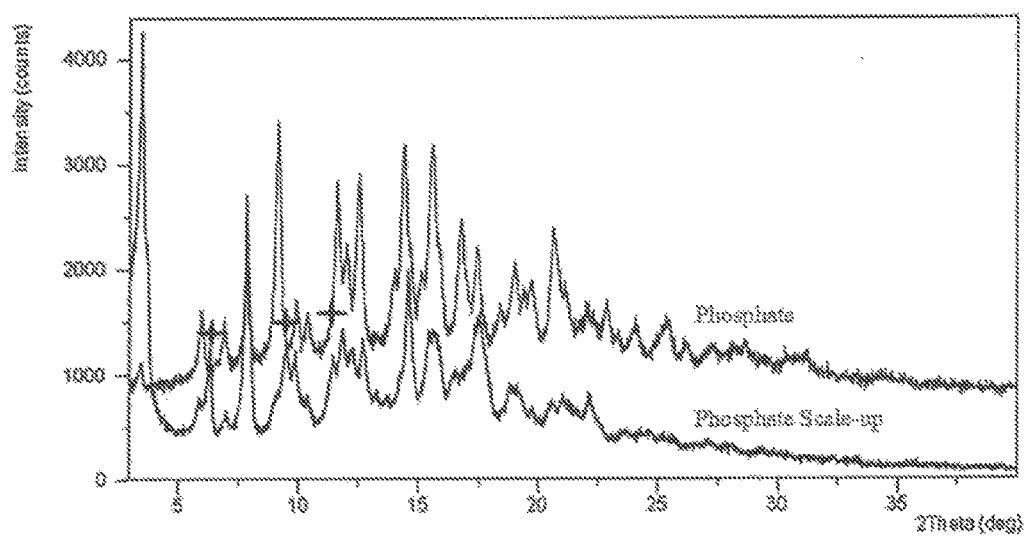
FIG. 37 is an XRPD of scaled-up SCY-078 phosphate Type A from Example 20.
Figure 38:
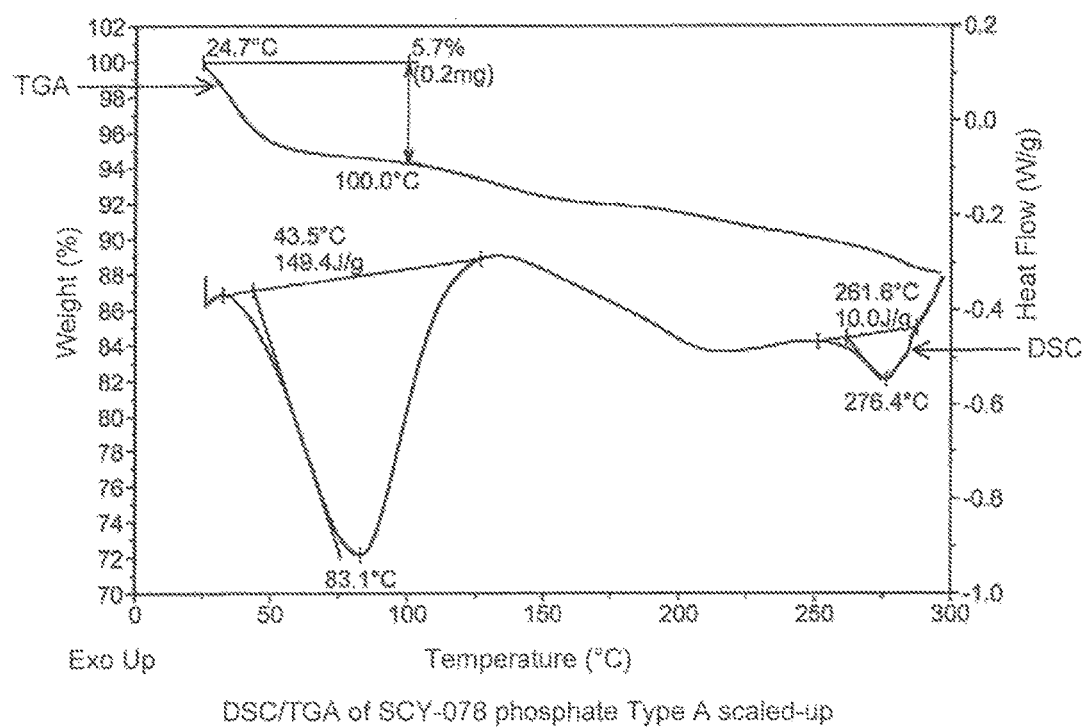
FIG. 38 is a DSC curve and a TGA curve of scaled-up SCY-078 phosphate Type A from Example 20.
Figure 39:
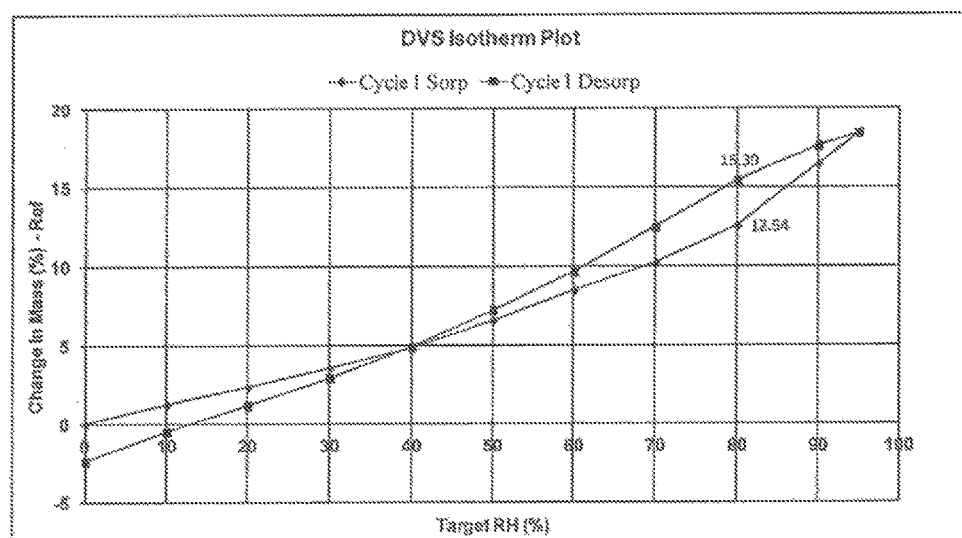
FIG. 39 is a DVS isotherm plot of scaled-up SCY-078 phosphate Type A from Example 20.

Characterization of scaled-up SCY-078 phosphate Type A included XRPD, DSC, TGA, and DVS (FIGS. 37-39). The XRPD pattern of the scaled-up SCY-078 phosphate Type A was compared with another phosphate sample. The comparison XRPD pattern evidenced certain peak shifts, which are signaled with an asterisk. The 2 theta and d-spacing values of SCY-078 phosphate Type A are summarized in Table 14. The DSC curve showed two endotherms at 43.5° C. and 261.6° C. (onset temperatures). The TGA curve showed a weight loss of 5.7% before 100° C. The DVS curve showed that the sample is hygroscopic with a water uptake of 12.5% at 25° C. and 80% RH. A second XRPD pattern performed after DVS showed SCY-078 phosphate Type A had no form change.

TABLE 14

| Pos. [°2 Th.] | Height [cts] | FWHM Left [°2 Th.] | d-spacing [Å] | Rel. Int. [%] |
|---|---|---|---|---|
| 3.510749 | 3822.958000 | 0.063960 | 25.16747 | 100.00 |
| 3.777221 | 1538.172000 | 0.089544 | 23.39256 | 40.24 |

TABLE 14-continued

| Pos.<br>[°2 Th.] | Height [cts] | FWHM Left<br>[°2 Th.] | d-spacing<br>[Å] | Rel. Int.<br>[%] |
|---|---|---|---|---|
| 6.351771 | 817.179700 | 0.089544 | 13.91551 | 21.38 |
| 6.974826 | 213.577600 | 0.153504 | 12.67379 | 5.59 |
| 7.884021 | 2248.860000 | 0.089544 | 11.21415 | 58.83 |
| 8.064520 | 922.909900 | 0.076752 | 10.96356 | 24.14 |
| 9.551988 | 811.444000 | 0.179088 | 9.25936 | 21.23 |
| 9.893185 | 731.339200 | 0.127920 | 8.94077 | 19.13 |
| 11.410930 | 713.463600 | 0.153504 | 7.75476 | 18.66 |
| 11.807790 | 1002.811000 | 0.127920 | 7.49500 | 26.23 |
| 12.234010 | 806.819600 | 0.153504 | 7.23483 | 21.10 |
| 12.657670 | 895.228700 | 0.127920 | 6.99361 | 23.42 |
| 14.562960 | 1550.900000 | 0.102336 | 6.08263 | 40.57 |
| 15.413370 | 939.681700 | 0.204672 | 5.74889 | 24.58 |
| 15.841220 | 831.733000 | 0.307008 | 5.59457 | 21.76 |
| 17.560630 | 1113.197000 | 0.409344 | 5.05048 | 29.12 |
| 18.775820 | 475.510700 | 0.153504 | 4.72626 | 12.44 |
| 20.576380 | 320.212100 | 0.307008 | 4.31657 | 8.38 |
| 22.143260 | 373.653900 | 0.204672 | 4.01454 | 9.77 |

Example 21

Preparation and Characterization of Scaled-Up SCY-078 Citrate Type A (Molar Equivalency—counter ion/API 1.0): To scale up SCY-078 citrate Type A, a solution of citric acid (130.7 mg) and SCY-078 MeOH desolvate (501.6 mg) in ACN (15.0 mL) was prepared. The suspension was then stirred (500 rpm) at room temperature for 30 hours. Following stirring, some slurry was filtered and the isolated solid was checked by XRPD to confirm SCY-078 citrate Type A. Finally, the suspension was filtered and dried at 30° C. for 4 hours in vacuum before characterization.

Figure 40:
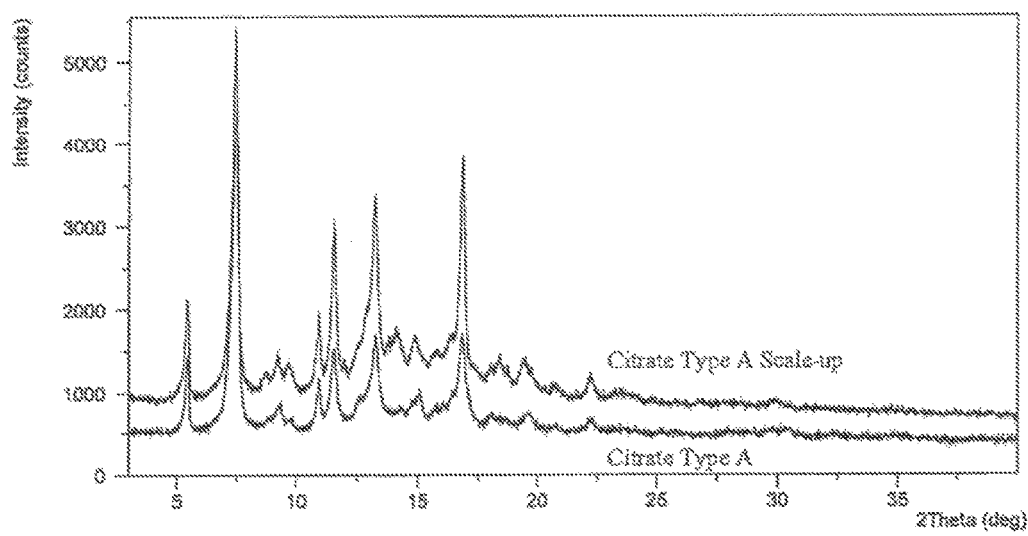
FIG. 40 is an XRPD of scaled-up SCY-078 citrate Type A from Example 21.
Figure 41:
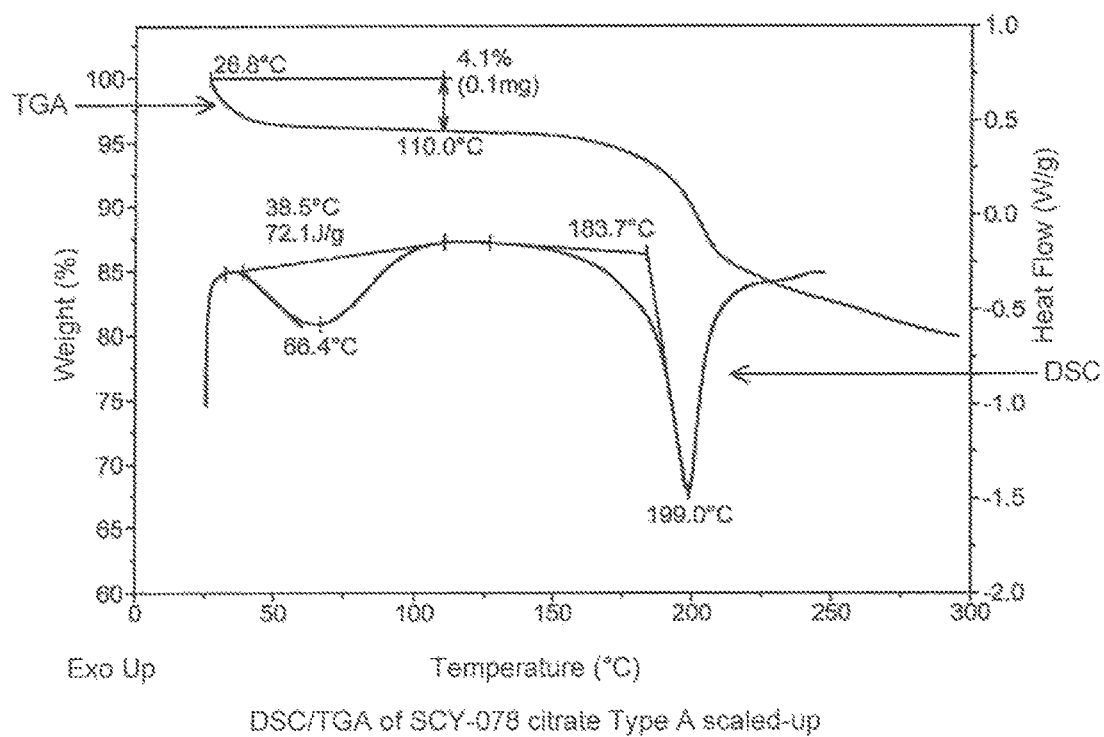
FIG. 41 is a DSC curve and a TGA curve of scaled-up SCY-078 citrate Type A from Example 21.
Figure 42:
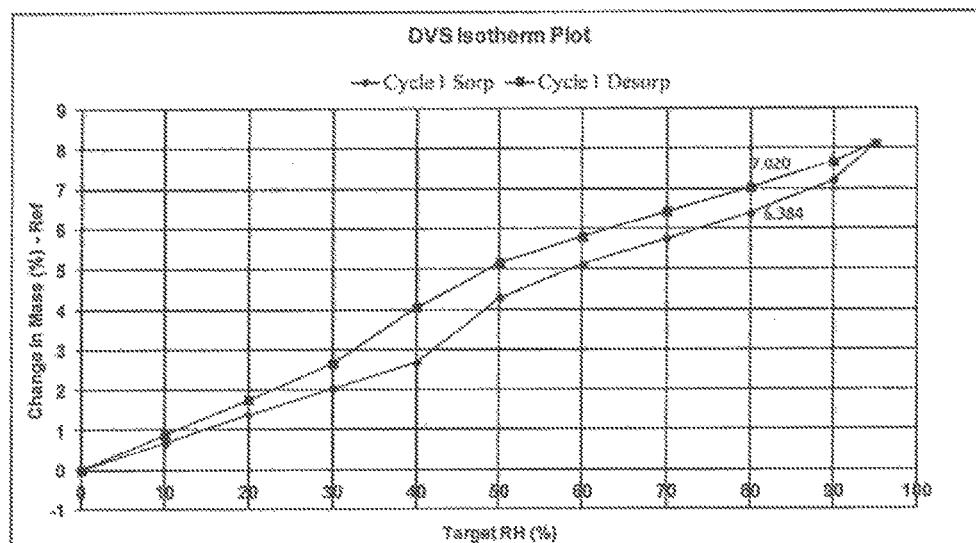
FIG. 42 is a DVS isotherm plot of scaled-up SCY-078 citrate Type A from Example 21.

Characterization of scaled-up SCY-078 citrate Type A included XRPD, DSC, TGA, and DVS (FIGS. 40-42). XRPD pattern evidenced that SCY-078 citrate Type A was successfully scaled up. The 2 theta and d-spacing values are summarized in Table 15. The DSC curve showed an endotherm at 38.5° C. and a melting endotherm at 183.7° C. (onset temperatures). The TGA curve showed a weight loss of 4.1% before 110° C. The DVS curve showed that the sample is hygroscopic with a water uptake of 6.4% at 80% RH, 25° C. A second XRPD pattern performed after DVS showed SCY-078 citrate Type A had no form change.

TABLE 15

| Pos.<br>[°2 Th.] | Height [cts] | FWHM Left<br>[°2 Th.] | d-spacing<br>[Å] | Rel. Int.<br>[%] |
|---|---|---|---|---|
| 5.448098 | 1112.016000 | 0.102336 | 16.22147 | 25.78 |
| 7.430264 | 4314.252000 | 0.153504 | 11.89794 | 100.00 |
| 8.687142 | 329.877800 | 0.153504 | 10.17913 | 7.65 |
| 9.219851 | 511.870400 | 0.153504 | 9.59216 | 11.86 |
| 9.657531 | 424.140300 | 0.255840 | 9.15840 | 9.83 |
| 10.883410 | 1078.439000 | 0.051168 | 8.12942 | 25.00 |
| 11.515250 | 2094.987000 | 0.115128 | 7.68474 | 48.56 |
| 13.187380 | 2396.469000 | 0.089544 | 6.71386 | 55.55 |
| 14.126680 | 799.280200 | 0.255840 | 6.26949 | 18.53 |
| 14.845300 | 757.431100 | 0.230256 | 5.96758 | 17.56 |
| 16.818410 | 2913.176000 | 0.127920 | 5.27165 | 67.52 |
| 18.364160 | 492.518400 | 0.153504 | 4.83127 | 11.42 |
| 19.381840 | 490.181800 | 0.307008 | 4.57983 | 11.36 |
| 20.774420 | 185.062500 | 0.307008 | 4.27587 | 4.29 |
| 22.213250 | 308.712600 | 0.204672 | 4.00205 | 7.16 |
| 23.587350 | 109.338400 | 0.818688 | 3.77193 | 2.53 |
| 29.871450 | 85.095400 | 0.307008 | 2.99120 | 1.97 |

Example 22

Chemical Characterization of SCY-078 Salts: The chemical purity of each of the scaled-up salts of SCY-078 (hippurate Type B, fumarate Type A, mesylate Type A, phosphate Type A, and citrate Type A) was tested using HPLC chromatographs. The chromatographs of the five compounds indicated that each compound has purity greater than 99% (Table 16).

TABLE 16

Chemical Characterization of SCY-078 Salts

| Compound | Purity |
|---|---|
| Hippurate Type B | 99.19 |
| Fumarate Type A | 99.90 |
| Mesylate Type A | 99.91 |
| Phosphate Type A | 99.91 |
| Citrate Type A | 99.89 |

Example 23

Evaluation of the pH Value of SCY-078 Salts in Water: The pH value for the saturated salt solutions of SCY-078 (i.e., hippurate Type B, fumarate Type A, mesylate Type A, phosphate Type A, and citrate Type A) was tested. To test the pH, a solution of each compound was equilibrated at room temperature using a rolling incubator (25 rpm) for 1 hour and 24 hours before measurement. The results (Table 17) suggested that the pH values of each of the salts tested is in the range of 3.0 to 5.0.

TABLE 17 pH value of saturated SCY-078 salt solutions in $H_2O$

| Salt Form | pH 1 hr | pH 24 hrs |
|---|---|---|
| Hippurate Type B | 4.6 | 4.2 |
| Fumarate Type A | 4.4 | 3.8 |
| Mesylate Type A | 3.4 | 3.6 |
| Phosphate Type A | 3.4 | 3.6 |
| Citrate Type A | 3.5 | 3.8 |

Example 24

Evaluation of the Kinetic Solubility of SCY-078 Salts: The kinetic solubilities of SCY-078 hippurate Type B, SCY-078 fumarate Type A, SCY-078 mesylate Type A, SCY-078 phosphate Type A, and SCY-078 citrate Type A were measured in dextrose buffer at pH 5.5, phosphate buffer at pH 6.0, phosphate buffer at pH 7.5, SGF media, FeSSIF media, and FaSSIF media according to the method described above. After filtration, 0.2 mL of supernatant was collected for HPLC quantification. The remaining solution was collected for pH measurement. The remaining solid was collected for XRPD characterization. The results appear in Table 18.

TABLE 18

Kinetic Solubility (mg/mL) of SCY-078 salts

| Media | Time (hours) | Hippurate Type B | Fumarate Type A | Mesylate Type A | Phosphate Type A | Citrate Type A |
|---|---|---|---|---|---|---|
| dextrose buffer (pH 5.5) | 1 hr | 0.54 | 0.05 | 1.4 | 0.10 | 0.67 |
| | 4 hrs | 1.7 | 0.46 | 2.5 | 0.09 | 4.2 |
| | 24 hrs | 4.4 | 2.1 | 4.3 | 0.04 | 8.3 |
| phosphate buffer (pH 6.0) | 1 hr | <LOQ | 0.07 | 0.16 | <LOQ | 0.75 |
| | 4 hrs | 0.04 | 1.2 | 0.13 | <LOQ | 4.7 |
| | 24 hrs | 0.47 | 4.7 | 0.04 | <LOQ | 7.5 |
| phosphate buffer (pH 7.5) | 1 hr | <LOQ | <LOQ | <LOQ | <LOQ | <LOQ |
| | 4 hrs | <LOQ | <LOQ | <LOQ | <LOQ | <LOQ |
| | 24 hrs | <LOQ | <LOQ | <LOQ | <LOQ | <LOQ |
| SGF | 1 hr | 12.4 | 13.4 | 17.8 | 9.2 | 20.6 |
| | 4 hrs | 15.0 | 17.7 | 20.5 | 16.0 | 21.4 |
| | 24 hrs | 21.8 | 23.4 | 22.5 | 21.2 | 21.1 |
| FeSSIF | 1 hr | 3.4 | 2.2 | 1.2 | 0.89 | 0.39 |
| | 4 hrs | <LOQ | 0.51 | 1.5 | 1.3 | 2.5 |
| | 24 hrs | 0.003 | 0.02 | 1.6 | 1.5 | 4.2 |
| FaSSIF | 1 hr | <LOQ | <LOD | <LOQ | 0.006 | 9.5 |
| | 4 hrs | 0.0007 | 2.8 | 0.29 | 0.17 | 20.7 |
| | 24 hrs | <LOQ | 17.0 | 0.44 | 1.0 | 21.6 |

LOD: 0.07 µg/mL
LOQ: 0.22 µg/mL

Example 25

Evaluation of the Stability of SCY-078 Salts: To test the chemical and physical stability of the salts, samples of the salts were placed under three different conditions for one week: (1) open dish at 25° C. with 60% RH; (2) open dish at 40° C. with 75% RH; and (3) closed dish at 60° C. with no humidity control.

The chemical and physical stability of SCY-078 fumarate Type A and SCY-078 citrate Type A were tested as described above (Table 19). XRPD indicated that neither SCY-078 fumarate Type A nor SCY-078 citrate Type A experienced form change during assessment.

TABLE 19

Stability result of SCY-078 salts

| Sample | Condition | Impurity % by HPLC |
|---|---|---|
| Citrate Type A | Initial | 0.34 |
| | 25° C./60% RH - 1 week | 0.09 |
| | 40° C./75% RH - 1 week | 0.10 |
| | 60° C. - 1 week | 0.17 |
| Fumarate Type A | Initial | 0.12 |
| | 25° C./60% RH - 1 week | 0.09 |
| | 40° C./75% RH - 1 week | 0.10 |
| | 60° C. - 1 week | 0.10 |

Example 26

Scaled-up SCY-078 Citrate Type A: A second scale-up of SCY-078 Citrate Type A was carried out to obtain 2.5 g via reactive ACN. To scale-up, SCY-078 MeOH desolvate (2.5 g) and citric acid (660 mg) were dissolved in ACN (80 mL). The resulting solution was stirred at a rate of 1000 rpm at room temperature for 30 hours and then the solid was isolated. The solid obtained was dried at 50° C. under vacuum overnight.

Figure 43:
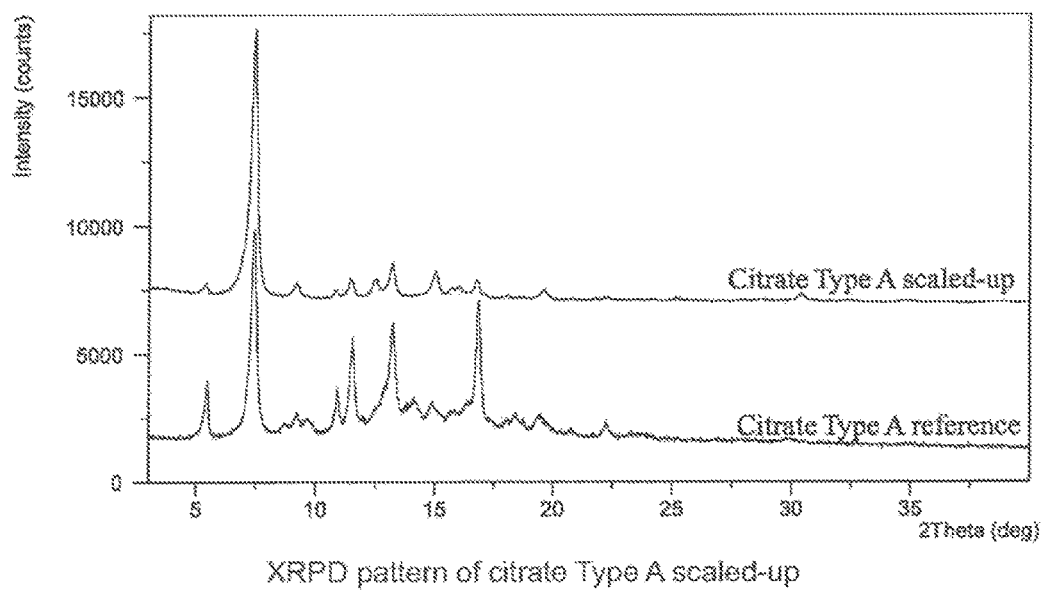
FIG. 43 is an XRPD of scaled-up SCY-078 citrate Type A from Example 26.
Figure 44:
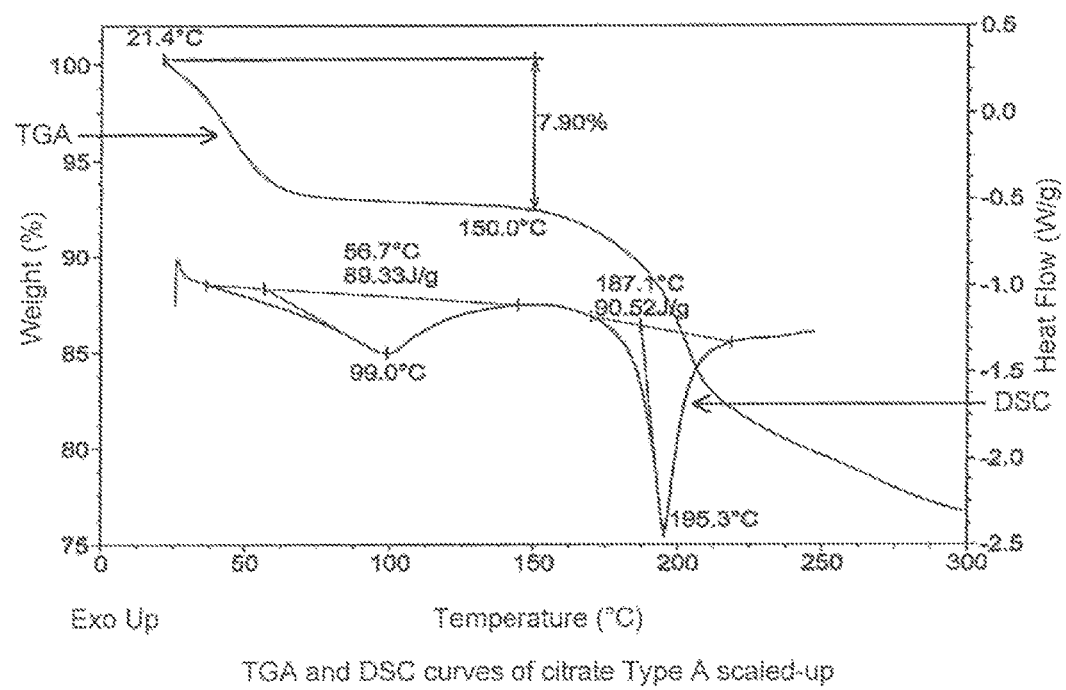
FIG. 44 is a DSC curve and a TGA curve of scaled-up SCY-078 citrate Type A from Example 26.

An XRPD pattern (FIG. 43) showed that SCY-078 citrate Type A was successfully scaled up and that it is highly crystalline. The 2 theta and d-spacing values are summarized in Table 20. DSC curve (FIG. 44) exhibited two endothermic peaks at 56.7° C. and 187.1° C. (onset temperatures). TGA curve (FIG. 44) showed 7.9% weight loss before 150° C.

TABLE 20

| Pos. [°2 Th.] | Height [cts] | FWHM Left [°2 Th.] | d-spacing [Å] | Rel. Int. [%] |
|---|---|---|---|---|
| 5.400273 | 434.322700 | 0.102336 | 16.36502 | 3.34 |
| 7.453872 | 13000.820000 | 0.191880 | 11.86031 | 100.00 |
| 9.201639 | 691.948300 | 0.204672 | 9.61110 | 5.32 |
| 10.831710 | 404.555000 | 0.153504 | 8.16811 | 3.11 |
| 11.485080 | 936.115200 | 0.179088 | 7.70486 | 7.20 |
| 12.491050 | 954.805500 | 0.179088 | 7.08652 | 7.34 |
| 13.191360 | 1776.320000 | 0.204672 | 6.71184 | 13.66 |
| 15.020350 | 1342.537000 | 0.204672 | 5.89842 | 10.33 |
| 15.664830 | 532.278900 | 0.179088 | 5.65717 | 4.09 |
| 15.955570 | 613.057500 | 0.127920 | 5.55474 | 4.72 |
| 16.751250 | 951.729000 | 0.153504 | 5.29264 | 7.32 |
| 17.978130 | 170.323300 | 0.204672 | 4.93412 | 1.31 |
| 19.591770 | 472.971000 | 0.204672 | 4.53123 | 3.64 |
| 22.213400 | 146.982900 | 0.204672 | 4.00202 | 1.13 |
| 23.845740 | 34.469910 | 0.614016 | 3.73164 | 0.27 |
| 25.160050 | 117.741100 | 0.307008 | 3.53961 | 0.91 |
| 28.761350 | 129.234400 | 0.255840 | 3.10407 | 0.99 |
| 30.356250 | 332.945100 | 0.230256 | 2.94452 | 2.56 |
| 32.317870 | 87.151140 | 0.307008 | 2.77014 | 0.67 |
| 34.725480 | 74.664570 | 0.511680 | 2.58339 | 0.57 |

Example 27

Approximate Solubility of SCY-078 Citrate Type A: The approximate solubility of SCY-078 citrate Type A from Example 26 was determined in 19 solvents at room temperature (25±3° C.) according to the procedure described above and is reported in Table 21 below.

TABLE 21

| Solvent | Solubility (mg/mL) |
|---|---|
| MeOH | >42.4 |
| EtOH | <1.0 |
| IPA | >40.0 |
| Acetic Acid | >41.0 |
| ACN | <1.1 |
| Acetone | 1.6 < S <1.7 |

TABLE 21-continued

| Solvent | Solubility (mg/mL) |
| --- | --- |
| MIBK | <1.0 |
| EtOAc | <1.0 |
| IPAc | <1.1 |
| MTBE | <1.0 |
| THF | >41.0 |
| 2-MeTHF | >41.8 |
| 1,4-Dioxane | >41.0 |
| NMP | >40.6 |
| DMSO | >40.6 |
| DCM | <1.0 |
| Toluene | <1.0 |
| Heptane | <1.1 |
| DMAc | >40.8 |

Example 28

Kinetic Solubility of SCY-078 Citrate Type A in Water: The kinetic solubility of SCY-078 citrate Type A from Example 26 was evaluated according to the procedure described above. After the samples were centrifuged, the residual solids analyzed by XRPD and the supernatant concentration measured by HPLC. Results (Table 22) indicated that SCY-078 citrate Type A partially converted to amorphous in water after 24 hours, and exhibited a slow rate of dissolution and increasing solubility in water from 1 hour to 24 hours.

TABLE 22

Kinetic Solubility of SCY-078 citrate Type A in Water

| | Initial | 1 hr | 4 hrs | 24 hrs |
| --- | --- | --- | --- | --- |
| pH | 8.0 | 3.3 | 3.3 | 3.4 |
| Solubility (mg/mL) | | 18.6 | 26.7 | 41.4 |
| Form | | Citrate Type A | Citrate Type A | Citrate Type A | Citrate Type A + amorphous |

Then the kinetic solubility of SCY-078 citrate Type A was compared with a mixture of SCY-078 amorphous freebase/citric acid. The kinetic solubility comparison was conducted in water at room temperature and was measured at 1 hour, 4 hours, and 24 hours with a ratio of solute to solvent of 20 mg/mL and 50 mg/mL. Results (Table 23) indicated that SCY-078 citrate Type A shows higher dissolution rate and equilibrium solubility in water than the mixture of SCY-078 amorphous freebase/citric acid.

TABLE 23

Kinetic solubility comparison between mixture of SCY-078 freebase/citric acid and SCY-078 citrate Type A

| Starting Material | Time | pH | XRPD Form | Solubility (mg/ML) |
| --- | --- | --- | --- | --- |
| Freebase Citric Acid 20 mg/mL | 1 hr | 2.7 | Amorphous | 3.0 |
| | 4 hrs | 2.9 | Amorphous | 5.1 |
| | 24 hrs | 3.5 | Amorphous | 10.1 |
| Freebase Citric Acid 50 mg/mL | 1 hr | 2.7 | Amorphous | 2.9 |
| | 4 hrs | 2.8 | Amorphous | 16.8 |
| | 24 hrs | 3.2 | Amorphous | 28.1 |
| Citrate Type A 20 mg/mL | 1 hr | 3.5 | Citrate Type A | 3.5 |
| | 4 hrs | 3.4 | Citrate Type A | 8.3 |
| | 24 hrs | 3.3 | Citrate Type A | 17.0 |
| Citrate Type A 50 mg/mL | 1 hr | 3.4 | Citrate Type A | 6.5 |
| | 4 hrs | 3.3 | Citrate Type A | 14.5 |
| | 24 hrs | 3.2 | Citrate Type A | 33.9 |

The remaining solids from the solubility measurement of physical mixture of freebase:citric acid at 1:1 molar ratio in water were amorphous. To determine the form of the amorphous, liquid NMR was performed on a Bruker 400M NMR Spectrometer using $CD_3OD$. The spectrum showed the number of hydrogen atoms assigned to citric acid as 3.12, corresponding to 0.78 equivalent of citric acid. This is less than 1:1 for mono-citrate and suggests it is a mixture that comprises a majority of amorphous citrate salt with a small quantity of amorphous freebase.

Example 29

Equilibrium Solubility of SCY-078 Salts in Water: Equilibrium solubility of SCY-078 citrate Type A from Example 26 in water was determined using the method described above. Results showed that SCY-078 citrate Type A exhibits 38.1 mg/mL solubility in water with the undissolved material having become amorphous after stirring in water for 24 hours.

Then to further study the solubility of SCY-078 citrate Type A in water, citrate Type A was tested for 24 hours at three ratios of solute to solvent: 0.3 mg/mL, 2.0 mg/mL, and 50.6 mg/mL. Each test used magnetic stirring and began with an initial pH of 8.0. The results (Table 24) indicated that SCY-078 citrate Type A exhibits a concentration-dependent solubility in water.

TABLE 24

Concentration dependent solubility of SCY-078 citrate Type A in water

| Ratio of Solid/Solvent (mg/mL) | Solubility after 24 hrs (mg/mL) | Final pH |
| --- | --- | --- |
| 0.3 | <0.3 (suspension) | 5.1 |
| 2.0 | >2.0 (clear) | 4.2 |
| 50.6 | 38.1 | 3.4 |

Example 30

Kinetic Solubility of SCY-078 Citrate Amorphous in Water: SCY-078 citrate amorphous was prepared under various conditions, including lyophilization from phosphate buffer (pH 6.0), lyophilization from water, and fast evaporation in THF. The results appear in Table 25. Where the table indicates "limited solid," there was not sufficient solid for XRPD analysis of the solid form.

Lyophilization in phosphate buffer (pH 6.0)—For lyophilization in phosphate buffer (pH 6.0), SCY-078 citrate amorphous was prepared by first preparing 50 mM pH 6.0 buffer. Then citrate Type A (30 mg) was weighed into a 20-mL vial. Then pH 6.0 buffer (20 mL) was added to the vial and was stirred at room temperature for 24 hours. The samples were filtered and the supernatant was cooled to −15° C. for 2 hours. Finally, the frozen samples were lyophilized at −50° C. for 12 hours. A larger batch (150 mg) was prepared using the same procedure noted above. The kinetic solubility of the second batch of the lyophilized product in water was measured according to the above procedure except that ~150 mg of solid and 1.0 mL of water were used. After the samples were centrifuged, the residual solids were analyzed by XRPD and the supernatant concentration was measured by HPLC.

Lyophilization in water—For lyophilization in water, amorphous citrate was prepared by first weighing citrate Type A (~150 mg) into a 20-mL vial. Then 10 mL of water was added to dissolve the solid completely. The solution was filtered and put in a condition of −20° C. until it froze. Finally, the sample was lyophilized under −50° C. for 24 hours. The kinetic solubility of the lyophilized product in water was measured according to the above procedure except that ~120 mg of solid and 1.5 mL of water were used. After the samples were centrifuged, the residual solids were analyzed by XRPD and the supernatant concentration was measured by HPLC.

Fast Evaporation in THF—For fast evaporation in THF, amorphous citrate was prepared by first weighing citrate Type A from Example 26 (~150 mg) into a 20-mL vial. Then THF (3 mL) was added to dissolve the solid completely. The solution was filtered under a fume hood for performance of fast evaporation. The kinetic solubility in water of the product in water was measured according to the above procedure except that ~120 mg of solid and 1.5 mL of water were used. After the samples were centrifuged, the residual solids were analyzed by XRPD and the supernatant concentration was measured by HPLC.

TABLE 25

Kinetic solubility of amorphous SCY-078 citrate in water

| Starting Solid | Time | Solubility (mg/mL) | pH | Form |
| --- | --- | --- | --- | --- |
| Lyophilization in pH 6.0 buffer | 1 hr | 0.14 | 5.1 | Amorphous |
|  | 4 hrs | 0.39 | 5.1 | Amorphous |
|  | 24 hrs | 1.5 | 5.1 | Amorphous |
| Lyophilization in water (pH 8.0) | 1 hr | 55.4 | 3.1 | Amorphous |
|  | 4 hrs | 54.7 | 3.3 | NA |
|  | 24 hrs | 55.5 | 3.2 | NA |
| Fast evaporation in THF (pH 8.0) | 1 hr | 44.5 | 3.2 | Amorphous |
|  | 4 hrs | 50.2 | 3.2 | NA |
|  | 24 hrs | 52.8 | 3.2 | NA |

NA: Limited solid for XRPD

Example 31

Slow Evaporation of SCY-078 Citrate Type A: Slow evaporation experiments were performed in 12 different solvent systems. SCY-078 citrate Type A from Example 26 (10 mg) was dissolved with solvent (0.05 mL-0.25 mL) for each sample in a 3-mL glass vial. The visually clear solutions were subjected to slow evaporation at room temperature to dryness. The solids obtained were then isolated for XRPD analysis, which showed that no crystalline form was obtained. The results appear in Table 26.

TABLE 26

Slow evaporation experiments

| Solvent | Form |
| --- | --- |
| MeOH | Amorphous |
| IPA | Amorphous |
| Acetic Acid | Amorphous |
| THF | Amorphous |
| MeOH/ACN, 9/1 | Amorphous |
| IPA/Acetone, 9/1 | Amorphous |
| THF/EtOAc, 9/1 | Amorphous |
| MeOH/H$_2$O, 9/1 | Amorphous |
| THF/Acetone, 9/1 | Amorphous |
| IPA/DCM, 9/1 | Amorphous |
| MeOH/MTBE, 9/1 | Amorphous |
| THF/EtOH, 9/1 | Amorphous |

Example 32

Slurry Conversion of SCY-078 Citrate Type A: Slurry conversion experiments were conducted under 50 conditions. SCY-078 citrate Type A from Example 26 (~10 mg) was suspended in each solvent (0.5 mL). The suspensions were stirred for 3 days at either room temperature (Table 27) or 50° C. (Table 28). After stirring, the solids were isolated for XRPD analysis. If the suspensions turned into clear solutions upon slurry, the clear solutions were subjected to slow evaporation at room temperature. The results revealed that SCY-078 citrate Type B and mixtures of SCY-078 citrate Type A and SCY-078 citrate Type B were discovered. All SCY-078 citrate Type C that was discovered was identified as freebase form.

TABLE 27

Slurry conversion experiments at RT

| Solvent | Form |
| --- | --- |
| EtOH | Type B |
| ACN | Type B |
| Acetone | Type B |
| MIBK | Type B |
| EtOAc | Type B |
| IPAc | Type B |
| MTBE | Amorphous |
| 1,4-Dioxane | Amorphous via slow evaporation |
| DCM | Type B |
| Toluene | Type B |
| Heptane | Type B |
| MeOH/Acetone, 1/19 | Type B |
| IPA/Heptane, 1/19 | Type B |
| THF/Toluene, 1/19 | Type B |
| NMP/EtOH, 1/19 | Amorphous |
| NMP/Acetone, 1/19 | Amorphous |
| NMP/IPAc, 1/19 | Amorphous |
| NMP/DCM, 1/19 | Type C |
| DMSO/ACN, 1/19 | Type C |
| DMSO/MIBK, 1/19 | Type C |
| DMSO/EtOAc, 1/19 | Type C |
| DMSO/Toluene, 1/19 | Type C |
| DMAc/EtOH, 1/19 | Type C |
| DMAc/Acetone, 1/19 | Type C |
| DMAc/MTBE, 1/19 | Type C |

TABLE 28

Slurry conversion experiments at 50° C.

| Solvent | Form |
| --- | --- |
| EtOH | Type B |
| ACN | Type B |
| Acetone | Type A + B |
| MIBK | Type B |
| EtOAc | Amorphous |
| IPAc | Type B |
| MTBE | Amorphous |
| 1,4-Dioxane | Amorphous via slow evaporation |
| DCM | Type B |

TABLE 28-continued

Slurry conversion experiments at 50° C.

| Solvent | Form |
|---|---|
| Toluene | Type A + B |
| Heptane | Type B |
| MeOH/Acetone, 1/19 | Type A + B |
| IPA/Heptane, 1/19 | Type B |
| THF/Toluene, 1/19 | Type A + B |
| NMP/EtOH, 1/19 | Amorphous |
| NMP/Acetone, 1/19 | Amorphous |
| NMP/IPAc, 1/19 | Amorphous |
| NMP/DCM, 1/19 | Amorphous |
| DMSO/ACN, 1/19 | Type C |
| DMSO/MIBK, 1/19 | Type C |
| DMSO/EtOAc, 1/19 | Type C |
| DMSO/Toluene, 1/19 | Type C |
| DMAc/EtOH, 1/19 | Amorphous |
| DMAc/Acetone, 1/19 | Type C |
| DMAc/MTBE, 1/19 | Type C |

Example 33

Reverse Anti-solvent addition of SCY-078 citrate Type A: Reverse anti-solvent addition experiments were conducted under 14 conditions. SCY-078 citrate Type A from Example 26 (~10 mg) was dissolved in each solvent (0.1 mL) to obtain a clear solution; This solution was added drop-wise into a glass vial containing 2.0 mL of each anti-solvent at room temperature. The precipitate was isolated for XRPD analysis. Slow evaporation experiments were conducted for the clear solutions. The results, which appear in Table 29, suggested that SCY-078 citrate Type E and SCY-078 citrate Type F were obtained. SCY-078 citrate Type D and SCY-078 citrate Type J were identified as freebase form.

TABLE 29

Reverse anti-solvent addition experiments at RT

| Solvent | Anti-solvent | Observation | Form |
|---|---|---|---|
| MeOH | IPAc | Precipitation | Type E |
| MeOH | DCM | Clear | Amorphous via slow evaporation |
| IPA | EtOH | Clear | Clear solution after slow evaporation RT for 2 weeks |
| IPA | MTBE | Precipitation | Amorphous |
| IPA | Toluene | Precipitation | Type F |
| THF | ACN | Precipitation | Type D |
| THF | MIBK | Precipitation | Amorphous |
| THF | Heptane | Precipitation | Amorphous |
| NMP | ACN | Clear | Clear solution after slow evaporation at RT for 2 weeks |
| NMP | Toluene | Clear | Clear solution after slow evaporation at RT for 2 weeks |
| DMSO | EtOH | Clear | Type J |
| DMSO | DCM | Clear | Amorphous via slow evaporation |
| DMAc | DCM | Clear | Amorphous via slow evaporation |
| DMAc | Toluene | Clear | Clear solution after slow evaporation at RT for 2 weeks |

Example 34

Solid vapor diffusion of SCY-078 Citrate Type A: Solid vapor diffusion experiments were conducted using four solvents at room temperature. SCY-078 citrate Type A from Example 26 (~10 mg) was placed into a 3-mL glass vial. Then the vial was sealed into a 20-mL glass vial with a solvent (3 mL). The system was kept at room temperature for six days, which was sufficient time for organic vapor to interact with the solids. The solids were characterized by XRPD to identify crystalline forms. The results (Table 30) indicated that SCY-078 citrate Type A and SCY-078 citrate Type B were generated.

TABLE 30

Solid vapor diffusion experiments

| Solvent | Form |
|---|---|
| EtOH | Type A |
| EtOAc | Type B |
| Acetone | Type A |
| DCM | Type A |

Example 35

Solution vapor diffusion of SCY-078 Citrate Type A: Solution vapor diffusion experiments were conducted under 5 conditions at room temperature. SCY-078 citrate Type A from Example 26 (~10 mg) was dissolved in a solvent to obtain a clear solution in a 3-mL glass vial. The vial was then sealed into a 20-mL glass vial with a volatile anti-solvent (3 mL). The system was kept at room temperature for six days, which allowed sufficient time for precipitation. As no precipitation was observed, the samples were evaporated slowly to dryness at room temperature. The solids were separated and analyzed by XRPD. The results (Table 31) indicated that no crystalline form was obtained.

TABLE 31

Solution vapor diffusion experiments

| Solvent | Anti-solvent | Observation | Form |
|---|---|---|---|
| Acetic Acid | EtOH | Clear | Amorphous via slow evaporation |
| DMSO | Acetone | Clear | Amorphous via slow evaporation |
| DMAc | IPAc | Clear | Clear solution after slow evaporation at RT for 2 weeks |
| IPA | DCM | Clear | Amorphous via slow evaporation |
| NMP | MTBE | Clear | Clear solution after slow evaporation at RT for 2 weeks |

Example 36

Polymer Induced Crystallization of SCY-078 Citrate Type A: Polymer induced crystallization experiments were performed under four conditions. SCY-078 citrate Type A from Example 26 (~10 mg) was dissolved in a solvent (0.1 mL-0.8 mL) in a 3-mL glass vial. A mixed polymer (~1.0 mg) was added into the visually clear solutions. The "mixed polymer" was a mixture of six polymers (polyvinyl alcohol, polyvinylchloride, polyvinyl pyrrolidone, polyvinyl acetate, hypromellose, and methyl cellulose) at the mass ration of 1.0. All the samples were then evaporated slowly at room temperature to dryness. The solids obtained were isolated for XRPD analysis. The results (Table 32) showed that no crystalline form was observed.

TABLE 32

Polymer induced crystallization experiments

| Solvent | Form |
| --- | --- |
| MeOH | Amorphous |
| THF | Amorphous |
| 1,4-Dioxane | Amorphous |
| MeOH/EtOH, 9/1 | Amorphous |
| MeOH/Acetone, 9/1 | Amorphous |

Example 37

Slow cooling of SCY-078 Citrate Type A: Slow cooling experiments were conducted under 10 conditions (Table 33). SCY-078 citrate Type A from Example 26 (~10 mg) was suspended in a solvent (0.1 mL-0.2 mL) at 50° C. Suspensions were filtered at 50° C., and the filtrates were collected and cooled from 50° C. to 5° C. at a rate of 0.1° C./min. All solutions were clear and subjected to slow evaporation at room temperature to induce precipitation. The solids were isolated for XRPD analysis. The results (Table 33) indicated that SCY-078 citrate Type C and SCY-078 citrate Type J were produced and that both SCY-078 citrate Type C and SCY-078 citrate Type J are freebase forms.

TABLE 33

Slow Cooling Experiments

| Solvent, v/v | Observation (5° C.) | Form |
| --- | --- | --- |
| MeOH/Toluene, 9/1 | Clear | Amorphous |
| IPA/ACN, 9/1 | Clear | Amorphous |
| IPA/EtOAc, 9/1 | Clear | Amorphous |
| THF/Toluene, 9/1 | Clear | Amorphous |
| THF/DCM, 9/1 | Clear | Amorphous |
| NMP/MTBE, 9/1 | Clear | Amorphous |
| DMSO/Acetone, 9/1 | Clear | Type C |
| DMAc/IPAc, 9/1 | Clear | Type J |
| DMAc/ACN, 9/1 | Clear | Type J |

Example 38

Figure 45:
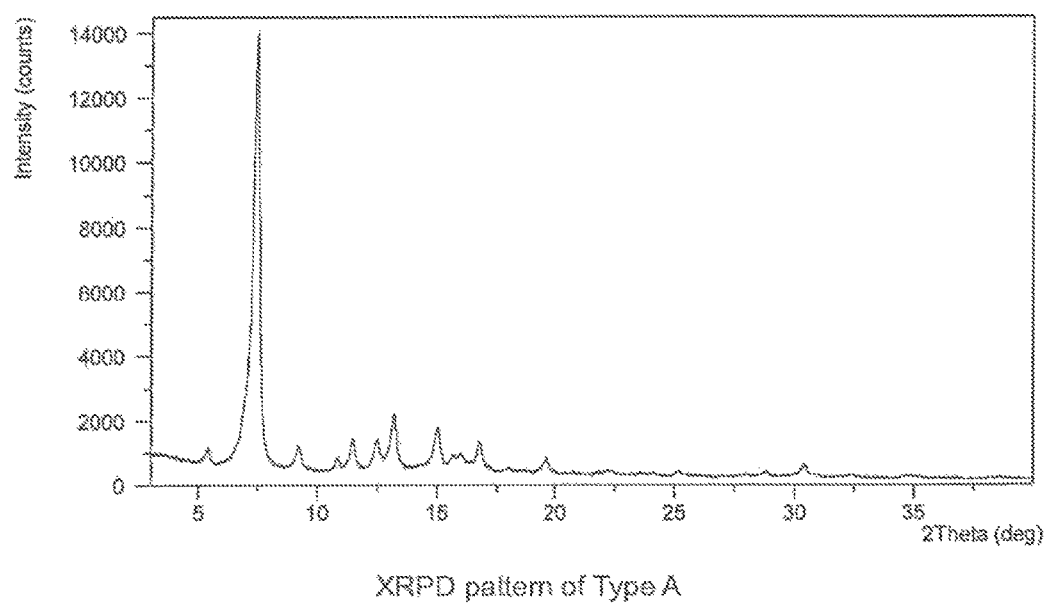
FIG. 45 is an XRPD of SCY-078 citrate Type A from Example 38.
Figure 46:
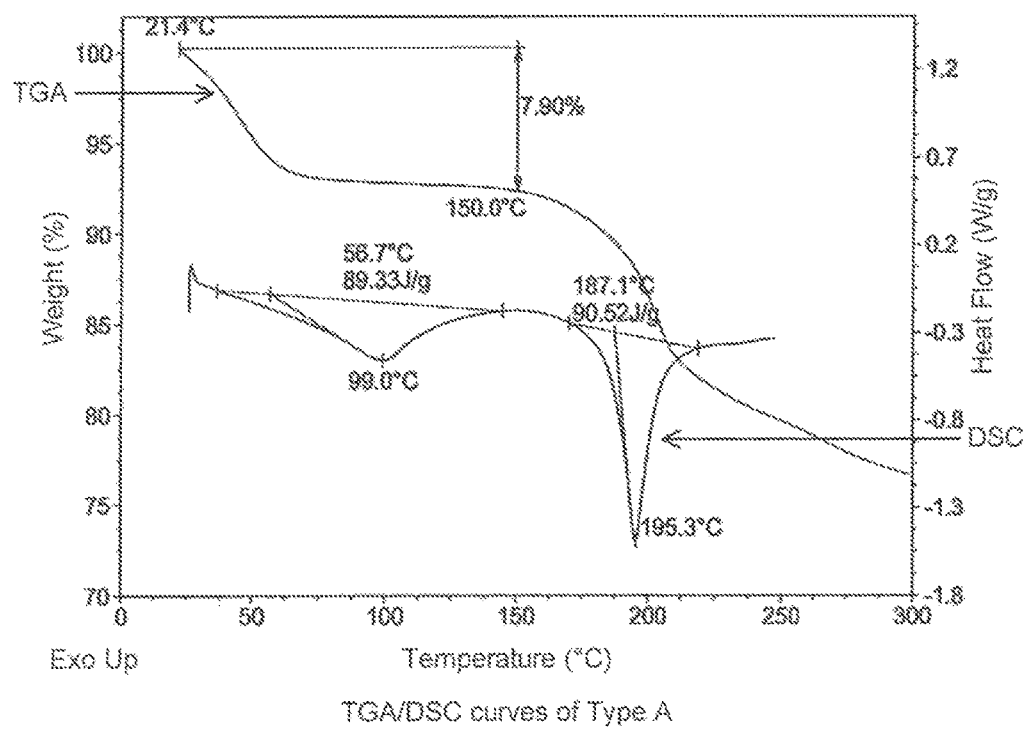
FIG. 46 is a DSC curve and a TGA curve of SCY-078 citrate Type A from Example 38.
Figure 47:
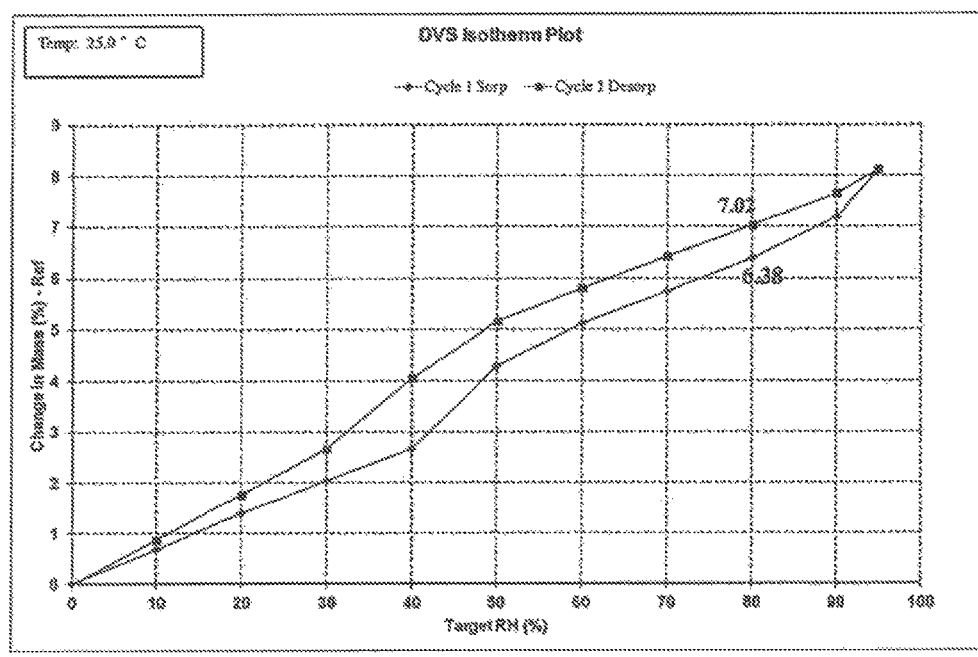
FIG. 47 is a DVS isotherm plot of SCY-078 citrate Type A from Example 38.
Figure 48:
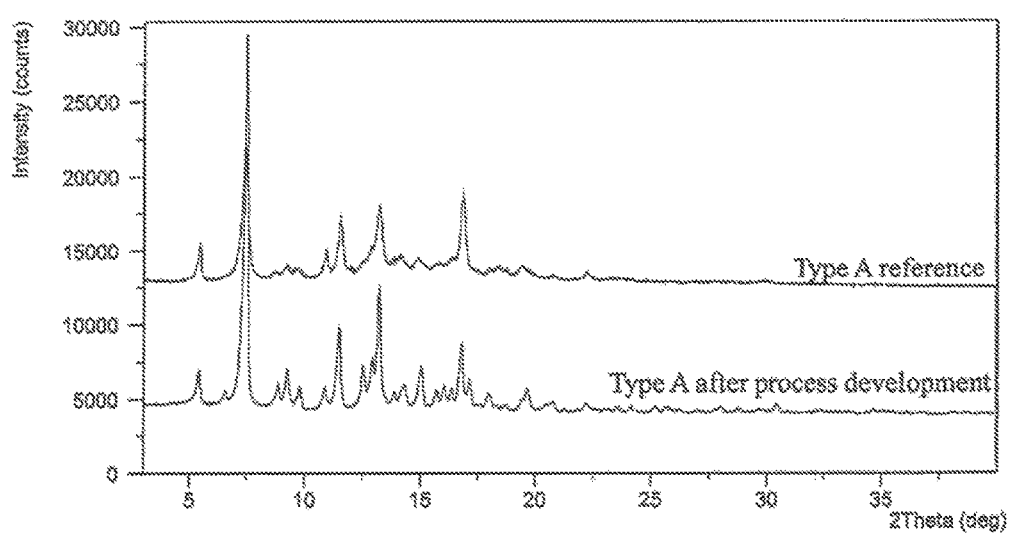
FIG. 48 is an XRPD of SCY-078 citrate Type A after process development from Example 38.

SCY-078 Citrate Type A via Reactive Crystallization: SCY-078 citrate Type A was obtained by reactive crystallization in ACN. The XRPD pattern showed distinctive diffraction peaks (FIG. 45). DSC curve showed two endothermic peaks at 56.7° C. and 187.1° C. (onset temperatures) (FIG. 46). TGA curve displayed a 7.9% weight loss up to 150° C. (FIG. 46). DVS plot showed a water uptake of 7.0% at 80% RH (FIG. 47). There was no form change after DVS analysis.

SCY-078 citrate Type A was also tested with variable temperature XRPD analysis. No form change was observed upon heating SCY-078 citrate Type A to 120° C. and then cooling back to 25° C., indicating that SCY-078 citrate Type A is an anhydrate.

Figure 49:
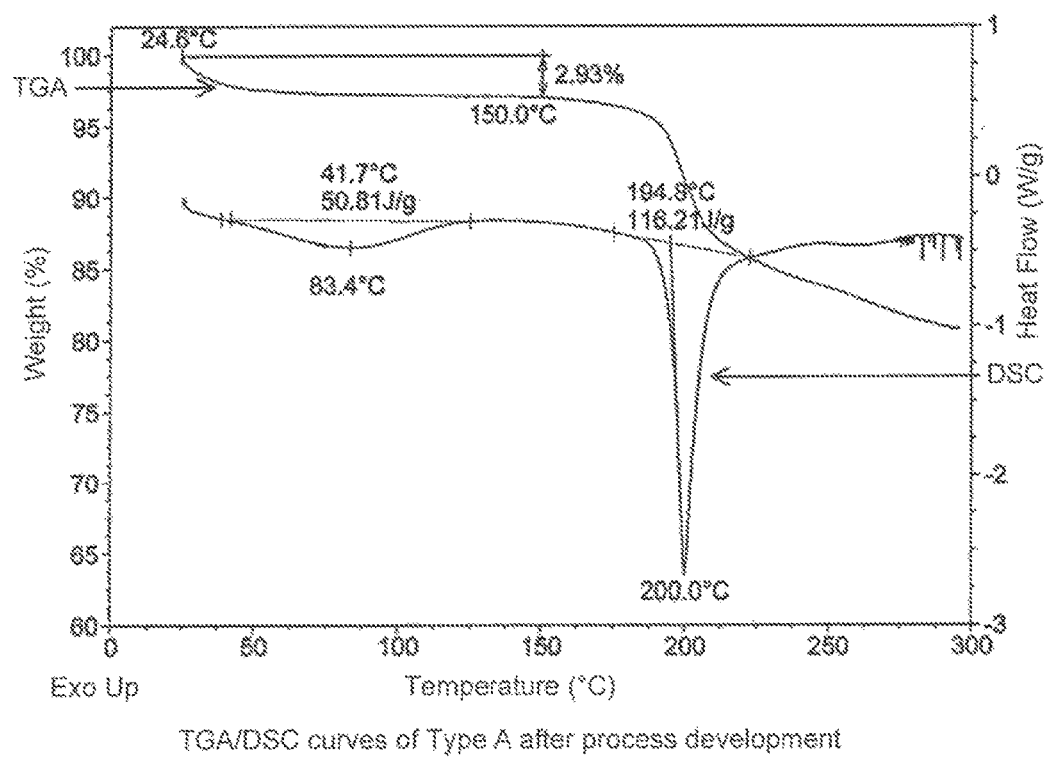
FIG. 49 is a DSC curve and a TGA curve of SCY-078 citrate Type A after process development from Example 38.
Figure 50:
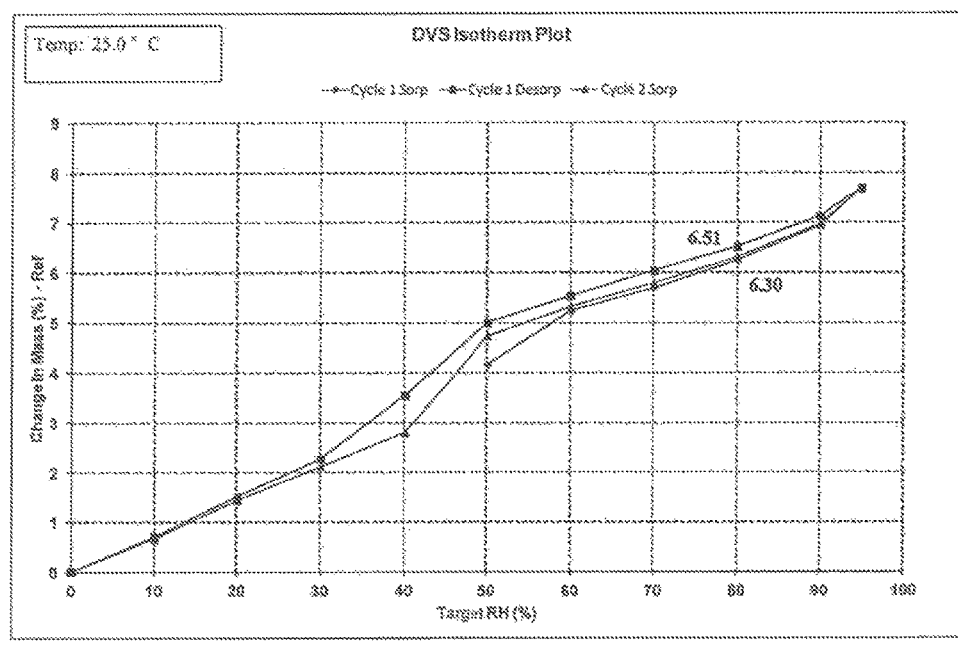
FIG. 50 is a DVS isotherm plot of SCY-078 citrate Type A after process development from Example 38.

After crystallization process development, SCY-078 citrate Type A exhibited higher crystallinity and less surface moisture adsorption was produced (FIG. 49). DSC curve showed two endothermic peaks at 41.7° C. and 194.8° C. (onset temperatures). TGA curve displayed 2.9% weight loss up to 150° C. DVS analysis showed a water uptake of 6.5% at 25° C. and 80% RH. No form change was observed after DVS analysis. $^1$H-NMR spectrum in $CD_3OD$ showed the molar ration of freebase and citric acid is 1:1, indicating that SCY-078 citrate Type A is mono-citrate.

Example 39

SCY-078 Citrate Type B: SCY-078 citrate Type B was obtained by slurry conversion at room temperature in ACN. SCY-078 citrate Type B can also be obtained by slurrying SCY-078 citrate Type A in various organic solvents such as EtOH, ACN, acetone, MIBK, EtOAc, IPAc, DCM, toluene, heptane, MeOH/acetone (1/19, v/v), IPA/heptane (1/19, v/v), and THF/toluene (1/19, v/v). SCY-078 citrate Type B converts to Type A rapidly under vacuum or upon $N_2$ flow at room or elevated temperature.

Figure 51:
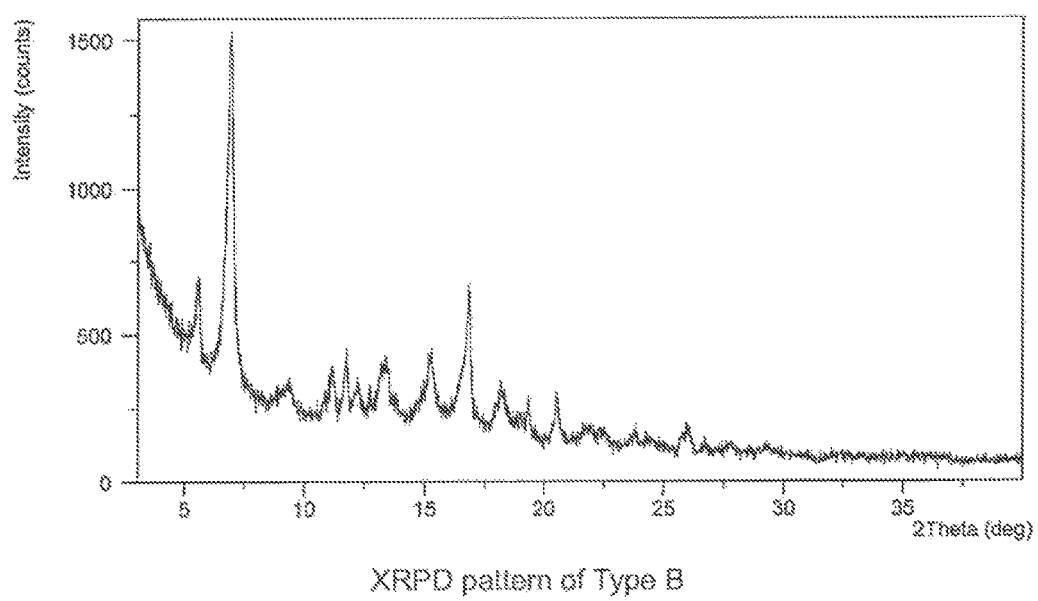
FIG. 51 is an XRPD of SCY-078 citrate Type B from Example 39.
Figure 52:
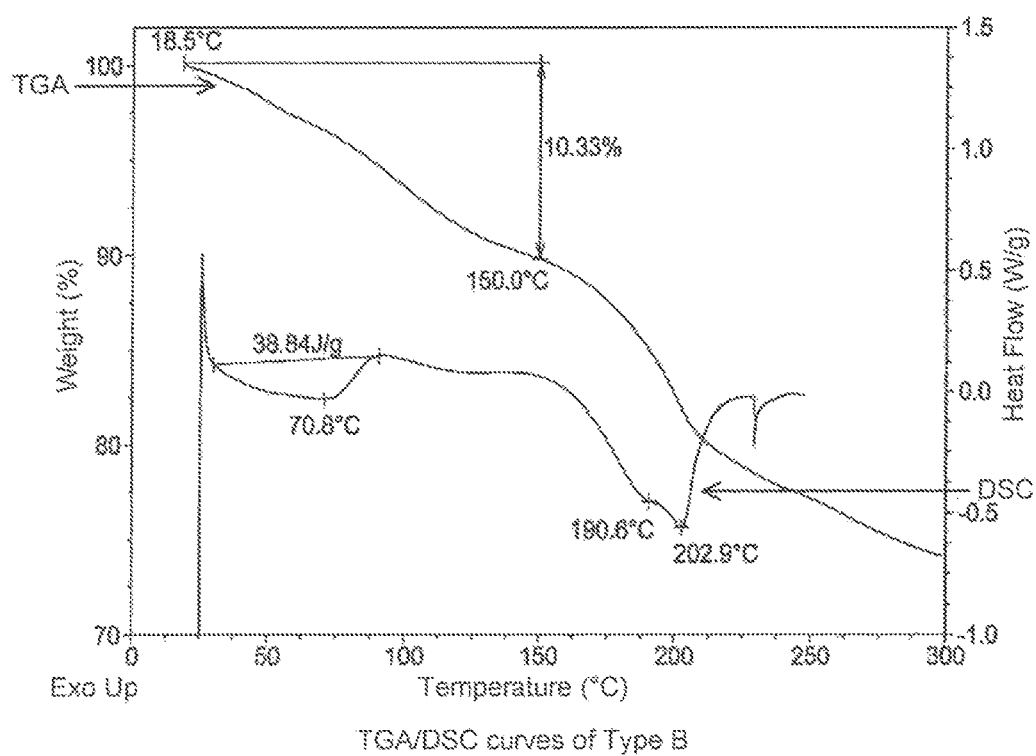
FIG. 52 is a DSC curve and a TGA curve of SCY-078 citrate Type B from Example 39.

The XRPD pattern of SCY-078 citrate Type B showed distinctive diffraction peaks (FIG. 51). DSC curve exhibited three endothermic peaks at 70.8° C., 190.6° C., and 202.9° C. (peak temperatures) (FIG. 52). TGA curve displayed 10.3% weight loss up to 150° C. (FIG. 52).

Example 40

Figure 53:
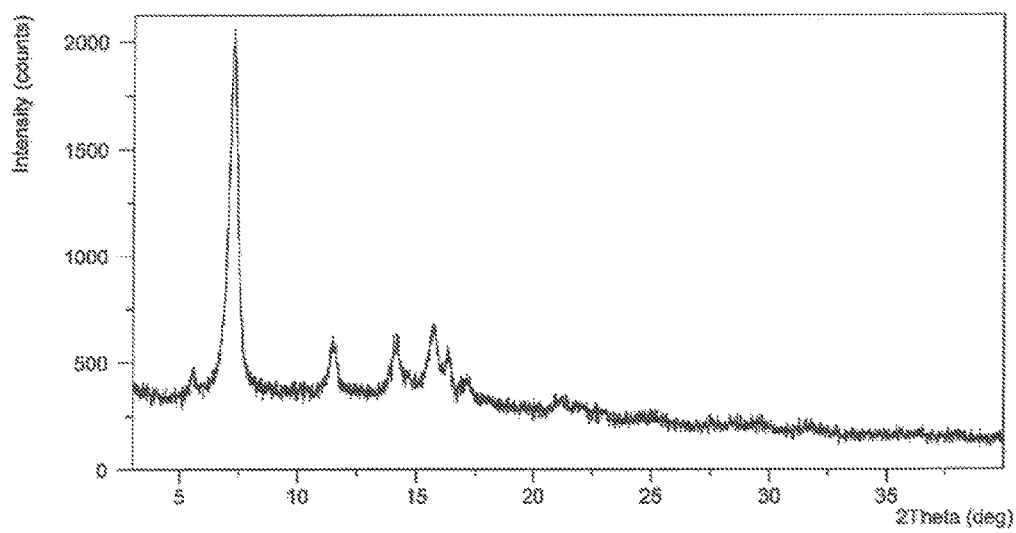
FIG. 53 is an XRPD of SCY-078 citrate Type E from Example 40.
Figure 54:
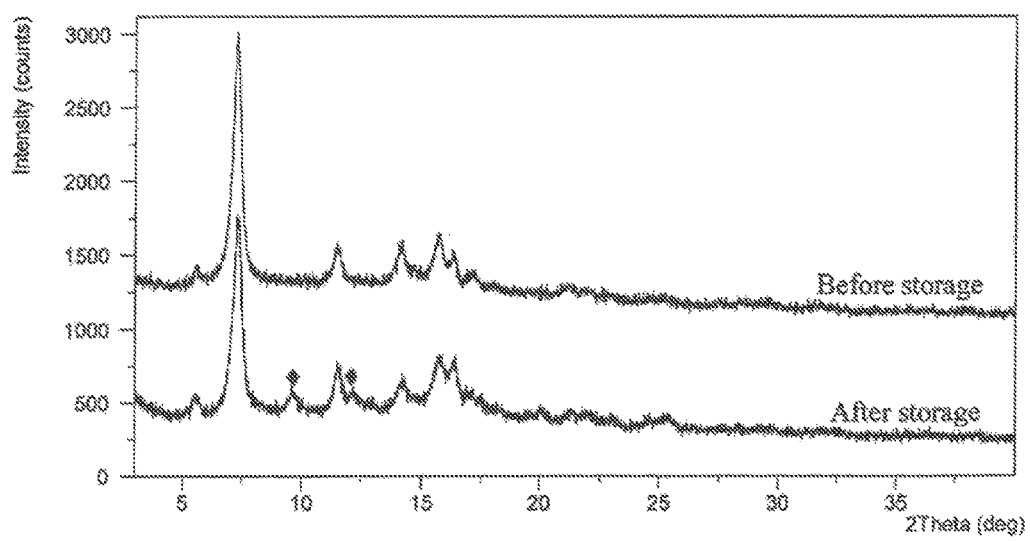
FIG. 54 is an XRPD of SCY-078 citrate Type E from Example 40 before and after storage.

SCY-078 Citrate Type E: SCY-078 citrate Type E was obtained by drying a metastable solvate SCY-078 citrate Type R from MeOH/IPAc. The XRPD pattern shows the crystalline form of the sample (FIG. 53). SCY-078 citrate Type E is not stable at ambient conditions, since it rapidly converts to a new form (SCY-078 citrate Type M) after exposing to air for 2 days (FIG. 54).

Example 41

Figure 55:
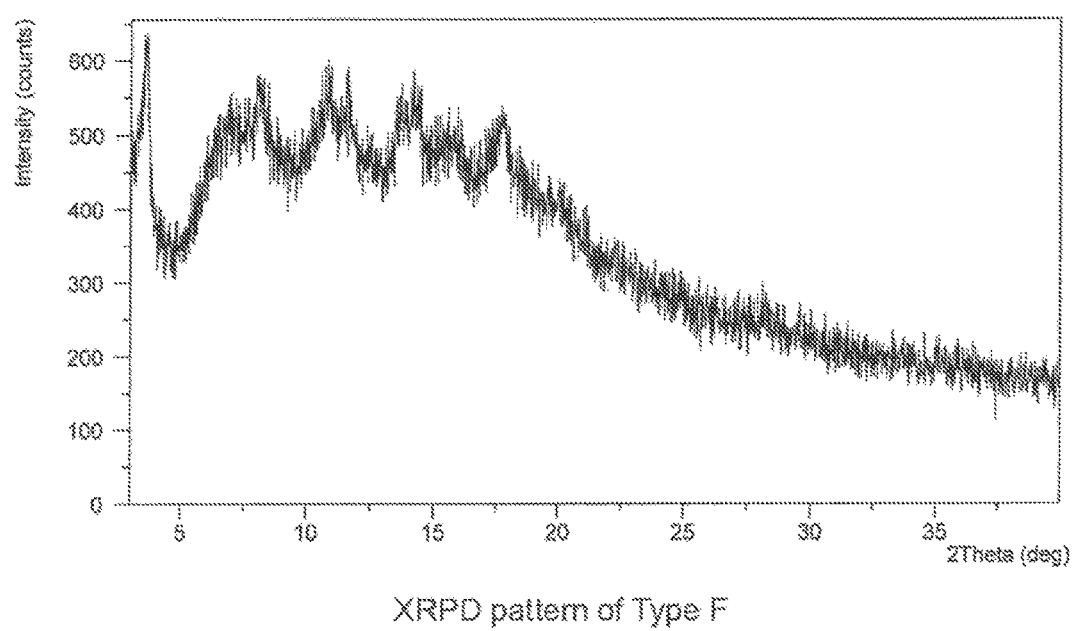
FIG. 55 is an XRPD of SCY-078 citrate Type F from Example 41.
Figure 56:
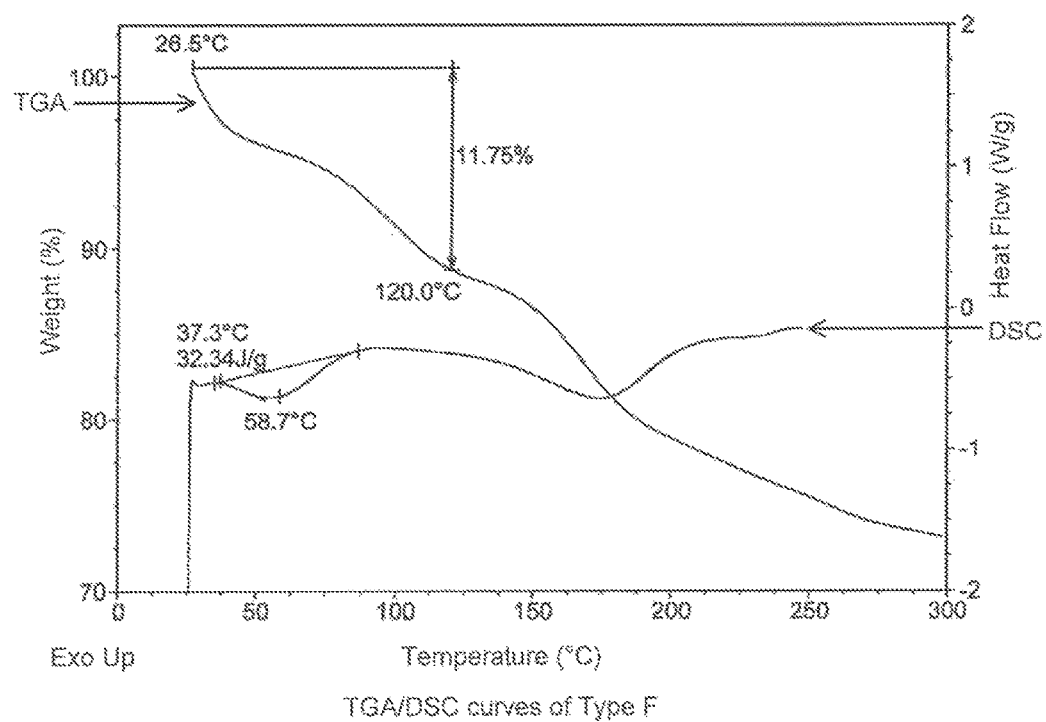
FIG. 56 is a DSC curve and a TGA curve of SCY-078 citrate Type F from Example 41.

SCY-078 Citrate Type F: SCY-078 citrate Type F was obtained by reverse anti-solvent addition in IPA/toluene according to the process described in Example 33 and Table 29. The XRPD pattern indicated that SCY-078 citrate Type F is weakly crystalline (FIG. 55). DSC curve exhibited a wide endothermic peak at 37.3° C. (onset temperature)(FIG. 56). TGA curve displayed a weight loss of 11.8% up to 120° C. (FIG. 56).

Example 42

Figure 57:
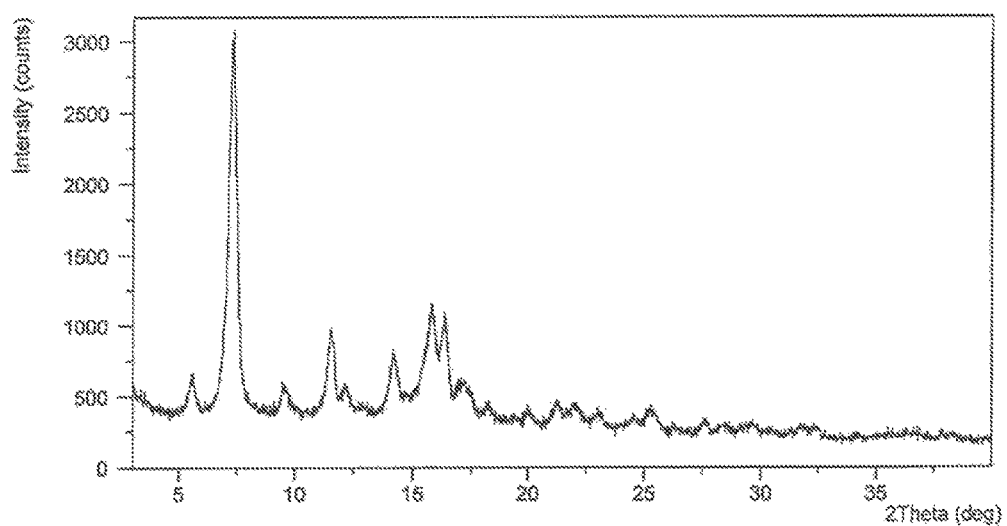
FIG. 57 is an XRPD of SCY-078 citrate Type M from Example 42.
Figure 58:
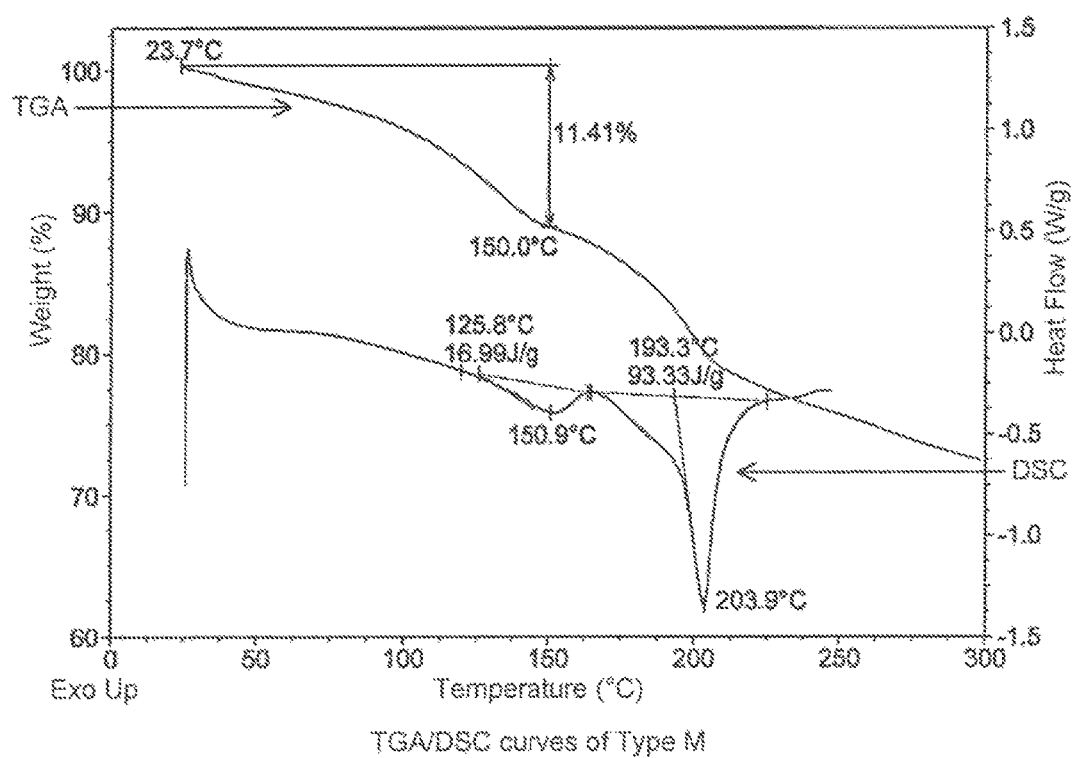
FIG. 58 is a DSC curve and a TGA curve of SCY-078 citrate Type M from Example 42.
Figure 59:
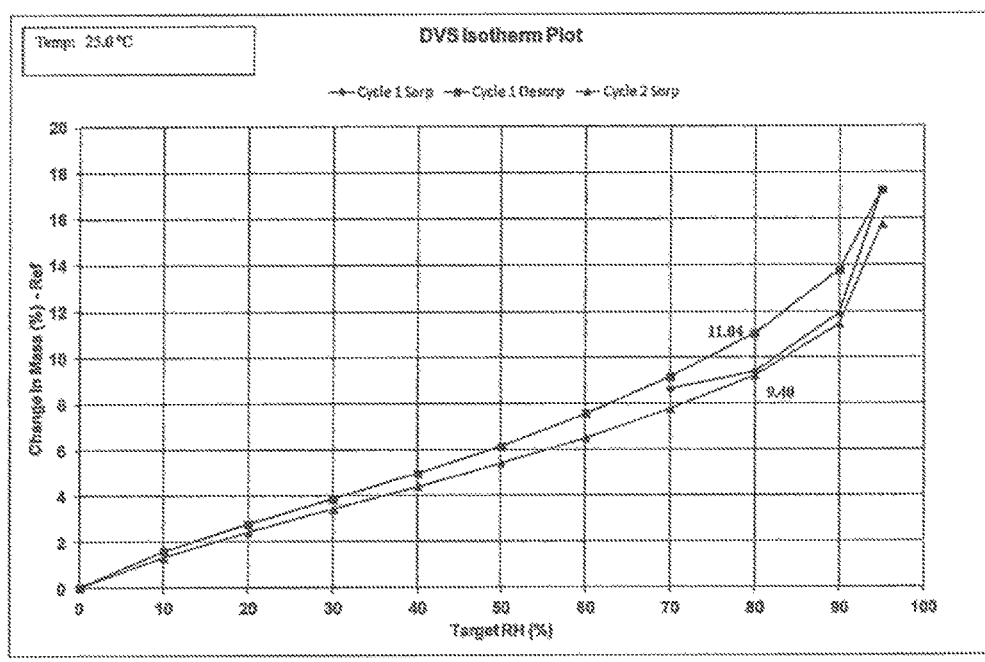
FIG. 59 is a DVS isotherm plot of SCY-078 citrate Type M from Example 42.

SCY-078 Citrate Type M: SCY-078 citrate Type M was obtained by storing SCY-078 citrate Type E in ambient conditions for 2 days. The XRPD pattern of SCY-078 citrate Type M displayed distinctive diffraction peaks (FIG. 57). DSC curve exhibited two endothermic peaks at 125.8° C. and 193.3° C. (onset temperatures) (FIG. 58). TGA curve displayed a 11.4% weight loss up to 150° C. (FIG. 58). DVS plot showed 11.0% water uptake at 25° C. and 80% RH (FIG. 59). After DVS, SCY-078 citrate Type M converts to partially amorphous.

Figure 60:
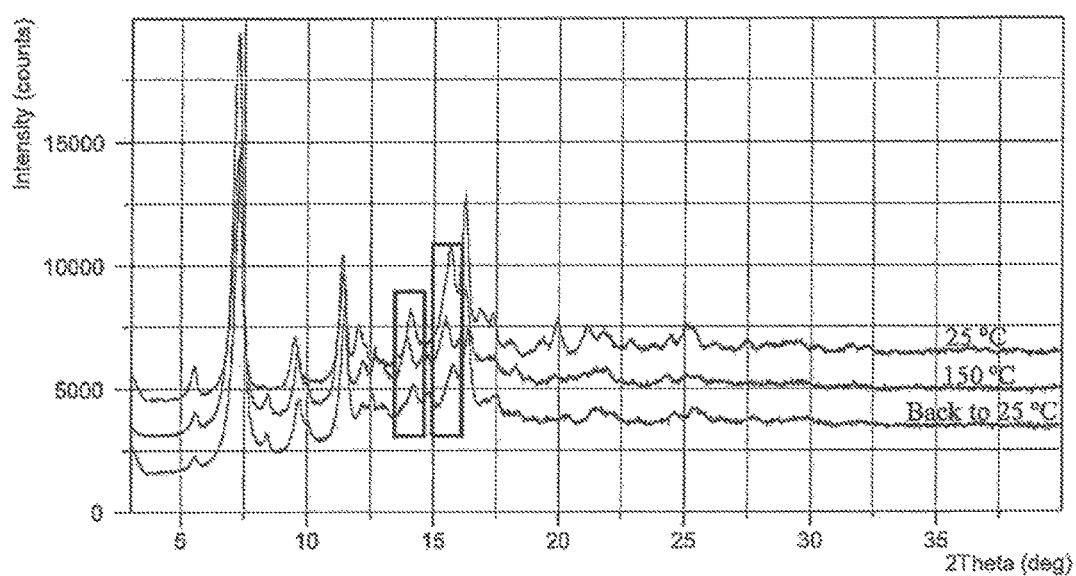
FIG. 60 is an XRPD of SCY-078 citrate Type M from Example 42 at variable temperatures.

XRPD analysis was also performed at variable temperatures wherein XRPD patterns were produced at 25° C., then at 150° C., and finally, again at 25° C. (FIG. 60). A shift in diffraction peaks was observed, indicating that Type M is probably a channel hydrate.

Example 43

Figure 61:
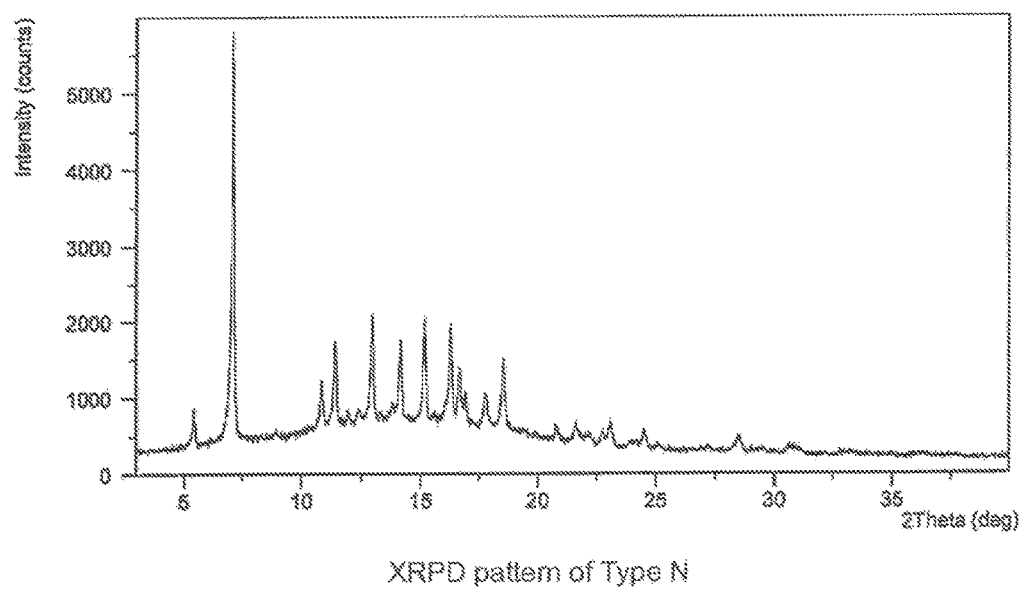
FIG. 61 is an XRPD of SCY-078 citrate Type N from Example 43.
Figure 62:
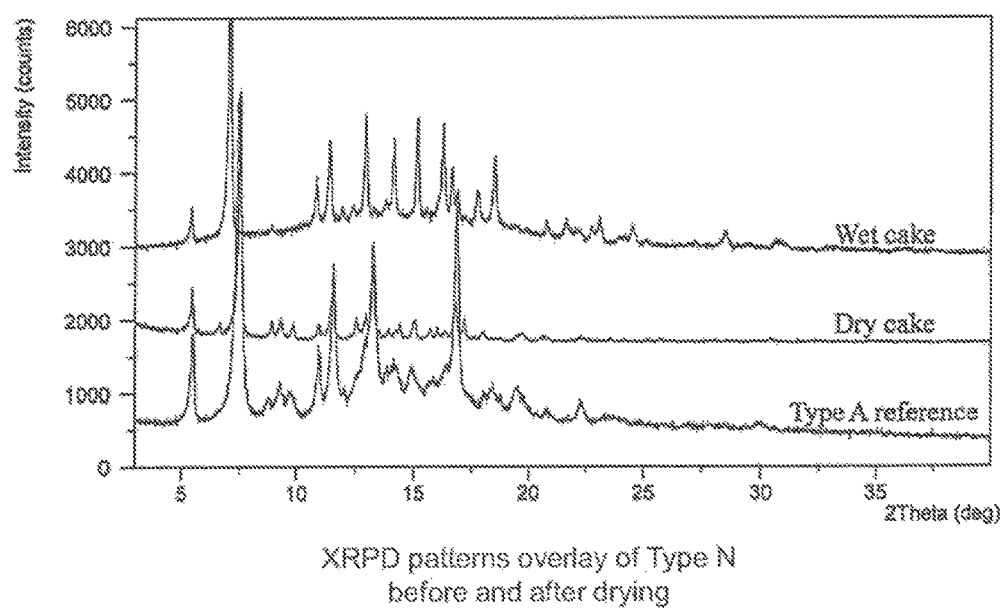
FIG. 62 is an XRPD of SCY-078 citrate Type N from Example 43 before and after drying.

SCY-078 Citrate Type N: SCY-078 citrate Type N was obtained by slurrying SCY-078 citrate Type B in EtOH at room temperature for two weeks. SCY-078 citrate Type N can also be obtained by exposing SCY-078 citrate Type A in EtOH vapor for 8 days or slurrying SCY-078 citrate Type A in EtOH for 2 hours. The XRPD pattern of SCY-078 citrate Type N indicates that it is highly crystalline (FIG. 61). SCY-078 citrate Type N converts to SCY-078 citrate Type A after vacuum drying at room temperature (FIG. 62), indicating SCY-078 citrate Type N is a metastable EtOH solvate, which rapidly converts to SCY-078 citrate Type A under vacuum or upon air/$N_2$ drying at ambient temperature or elevated temperature.

Example 44

Figure 63:
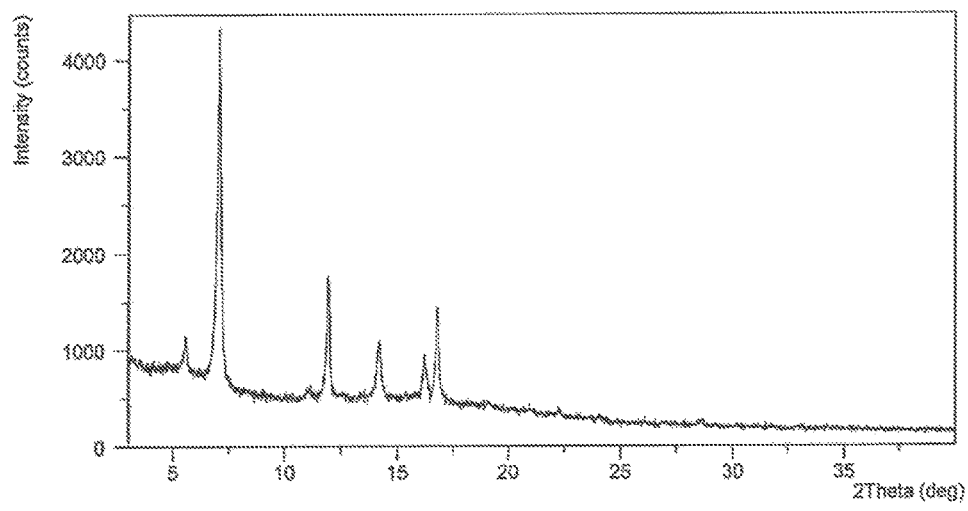
FIG. 63 is an XRPD of SCY-078 citrate Type O from Example 44.

SCY-078 Citrate Type O: SCY-078 citrate Type O was obtained by slurrying SCY-078 citrate Type M in acetone at room temperature for 19 hours. The XRPD pattern of SCY-078 citrate Type O indicated that it is highly crystalline with distinctive diffraction peaks (FIG. 63). SCY-078 citrate Type O converts to SCY-078 citrate Type S under ambient or vacuum conditions.

Example 45

Figure 64:
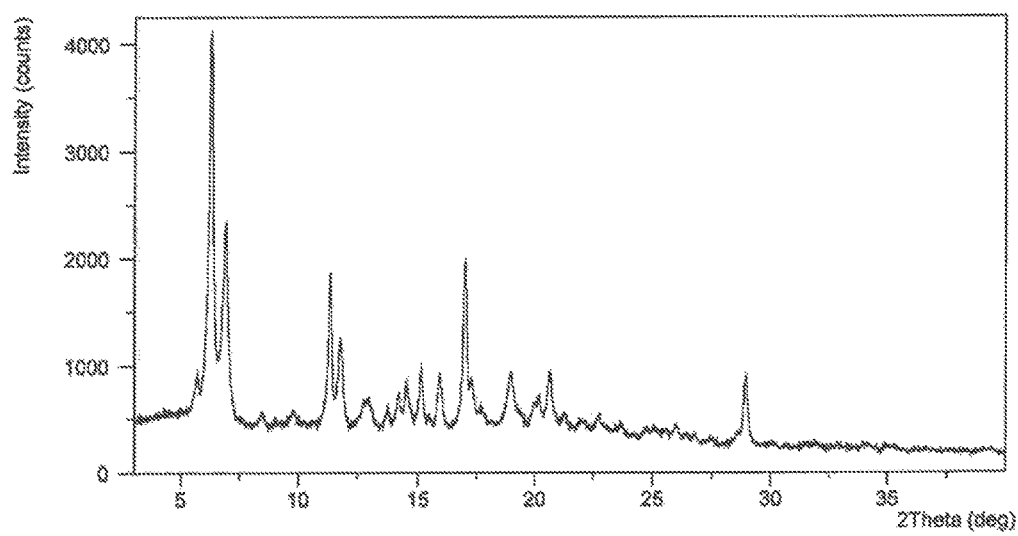
FIG. 64 is an XRPD of SCY-078 citrate Type Q from Example 45.
Figure 65:
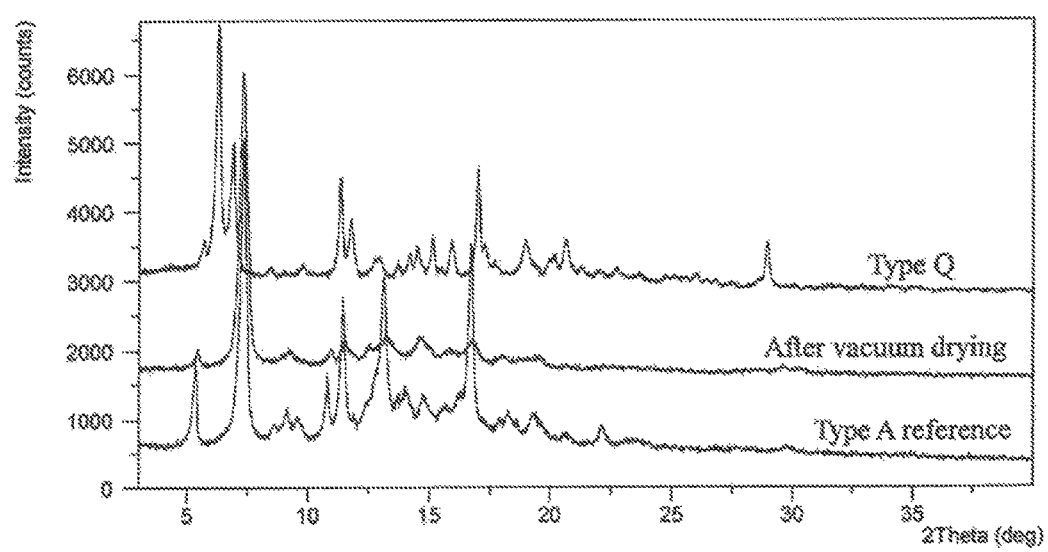
FIG. 65 is an XRPD of SCY-078 citrate Type Q from Example 45 before and after drying.

SCY-078 Citrate Type Q: SCY-078 citrate Type Q was obtained when performing reactive crystallization of freebase and citric acid (1:1) in EtOH without seeds. SCY-078 citrate Type N was consistently obtained when the reactive crystallization was performed using SCY-078 citrate Type N or SCY-078 citrate Type A seeds. The XRPD pattern showed SCY-078 citrate Type Q is highly crystalline with distinctive diffraction peaks (FIG. 64). SCY-078 citrate Type Q can convert to SCY-078 citrate Type A after vacuum drying at room temperature, indicating that SCY-078 citrate Type Q is a metastable EtOH solvate (FIG. 65).

The stability of the two EtOH solvates, SCY-078 citrate Type N and SCY-078 citrate Type Q, was evaluated by measuring their solubility at 5° C. and 20° C. (Table 34). The solubility was measured by slurrying SCY-078 citrate Type N and SCY-078 citrate Type Q samples in EtOH for 24 hours with a magnetic stirring rate of 1000 rpm. SCY-078 citrate Type Q exhibited lower solubility than SCY-078 citrate Type N in EtOH at 5° C. and 20° C., indicating that SCY-078 citrate Type Q is thermodynamically more stable in EtOH from 5° C. to 20° C. XRPD analysis of the remaining wet cakes from the solubility experiments showed no form change for both SCY-078 citrate Type Q and SCY-078 citrate Type N.

TABLE 34

Solubility (mg/mL) of SCY-078 citrate Type N and SCY-078 citrate Type Q in EtOH at different temperatures

| Temperature (° C.) | Type N | Type Q |
| --- | --- | --- |
| 5 | 24.4 | 17.4 |
| 20 | 27.1 | 25.9 |

Example 46

Figure 66:
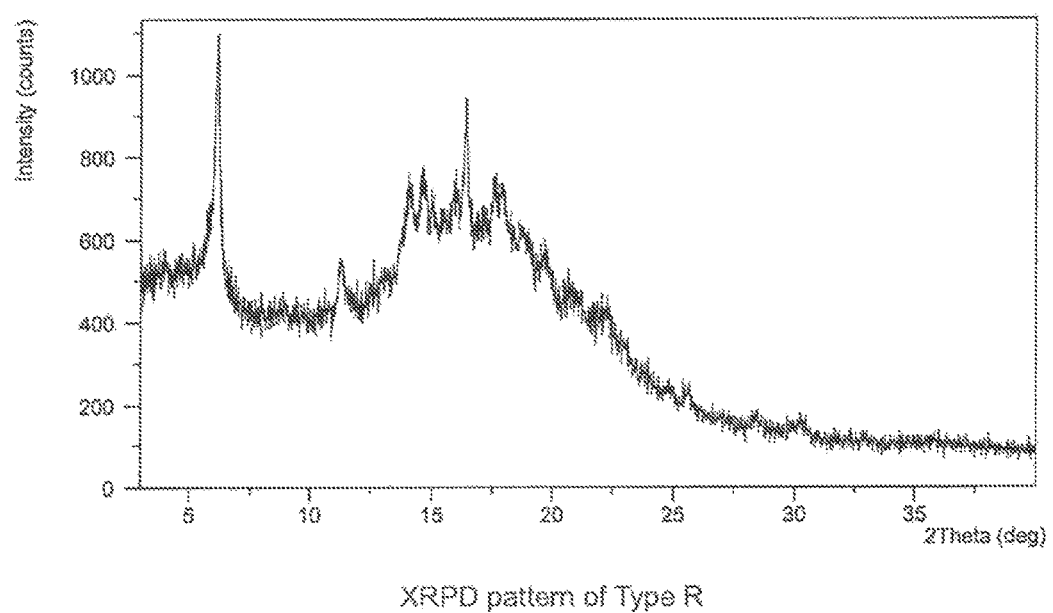
FIG. 66 is an XRPD of SCY-078 citrate Type R from Example 46.
Figure 67:
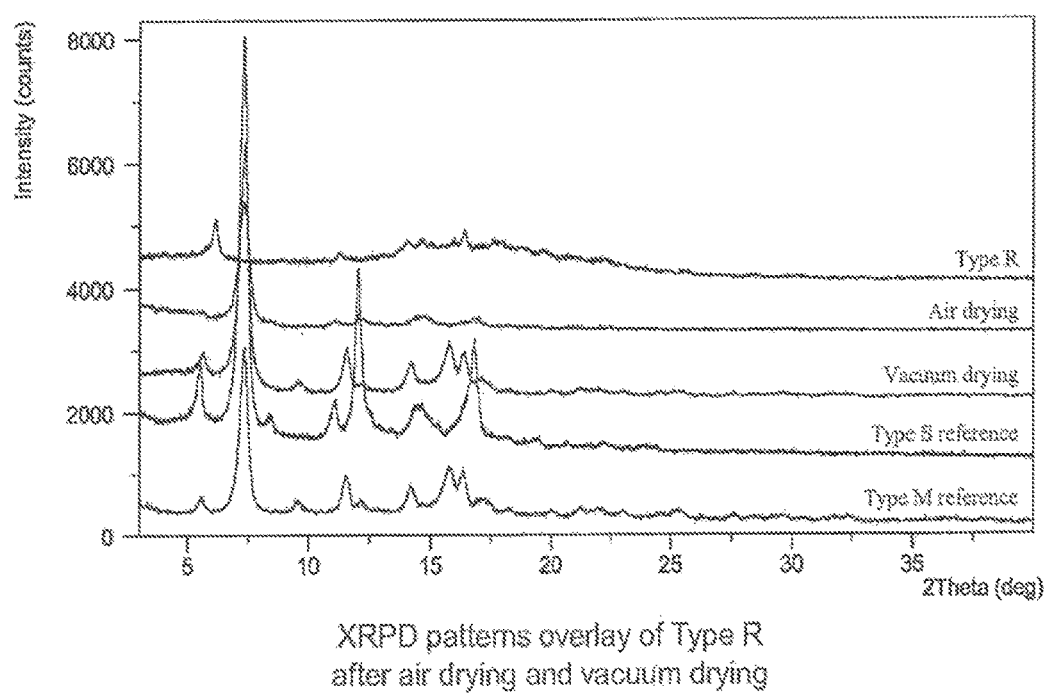
FIG. 67 is an XRPD of SCY-078 citrate Type R from Example 46 before and after drying.

SCY-078 Citrate Type R: SCY-078 citrate Type R was obtained by slurrying SCY-078 citrate Type M in MeOH/IPAc (1/14, v/v) for 17 hours. SCY-078 citrate Type R can also be obtained by reverse anti-solvent addition in MeOH/IPAc. The XRPD pattern indicated that SCY-078 citrate Type R is weakly crystalline (FIG. 66). XRPD analysis also indicated that SCY-078 citrate Type R is a metastable solvate that can easily convert to SCY-078 citrate Type S upon air drying and to SCY-078 citrate Type M after vacuum drying (FIG. 67).

Example 47

Figure 68:
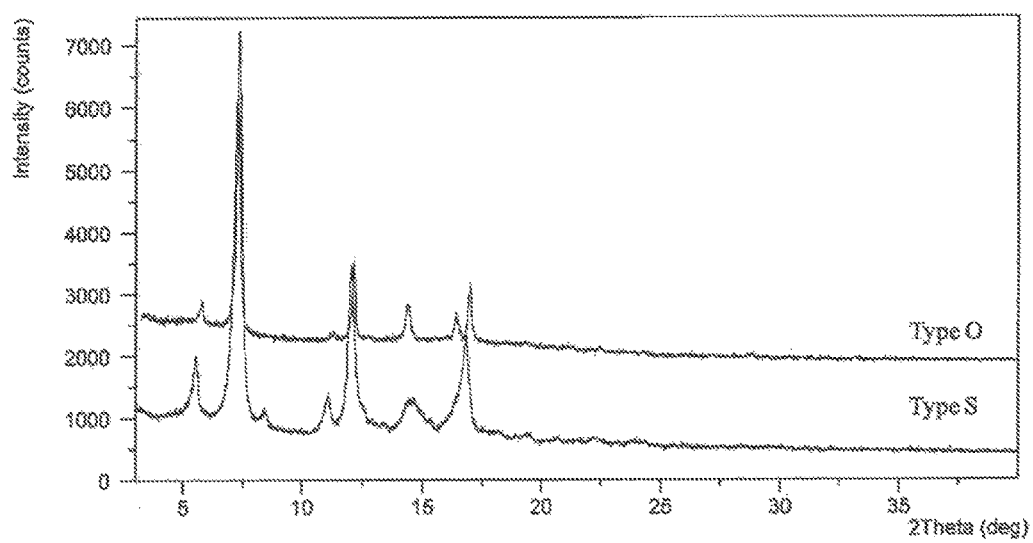
FIG. 68 is an XRPD of SCY-078 citrate Type S from Example 47.
Figure 69:
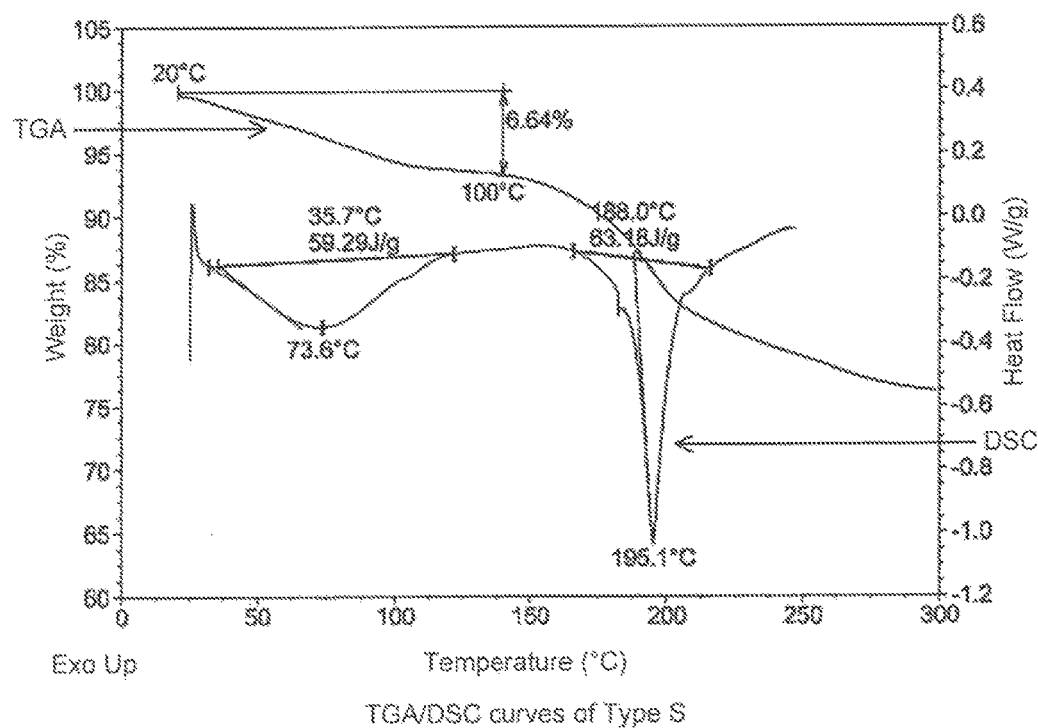
FIG. 69 is a DSC curve and a TGA curve of SCY-078 citrate Type S from Example 47.
Figure 70:
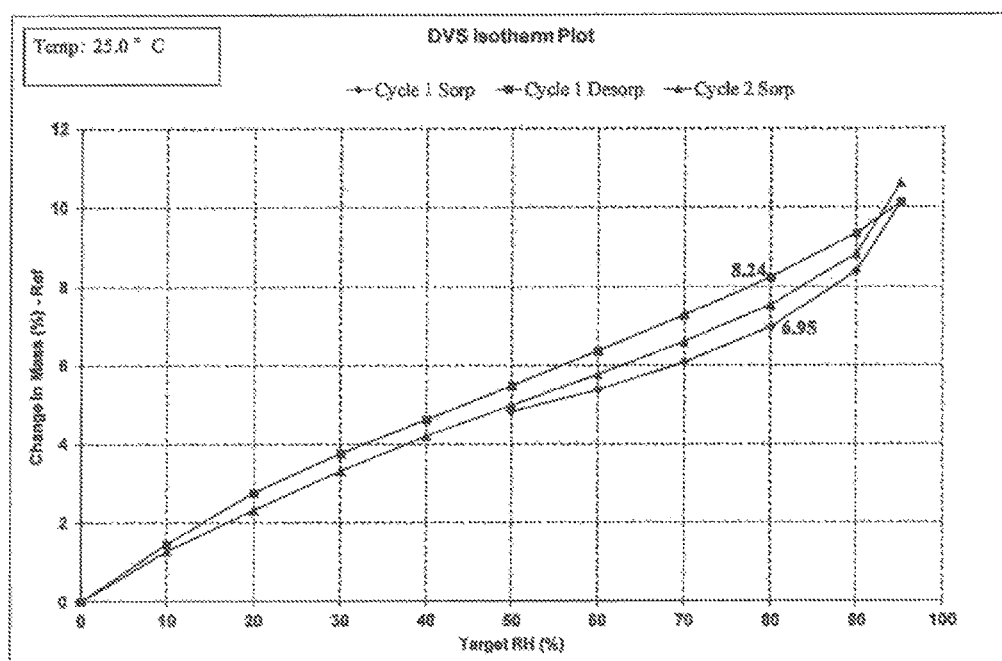
FIG. 70 is a DVS isotherm plot of SCY-078 citrate Type S from Example 47.
Figure 71:
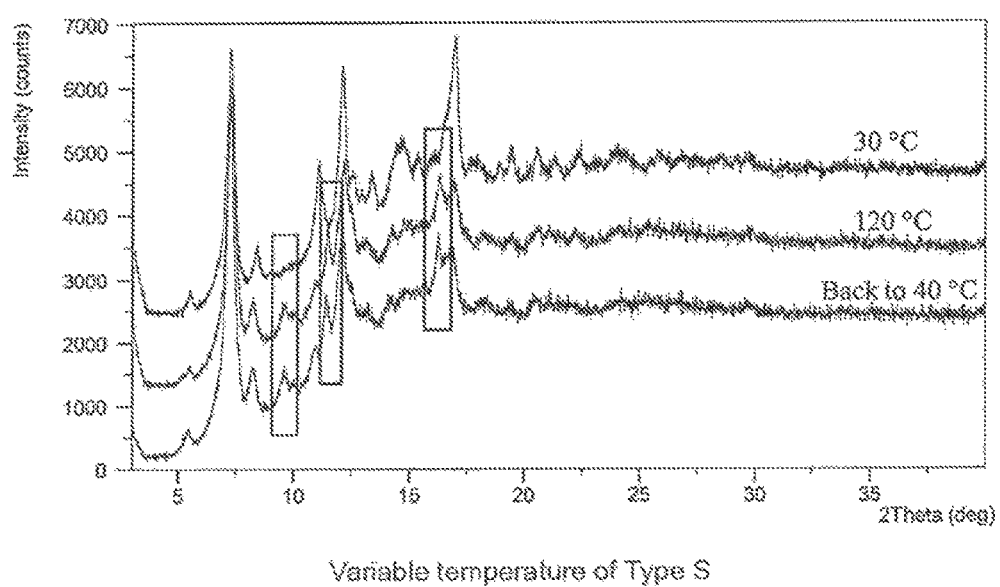
FIG. 71 is an XRPD of SCY-078 citrate Type S from Example 47 at variable temperatures.

SCY-078 Citrate Type S: SCY-078 citrate Type S can be obtained by drying SCY-078 citrate Type O sample under ambient or vacuum condition. The XRPD patterns showed shift of diffraction peaks after conversion from SCY-078 citrate Type O to SCY-078 citrate Type S (FIG. 68). DSC curve exhibited two endothermic peaks at 35.7° C. and 188.0° C. (onset temperatures) (FIG. 69). TGA curve displayed 6.6% weight loss up to 100° C. (FIG. 69). DVS plot showed 8.2% water uptake at 25° C. and 80% RH for SCY-078 citrate Type S (FIG. 70). XRPD analysis after DVS showed peak shifts. XRPD analysis was further performed at variable temperatures 30° C. to 120° C. and back to 40° C., which showed a shift of diffraction peaks (FIG. 71).

Example 48

Figure 72:
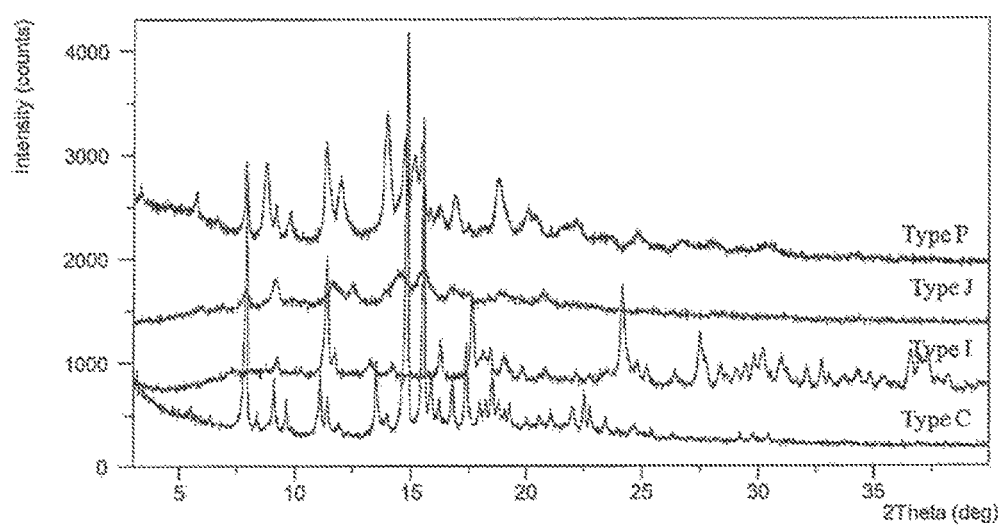
FIG. 72 shows XRPD patterns of SCY-078 citrate Types C, I, J, and P from Example 48.

Disproportionation of SCY-078 Citrate Salt: Crystalline forms of SCY-078 citrate named Type C, Type I, Type J, and Type P were observed either during polymorph study or when investigating the inter-conversion relationship of different SCY-078 citrate forms. XRPD patterns of the four forms (FIG. 72) demonstrated that SCY-078 citrate Type C and SCY-078 citrate Type J are freebase forms and that SCY-078 citrate Type I and SCY-078 citrate Type P are likely freebase forms.

SCY-078 citrate Type I was obtained in DMSO/EtOH system. SCY-078 citrate Type P was obtained by slurrying SCY-078 citrate Type M in acetone/$H_2O$ system. SCY-078 citrate Type A disproportionated to the freebase (SCY-078 citrate Type C, which converts to SCY-078 citrate Type J upon drying) when slurrying in EtOH/$H_2O$, acetone/$H_2O$, and BuOH/$H_2O$ systems. Slurrying SCY-078 citrate Type A or evaporating the citrate solution in DMSO, DMAc and DCM-related co-solvents also resulted in disproportionation.

Example 49

Inter-conversion Between SCY-078 Citrate Type A and Citrate Type B: Slurry experiments were performed with SCY-078 citrate Type A in different organic solvents in order to understand the inter-conversion between SCY-078 citrate Type A and SCY-078 citrate Type B. SCY-078 citrate Type A (~20 mg) was suspended into a solvent (0.5 mL) in a 1.5-mL glass vial. After the suspensions were ultrasonicated for 1 hour or stirred for 6 hours at room temperature, the remaining solids were isolated for XRPD analysis. The results (Table 35) indicated that SCY-078 citrate Type B can be obtained from various organic solvents. SCY-078 citrate Type B was also prepared from SCY-078 citrate Type A by slurry in EtOH, ACN, acetone, MIBK, EtOAc, IPAc, DCM, toluene, heptane, MeOH/acetone (1/19), IPA/heptane (1/19), THF/toluene (1/19) or by solid vapor diffusion in EtOAc. SCY-078 citrate Type B can convert to SCY-078 citrate Type A via drying under $N_2$ or vacuum at room temperature.

TABLE 35

Summary of preparation methods of SCY-078 citrate Type B

| Solvent | Preparation | Form, Wet Slurry | Form, Vacuum filtered slurry | Form after $N_2$ drying at RT |
| --- | --- | --- | --- | --- |
| ACN | Ultrasonication for 1 hr | Type B | Type A | Type A |

TABLE 35-continued

Summary of preparation methods of SCY-078 citrate Type B

| Solvent | Preparation | Form, Wet Slurry | Form, Vacuum filtered slurry | Form after N$_2$ drying at RT |
|---|---|---|---|---|
| DCM | Ultrasonication for 1 hr | Type B | Type A | Type A |
| EtOAc | Stirring for 6 hrs | Type B | Type B | Type A |

Example 50

Figure 73:
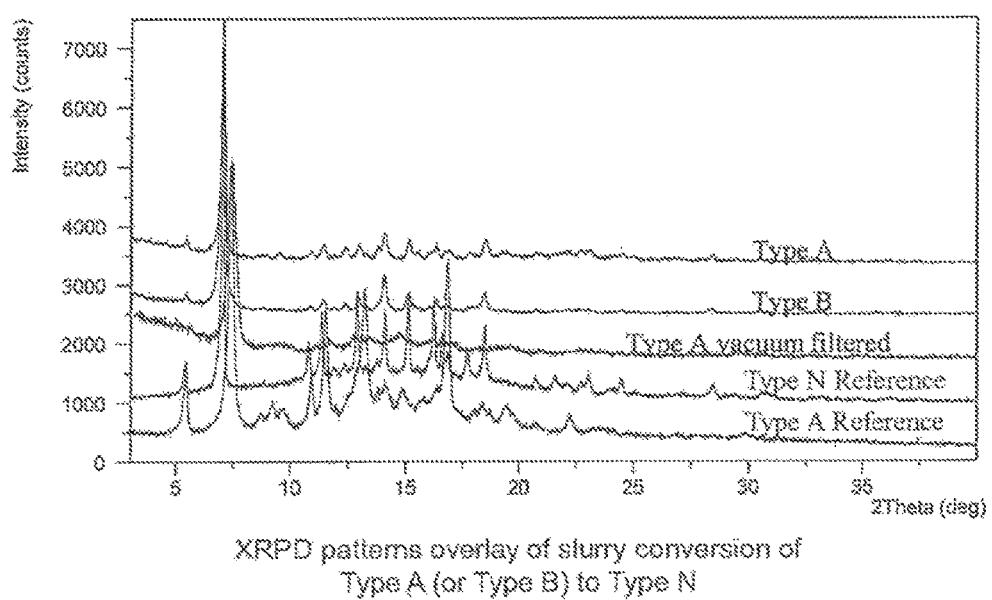
FIG. 73 shows XRPD patterns of slurry conversion of SCY-078 citrate Type A or Type B to Type N from Example 50.

Inter-conversion between SCY-078 citrate Type A and SCY-078 citrate Type N and SCY-078 citrate Type Q: SCY-078 citrate Type N can be obtained by slurrying SCY-078 citrate Type A (or SCY-078 citrate Type B) in EtOH with ultrasonication or at room temperature for 1 hour. SCY-078 citrate Type N rapidly converts to SCY-078 citrate Type A via vacuum filtration (FIG. 73).

Figure 74:
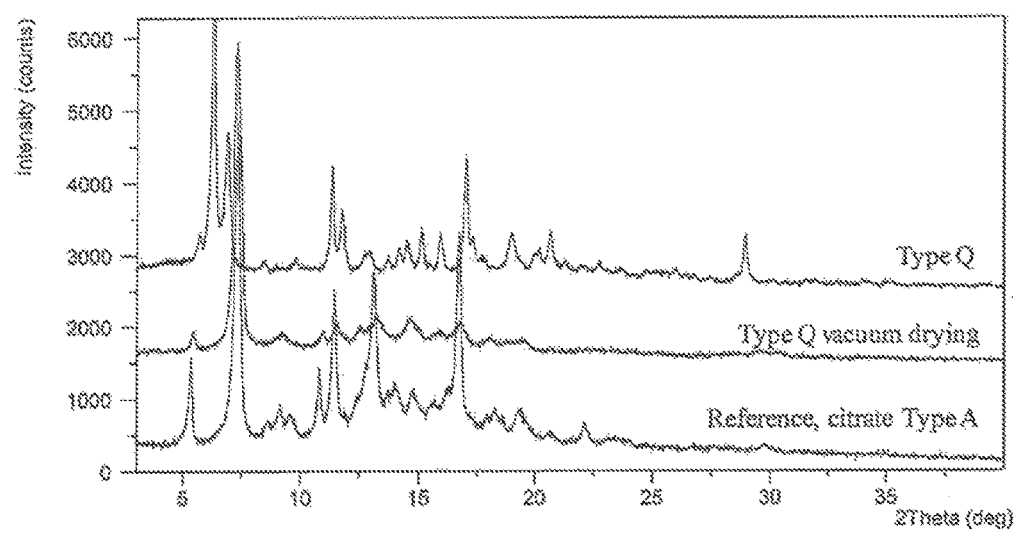
FIG. 74 shows XRPD patterns of SCY-078 citrate Type Q after drying from Example 50.

SCY-078 citrate Type Q was obtained by reactive crystallization of freebase MeOH desolvate and citric acid (1:1) in EtOH without seeds. After drying in vacuum at room temperature, SCY-078 citrate Type Q converts to SCY-078 citrate Type A (FIG. 74). The study of the inter-conversion between SCY-078 citrate Type A and SCY-078 citrate Type N and SCY-078 citrate Type Q is summarized below in Table 36.

TABLE 36

Slurry conversion of SCY-078 citrate Type A or SCY-078 citrate Type B to SCY-078 citrate Type N

| Starting Material | Method | Solvent | Form, Wet Slurry | Form, Vacuum Dry |
|---|---|---|---|---|
| Type A | Ultrasonication | EtOH | Type N | Type A |
| Type B | Ultrasonication | EtOH | Type N | Not Measured |
| MeOH desolvate/ citric acid (1:1) | Reactive crystallization | EtOH | Type Q | Type A |

Example 51

Figure 75:
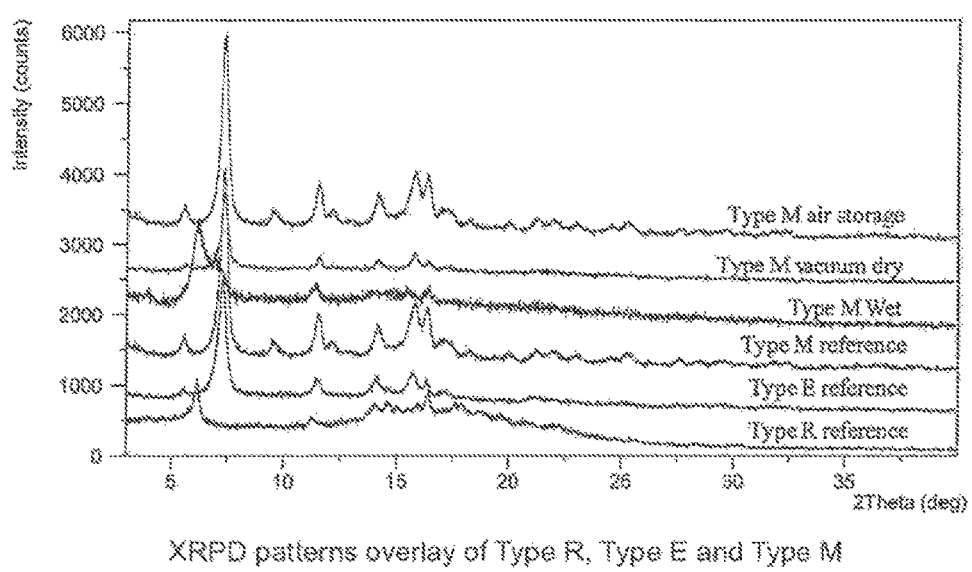
FIG. 75 shows XRPD patterns of SCY-078 citrate Types R, E, and M from Example 51.

Inter-conversion Relationship Around Channel Hydrate SCY-078 Citrate Type M: Metastable solvate SCY-078 citrate Type R was obtained by reverse anti-solvent addition in MeOH/IPAc. SCY-078 citrate Type R converted to SCY-078 citrate Type E after drying in vacuum at room temperature, and then SCY-078 citrate Type M was obtained by storing SCY-078 citrate Type E under ambient conditions for 2 days (FIG. 75). SCY-078 citrate Type R was found to convert to SCY-078 citrate Type M directly upon vacuum drying at room temperature.

Figure 76:
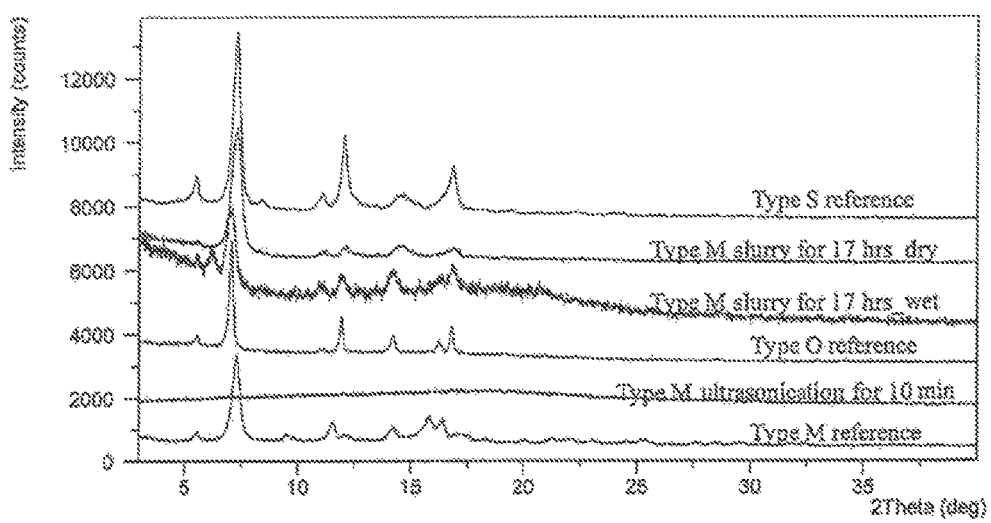
FIG. 76 shows XRPD patterns of SCY-078 citrate Type M slurry in acetone from Example 51.
Figure 77:
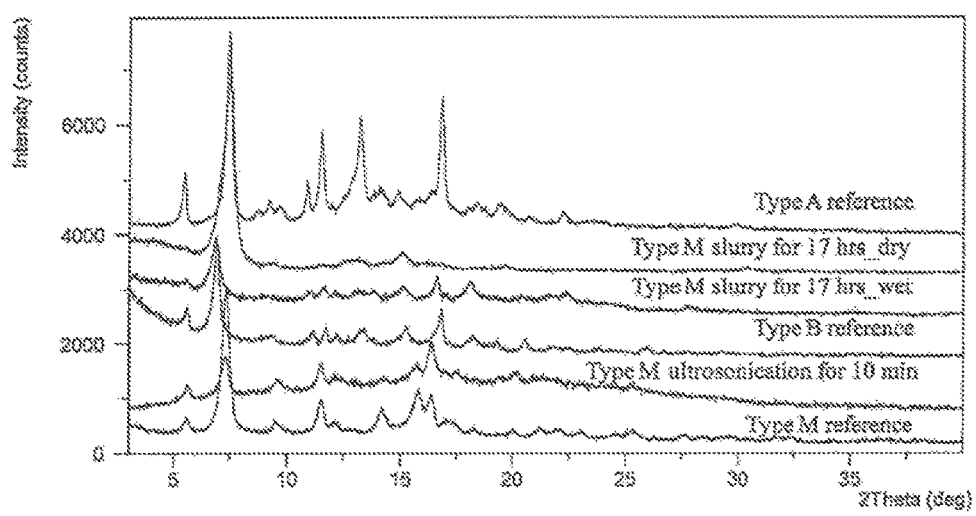
FIG. 77 shows XRPD patterns of SCY-078 citrate Type M slurry in acetonitrile from Example 51.
Figure 78:
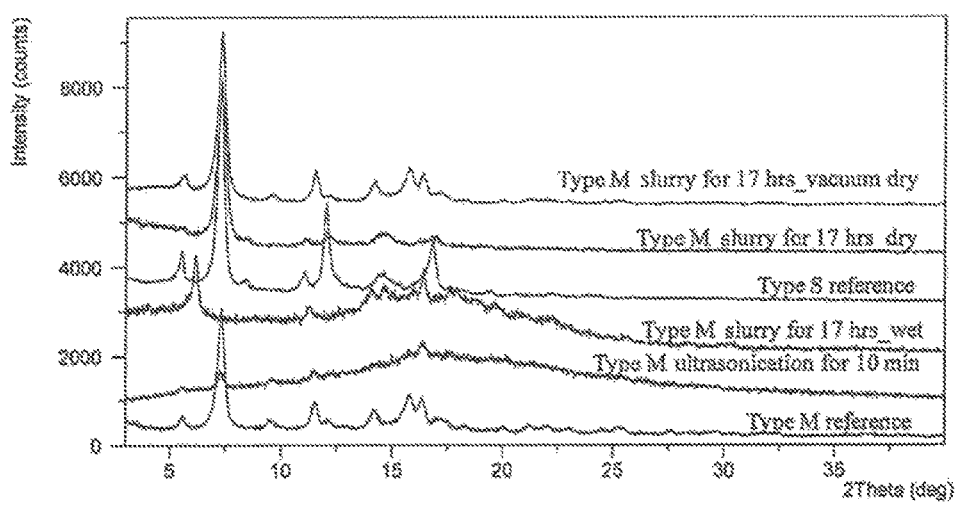
FIG. 78 shows XRPD patterns of SCY-078 citrate Type M slurry in MeOH/IPAc from Example 51.
Figure 79:
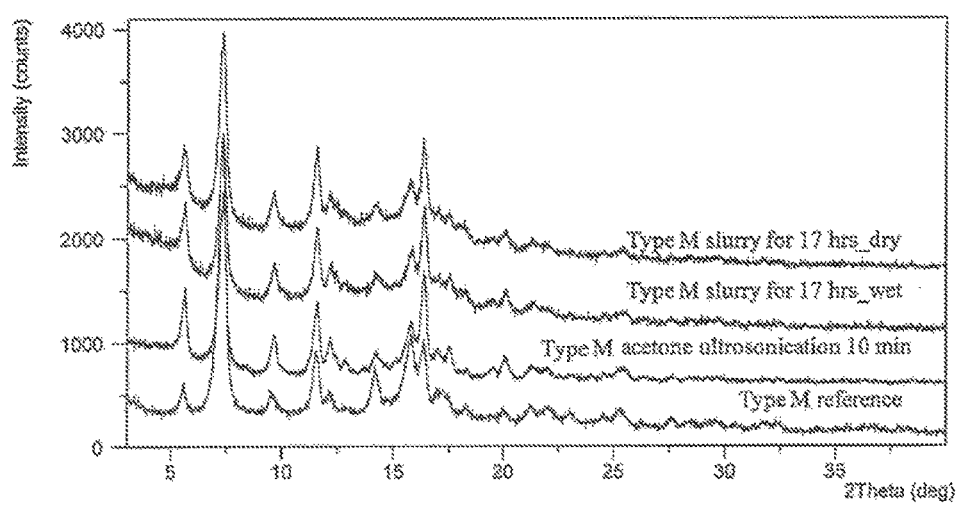
FIG. 79 shows XRPD patterns of SCY-078 citrate Type M slurry in heptane from Example 51.

Slurry experiments were performed on SCY-078 citrate Type M in selected organic solvents. The results (Table 37) indicated that SCY-078 citrate Type M converted to SCY-078 citrate Type O after slurrying in acetone for 17 hours, and SCY-078 citrate Type O converted to SCY-078 citrate Type S after air drying (FIG. 76). SCY-078 citrate Type M converted to SCY-078 citrate Type A when slurried in ACN (FIG. 77), and converted to metastable solvate SCY-078 citrate Type R in MeOH/IPAc co-solvent (FIG. 78). SCY-078 citrate Type R converted to SCY-078 citrate Type S upon air drying and converted back to SCY-078 citrate Type M through vacuum drying at room temperature. No form change was observed by slurrying SCY-078 citrate Type M in heptane (FIG. 79).

TABLE 37

Slurry experiments result of SCY-078 citrate Type M in organic solvents

| Solvent | Condition | Solid Form |
|---|---|---|
| Acetone | 10 mins ultrasonication/wet | Amorphous |
| | 17 hrs (slurry) wet | Type O |
| | 17 hrs (slurry) dry under ambient conditions | Type S |
| ACN | 10 mins ultrasonication/wet | Type M |
| | 17 hrs (slurry) wet | Type B |
| | 17 hrs (slurry) dry under ambient conditions | Type A |
| Heptane | 10 mins ultrasonication/wet | Type M |
| | 17 hrs (slurry) wet | Type M |
| | 17 hrs (slurry) dry under ambient conditions | Type M |
| MeOH/IPAc (5/70, v/v) | 10 mins ultrasonication/wet | Type M |
| | 17 hrs (slurry) wet | Type R* |
| | 17 hrs (slurry) dry under ambient conditions | Type S |

*Type R converts to Type M after vacuum drying at RT

Example 52

Figure 80:
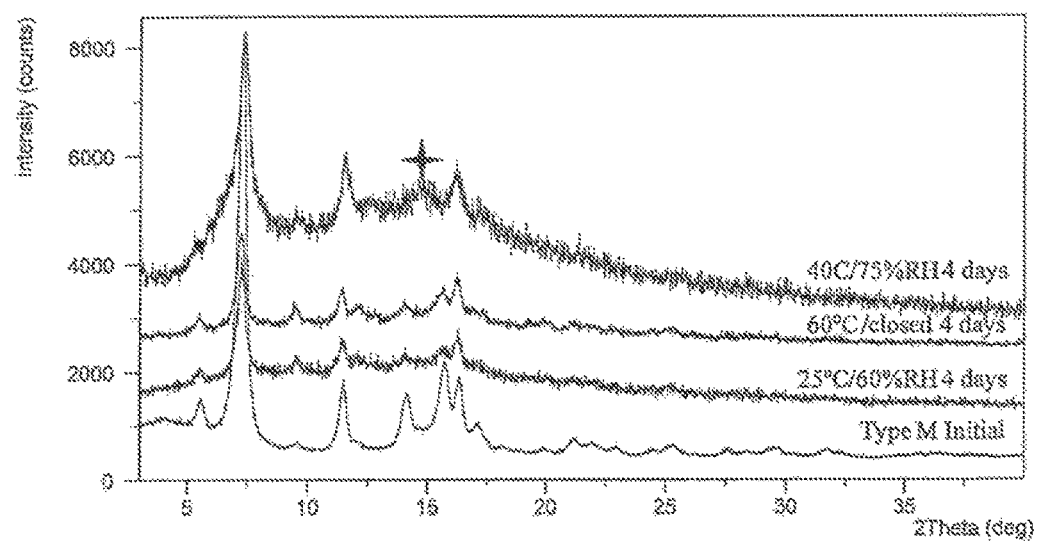
FIG. 80 shows XRPD patterns of SCY-078 citrate Type M after stability testing from Example 52.
Figure 81:
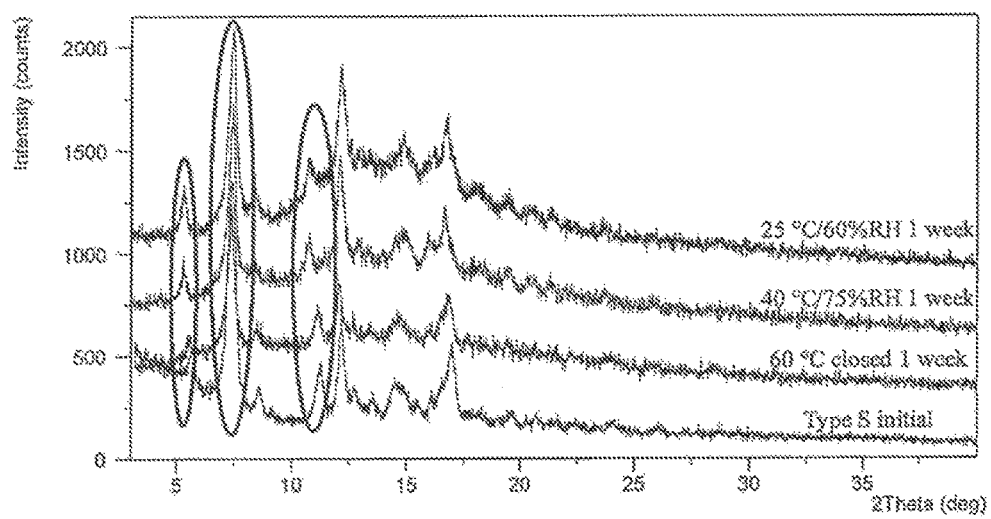
FIG. 81 shows XRPD patterns of SCY-078 citrate Type S after stability testing from Example 52.

Stability Study of SCY-078 Citrate Type A, SCY-078 Citrate Type M, and SCY-078 Citrate Type S: As described in Example 25 and Table 19, SCY-078 citrate Type A is physically/chemically stable at the tested conditions for at least 1 week. To test the physical and chemical stability of SCY-078 citrate Type M and SCY-078 citrate Type S, each was placed under three different conditions: (1) open dish at 25° C. with 60% RH; (2) open dish at 40° C. with 75% RH; and (3) closed dish at 60° C. with no humidity control. SCY-078 citrate Type M was tested for 4 days and SCY-078 citrate Type S was tested for 1 week (FIGS. 80-81).

The results (Table 38) showed that SCY-078 citrate Type M was physically and chemically stable at 25° C. and 60% RH for at least 4 days. One diffraction peak change and partial crystallinity loss was observed in the XRPD pattern of SCY-078 citrate Type M after storage at 40° C. and 75% RH. This is consistent with the previous observation in Example 42 that SCY-078 citrate Type M partially converts to amorphous after DVS analysis. The impurity of SCY-078 citrate Type M increased under closed conditions at 60° C. for 4 days.

SCY-078 citrate Type S is physically and chemically stable under 60° C. closed conditions for one week. Diffraction peak shifts were observed for the samples stored at 25° C. and 60% RH and 40° C. and 75% RH.

TABLE 38

Physical and Chemical Stability of SCY-078 citrate Type M and SCY-078 citrate Type S

| Sample | Condition | Impurity % by HPLC | Solid Form |
|---|---|---|---|
| Type M (4 days) | Initial | 0.42 | Type M |
| | 25° C./60% RH | 0.39 | Type M |
| | 40° C./75% RH | 0.00 | Type M* |
| | 60° C. closed | 0.63 | Type M |
| Type S (1 week) | Initial | 0.10 | Type S |
| | 25° C./60% RH | 0.03 | Type S** |

TABLE 38-continued

Physical and Chemical Stability of SCY-078 citrate Type M and SCY-078 citrate Type S

| Sample | Condition | Impurity % by HPLC | Solid Form |
|---|---|---|---|
| | 40° C./75% RH | 0.03 | Type S** |
| | 60° C. closed | 0.11 | Type S |

*One peak change was observed for the sample
**Peak shifts were observed for the samples

Example 53

Alternative Preparation of SCY-078 Citrate Type A: A 10-L reactor was charged with SCY-078 phosphate (450 g; freebase content in phosphate was 85.6% by HPLC). 2-MeTHF (2.25 L) was charged into the same reactor. A 10% $Na_2CO_3$ water solution (2.25 L) at 20° C. was charged into the reaction in 25 min. The suspension was stirred at 20° C. for 20 min and then allowed to settle for 30 min. The organic layer was collected and washed with 1.8 L of saturated NaCl water solution twice, and then further washed with 1.8 L deionized water once.

The organic layer was transferred to a 4-L crystallizer. The reactor was rinsed with 250 mL 2-MeTHF and the liquid was transferred into the crystallizer containing the organic layer. The solution was concentrated in the crystallizer to 900 mL at 50° C. The crystallizer was charged with 900 mL methanol and the mixture was cooled to 40° C. The mixture was stirred at 40° C. for 1 hour (clear). 4.5 g of seeds were added to the crystallizer and the suspension was aged at 40° C. for 1 hour. The mixture was then concentrated to 900 mL at 40° C. The crystallizer was then charged with 900 mL methanol and again concentrated to 900 mL at 40° C. This step was repeated twice more and the mother liquor was assayed by gas chromatography. The mixture was cooled to 10° C. in 2 hours and then aged at 10° C. for no less than three hours. The mother liquor was sampled for solution concentration by HPLC. The suspension was filtered and the cake was dried in a vacuum over at 35° C. for 12 hours.

To generate the citrate salt, a 10-L jacketed crystallizer with a twin-impeller over-head agitator was used. The diameter of the impeller is 13 cm. First, EtOH (500 mL) was added into a 10-L crystallizer (Crystallizer 1) and was agitated (300 rpm). The temperature of Crystallizer 1 was maintained at 25° C. The SCY-078 freebase (242.09 g) was added to Crystallizer 1. Another volume of EtOH (500 mL) was charged into Crystallizer 1. Crystallizer 1 was heated to 50° C. A citric acid solution, prepared by dissolving citric acid (58.22 g) into EtOH (758 mL), was charged into Crystallizer 1 in 35 min. Crystallizer 1 was heated to 55° C. and stirred for 20 minutes. Then Crystallizer 1 was cooled to 50° C. for 20 minutes.

After cooling, the extraneous matter was filtered (pore size of 30-50 μm) and the filtrate was transferred to another 10-L crystallizer (Crystallizer 2). The filter was washed with EtOH (5 mL) and transferred into Crystallizer 2. The mixture in Crystallizer 2 was stirred at 50° C. for 30 minutes. Next a seed slurry, which was prepared from seeds (13.22 g) that were sonicated and dispersed in 50/50 EtOH/n-heptane (68 mL), was rapidly charged into Crystallizer 2. The mixture in Crystallizer 2 was aged at 50° C. for 2 hours. Crystallizer 2 was then charged with n-heptane (1758 mL) for 12 hours at 50° C. The mixture was again aged at 50° C. for 2 hours. From the resulting mixture, a sample was taken for XRPD analysis and microscopy.

The mixture was cooled to 20° C. in 2 hours and then stirred at 20° C. for 3 hours. The batch was filtered and the cake was washed with a solution of 1:1 EtOH/n-heptane (500 mL). The cake was blown with $N_2$ for 60 minutes. Finally, the cake was dried at 45-55° C. with $N_2$ blowing.

Figure 82:
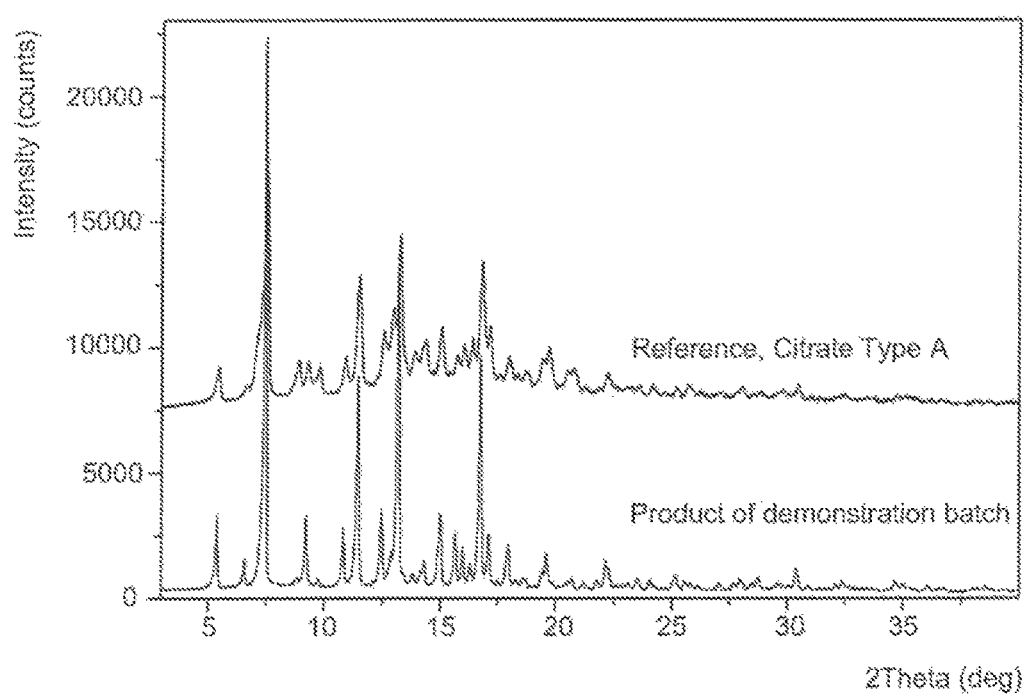
FIG. 82 is an XRPD of SCY-078 citrate Type A from Example 53.
Figure 83:
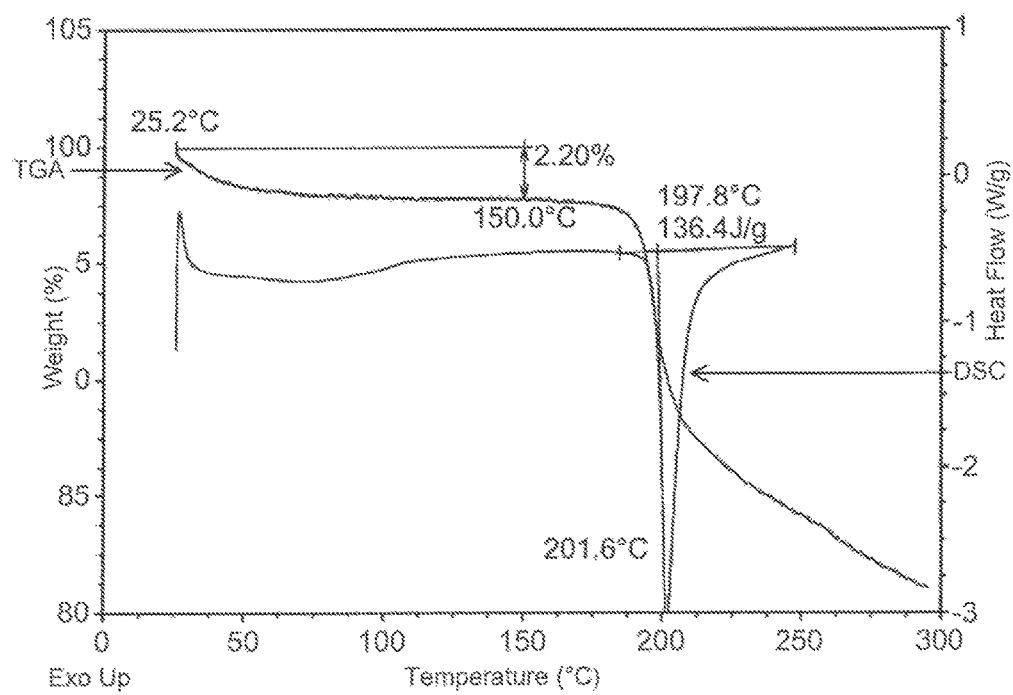
FIG. 83 is a DSC curve and a TGA curve of SCY-078 citrate Type A from Example 53.
Figure 84:
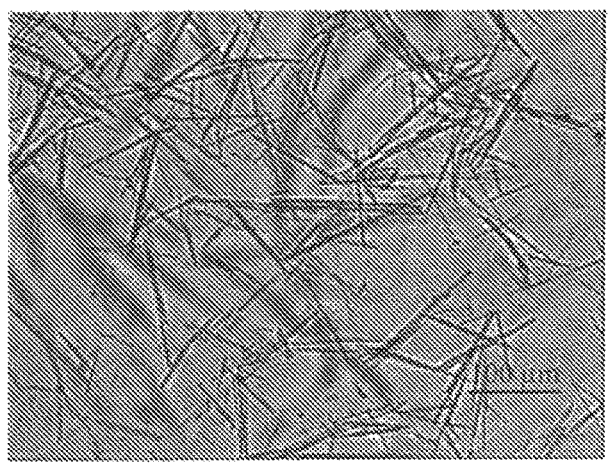
FIG. 84 is a DSC curve and a TGA curve of SCY-078 citrate Type A from Example 53.

Ultimately 241 grams of product was obtained with a 86.4% yield. XRPD analysis showed that the product was highly crystalline SCY-078 citrate Type A (FIG. 82). TGA curve showed a weight loss of 2.2% before 150° C. (FIG. 83). The DSC curve showed a melting point of 197.8° C. (onset temperature) (FIG. 83). The resulting crystals were rod-like with an average size of 34.2 μm (FIG. 84).

Example 54

Preparation and characterization of SCY-078 Trifluoroacetate Type A: SCY-078 amorphous freebase (994.3 mg) and trifluoroacetic acid (freebase/acid molar ratio—1/1) were weighted into a 5-mL vial, followed by addition of 5 mL acetonitrile. The mixture was slurried at RT with a magnetic stirring rate of 1000 rpm for 4 days. The suspension was centrifuged and vacuum dried at RT overnight.

Figure 85:
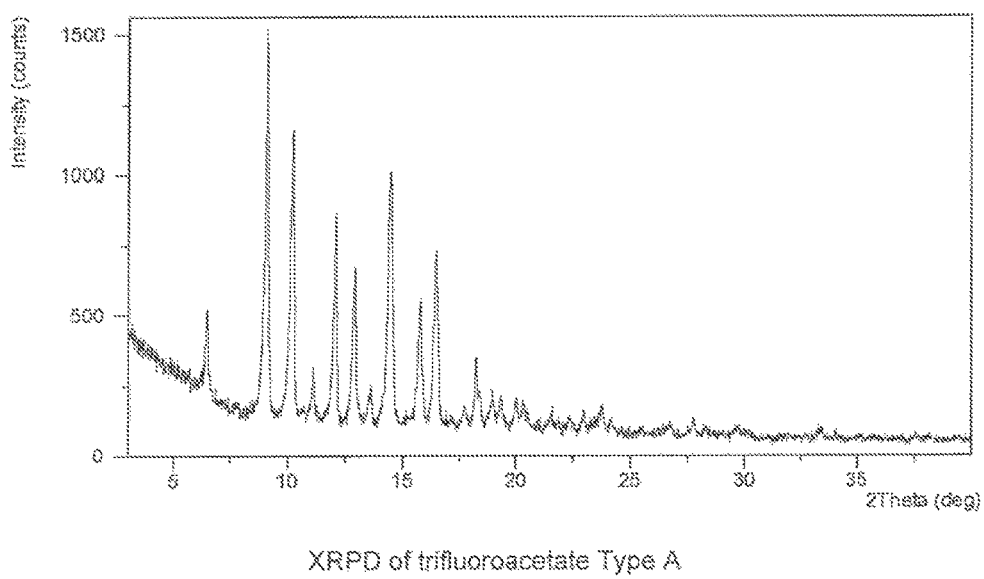
FIG. 85 is an XRPD of SCY-078 Trifluoroacetate Type A from Example 54.
Figure 86:
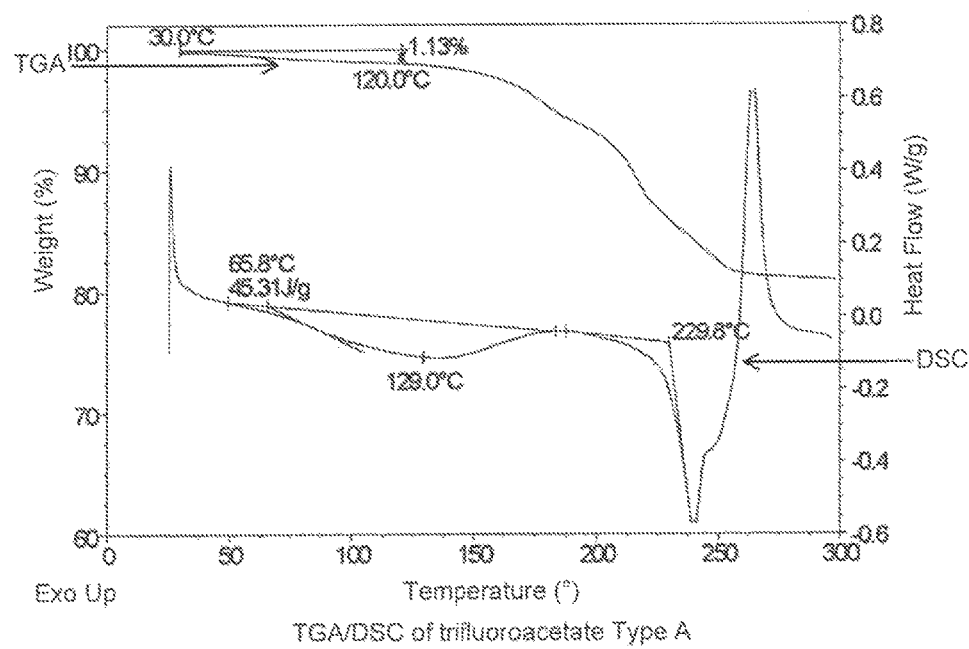
FIG. 86 is a DSC curve and a TGA curve of SCY-078 Trifluoroacetate Type A from Example 54.
Figure 87:
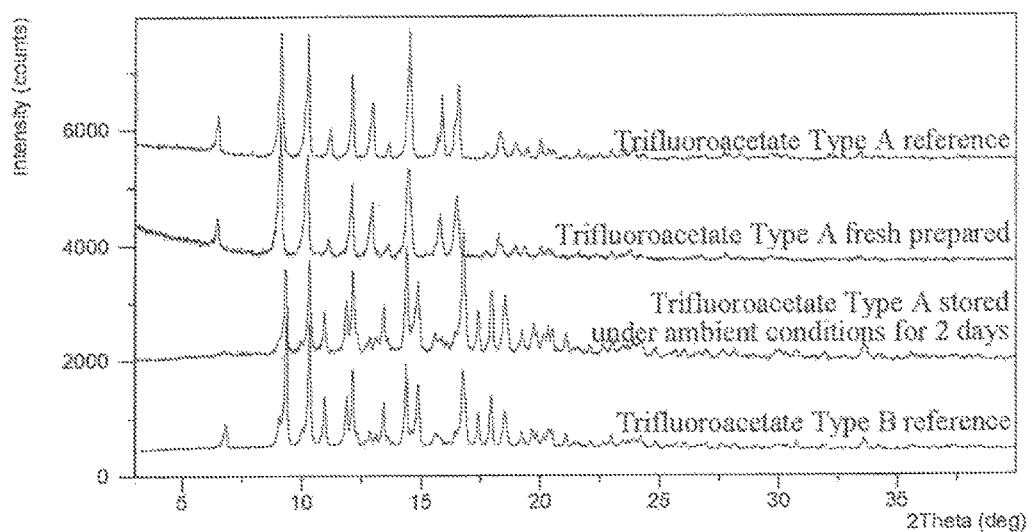
FIG. 87 is an XRPD of SCY-078 Trifluoroacetate Type A before and after storage from Example 54.

SCY-078 Trifluoroacetate Type A is highly crystalline as shown in the XRPD (FIG. 85). A weight loss of 1.1% is observed up to 120° C. in the TGA curve (FIG. 86). The DSC (FIG. 86) shows two endothermic peaks, one at 65.8° C. and 229.8° C. Trifluoroacetate Type A converted to Type B after stored under ambient conditions for 2 days (FIG. 87). The molar ratio of trifluoroacetate Type A (acid:freebase) was determined to be 1:1 via HPLC-IC confirmation.

Example 55

Preparation and characterization of SCY-078 Trifluoroacetate Type B: Trifluoroacetic acid (331.5 mg) was added into acetonitrile (8 mL) in a 20-mL glass vial, followed by addition of amorphous SCY-078 freebase Type A (freebase/acid molar ratio=1/1). The mixture was stirred at RT with a magnetic stirring rate of 600 rpm for 24 hours. The suspension was vacuum filtered and dried at RT for 20 hours. Trifluoroacetate Type A was obtained (2.18 g), which converted to Trifluoroacetate Type B after storage at ambient conditions for almost 1 month.

Figure 88:
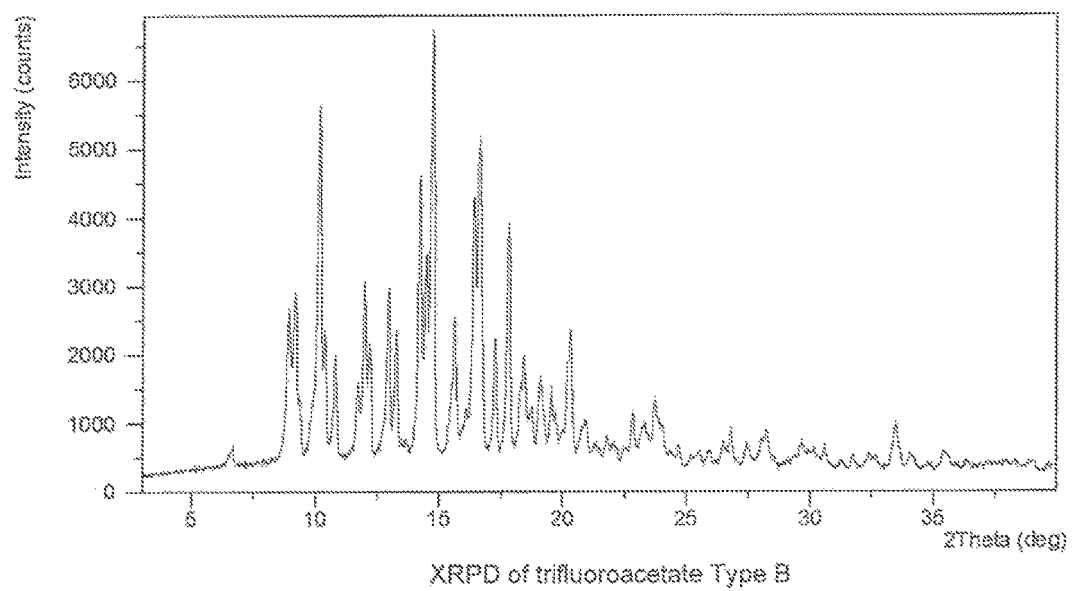
FIG. 88 is an XRPD of SCY-078 Trifluoroacetate Type B from Example 55.
Figure 89:
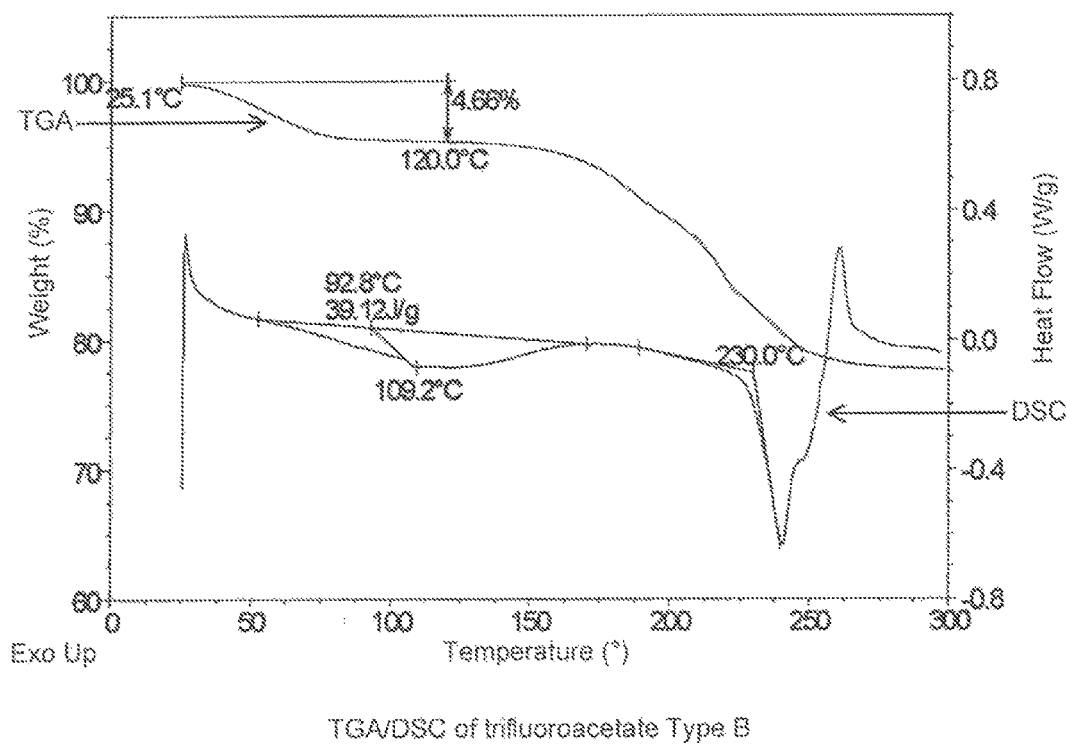
FIG. 89 is a DSC curve and a TGA curve of SCY-078 Trifluoroacetate Type B from Example 55.

SCY-078 Trifluoroacetate Type B is highly crystalline as shown in the XRPD (FIG. 88). A weight loss of 4.7% is observed up to 120° C. in the TGA curve (FIG. 89). The DSC (FIG. 89) shows two endothermic peaks, one at 92.8° C. and 230.0° C. Due to the reversible conversation of Trifluoroacetate Type A and Type B, the molar ratio of Trifluoroacetate Type B (acid:freebase) is postulated to be 1:1, same as Type A.

Figure 90:
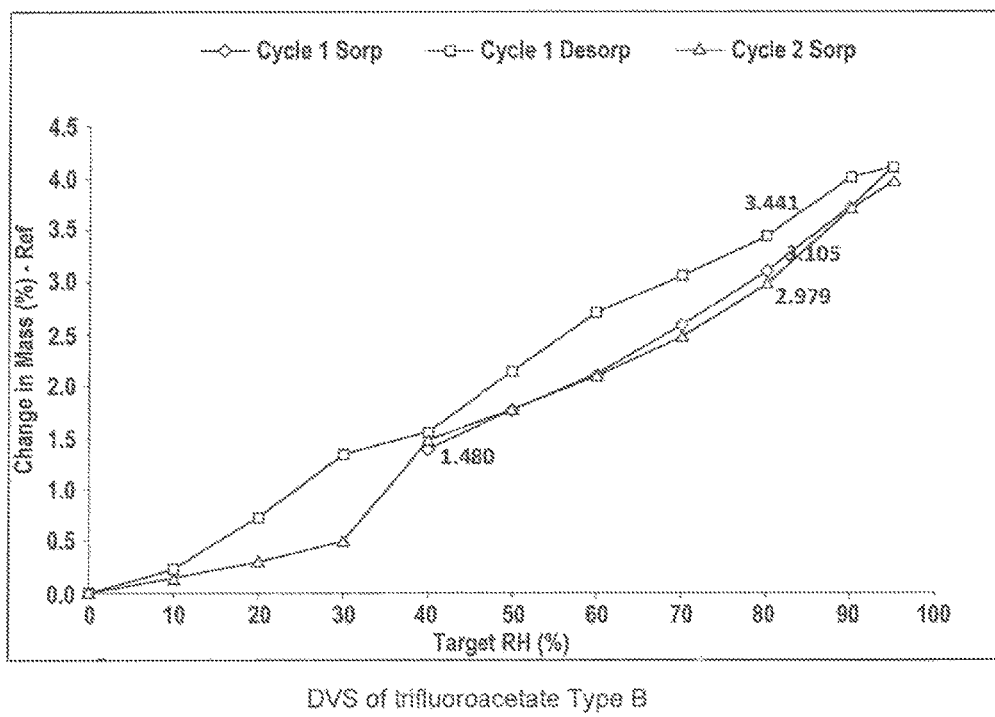
FIG. 90 is a DVS curve of SCY-078 Trifluoroacetate Type B from Example 55.
Figure 91:
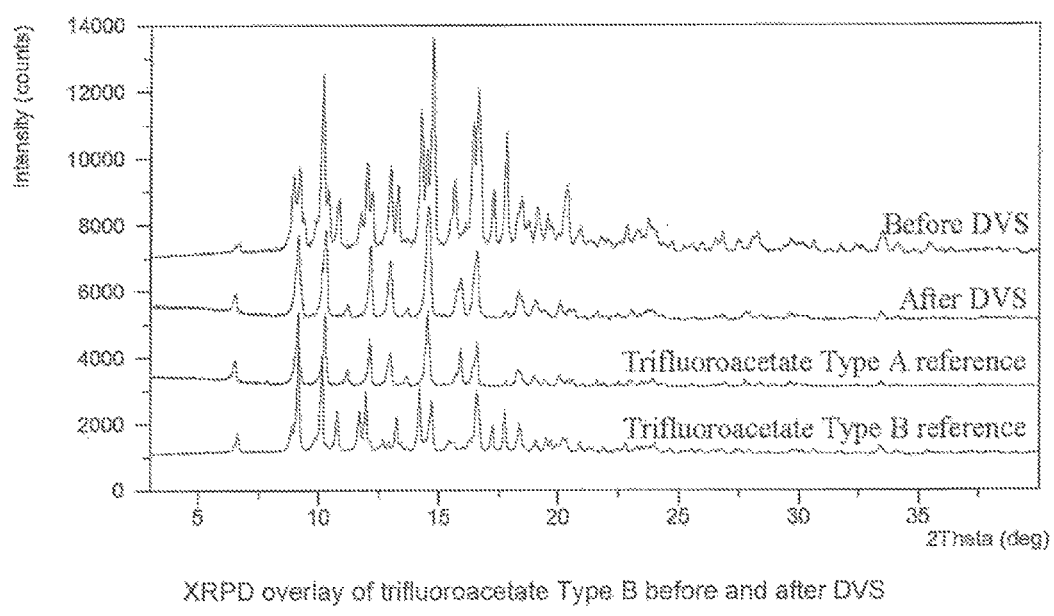
FIG. 91 is an XRPD overlay of SCY-078 Trifluoroacetate Type B before and after DVS from Example 55.

From the DVS (FIG. 90), 3.4 wt % of water uptake was observed at 25° C./80% RH, indicating that Type B is moderately hygroscopic. The DVS revealed potential form change with respect to RH, estimated to be between 30% RH and 40% RH. SCY-078 Trifluoroacetate Type B converted to Type A after DVS as shown in FIG. 91.

Figure 92:
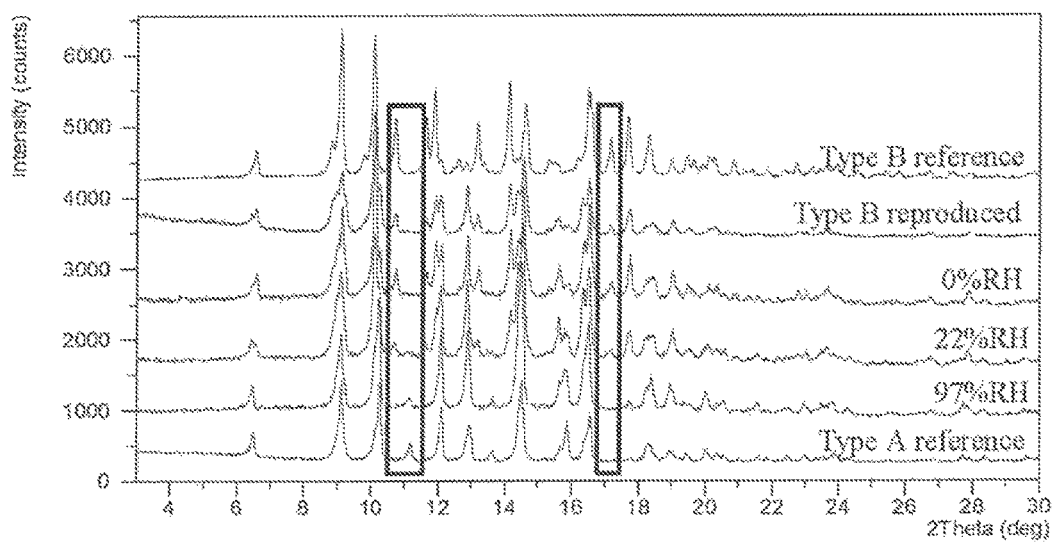
FIG. 92 is an XRPD overlay of SCY-078 Trifluoroacetate Type B at varying relative humidity from Example 55.
Figure 93:
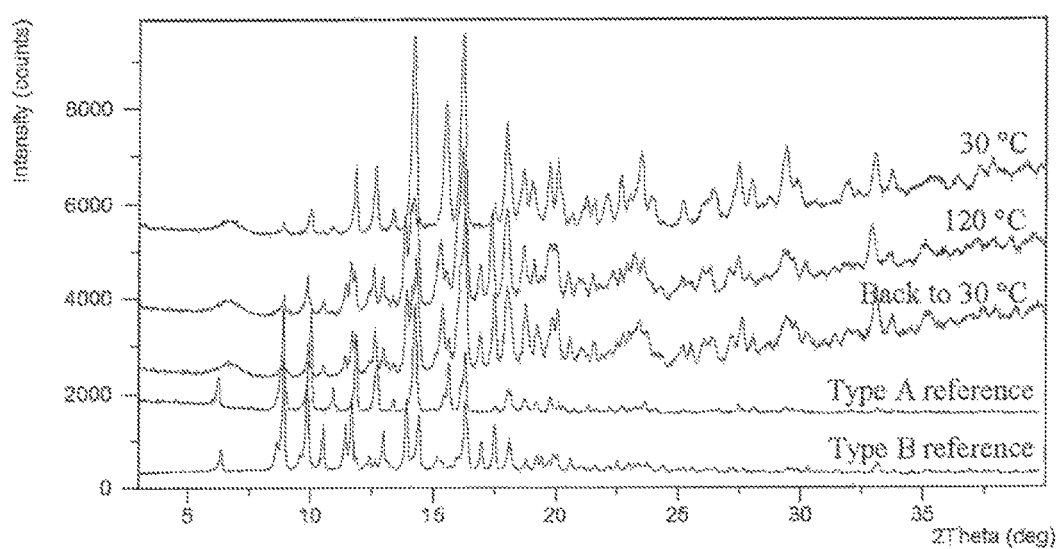
FIG. 93 is a VT-XRPD overlay of SCY-078 Trifluoroacetate Type A from Example 55.

To investigate transition relationship of trifluoroacetate Type A and Type B, both samples were stored in chambers with varying relative humidity to monitor any form change. Summary of trifluoroacetate Type B stored at varying relative humidity is listed in Table 39, and XRPD patterns overlay is displayed in FIG. 92. Trifluoroacetate Type B converted to Type A only at high relative humidity (97% RH) while Type B is stable at low relative humidity (<22% RH). Varying temperature (VT)-XRPD of trifluoroacetate Type A was performed. VT-XRPD patterns overlay is displayed in FIG. 93. Type A converted to Type B after heated to 120° C.

TABLE 39

| Relativity Humidity | 0% | 22% | 97% |
|---|---|---|---|
| TFA Type B | Type B | Type B | Type A |

The XRPD patterns were collected after storage for 24 hours.

Example 56

Preparation and characterization of SCY-078 HCl Type I: 342.7 μL of concentrated HCl (37.5%) was dispersed in 40 mL of acetone. 2.0 mg of SCY-078 freebase Type A (freebase/acid molar ratio=1/1.5) was added. The suspension was settled in a biochemical incubator to perform heat-cooling cycles (50° C.~20° C.) with a magnetic stirring rate of 600 rpm. The suspension was cooled to 5° C. at a rate of 0.1° C./min and aged at 5° C. for 17 hours. The wet cake was vacuum filtered and dried at RT for 20 hours. SCY-078 HCl Type I (2.06 g) was obtained.

Figure 94:
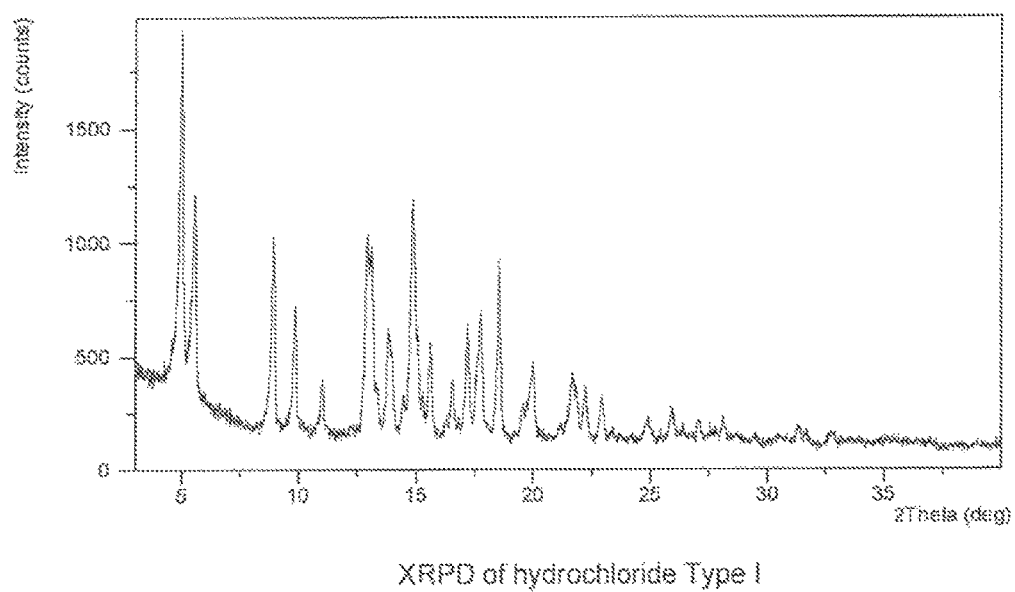
FIG. 94 is an XRPD of SCY-078 HCl Type I from Example 56.
Figure 95:
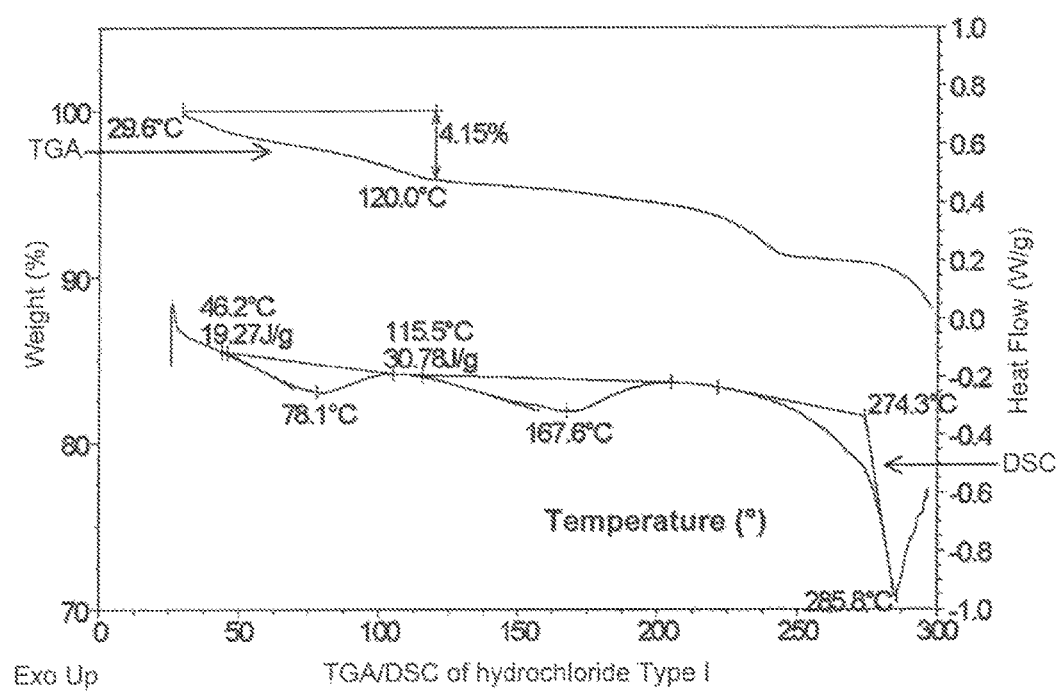
FIG. 95 is a DSC curve and a TGA curves of SCY-078 HCl Type I from Example 56.

SCY-078 HCl Type I is highly crystalline as shown in the XRPD (FIG. 94). A weight loss of 4.2% is observed up to 120° C. in the TGA curve (FIG. 95). The DSC (FIG. 95) shows three endothermic peaks, one at 46.2° C., one at 115.5° C. and one at 274.3° C. The molar ratio of SCY-078 HCl Type I (acid:freebase) was determined to be 1.5:1 via HPLC-IC.

Figure 96:
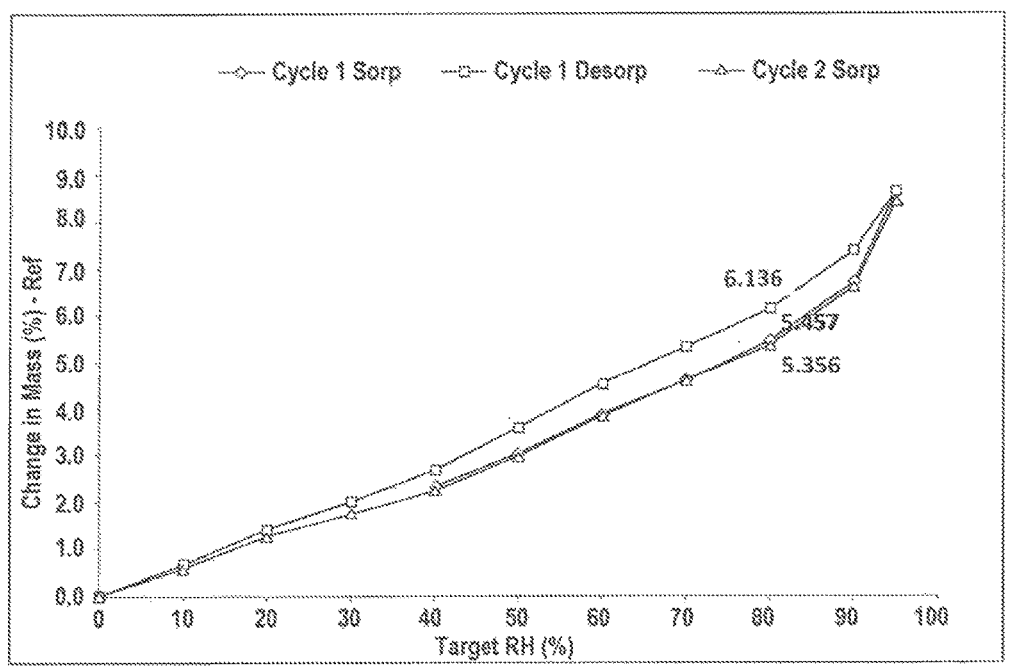
FIG. 96 is a DVS curve of SCY-078 HCl Type I from Example 56.
Figure 97:
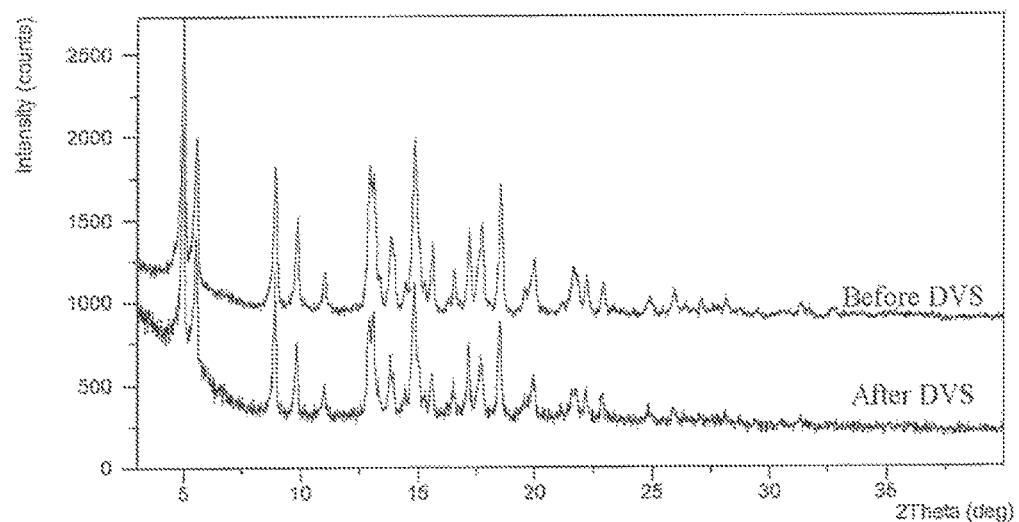
FIG. 97 is an XRPD overlay of SCY-078 HCl Type I before and after DVS from Example 56.

From the DVS (FIG. 96), 6.1 wt % of water uptake was observed at 25° C./80% RH, indicating HCl Type I is moderately hygroscopic. No form change was observed after DVS characterization as shown in FIG. 97.

Example 57

Figure 98:
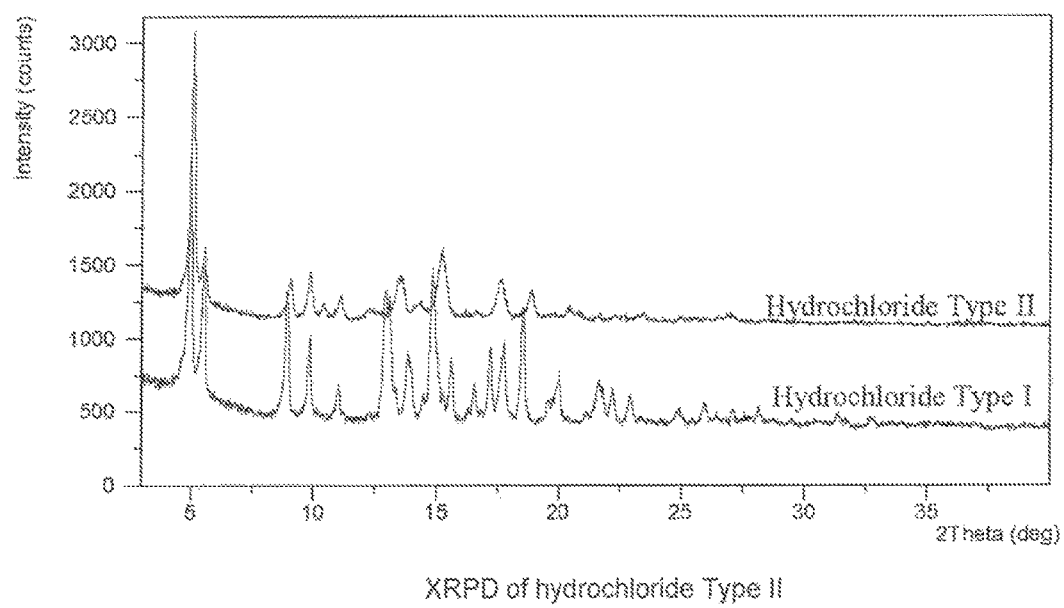
FIG. 98 is an XRPD of SCY-078 HCl Type II from Example 57.
Figure 99:
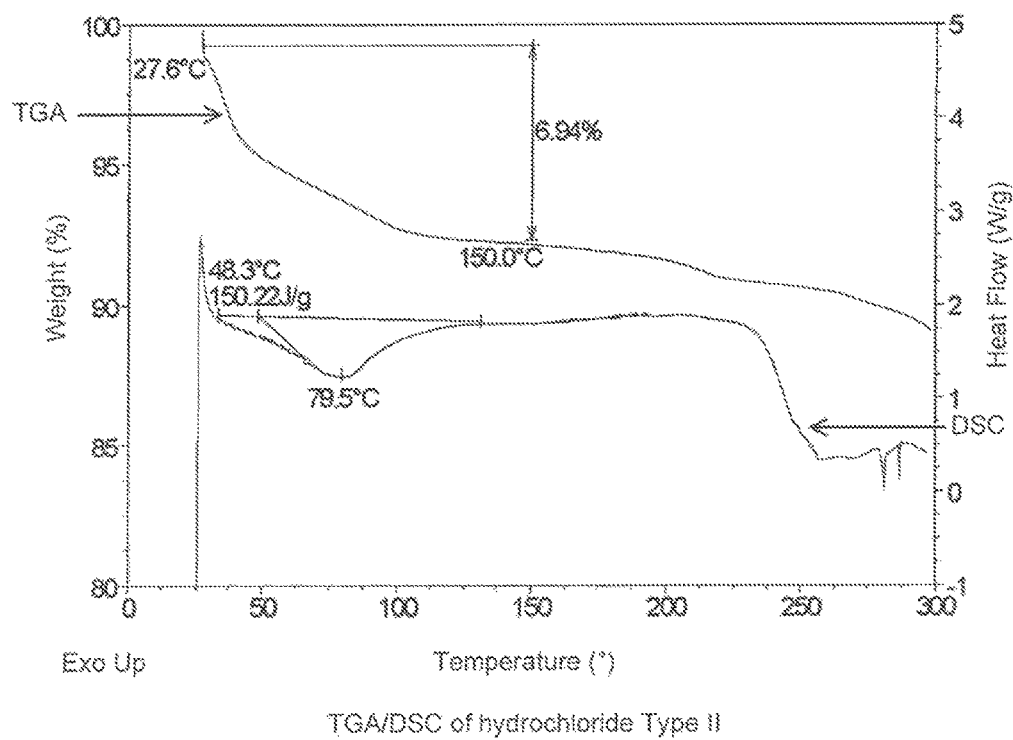
FIG. 99 is a DSC curve and TGA curve of SCY-078 HCl Type II from Example 57.

Preparation and characterization of SCY-078 HCl Type II: SCY-078 HCl Type II was obtained by suspending HCl Type I in acetate buffer (pH 5.5) for 4 hours. The XRPD pattern (FIG. 98) indicates Type II is highly crystalline. The TGA shows that HCl Type II exhibits a weigh loss of 6.9% up to 150° C. and the DSC shows an endothermic peak at 48.3° C. (onset temperature), as shown in FIG. 99.

Example 58

Figure 100:
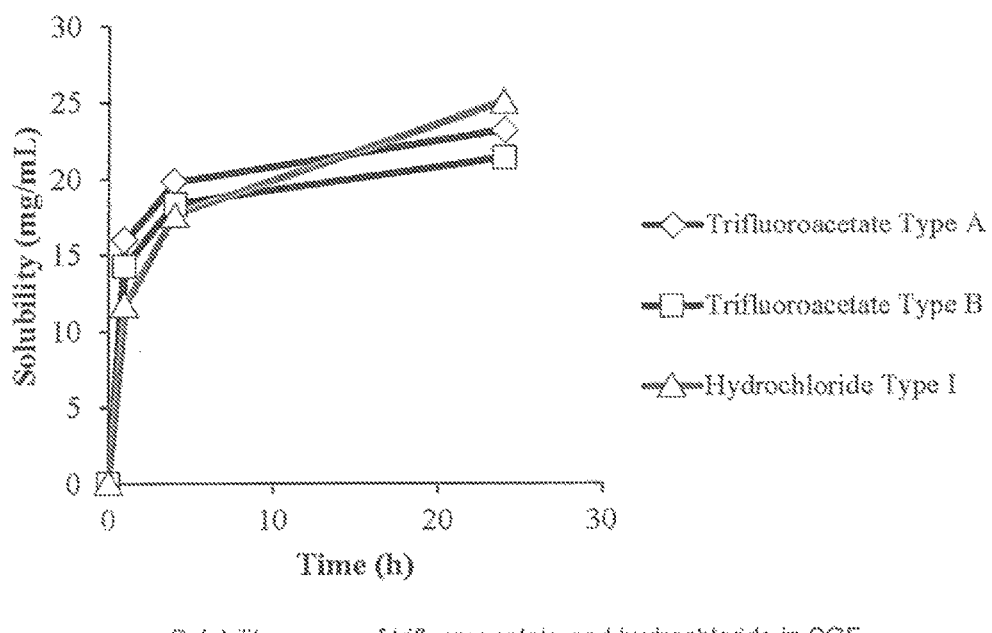
FIG. 100 shows the kinetic solubility curves of SCY-078 Trifluoroacetate Types A and B and SCY-078 HCl Type I in SGF from Example 58.
Figure 101:
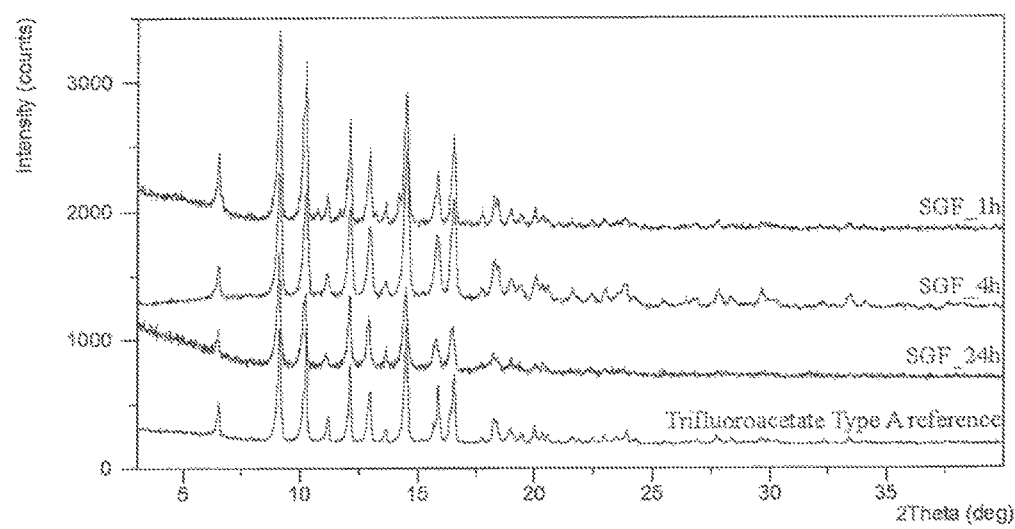
FIG. 101 is an XRPD overlay of SCY-078 Trifluoroacetate Type A in SGF from Example 58.
Figure 102:
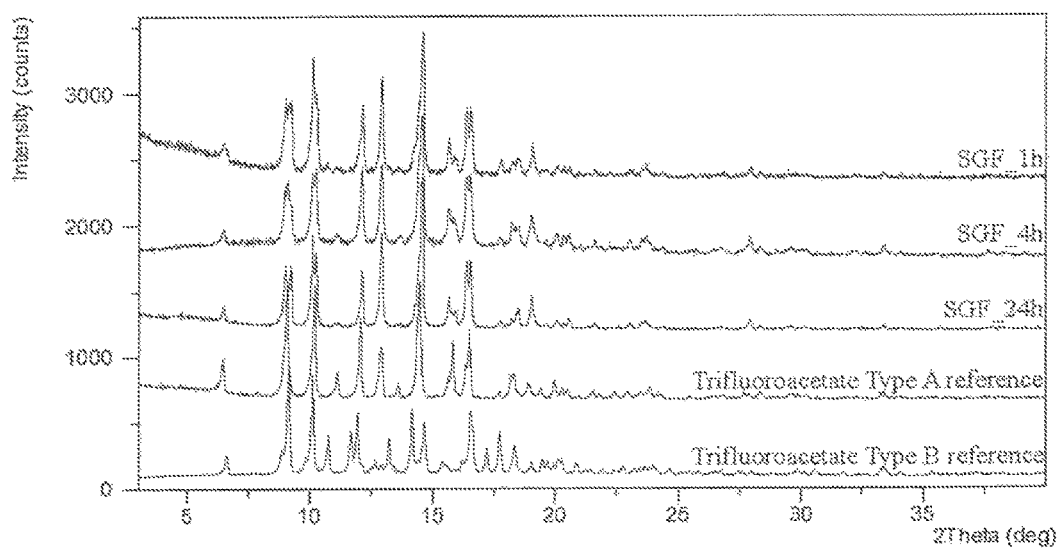
FIG. 102 is an XRPD overlay of SCY-078 Trifluoroacetate Type B in SGF from Example 58.
Figure 103:
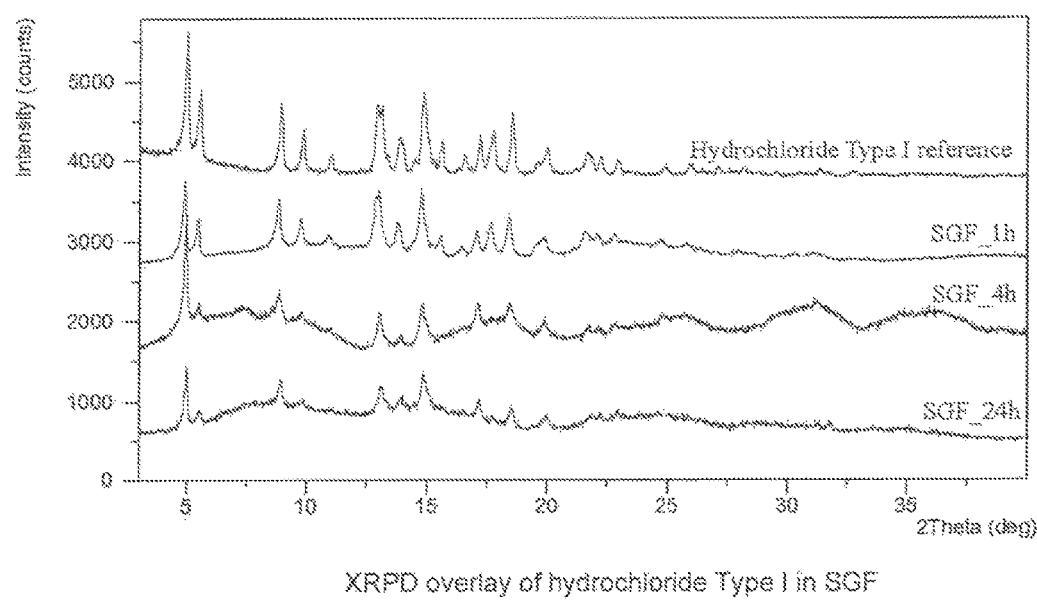
FIG. 103 is an XRPD overlay of SCY-078 HCl Type I in SGF from Example 58.

The solubility of trifluoroacetate Type A, Type B and HCl Type I was measured in SGF at ambient temperature. Approximately 90 mg of solid sample was weighted into a 4-mL centrifuge tube, and 3 mL of SGF buffer was added before leaving the suspension on a rolling incubator (25 r/min). 1.0 mL aliquot of the suspension was sampled for centrifugation (10000 rpm, 3 mins) the supernatant was analyzed by HPLC and pH measurement and solid by XRPD characterization at 1 hr, 4 hr and 24 hrs, respectively. The results are summarized in Table 40 and the solubility curves are displayed in FIG. 100. All three salts exhibit high solubility in SGF (>20 mg/mL at 24 hrs). Trifluoroacetate Type B converted to Type A in SGF after an hour. However, no form change was observed of trifluoroacetate Type A and HCl Type I in SGF. The XRPD patterns of residual solid are shown in FIG. 101, FIG. 102, and FIG. 103.

TABLE 40

| | 1 hr | | | 4 hrs | | | 24 hrs | | |
|---|---|---|---|---|---|---|---|---|---|
| Starting Material | S | pH | Form change | S | pH | Form change | S | pH | Form change |
| TFA Type A | 15.9 | 2.2 | No | 19.8 | 2.2 | No | 23.2 | 2.1 | No |
| TFA Type B | 14.3 | 2.0 | Yes (Type A) | 18.4 | 2.0 | Yes (Type A) | 21.4 | 1.8 | Yes (Type A) |
| HCl Type I | 11.7 | 1.7 | No | 17.7 | 1.9 | No | 25.1 | 1.8 | No |

S: solubility, mg/mL.

Example 59

Figure 104:
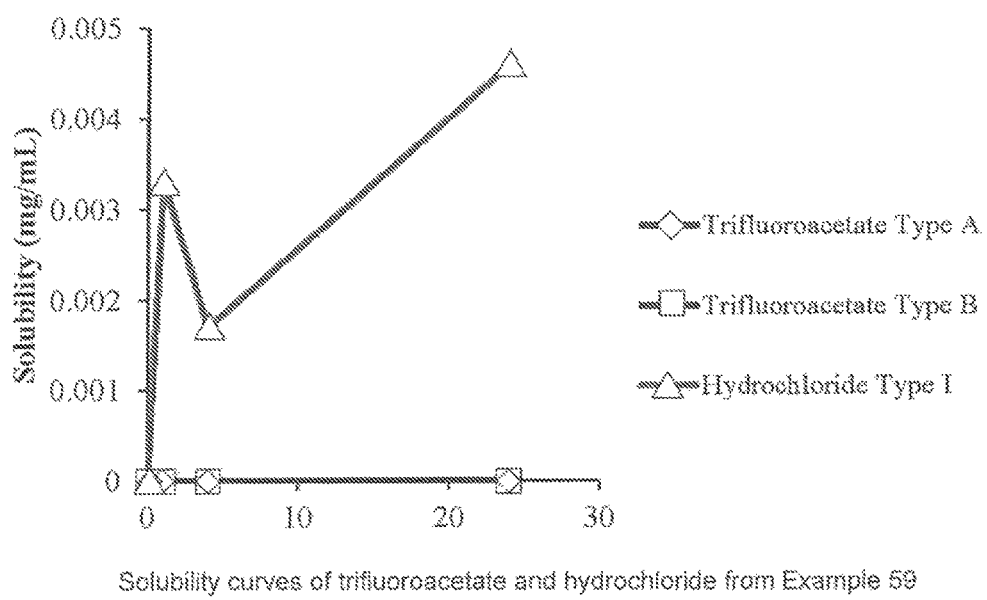
FIG. 104 shows the kinetic solubility curves of SCY-078 Trifluoroacetate Types A and B and SCY-078 HCl Type I from Example 59.
Figure 105:
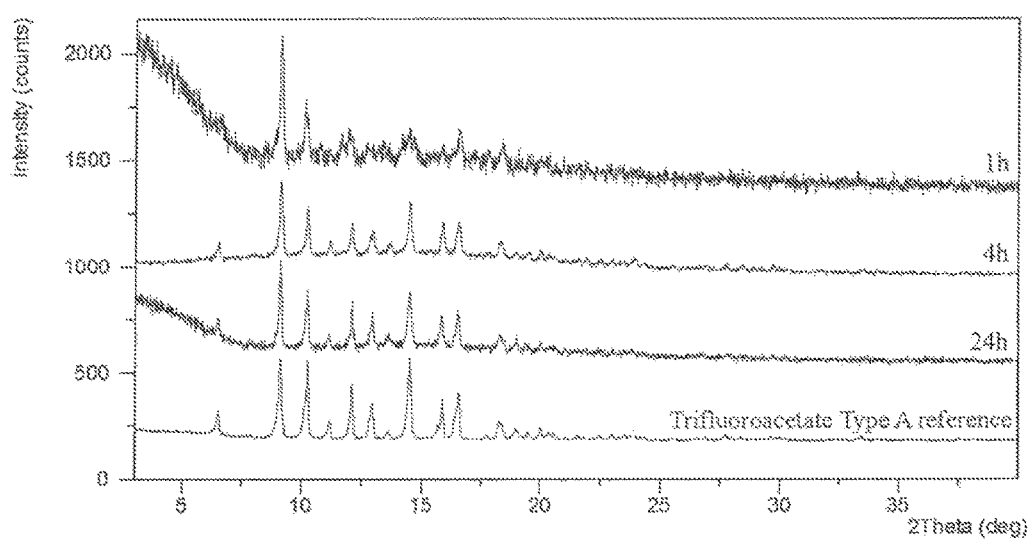
FIG. 105 is an XRPD overlay of SCY-078 Trifluoroacetate Type A from Example 59.
Figure 106:
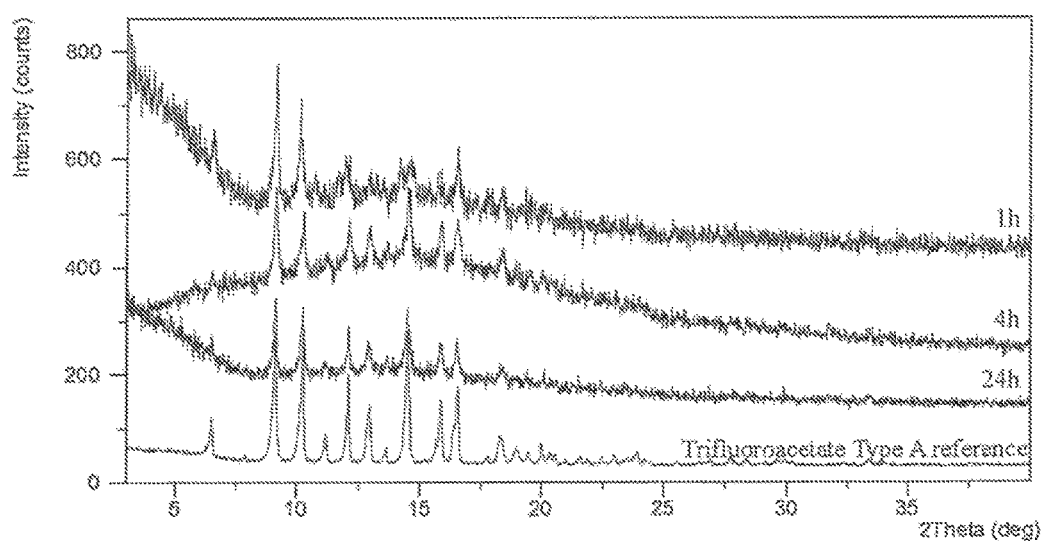
FIG. 106 is an XRPD overlay of SCY-078 Trifluoroacetate Type B from Example 59.
Figure 107:
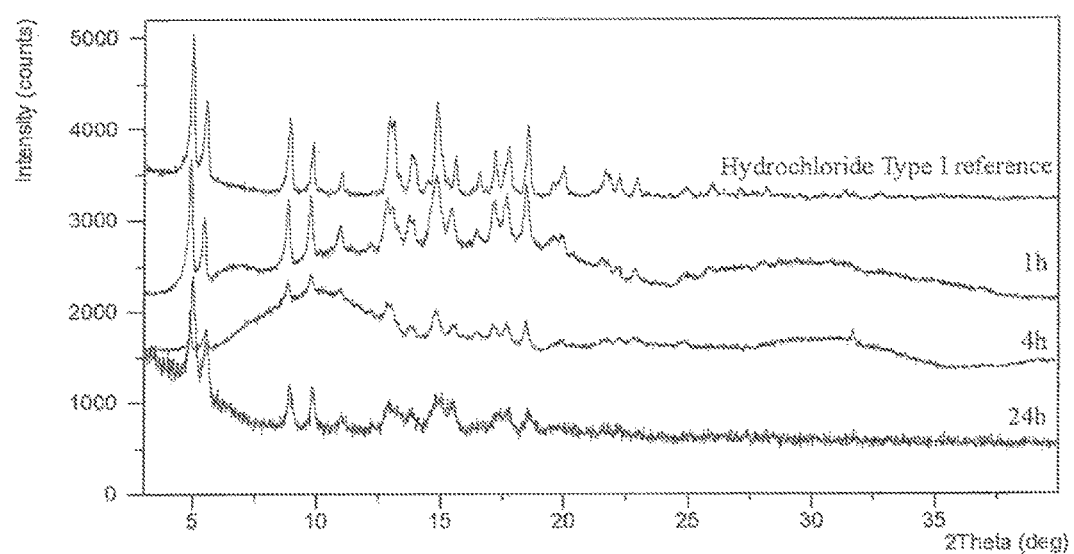
FIG. 107 is an XRPD overlay of SCY-078 HCl Type I from Example 59.

The solubility of trifluoroacetate Type A, Type B and hydrochloride Type I was measured in the FaSSIF alternative media at ambient temperature. Approximately 15 mg of solid sample was weighted into a 4-mL plastic tube, and 3 mL of the media was added before leaving the suspension on a rolling incubator (25 r/min). 1.0 mL aliquot of the suspension was sampled for centrifugation with the supernatant submitted for HPLC and pH measurement and solid for XRPD characterization at 1 hr, 4 hr and 24 hrs, respectively. The results are summarized in Table 41 and the solubility curves are displayed in FIG. 104. All three salts exhibit poor solubility in the FaSSIF alternative media (<0.01 mg/mL at 24 the kinetic hrs). Trifluoroacetate Type B converted to Type A after an hour. However, no form change was observed of trifluoroacetate Type A and HCl Type I. The XRPD patterns of residual solid are shown in FIG. 105, FIG. 106, and FIG. 107.

TABLE 41

| | 1 hr | | | 4 hrs | | | 24 hrs | | |
|---|---|---|---|---|---|---|---|---|---|
| Starting Material | S | pH | Form change | S | pH | Form change | S | pH | Form change |
| TFA Type A | <LOD | 6.5 | No | <LOD | 6.4 | No | <LOD | 6.4 | No |
| TFA Type B | <LOD | 6.4 | Yes (Type A) | <LOD | 6.4 | Yes (Type A) | <LOD | 6.3 | Yes (Type A) |
| HCl Type I | 0.0033 | 5.0 | No | 0.0017 | 5.3 | No | 0.0046 | 5.1 | No |

S: solubility, mg/mL; LOD: 0.00064 mg/mL.

Example 60

Figure 108:
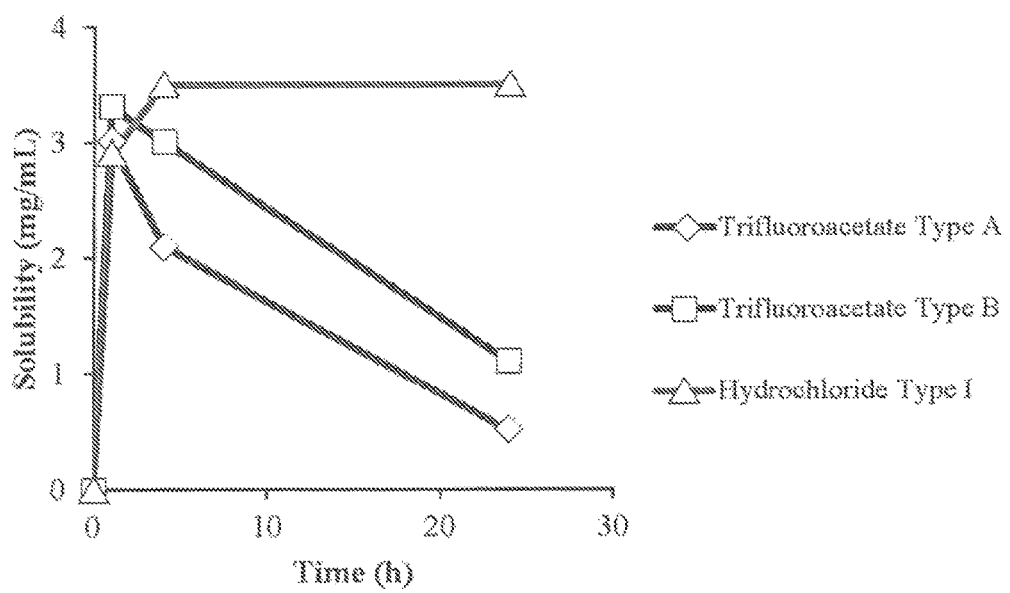
FIG. 108 shows the kinetic solubility curves of SCY-078 Trifluoroacetate Types A and B and SCY-078 HCl Type I from Example 60.
Figure 109:
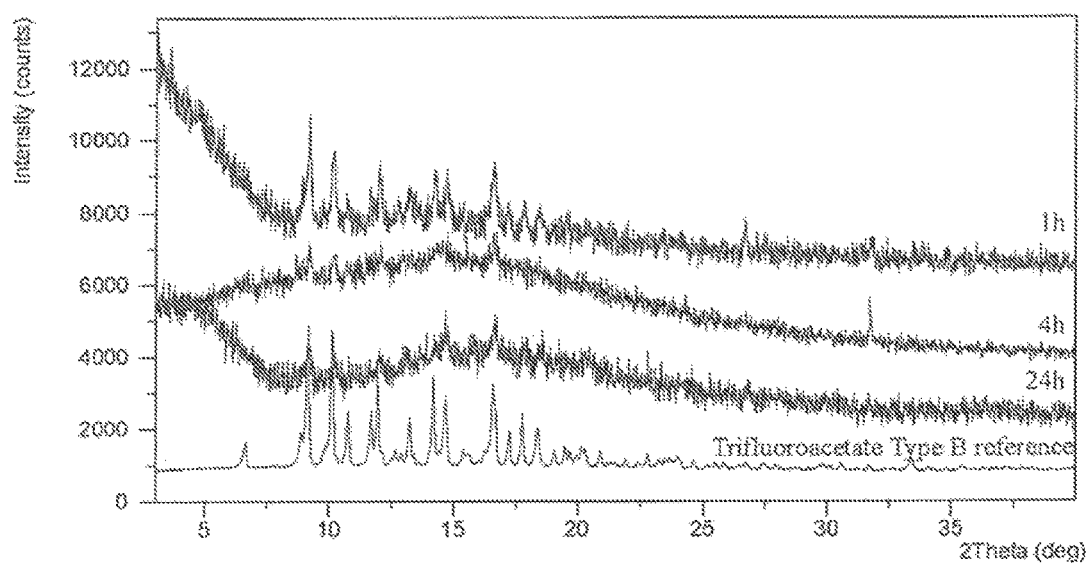
FIG. 109 is an XRPD overlay of SCY-078 Trifluoroacetate Type A from Example 60.
Figure 110:
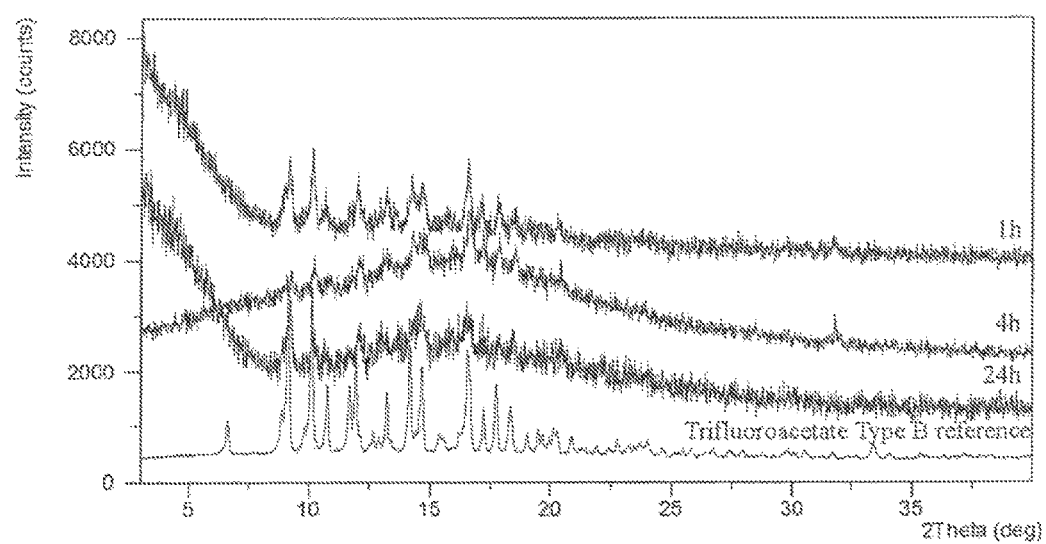
FIG. 110 is an XRPD overlay of SCY-078 Trifluoroacetate Type B from Example 60.
Figure 111:
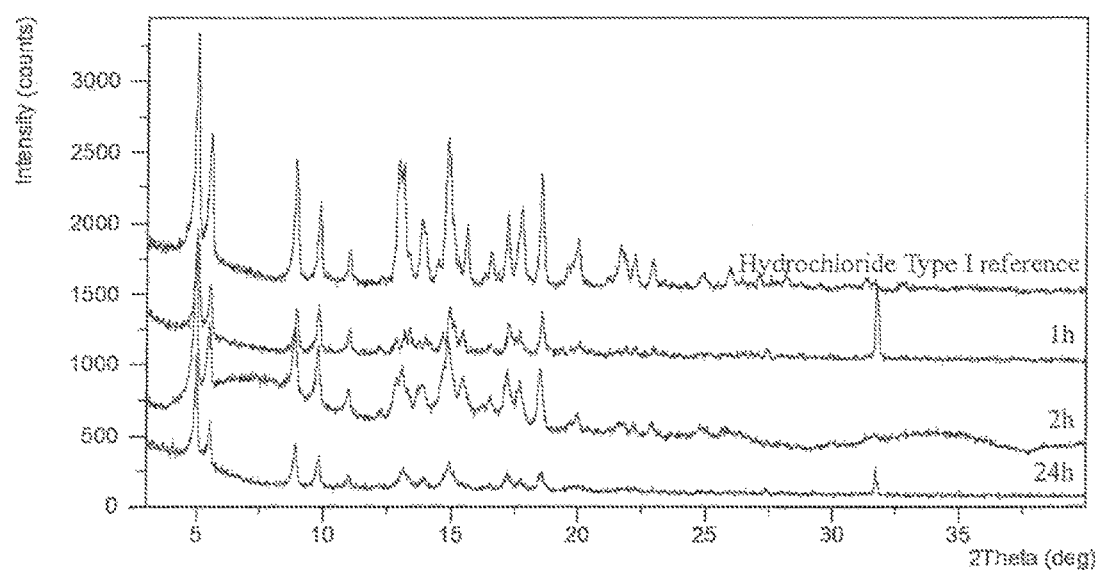
FIG. 111 is an XRPD overlay of SCY-078 HCl Type I from Example 60.

The solubility of trifluoroacetate Type A, Type B and HCl Type I was measured in the FeSSIF alternative media at ambient temperature. Approximately 36 mg of solid sample was weighted into a 4-mL plastic tube, and 3 mL of the media was added before leaving the suspension on a rolling incubator (25 r/min). 1.0 mL aliquot of the suspension was sampled for centrifugation with the supernatant submitted for HPLC and pH measurement and solid for XRPD characterization at 1 hr, 4 hr and 24 hrs, respectively. The results are summarized in Table 42 and the solubility curves are displayed in FIG. 108. All three salts exhibit a solubility of ~3 mg/mL at first one hour. HCl Type I exhibits an equilibrium solubility of 3.5 mg/mL at 24 hrs, while trifluoroacetate (both Type A and Type B) exhibit a decreasing solubility after an hour. Trifluoroacetate Type A converted to Type B after an hour. However, no form change was observed of trifluoroacetate Type B and hydrochloride Type I. The XRPD patterns of residual solid were included in FIG. 109, FIG. 110, and FIG. 111.

TABLE 42

| Starting Material | 1 hr | | | 4 hrs | | | 24 hrs | | |
|---|---|---|---|---|---|---|---|---|---|
| | S | pH | Form change | S | pH | Form change | S | pH | Form change |
| TFA Type A | 3.0 | 5.0 | Yes (Type B) | 2.1 | 5.0 | Yes (Type B) | 0.5 | 5.0 | Yes (Type B) |
| TFA Type B | 3.3 | 5.0 | No | 3.0 | 5.0 | No | 1.1 | 4.9 | No |
| HCl Type I | 2.9 | 4.8 | No | 3.5 | 4.8 | No | 3.5 | 4.9 | No |

S: solubility, mg/mL.

Example 61

Figure 112:
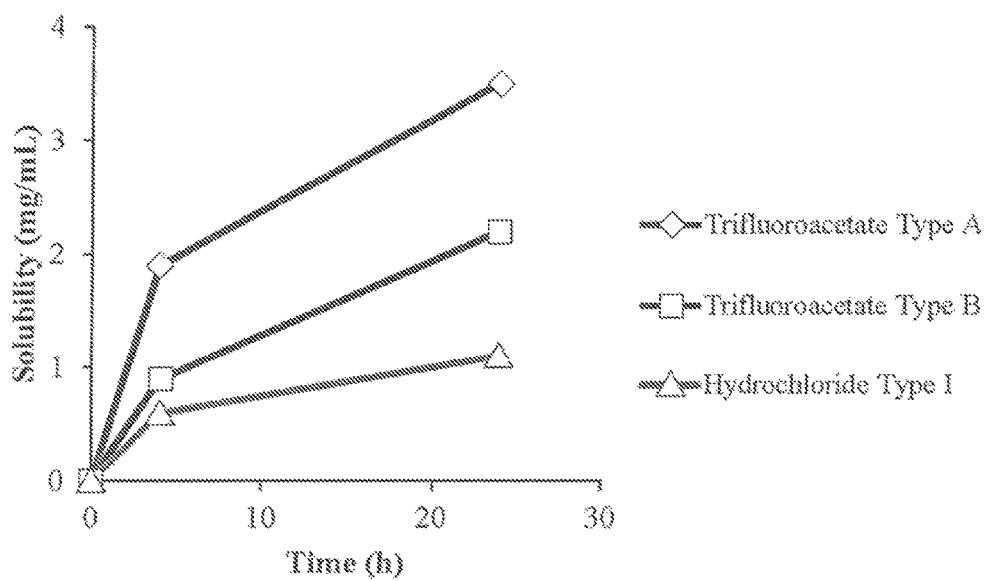
FIG. 112 shows the kinetic solubility curves of SCY-078 Trifluoroacetate Types A and B and SCY-078 HCl Type I from Example 61.
Figure 113:
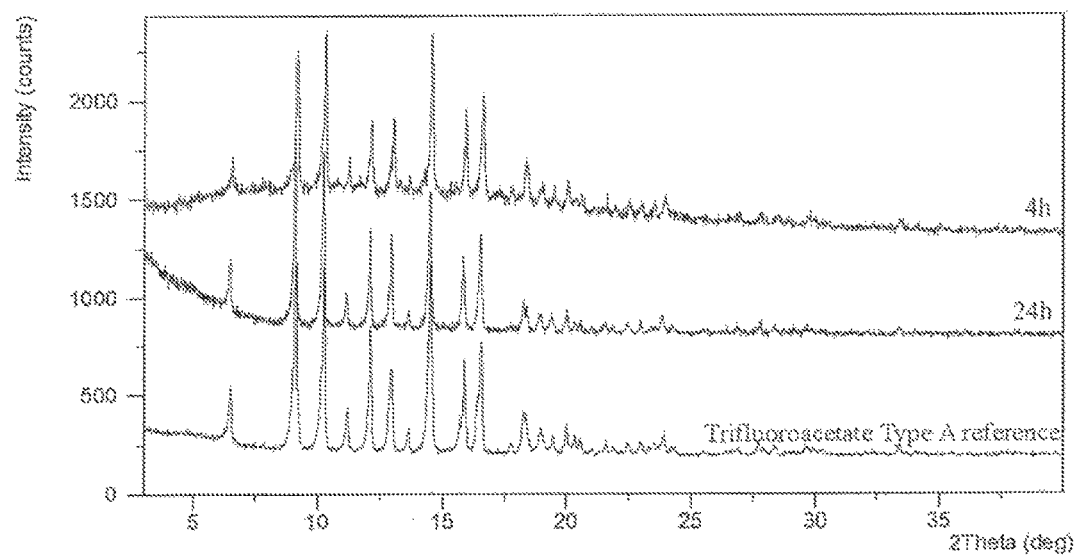
FIG. 113 is an XRPD overlay of SCY-078 Trifluoroacetate Type A from Example 61.
Figure 114:
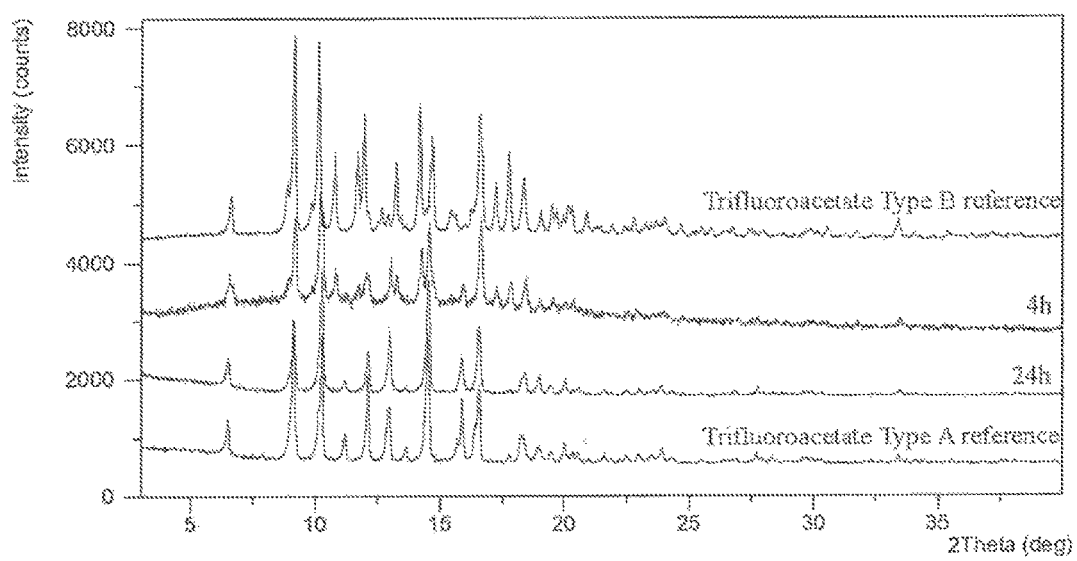
FIG. 114 is an XRPD overlay of SCY-078 Trifluoroacetate Type B from Example 61.
Figure 115:
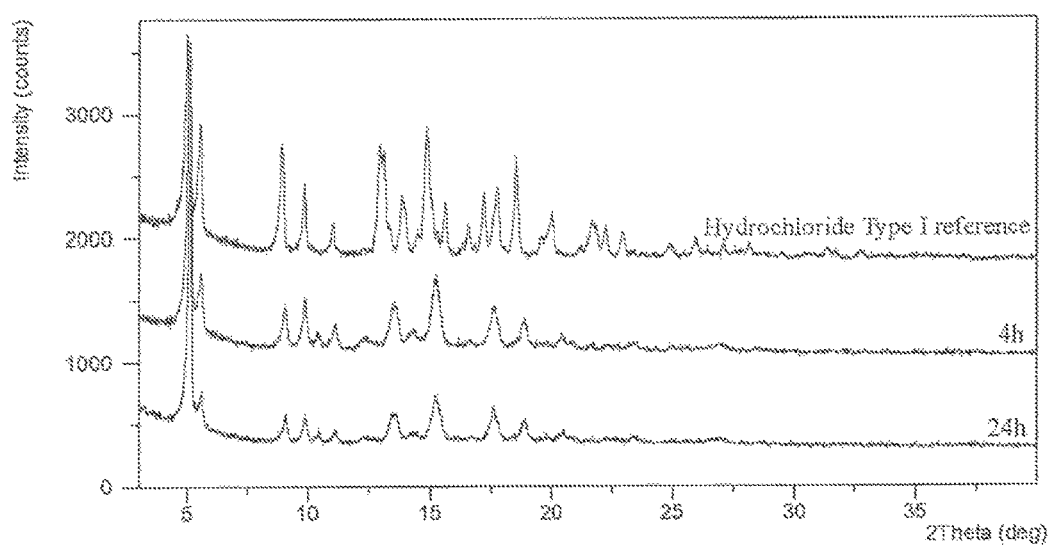
FIG. 115 is an XRPD overlay of SCY-078 HCl Type I from Example 61.

The solubility of trifluoroacetate Type A, Type B and HCl Type I was measured in acetate buffer (pH 5.5) at ambient temperature. Approximately 15 mg of solid sample was weighted into a 4-mL plastic tube, and 3 mL of acetate pH 5.5 buffer was added before leaving the suspension on a rolling incubator (25 r/min). 1.0 mL aliquot of the suspension was sampled for centrifugation with the supernatant submitted for HPLC and pH measurement and solid for XRPD characterization at 4 hr and 24 hrs, respectively. The results are summarized in Table 43 and the solubility curves are displayed in FIG. 112. Trifluoroacetate Type A exhibits higher solubility in acetate pH 5.5 buffer, and no form change was observed. However, Type B converted to Type A in acetate pH 5.5 buffer. While HCl Type I exhibits lower solubility in acetate pH 5.5 buffer comparing with trifluoroacetate, and HCl Type I converted to Type II in acetate pH 5.5 buffer. The XRPD patterns of residual solid were included in FIG. 113, FIG. 114, and FIG. 115.

TABLE 43

| Starting Material | 4 hrs | | | 24 hrs | | |
|---|---|---|---|---|---|---|
| | S | pH | Form change | S | pH | Form change |
| TFA Type A | 1.9 | 5.5 | No | 3.5 | 5.4 | No |
| TFA Type B | 0.89 | 5.4 | Yes (Type A + B) | 2.2 | 5.2 | Yes (Type A) |
| HCl Type I | 0.59 | 4.8 | Yes (Type II) | 1.1 | 4.9 | Yes (Type II) |

S: solubility, mg/mL.

Example 62

Figure 116:
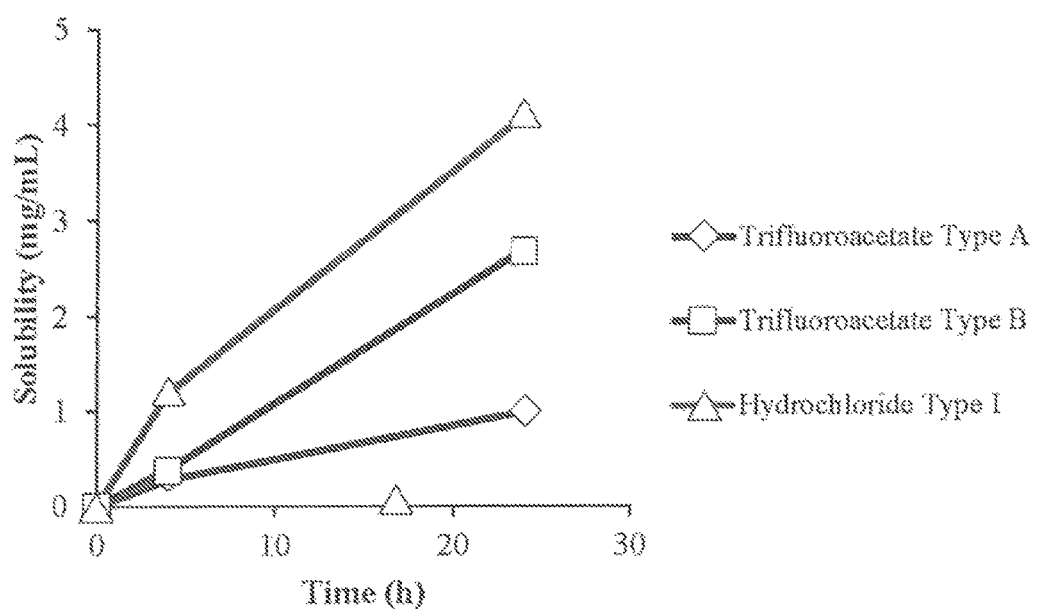
FIG. 116 shows the kinetic solubility curves of SCY-078 Trifluoroacetate Types A and B and SCY-078 HCl Type I from Example 62.
Figure 117:
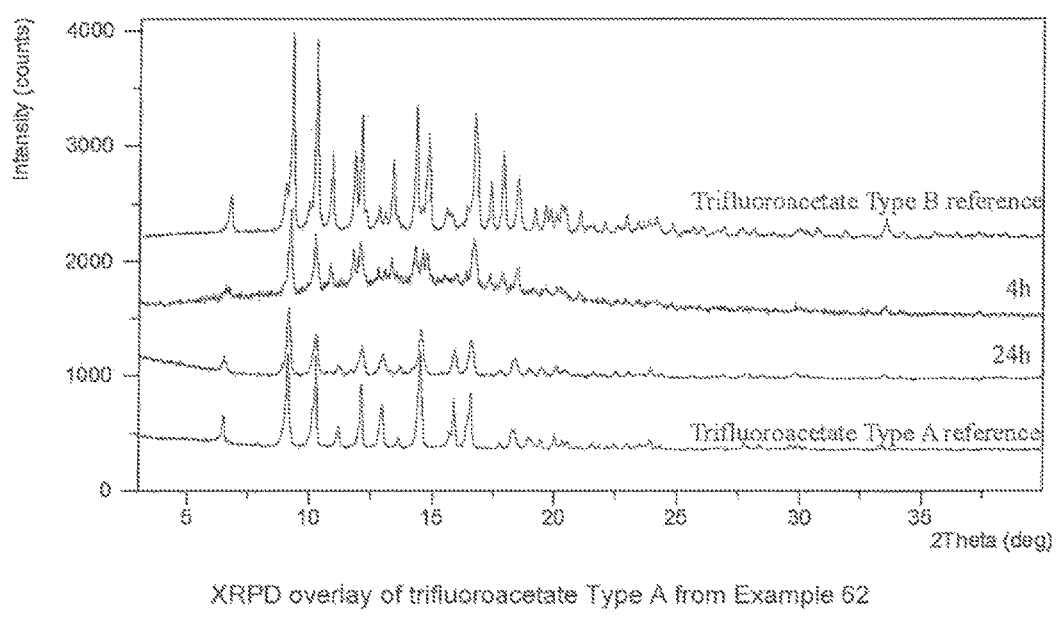
FIG. 117 is an XRPD overlay of SCY-078 Trifluoroacetate Type A from Example 62.
Figure 118:
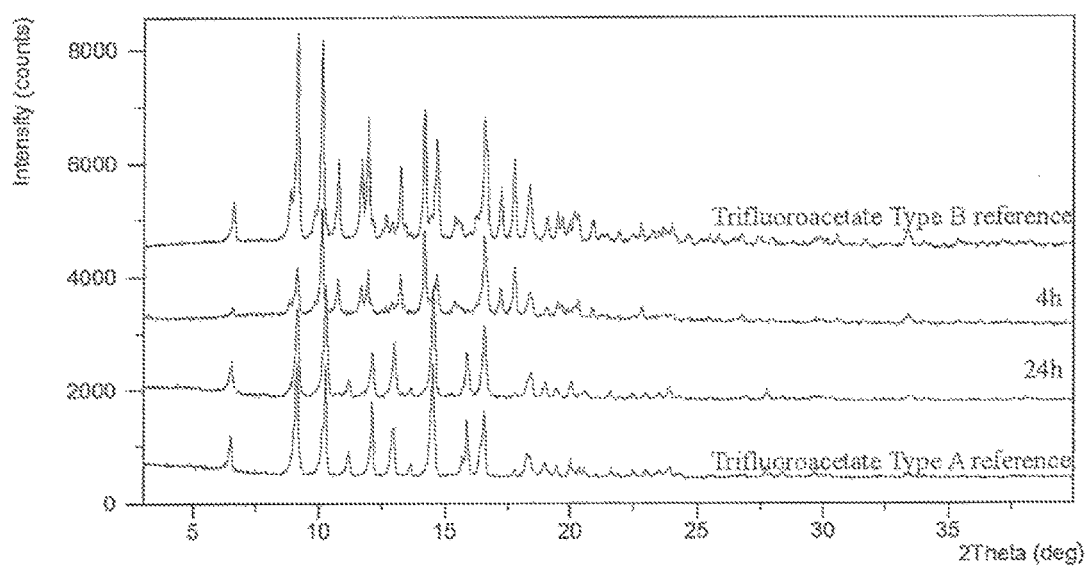
FIG. 118 is an XRPD overlay of SCY-078 Trifluoroacetate Type B from Example 62.
Figure 119:
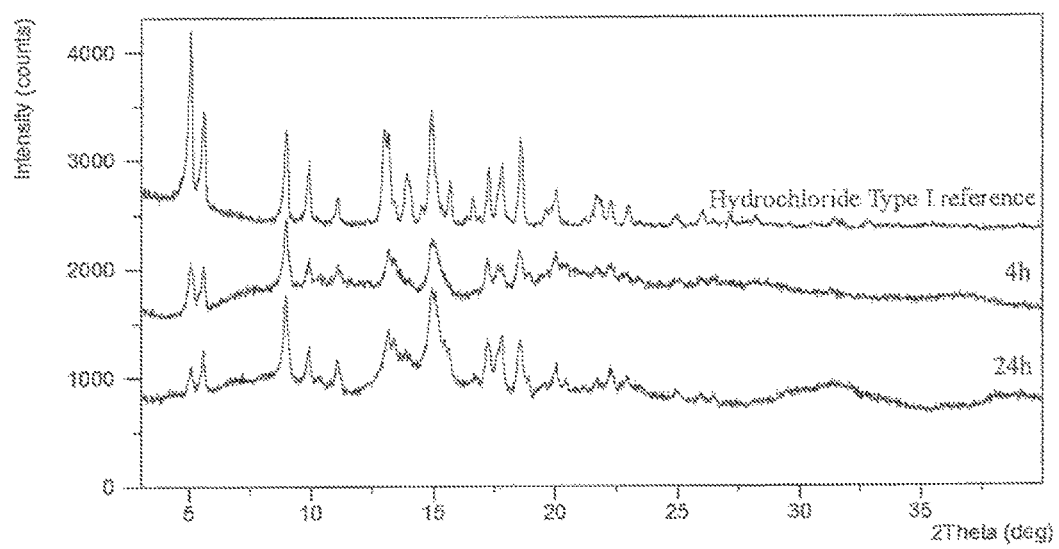
FIG. 119 is an XRPD overlay of SCY-078 HCl Type I from Example 62.
Figure 120:
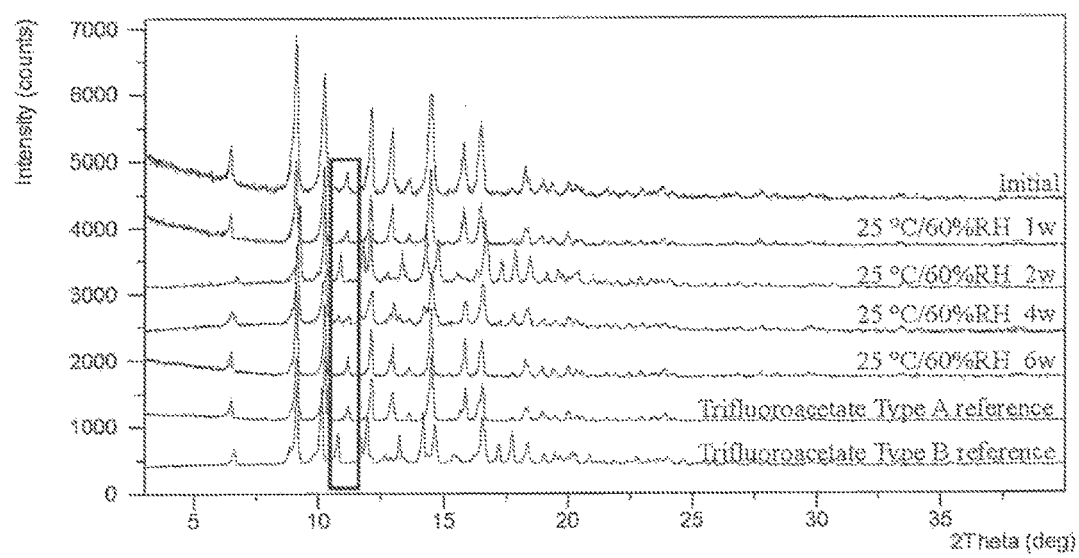
Figure 121:
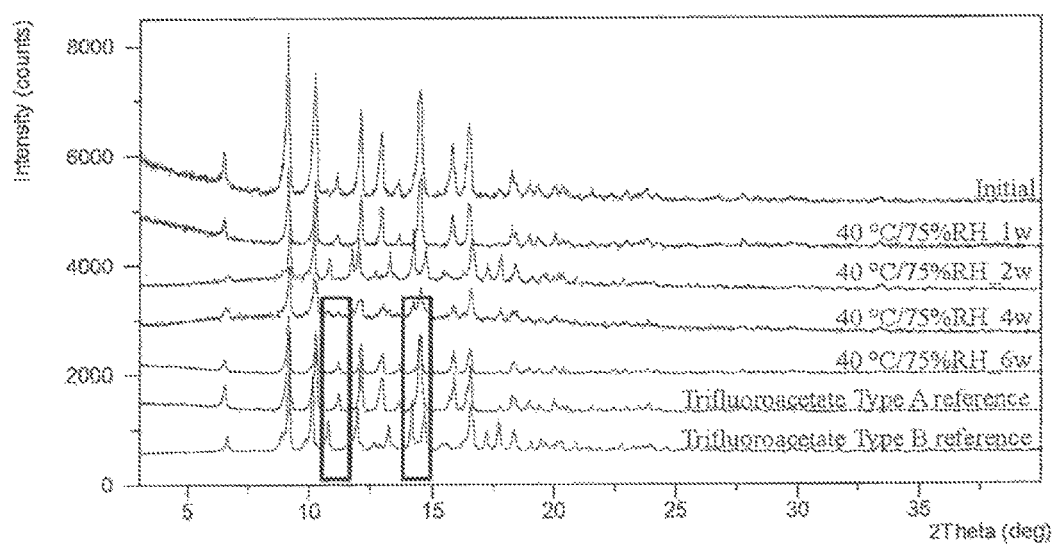
Figure 122:
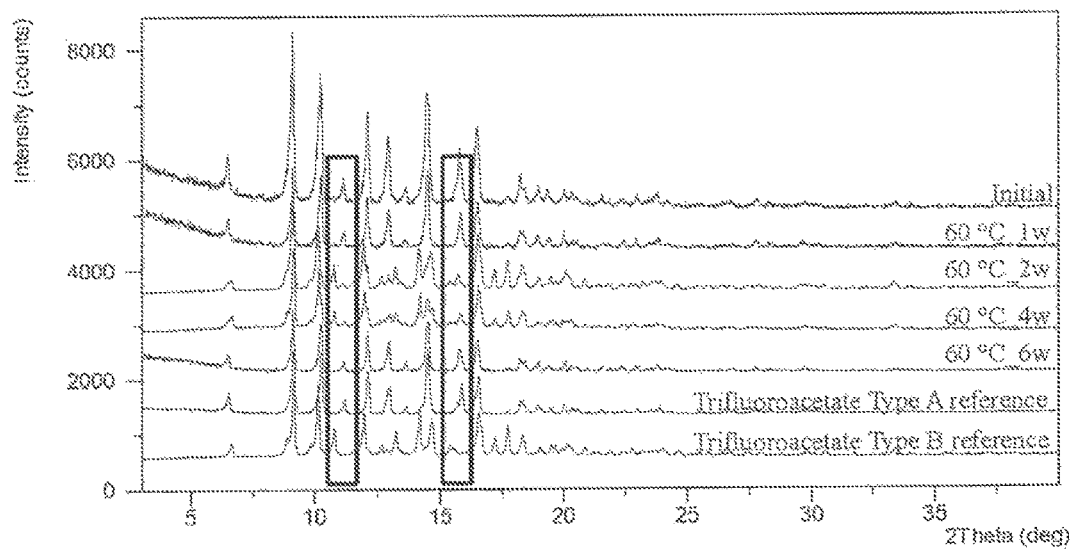
Figure 123:
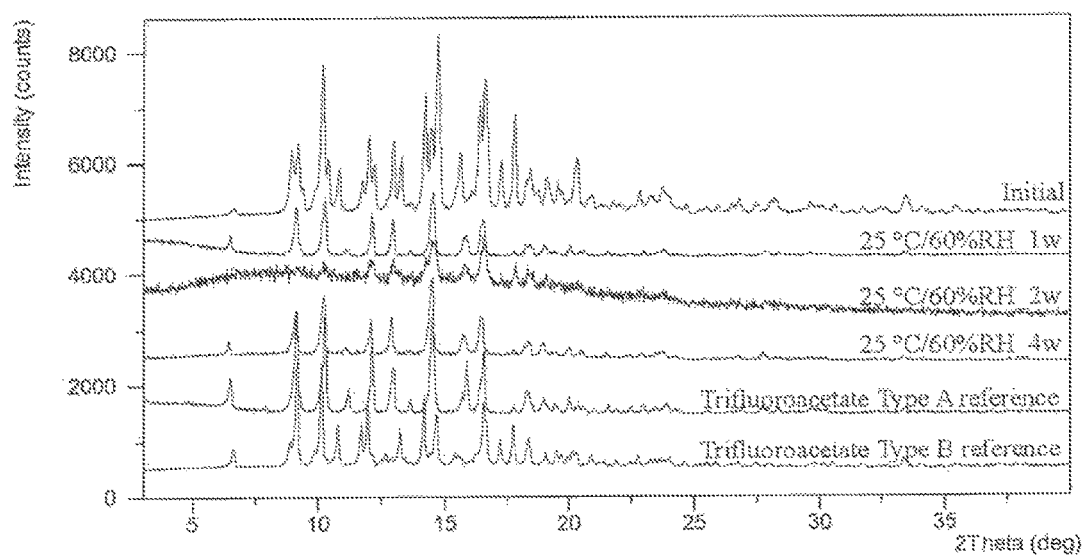
Figure 124:
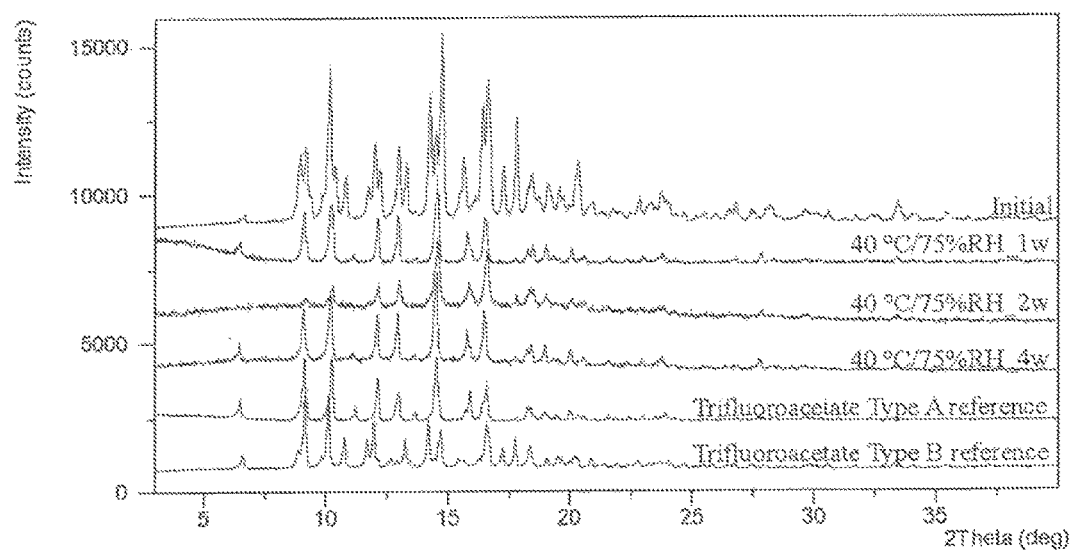
Figure 125:
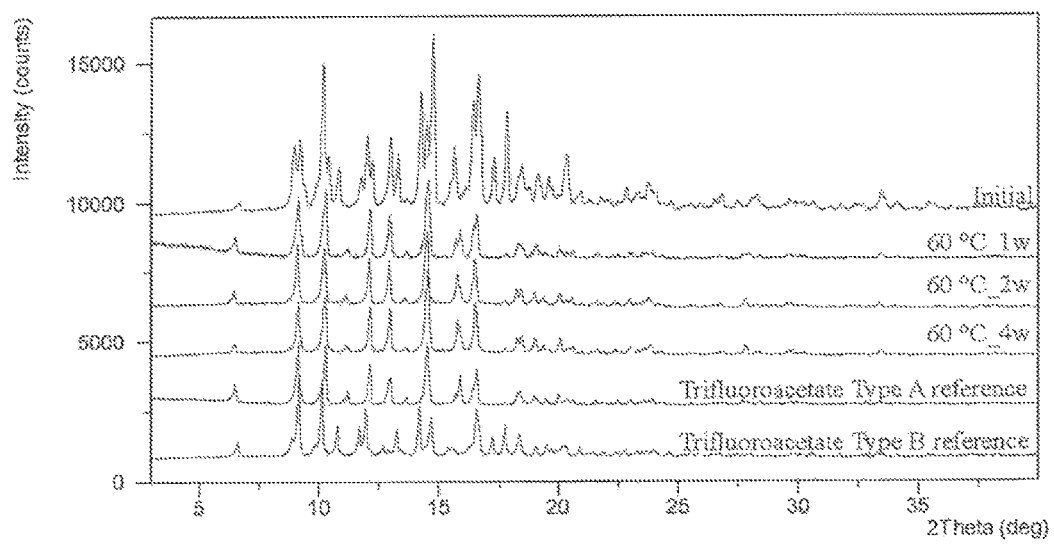
Figure 126:
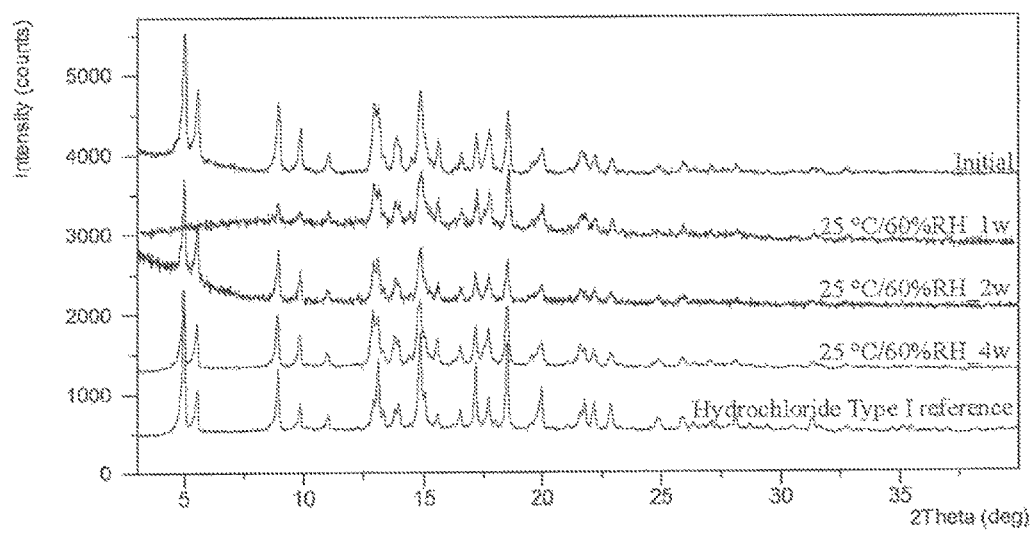
Figure 127:
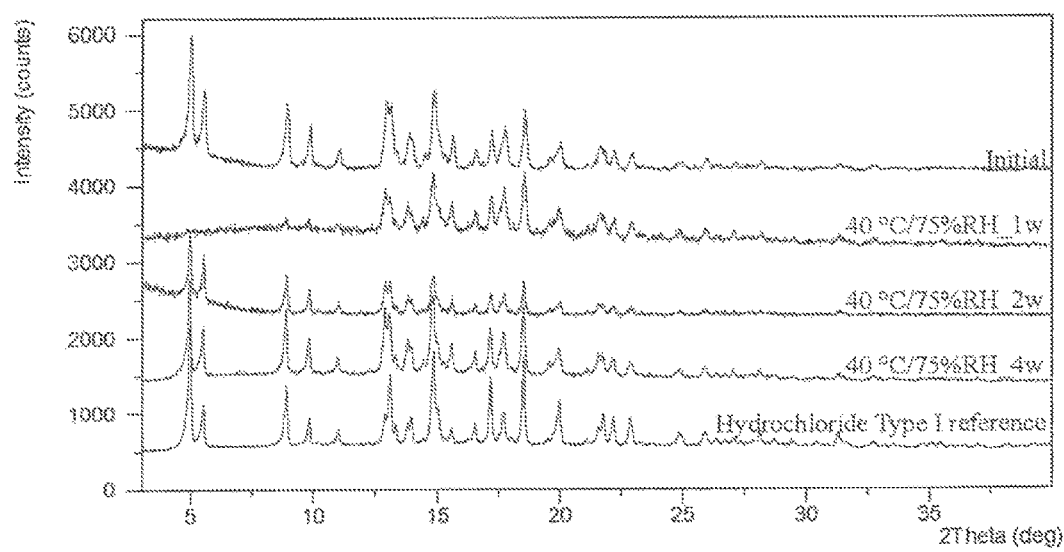
Figure 128:
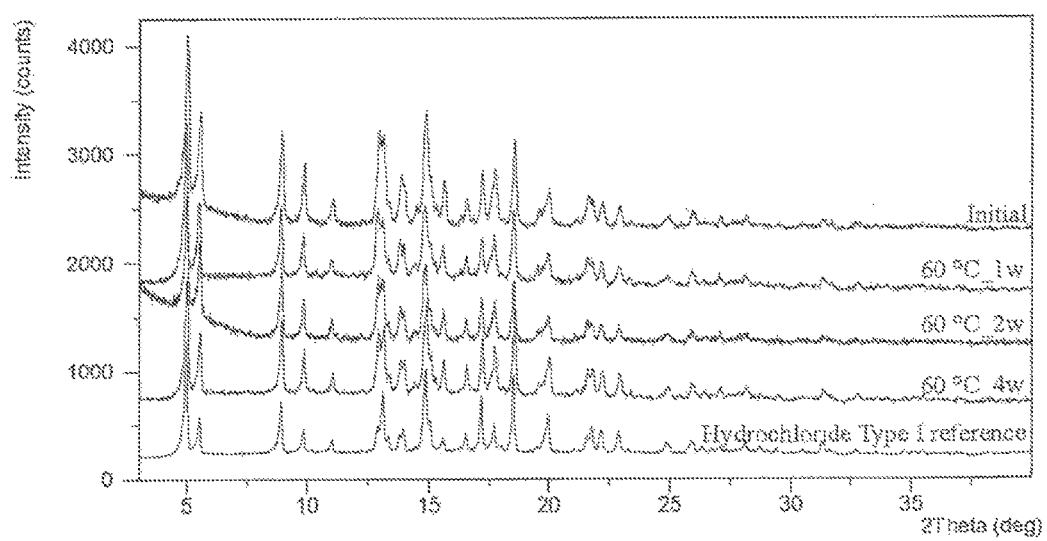

The solubility of trifluoroacetate Type A, Type B and HCl Type I was measured in the phosphate (pH 6.0) alternative media at ambient temperature. Approximately 15 mg of solid sample was weighted into a 4-mL plastic tube, and 3 mL of media was added before leaving the suspension on a rolling incubator (25 r/min). 1.0 mL aliquot of the suspension was sampled for centrifugation with the supernatant for HPLC and pH measurement and solid for XRPD characterization at 4 hr and 24 hrs, respectively. The results are summarized in Table 44, and the solubility curves are displayed in FIG. 116. HCl Type I exhibits higher solubility, while trifluoroacetate Type A exhibits lower solubility. Trifluoroacetate Type A firstly converted to Type B at 4 hrs and back to Type A at 24 hrs, while Type B converted to Type A at 24 hrs. No form change was observed of HCl Type I. The XRPD patterns of residual solid were included in FIG. 117, FIG. 118, and FIG. 119.

TABLE 44

| Starting Material | 4 hrs | | | 24 hrs | | |
|---|---|---|---|---|---|---|
| | S | pH | Form change | S | pH | Form change |
| TFA Type A | 0.28 | 5.8 | Yes (Type B) | 0.99 | 5.5 | Back to Form A |
| TFA Type B | 0.39 | 5.3 | No | 2.7 | 4.9 | Yes (Type A) |
| HCl Type I | 1.2 | 3.9 | No | 4.1 | 4.4 | No |

S: solubility, mg/mL.

Example 63

Physical and chemical stability evaluation of trifluoroacetate Type A, trifluoroacetate Type B, and HCl Type I was performed at 25° C./60% RH, 40° C./75% RH and 60° C. for 1, 2, 4 and 8 weeks. In the experiments, approximately 20 mg of solid was placed into a 1.5-mL glass vial. The vials were stored under 25° C./60% RH (uncapped), 40° C./75% RH (uncapped) and 60° C. (capped) conditions for 8 weeks. XRPD analysis was then employed to check the crystalline form of the solid, and HPLC was utilized to determine the purity profile at 1, 2, 4 and 8 weeks. From the stability results summarized in Table 45, both trifluoroacetate Type A and HCl Type I are physically and chemically stable under 25° C./60% RH, 40° C./75% RH and 60° C. conditions for 8 weeks. The solid form change of trifluoroacetate Type A at 2 and 4 weeks was postulated to the air-exposure when the sample was taken out for XRPD characterization. Trifluoroacetate Type B is chemically stable, however, physically unstable evidenced by conversion to Type A under these conditions. XRPD patterns overlay of trifluoroacetate Types A and B and HCl Type I at stressed conditions are displayed from FIG. 120 to FIG. 128.

TABLE 45

| Salt | Initial HPLC purity | Time point (weeks) | 25° C./60% RH HPLC purity | 25° C./60% RH Solid form | 40° C./75% RH HPLC purity | 40° C./75% RH Solid form | 60° C. (capped) HPLC purity | 60° C. (capped) Solid form |
|---|---|---|---|---|---|---|---|---|
| TFA Type A | 99.9% | 1 | 99.9% | Type A | 99.9% | Type A | 99.9% | Type A |
| | | 2 | 99.9% | Type B | 99.9% | Type B | 99.9% | Type B |
| | | 4 | 99.9% | Type A + B | 99.9% | Type A + B | 99.9% | Type A + B |
| | | 6 | — | Type A | — | Type A | — | Type A |
| | | 8 | 99.9% | Type A | 99.9% | Type A | 99.9% | Type A |
| TFA Type B | 99.9% | 1 | 99.9% | Type A | 99.9% | Type A | 99.9% | Type A |
| | | 2 | 99.9% | Type A | 99.9% | Type A | 99.9% | Type A |
| | | 4 | 99.9% | Type A | 99.9% | Type A | 99.9% | Type A |
| | | 8 | 99.9% | Type A | 99.9% | Type A | 99.9% | Type A |
| HCl Type I | 99.9% | 1 | 99.9% | Type I | 99.9% | Type I | 99.9% | Type I |
| | | 2 | 99.9% | Type I | 99.9% | Type I | 99.9% | Type I |
| | | 4 | 99.9% | Type I | 99.9% | Type I | 99.9% | Type I |
| | | 8 | 99.9% | Type I | 99.9% | Type I | 99.9% | Type I |

The solid form change of TFA Type A at 2 and 4 weeks was postulated to the air-exposure taken out for XRPD characterization.

The invention claimed is:

1. A method of treating a fungal infection in a patient in need thereof, comprising administering to the patient a pharmaceutical composition comprising an effective amount of a pharmaceutically acceptable salt of compound 1:

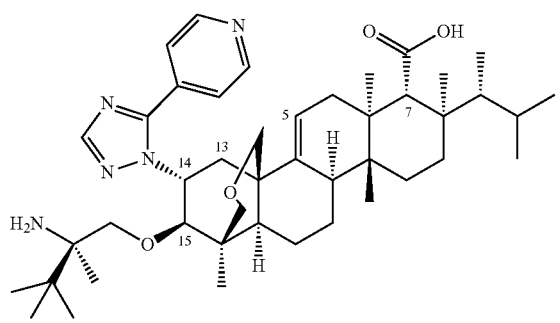

wherein the pharmaceutically acceptable salt is selected from citrate, hippurate, mesylate, and fumarate, and wherein the pharmaceutically acceptable salt of compound 1 used to prepare the pharmaceutical composition has a water sorption of from 2% to 7% at 25° C. and 80% relative humidity as determined by DVS.

2. The method of claim 1, wherein the pharmaceutical composition further comprises a pharmaceutically acceptable carrier, and wherein the pharmaceutical composition is suitable for injection into the patient.

3. The method of claim 1, wherein the pharmaceutical composition further comprises a pharmaceutically acceptable carrier, and wherein the pharmaceutically acceptable salt of compound 1 is dissolved in the pharmaceutically acceptable carrier prior to administering the pharmaceutical composition to the patient.

4. The method of claim 3, wherein the administering comprises administration by intravenous injection.

5. The method of claim 1, wherein the pharmaceutically acceptable salt of compound 1 used to prepare the pharmaceutical composition has a water sorption of from 3% to 7% at 25° C. and 80% relative humidity as determined by DVS.

6. The method of claim 1, wherein the pharmaceutically acceptable salt of compound 1 used to prepare the pharmaceutical composition has a water sorption of from 6% to 7% at 25° C. and 80% relative humidity as determined by DVS.

7. The method of claim 1, wherein the pharmaceutically acceptable salt of compound 1 is a citrate salt of compound 1.

8. The method of claim 1, wherein the fungal infection is a Candida and/or Aspergillus fungal infection.

9. The method of claim 1, wherein the fungal infection is Invasive Candidiasis and/or Invasive Aspergillosis.

10. A method of treating a fungal infection in a patient in need thereof, comprising administering to the patient a pharmaceutical composition comprising an effective amount of a citrate salt of compound 1:

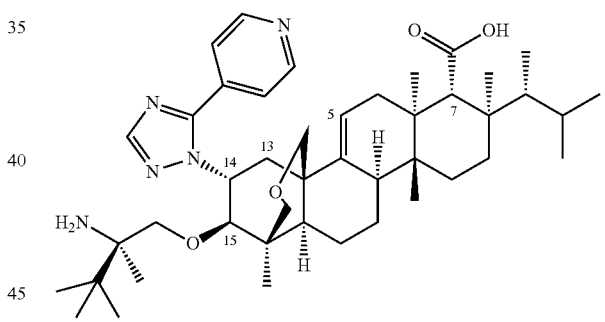

wherein the citrate salt of compound 1 used to prepare the pharmaceutical composition comprises at least one of Type A, Type B, Type E, Type F, Type M, Type N, Type O, Type Q, Type R, and Type S citrate crystal forms.

11. The method of claim 10, wherein the pharmaceutical composition further comprises a pharmaceutically acceptable carrier, and the pharmaceutical composition is suitable for injection into the patient.

12. The method of claim 10, wherein the citrate salt of compound 1 is dissolved in a pharmaceutically acceptable carrier prior to administering the pharmaceutical composition to the patient.

13. The method of claim 12, wherein the administering comprises administration by intravenous injection.

14. The method of claim 10, wherein the citrate salt of compound 1 used to prepare the pharmaceutical composition comprises Type A.

15. The method of claim 10, wherein the citrate salt of compound 1 used to prepare the pharmaceutical composition consists essentially of Type A.

16. The method of claim 10, wherein the citrate salt of compound 1 used to prepare the pharmaceutical composition comprises at least 98% Type A.

17. The method of claim 10, wherein the citrate salt of compound 1 used to prepare the pharmaceutical composition comprises at least 99% Type A.

18. The method of claim 14, wherein the Type A has an XRPD pattern comprising peaks at d-spacing of 11.86, 6.71, and 5.90 Angstroms.

19. The method of claim 14, wherein the Type A has an XRPD pattern comprising peaks at d-spacing of 11.86, 7.70, 7.09, 6.71, 5.90, and 5.29 Angstroms.

20. The method of claim 14, wherein the Type A has an XRPD pattern comprising peaks at degrees 2 theta of 7.45, 11.49, 12.49, 13.19, 15.02, and 16.75.

21. The method of claim 14, wherein the Type A has an XRPD pattern comprising peaks at degrees 2 theta of 7.45, 13.19, and 15.02.

22. The method of claim 14, wherein the Type A is stable for at least 1 week when stored at 60° C.

23. The method of claim 14, wherein the Type A is stable for at least 1 week when stored at 25° C. and 60% relative humidity.

24. The method of claim 14, wherein the Type A is stable for at least 1 week when stored at 40° C. and 75% relative humidity.

25. The method of claim 14, wherein the Type A has an equilibrium solubility of 38 mg/mL in non-buffered water at room temperature.

26. The method of claim 14, wherein the Type A has an approximate solubility of from 40 mg/mL to 42 mg/mL at room temperature in at least one solvent selected from methanol, isopropyl alcohol, acetic acid, tetrahydrofuran, 2-methyl-tetrahydrofuran, 1,4-dioxane, n-methyl-2-pyrrolidone, dimethyl sulfoxide, and dimethylacetamide.

27. The method of claim 14, wherein the Type A has a kinetic solubility of 4 mg/mL at 4 hours in dextrose buffer at pH 5.5.

28. The method of claim 14, wherein the Type A has a kinetic solubility of 8 mg/mL at 24 hours in dextrose buffer at pH 5.5.

29. The method of claim 14, wherein the Type A has a kinetic solubility of 5 mg/mL at 4 hours in phosphate buffer at pH 6.0.

30. The method of claim 14, wherein the Type A has a kinetic solubility of 8 mg/mL at 24 hours in phosphate buffer at pH 6.0.

31. The method of claim 14, wherein the Type A has a kinetic solubility of 21 mg/mL at 1 hour in SGF media.

32. The method of claim 14, wherein the Type A has a kinetic solubility of 4 mg/mL at 24 hours in FeSSIF media.

33. The method of claim 14, wherein the Type A has a kinetic solubility of 10 mg/mL at 1 hour in FaSSIF media.

34. The method of claim 14, wherein the Type A has a kinetic solubility of 21 mg/mL at 4 hours in FaSSIF media.

35. The method of claim 14, wherein the Type A has a water sorption of 6% at 25° C. and 80% relative humidity as determined by DVS.

36. The method of claim 10, wherein the fungal infection is a *Candida* and/or *Aspergillus* fungal infection.

37. The method of claim 10, wherein the fungal infection is *Invasive Candidiasis* and/or *Invasive Aspergillosis*.

* * * * *